(12) United States Patent
Schultheiβ et al.

(10) Patent No.: US 8,373,022 B2
(45) Date of Patent: Feb. 12, 2013

(54) METHODS FOR INCREASING THE RESISTANCE IN PLANTS TO BIOTROPIC FUNGI

(75) Inventors: Holger Schultheiβ, Neustadt (DE); Markus Frank, Neustadt (DE); Caroline Höfle, Wolfersdorf (DE)

(73) Assignee: BASF Plant Science GmbH, Ludwigshafen (DE)

( * ) Notice: Subject to any disclaimer, the term of this patent is extended or adjusted under 35 U.S.C. 154(b) by 552 days.

(21) Appl. No.: 12/446,641

(22) PCT Filed: Oct. 24, 2007

(86) PCT No.: PCT/EP2007/061436
§ 371 (c)(1),
(2), (4) Date: Apr. 22, 2009

(87) PCT Pub. No.: WO2008/049865
PCT Pub. Date: May 2, 2008

(65) Prior Publication Data
US 2010/0088777 A1    Apr. 8, 2010

(30) Foreign Application Priority Data
Oct. 24, 2006    (EP) ..................................... 06122870

(51) Int. Cl.
*C12N 15/09*    (2006.01)
*C12N 15/82*    (2006.01)
(52) U.S. Cl. ........ 800/279; 800/278; 800/312; 800/298; 435/320.1; 435/69.1
(58) Field of Classification Search .................. None
See application file for complete search history.

(56) References Cited

U.S. PATENT DOCUMENTS

| 6,229,067 | B1 | 5/2001 | Sonnewald et al. | |
|---|---|---|---|---|
| 6,451,604 | B1 * | 9/2002 | Flinn et al. .................. | 435/468 |
| 2003/0009785 | A1 | 1/2003 | Reed | |
| 2006/0064775 | A1 | 3/2006 | Frank et al. | |

FOREIGN PATENT DOCUMENTS

| EP | 0864650 A2 | 9/1998 |
|---|---|---|
| WO | WO-00/26391 | 5/2000 |
| WO | WO-02/101079 A2 | 12/2002 |
| WO | WO-2004/081217 A1 | 9/2004 |
| WO | WO-2007/080143 A1 | 7/2007 |

OTHER PUBLICATIONS

Mittler et al. Plant Cell (1996) 8:1991-2001.*
"*Brassica napus* Bax Inhibitor 1 (BI-1) mRNA, Complete cds.", EMBL Database, Accession No. AF390555, Jul. 17, 2001.
"*Arabidopsis thaliana* AtBI-1 mRNA for Bax Inhibitor-1, Complete cds.", EMBL Database, Accession No. AB025927, Jan. 19, 2000.
"*Nicotiana tabacum* Bax Inhibitor 1 (BI-1) mRNA, Complete cds.", EMBL Database, Accession No. AF390556, Jul. 17, 2001.
"*Oryza sativa* BI-1 mRNA for Bax Inhibitor-1, Complete cds.", EMBL Database, Accession No. AB025926, Jan. 19, 2000.
Imani J., et al., "Expression of Barley BAX Inhibitor-1 in Carrots Confers Resistance to *Botrytis cinerea*", Molecular Plant Pathology, 2006, vol. 7, No. 4, pp. 279-284.
Eichmann, R., et al., 'The Barley Apoptosis Suppressor Homologue Bax Inhibitor-1 Compromises Nonhost Penetration Resistance of Barley to the Inappropriate Pathogen *Blumeria graminis* f. sp. *tritici*, Molecular Plant Microbe Interactions, 2004, vol. 17, No. 5, pp. 484-490.
Hückelhoven, R., et al., "Overexpression of Barley BAX Inhibitor 1 Induces Breakdown of *mlo*-Mediated Penetration Resistance to *Blumeria graminis*", Proc. Natl. Acad. Sci. U.S.A., 2003, vol. 100, No. 9, pp. 5555-5560.
Hückelhoven, R., et al., "Differential Expression of Putative Cell Death Regulator Genes in Near-Isogenic, Resistant and Susceptible Barley Lines during Interaction with the Powdery Mildew Fungus", Plant Molecular Biology, 2001, vol. 47, pp. 739-748.
Sanchez, P., et al., "AtBI-1, a Plant Homologue of Bax Inhibitor-1, Suppresses Bax-Induced Cell Death in Yeast and is Rapidly Upregulated during Wounding and Pathogen Challenge", The Plant Journal, 2000, vol. 21, No. 4, pp. 393-399.
Adendorff, R., et al., "Scanning Electron Microscopy of Direct Host Leaf Penetration by Urediospore-Derived Infection Structures of *Phakopsora apoda*", Mycological Research, 2000, vol. 104, No. 3, pp. 317-324.
Chae, H.-J., et al., "Evolutionary Conserved Cytoprotection Provided by Bax Inhibitor-1 Homologs from Animals, Plants, and Yeast", Gene, 2003, vol. 323, pp. 101-113.
Lacomme, C., et al., "Bax-Induced Cell Death in Tobacco is Similar to the Hypersensitive Response", Proc. Natl. Acad. Sci. U.S.A., 1999, vol. 96, pp. 7956-7961.
Kawal-Yamada, M., et al., "Dissection of *Arabidopsis* Bax Inhibitor-1 Suppressing Bax-, Hydrogen Peroxide-, and Salicylic Acid-Induced Cell Death", The Plant Cell, 2004, vol. 16, pp. 21-32.
Hückelhoven, R., "BAX Inhibitor-1, an Ancient Cell Death Suppressor in Animals and Plants with Prokaryotic Relatives", Apoptosis, 2004, vol. 9, pp. 299-307.
Bolduc, N., et al., "Molecular Characterization of Two Plant BI-1 Homologues which Suppress Bax-Induced Apoptosis in Human 293 Cells", Planta, 2003, vol. 216, pp. 377-386.
Xu, Q., et al., "Bax inhibitor-1, a Mammalian Apoptosis Suppressor Identified by Functional Screening in Yeast", Molecular Cell, 1998, vol. 1, pp. 337-346.
Matsumura, H., et al., "Overexpression of Bax Inhibitor Suppresses the Fungal Elicitor-Induced Cell Death in Rice (*Oryza saliva* L.) Cells", The Plant Journal, 2003, vol. 33, pp. 425-434.

(Continued)

*Primary Examiner* — Medina A Ibrahim
(74) *Attorney, Agent, or Firm* — Novak Druce Connolly Bove + Quigg LLP

(57) ABSTRACT

The present invention relates to methods of generating or increasing resistance to at least one biotrophic pathogen in a plant or a part of a plant by increasing the protein quantity or function of at least one Bax Inhibitor-1 (BI-1) protein in at least one part of the plant. Moreover, the invention relates to polypeptide sequences and nucleic acid sequences which code for a BI-1 protein, and to expression cassettes, vectors and organisms which comprise such sequences or such a protein.

16 Claims, 15 Drawing Sheets

OTHER PUBLICATIONS

Baek, D., et al., "Bax-induced Cell Death of *Arabidopsis* is Meditated through Reactive Oxygen-Dependent and -Independent Processes", Plant Molecular Biology, 2004, vol. 56, pp. 15-27.

Bolduc, N., et al., "Antisense Down Regulation of NtBI-1 in Tobacco BY-2 Cells Induces Accelerated Cell Death upon Carbon Starvation", FEBS Letters, 2002, vol. 532, pp. 111-114.

Watanabe, N., et al., "*Arabidopsis* Sax Inhibitor-1 Functions as an Attenuator of Biotic and Abiotic Types of Cell Death", The Plant Journal, 2006, vol. 45, pp. 884-894.

Roth, W., et al., "Apoptosis and Cancer: When BAX is Trailing Away", Nature Medicine, 2002, vol. 8, No. 3, pp. 216-218.

Kawai, M., et al., "Evolutionary Conserved Plant Homologue of the Bax Inhibitor-1 (BI-1) Gene Capable of Suppressing Bax-Induced Cell Death in Yeast", FEBS Letters, 1999, vol. 464, pp. 143-147.

Kawai-Yamada, M., et al., "Mammalian Bax-Induced Plant Cell Death Can Be Down-Regulated by Overexpression of *Arabidopsis Bax* Inhibitor-1 (AtBI-1)", PNAS, 2001, vol. 98, No. 21, pp. 12295-12300.

Lincoln, J., et al., "Expression of the Antiapoptotic Baculovirus p35 Gene in Tomato Blocks Programmed Cell Death and Provides Broad-Spectrum Resistance to Disease", Proceedings of the National Academy of Sciences of the U.S., vol. 99, No. 23 (2002), pp. 15217-15221.

Shirasu, K., et al., "Regulators of Cell Death in Disease Resistance", Plant Molecular Biology, vol. 44 (2000), pp. 371-385.

"*Hordeum vulgare* mRNA for BAX Inhibitor-1 (pBI-1 Gene)", GenBank Accession No. AJ290421, Jan. 18, 2002.

Nelson, H., et al. "Respective roles of the epidermis and mesophyll in the resistance of barley to powdery mildew", Ann. Phytopath. Soc. Japan (1989) 55: 156-160.

Ryals, J.A., et al., "Systemic Acquired Resistance",The Plant Cell (1996) vol. 8: 1809-1819.

* cited by examiner

Figure 1a (Page 1 of 3)

```
          1                                                          50
   AtBI-1    (1)  ---------MDAFSSFFDSQPGS---RSWSYDSLKNFRQISPAVQNHLKR
   BnBI-1    (1)  ---------MDSFSSFFDSQPGS---RSWSYDSLKNLRQISPSVQNHLKR
    GmBI2    (1)  -----RLQAMDAFNSFFDS------RNRWNYDTLKNFRQISPVVQNHLKQ
    GmBI3    (1)  ITKTIRFDSLFSMDTFFKSPSSSSSRSRWSYDTLKNFREISPLVQNHIKL
   HVBI-1    (1)  ----------MDAFYSTS---SAAASGWGHDSLKNFRQISPAVQSHLKL
   NtBI-1    (1)  ---------MESCTSFFNSQSASS-RNRWSYDSLKNFRQISPFVQTHLKK
   OsBI-1    (1)  ----------MDAFYSTSSAYGAAASGWGYDSLKNFRQISPAVQSHLKL
   TaBI11    (1)  --------------------------------------------------
   TaBI18    (1)  -----------------FSGTFRNSRSDDFVLCELQRELPRCRDATLTV
  TaBI5 new  (1)  --------------------------------------------VAMPGR
   ZmBI14    (1)  --------------------------------------------------
   ZmBI16    (1)  --------------------------------------------------
   ZmBI33    (1)  --------------------------------------------------
    ZmBI8    (1)  --------------------------------------------------
Consensus    (1)                   F  S         W YDSLKN R ISP VQ HLK 51                                                     100
   AtBI-1   (39)  VYLTLCCALVASAFGAYLHVLWNIGGILTTIGCIGTMIWLLSCPPYEHQK
   BnBI-1   (39)  VYLTLCCALVASAFGAYLHVLWNIGGILTTIGCFGSMIWLLSCPPYEQQK
    GmBI2   (40)  VYFTLCFAVVAAAVGAYLHVLLNIGGFLTTVACMGSSFWLLSTPPFEERK
    GmBI3   (51)  VYFTLCCAVVAAAVGAFLHVLWNIGGFLTTLASIGSMFWLLSTPPFEEKK
   HVBI-1   (37)  VYLTLCFALASSAVGAYLHIALNIGGMLTMLACVGTIAWMFSVPVYEERK
   NtBI-1   (41)  VYLSLCCALVSAAGAYLHILWNIGGLLTTLGCVGSIVWLMATPLYEEQK
   OsBI-1   (40)  VYLTLCVALAASAVGAYLHVALNIGGMLTMLGCVGSIAWLFSVPVFEERK
   TaBI11    (1)  --------------------------------------------------
   TaBI18   (33)  VYVIPIVGRIKSAAGAYLHIALNIGGMLTMLACIGTIAWMFSVPVYEERK
  TaBI5 new  (7)  RFRLTYALPGLICRGCLPAHCPEHWRDADNARVYRNHRLDVLGASLRGEE
   ZmBI14    (1)  -----------------------------GSIAWLFSVPVYEERK
   ZmBI16    (1)  -------------------WNIGVRLTMLGCIGSIDWLFSVPVYEERK
   ZmBI33    (1)  -------------------WNIGGTLTMLGCVGSIAWLFSVPVYEERK
    ZmBI8    (1)  --------------------------------------------------
Consensus   (51)  VY TLC AL ASA GAYLHV  NIGG LT LGCIGSI WL S PVYEERK 101                                                    150
   AtBI-1   (89)  RLSLLFVSAVLEGASVGPLIKVAIDVDPSILITAFVGTAIAFVCFSAAAM
   BnBI-1   (89)  RLSLLFLSAVLEGASVGPLIKVAVDFDPSILITAFVGTAIAFICFSGAAM
    GmBI2   (90)  RVTLLMAASLFQGSSIGPLIDLAIHIDPSLIFSAFVGTALAFACFSGAAL
    GmBI3  (101)  RLSLLMASALFQGASIGPLIDLAFAIDPGLIIGAFVATSLAFACFSAVAL
   HVBI-1   (87)  RFGLLMGAALLEGASVGPLIELAIDFDPSILVTGFVGTAIAFGCFSGAAI
   NtBI-1   (91)  RIALLMAAALFKGASIGPLIELAIDFDPSIVIGAFVGCAVAFGCFSAAAM
   OsBI-1   (90)  RFGILLAAALLEGASVGPLIKLAVDFDSSILVTAFVGTAIAFGCFTCAAI
   TaBI11    (1)  --------------------------------------------AAI
   TaBI18   (83)  RFGLLMGAALLEGASVGPLIELAIDFDPSILVTGFVGTAIAFGCFSGAAI
  TaBI5 new (57)  EVWAADGCSLLEGASVGPLIELAIDFDPSILVTGFVGTAIAFGCFSGAAI
   ZmBI14   (17)  RYWLLMAAALLEGASVGPLIKLAVEFDPSILVTAFVGTAIAFACFSCAAM
   ZmBI16   (30)  RYGLLMAAALLEGASVGPLVKLAVEFDPSILVTAFVGTAIAFACFSGAAM
   ZmBI33   (30)  RYGLLMAAALLEGASVGPLVKLAVEFDPSILVTAFVGTAIAFACFSGAPW
    ZmBI8    (1)  ---------------------VIDLDSRILVTAFVGTAVAFACFSGAAI
Consensus  (101)  R   LLMAAALLEGASVGPLI LAIDFDPSILVTAFVGTAIAFACFSGAAI
```

Figure 1b (Page 2 of 3)

```
                 151                                              200
    AtBI-1 (139) LARRREYLYLGGLLSSGLSMLMWLQFASSIFG-GSASIFKFELYFGLLIF
    BnBI-1 (139) LARRREYLYLGGLLSSGLSMLMWLQFASSIFG-GSASIFKFELYFGLLIF
     GmBI2 (140) VARRREYLYLGGLVSSGLSILLWLHFASSIFG-GSTALFKFELYFGLLVF
     GmBI3 (151) VARRREYLYLGGLLSSWLSILMWLHSDSSLFG-GSIALFKFELYFGLLVF
    HVBI-1 (137) IAKRREYLYLGGLLSSGLSILLWLQFVTSIFGHSS-GSFMFEVYFGLLIF
    NtBI-1 (141) VARRREYLYLGGLLSSGLSILFWLHFASSIFG-GSMALFKFEVYFGLLVF
    OsBI-1 (140) VAKRREYLYLGGLLSSGLSILLWLQFAASIFGHST-GSFMFEVYFGLLIF
    TaBI11   (4) IAKRREYLYLGGLLSSGLSILLWLQFATSIFGHSS-GSFMFEVYFGLLIF
    TaBI18 (133) IAKRREYLYLGGLLSSG------------------------LTIL
 TaBI5 new (107) IAKRREYLYLGGLLSSGLSILLWLQFATSIFGHSS-GSFMFEVYFGLLIF
    ZmBI14  (67) VAKRREYLYLGGLLSSGLSILLWLQFAASIFGHQSTSSFMFEVYFGLLIF
    ZmBI16  (80) VARRREYLYLGGLLSSGLSILLWLQLAASIF-GHSATSFMFEVYFGLLIF
    ZmBI33  (80) WQAR-EYLYLGGCSRRGSPSCSGCSSPPPSS--ALRNSFMFEVYFGLLIL
     ZmBI8  (29) IAKRREYLYLGGLLSSGLSILLWLQFATSIFGHTS-ATFMFELYFGLLVF
 Consensus (151) VAKRREYLYLGGLLSSGLSILLWLQFASSIFG  S ASFMFEVYFGLLIF 201                                              250
    AtBI-1 (188) VGYMVVDTQEIIEKAHLGDMDYVKHSLTLFTDFVAVFVRILIIMLKNSAD
    BnBI-1 (188) VGYMVVDTQDIIEKAHLGDMDYVKHSLTLFTDFVAVFVRVLIIMLKNSAD
     GmBI2 (189) VGYIVVDTQEIVERAHLGDLDYVKHALTLFTDLVAAIFVRILVIMLKNSTE
     GmBI3 (200) VGYVVIVDTQEIIERAHFGDLDYVKHALTLFTDLAAIFVRILIIMLKNSSE
    HVBI-1 (186) LGYMVYDTQEIIERAHLGDMDYIKHALTLFTDFVAVLVRVLIIMLKNAGD
    NtBI-1 (190) VGYIIFDTQDIIEKAHLGDLDYVKHALTLFTDFVAVFVRILIIMLKNASD
    OsBI-1 (189) LGYMVYDTQEIIERAHHGDMDYIKHALTLFTDFVAVLVRILVIMLKNASD
    TaBI11  (53) LGYMVYDTQEIIERAHHGDMDYIKHALTLFTDFVAVLVRILIIMLKNAGD
    TaBI18 (154) L------------------------------------------------
 TaBI5 new (156) LGYMVYDTQEIIERAHHGDMDYIKHALTLFTDFVAVLVRVLIILLKNAAD
    ZmBI14 (117) LGYMVYDTQEVIERAHHG-------------------------------
    ZmBI16 (129) LGYVVYDT-----------------------------------------
    ZmBI33 (127) LG-----------------------------------------------
     ZmBI8  (78) LGYMVFDTQEIIERAHRGDMDYIKHALTLFTDFVAVLVRILVIMMKNAQE
 Consensus (201) LGYMVYDTQEIIERAH GDMDYIKHALTLFTDFVAV VRILIIMLKNA D 251                                              300
    AtBI-1 (238) KEEKKKKRRN------GDVK-I-LYGCYRVWPL-RYYLLALSIGDQTCF
    BnBI-1 (238) KEDKKKRRRN------D-KVRKKAK-SGCYVCFKK------------KRVG
     GmBI2 (239) RNEKKKKRRD---------------------------------------
     GmBI3 (250) RNEKKKKRRD--ADRPTRAQASLQ-FSLWRIHN--------LFR-CWSLV-
    HVBI-1 (236) KSEDKKKRKRG------------------S-------------------
    NtBI-1 (240) KEEKKKKRRN----CISGYSKTL-L-NLAFSCS---TSVDLRQVCC--FG
    OsBI-1 (239) KSEEKKRKKRS-ELLFPLCT-EKTTAAIASTYYDRAALQLGFMVNTSSFA
    TaBI11 (103) KSEDKKKRKRRS-------------------------------------
    TaBI18 (155) -------------------------------------------------
 TaBI5 new (206) KVGGQEEEEEKS-------------------------------------
    ZmBI14 (135) -------------------------------------------------
    ZmBI16 (137) -------------------------------------------------
    ZmBI33 (129) -------------------------------------------------
     ZmBI8 (128) KSQDEKKRK----------------------------------------
 Consensus (251) K E KKKRR
```

Figure 1c (Page 3 of 3)

```
                301                                                 350
AtBI-1   (278)  H-KG-SACFTSAQVPSSDCK---------------LECCSSFHKLLFFKSL
BnBI-1   (269)  VISTDMIALVFFTCLEQFW------------QHTLRICVFLLVTPDCEWI
GmBI2    (249)  --------------------------------------------------
GmBI3    (288)  LVSYVFAVMVNVRISFKHLHMYLPIS-CVV-HHTLV-KKKKKKKKKKKKK
HVBI-1   (248)  --------------------------------------------------
NtBI-1   (279)  NASD-AARLCYAACQCGYGGT-MVLF----PKHTIK-HACLHYIDNLRVY
OsBI-1   (287)  FC-YGVNLLRFVVVVALQILACYMTRIFL-WWSR-SKRENTSSFATNLFA
Consensus (301)

351                                                 400
AtBI-1   (312)  VLLIASYQAKNNVGK----------SCLNFLKCVHFRKKKKKKKKK-----
BnBI-1   (307)  SILKLC-KLSVGS-------------------------------------
GmBI2    (249)  --------------------------------------------------
GmBI3    (335)  KKKKKXXXXXXXXXXXXX--XXXXXGVCGLRYSRHSSNH-EGSLW-PGLC-
HVBI-1   (248)  --------------------------------------------------
NtBI-1   (322)  YLFLLPFAVLGCS-LYS-FSVMLDHLLS-RLISHIDGRNENSHRRPNLFK
OsBI-1   (334)  FW-LMMILSPKKKK------------------------------------
Consensus (351)

401                                                 450
AtBI-1   (348)  --------------------------------------------------
BnBI-1   (319)  --------------------------------------------------
GmBI2    (249)  --------------------------------------------------
GmBI3    (380)  ACIDTVH-FGCNLCANS-YNVE-FI-EK-EEEEERLIG-PIAMCRVIWFV
HVBI-1   (248)  --------------------------------------------------
NtBI-1   (369)  TEAQL---------------------------------------------
Consensus (401)

451                                                 500
GmBI3    (424)  ENT-LAV-KLLVPLCS--LAMCLL-W-MSGFLLNIFICIC---S-YIV-TS
Consensus (451)

501       512
GmBI3    (464)  FLGLKKEKKKKK
Consensus (501)
```

Figure 6

```
H.vul.  MDDFYSTSS----AAASGUGHDSLKTPRGISPAVQSHLKLVYLTLCFALASSAWGAYLHIA  57
O.sat.  MDDFYSTSSAYGAAASGUGYDSLKTPRGISPAVQSHLKLVYLTLGVALAASAWGAYLHVA  60
A.tha.  MDDFSSFFDS-QPGSRSWSYDSLKNPRGISPAVQMHLKRVYLTLGCALVASDFGAYLHVL  59
H.sap.  MNDFDRKIN-----------FDALLKFSHITPSTQCHLKRVYASFALCMFVAAAGAYWHMV  50

H.vul.  LN---IGGMLTMLACVGTIADMFSVPVYEE---RKRFGLLMGADLLEGASVGPLIELAIDFD  113
O.sat.  LN---IGGMLTMLGCVGSIADLFSVPVFEE---RKRFGILLADLLEGASVGPLIKLAVDFD  116
A.tha.  UN---IGGILTTIGCIGTMIWLLSCPPYEH---QKRLSLLFVSDVLEGASVGPLIKVAIDVD  115
H.sap.  THFIQACLLSALGSLILMIDLNATPHSHETEQKRLGLLAGFDFLTGVGLGPALEFCIAVN  110

H.vul.  PSILVIGFVGTADIFGCFSGADIIAKRREYLVLGGLLSSGLSILLWLQFVTSIFGHSSGS  173
O.sat.  SSILVTAFVGTADIFGCFTCADIVAKRREYLVLGGLLSSGLSILLWLQFAASIFGHSTGS  176
A.tha.  PSILITAFVGTADIFVCFSADAHLAPRREYLVLGGLLSSGLSMIWMLQFASSIFGGSASI  175
H.sap.  PSILPTAFNGTAMIFTCFTLSALYARRESYLFLGGIDMSALSLLLLSSLGNVFPG-SIWP  169

H.vul.  FMFEVYFGLLIFLGYMVYDTCEIIERAHHGDLDYIKHALTLFTDFVAVLVRVLIIMLKNA  233
O.sat.  FMFEVYFGLLIFLGYMVYDTCEIIERAHHGDLDYIKHALTLFTDFVAVLVRILVIMLKNA  236
A.tha.  FKFELYFGLLIFVGYMVVDTCEIIERAHLGDMDYVKHSLTLFTDFVAVFWRILIIMLKNS  235
H.sap.  FQANLYVGLVVMCGFVLVDTCLIIERMEHGDQDYIWHCIDLFLDFITWFRKLMMILAMNE  229

H.vul.  GDRSEDKRKRKRGS  247
O.sat.  SDRSEEKPRKKRS-  249
A.tha.  ADR-EEKRKKREN-  247
H.sap.  KDR----KREKK--  237
```

Figure 10

| Experiment | Constructs used | Transformed cells which interact with soybean rust | Transformed cells which are penetrated by soybean rust | Penetration rate of the transformed cells [%] |
|---|---|---|---|---|
| 1 | pGY1-GFP+pGY1 | 46 | 19 | 41.30 |
|   | pGY1-GFP+ pGY1-HvBI | 13 | 3 | 23.08 |
| 2 | pGY1-GFP+pGY1 | 65 | 36 | 55.38 |
|   | pGY1-GFP+ pGY1-HvBI | 136 | 62 | 45.59 |
| 3 | pGY1-GFP+pGY1 | 126 | 79 | 62.70 |
|   | pGY1-GFP+ pGY1-HvBI | 203 | 91 | 44.83 |

|  | Control | HvBI-1 |
|---|---|---|
| Overall mean averaged over the experiments | 53.13 | 37.83 |
| standard deviation | 10.88 | 12.78 |
| t-test | 0.0309 |  |

Figure 11a (Page 1 of 2)

| Barley | Plant No. | Spores | Spores with appressoria | Appressoria with papillae | HR of infected cells |
|---|---|---|---|---|---|
| 1#6 (1)E8L1 (T1) | 1 | 139 | 122 | 33 | 55 |
| 1#6 (1)E8L1 (T1) | 2 | 167 | 136 | 76 | 23 |
| 1#6 (1)E8L1 (T1) | 3 | 167 | 131 | 87 | 21 |
| 1#6 (1)E8L1 (T1) | 4 | 194 | 124 | 81 | 26 |
| 1#6 (1)E8L1 (T1) | 6 | 169 | 121 | 71 | 34 |
| 1#6 (1)E8L1 (T1) | 7 | 188 | 123 | 73 | 28 |
| 1#6 (1)E8L1 (T1) | 8 | 143 | 123 | 84 | 33 |
| 1#6 (1)E8L1 (T1) | 9 | 156 | 122 | 82 | 16 |
| 1#6 (1)E8L1 (T1) | 20 | 147 | 103 | 61 | 24 |
| 1#6 (1)E8L1 (T1) | 18 | 175 | 138 | 97 | 25 |
| 1#6 (1)E8L1 (T1) | 17 | 134 | 129 | 94 | 16 |
| 1#6 (1)E8L1 (T1) | 16 | 176 | 122 | 50 | 51 |
| 1#6 (1)E8L1 (T1) | 15 | 168 | 123 | 100 | 23 |
| 1#6 (1)E8L1 (T1) | 14 | 168 | 124 | 77 | 11 |
| 1#6 (1)E8L1 (T1) | 13 | 143 | 125 | 86 | 20 |
| 1#6 (1)E8L1 (T1) | 12 | 153 | 122 | 83 | 25 |
| 1#6 (1)E8L1 (T1) | 11 | 141 | 122 | 82 | 31 |
| 1#6 (2)E15L7P2 (T2) | 1 | 156 | 136 | 72 | 12 |
| 1#6 (2)E15L7P2 (T2) | 2 | 151 | 125 | 78 | 13 |
| 1#6 (2)E15L7P2 (T2) | 4 | 173 | 127 | 77 | 21 |
| 1#6 (2)E15L7P2 (T2) | 14 | 131 | 111 | 40 | 35 |
| 1#6 (2)E15L7P2 (T2) | 13 | 177 | 122 | 58 | 44 |
| 1#6 (2)E15L7P2 (T2) | 10 | 175 | 127 | 60 | 22 |
| 1#6 (2)E15L7P2 (T2) | 9 | 164 | 114 | 60 | 16 |
| 1#6 (2)E15L7P2 (T2) | 8 | 175 | 126 | 96 | 17 |
| 1#6 (2)E15L7P2 (T2) | 7 | 152 | 131 | 52 | 18 |
| 1#6 (2)E15L7P2 (T2) | 6 | 181 | 128 | 53 | 10 |
| 1#6 (2)E15L7P2 (T2) | 5 | 207 | 129 | 74 | 19 |
| GP-WT | 1 | 159 | 115 | 54 | 42 |
| GP-WT | 2 | 150 | 127 | 54 | 58 |
| GP-WT | 3 | 169 | 123 | 21 | 80 |
| GP-WT | 4 | 175 | 120 | 68 | 35 |
| GP-WT | 5 | 162 | 125 | 52 | 66 |
| GP-WT | 6 | 160 | 121 | 53 | 61 |
| GP-WT | 7 | 137 | 124 | 45 | 59 |
| GP-WT | 8 | 160 | 120 | 43 | 63 |
| GP-WT | 9 | 161 | 126 | 30 | 90 |
| GP-WT | 10 | 125 | 119 | 46 | 64 |
| GP-WT | 11 | 165 | 138 | 43 | 53 |
| GP-WT | 12 | 146 | 126 | 55 | 33 |
| GP-WT | 13 | 139 | 113 | 34 | 51 |
| GP-WT | 14 | 147 | 123 | 47 | 50 |
| GP-WT | 15 | 151 | 130 | 25 | 65 |
| GP-WT | 16 | 209 | 124 | 33 | 75 |
| GP-WT | 17 | 210 | 147 | 29 | 46 |
| GP-WT | 18 | 151 | 132 | 72 | 42 |
| GP-WT | 19 | 207 | 122 | 50 | 50 |
| GP-WT | 20 | 199 | 133 | 52 | 52 |

Figure 11b (Page 2 of 2)

| Barley | Plant No. | Spores | Spores with appressoria | Appressoria with papillae | HR of infected cells |
|---|---|---|---|---|---|
| 1#6 (2) E15L7P1 (T2) | 20 | 149 | 100 | 46 | 26 |
| 1#6 (2) E15L7P1 (T2) | 19 | 176 | 120 | 81 | 15 |
| 1#6 (2) E15L7P1 (T2) | 18 | 181 | 129 | 94 | 12 |
| 1#6 (2) E15L7P1 (T2) | 17 | 200 | 122 | 70 | 21 |
| 1#6 (2) E15L7P1 (T2) | 16 | 170 | 121 | 76 | 20 |
| 1#6 (2) E15L7P1 (T2) | 15 | 170 | 128 | 62 | 22 |
| 1#6 (2) E15L7P1 (T2) | 14 | 156 | 126 | 44 | 43 |
| 1#6 (2) E15L7P1 (T2) | 13 | 116 | 94 | 34 | 32 |
| 1#6 (2) E15L7P1 (T2) | 12 | 204 | 130 | 75 | 30 |
| 1#6 (2) E15L7P1 (T2) | 11 | 194 | 122 | 69 | 30 |
| 1#6 (2) E15L7P1 (T2) | 10 | 145 | 121 | 60 | 20 |
| 1#6 (2) E15L7P1 (T2) | 9 | 165 | 121 | 64 | 30 |
| 1#6 (2) E15L7P1 (T2) | 8 | 192 | 122 | 80 | 23 |
| 1#6 (2) E15L7P1 (T2) | 7 | 184 | 127 | 74 | 28 |
| 1#6 (2) E15L7P1 (T2) | 6 | 167 | 121 | 85 | 13 |
| 1#6 (2) E15L7P1 (T2) | 5 | 169 | 129 | 67 | 20 |
| 1#6 (2) E15L7P1 (T2) | 4 | 182 | 124 | 80 | 22 |
| 1#6 (2) E15L7P1 (T2) | 3 | 147 | 117 | 77 | 24 |
| 1#6 (2) E15L7P1 (T2) | 2 | 131 | 121 | 81 | 25 |
| 1#6 (2) E15L7P1 (T2) | 1 | 174 | 119 | 59 | 23 |
| 1#6 (1)E4L3P5 (T2) | 20 | 153 | 121 | 74 | 36 |
| 1#6 (1)E4L3P5 (T2) | 19 | 150 | 143 | 82 | 39 |
| 1#6 (1)E4L3P5 (T2) | 18 | 152 | 122 | 82 | 19 |
| 1#6 (1)E4L3P5 (T2) | 17 | 143 | 131 | 81 | 12 |
| 1#6 (1)E4L3P5 (T2) | 16 | 179 | 149 | 76 | 39 |
| 1#6 (1)E4L3P5 (T2) | 15 | 153 | 121 | 46 | 43 |
| 1#6 (1)E4L3P5 (T2) | 14 | 155 | 124 | 58 | 41 |
| 1#6 (1)E4L3P5 (T2) | 13 | 145 | 126 | 67 | 33 |
| 1#6 (1)E4L3P5 (T2) | 12 | 160 | 125 | 67 | 45 |
| 1#6 (1)E4L3P5 (T2) | 11 | 169 | 123 | 65 | 46 |
| 1#6 (1)E4L3P5 (T2) | 10 | 157 | 124 | 57 | 46 |
| 1#6 (1)E4L3P5 (T2) | 9 | 180 | 124 | 68 | 47 |
| 1#6 (1)E4L3P5 (T2) | 8 | 168 | 120 | 78 | 25 |
| 1#6 (1)E4L3P5 (T2) | 7 | 153 | 128 | 76 | 15 |
| 1#6 (1)E4L3P5 (T2) | 6 | 165 | 127 | 78 | 37 |
| 1#6 (1)E4L3P5 (T2) | 5 | 144 | 136 | 68 | 37 |
| 1#6 (1)E4L3P5 (T2) | 4 | 134 | 132 | 53 | 55 |
| 1#6 (1)E4L3P5 (T2) | 3 | 188 | 156 | 75 | 34 |
| 1#6 (1)E4L3P5 (T2) | 2 | 158 | 130 | 77 | 14 |
| 1#6 (1)E4L3P5 (T2) | 1 | 162 | 123 | 51 | 30 |

SEQUENCE LISTING

```
<160> NUMBER OF SEQ ID NOS: 61

<210> SEQ ID NO 1
<211> LENGTH: 744
<212> TYPE: DNA
<213> ORGANISM: Hordeum vulgare
<220> FEATURE:
<221> NAME/KEY: CDS
<222> LOCATION: (1)..(741)
<223> OTHER INFORMATION: coding for BI1-protein

<400> SEQUENCE: 1 atg gac gcc ttc tac tcg acc tcg tcg gcg gcg gcg agc ggc tgg ggc      48
Met Asp Ala Phe Tyr Ser Thr Ser Ser Ala Ala Ala Ser Gly Trp Gly
 1               5                  10                  15 cac gac tcc ctc aag aac ttc cgc cag atc tcc ccc gcc gtg cag tcc      96
His Asp Ser Leu Lys Asn Phe Arg Gln Ile Ser Pro Ala Val Gln Ser
             20                  25                  30 cac ctc aag ctc gtt tac ctg act cta tgc ttt gca ctg gcc tca tct     144
His Leu Lys Leu Val Tyr Leu Thr Leu Cys Phe Ala Leu Ala Ser Ser
         35                  40                  45 gcc gtg ggt gct tac cta cac att gcc ctg aac atc ggc ggg atg ctg     192
Ala Val Gly Ala Tyr Leu His Ile Ala Leu Asn Ile Gly Gly Met Leu
     50                  55                  60 aca atg ctc gct tgt gtc gga act atc gcc tgg atg ttc tcg gtg cca     240
Thr Met Leu Ala Cys Val Gly Thr Ile Ala Trp Met Phe Ser Val Pro
 65                  70                  75                  80 gtc tat gag gag agg aag agg ttt ggg ctg ctg atg ggt gca gcc ctc     288
Val Tyr Glu Glu Arg Lys Arg Phe Gly Leu Leu Met Gly Ala Ala Leu
                 85                  90                  95 ctg gaa ggg gct tcg gtt gga cct ctg att gag ctt gcc ata gac ttt     336
Leu Glu Gly Ala Ser Val Gly Pro Leu Ile Glu Leu Ala Ile Asp Phe
            100                 105                 110 gac cca agc atc ctc gtg aca ggg ttt gtc gga acc gcc atc gcc ttt     384
Asp Pro Ser Ile Leu Val Thr Gly Phe Val Gly Thr Ala Ile Ala Phe
        115                 120                 125 ggg tgc ttc tct ggc gcc gcc atc atc gcc aag cgc agg gag tac ctg     432
Gly Cys Phe Ser Gly Ala Ala Ile Ile Ala Lys Arg Arg Glu Tyr Leu
    130                 135                 140 tac ctc ggt ggc ctg ctc tcg tct ggc ctg tcg atc ctg ctc tgg ctg     480
Tyr Leu Gly Gly Leu Leu Ser Ser Gly Leu Ser Ile Leu Leu Trp Leu
145                 150                 155                 160 cag ttt gtc acg tcc atc ttt ggc cac tcc tct ggc agc ttc atg ttt     528
Gln Phe Val Thr Ser Ile Phe Gly His Ser Ser Gly Ser Phe Met Phe
                165                 170                 175 gag gtt tac ttt ggc ctg ttg atc ttc ctg ggg tac atg gtg tac gac     576
Glu Val Tyr Phe Gly Leu Leu Ile Phe Leu Gly Tyr Met Val Tyr Asp
            180                 185                 190 acg cag gag atc atc gag agg gcg cac cat ggc gac atg gac tac atc     624
```

```
Thr Gln Glu Ile Ile Glu Arg Ala His His Gly Asp Met Asp Tyr Ile
        195                 200                 205 aag cac gcc ctc acc ctc ttc acc gac ttt gtt gcc gtc ctc gtc cga       672
Lys His Ala Leu Thr Leu Phe Thr Asp Phe Val Ala Val Leu Val Arg
    210                 215                 220 gtc ctc atc atc atg ctc aag aac gca ggc gac aag tcg gag gac aag       720
Val Leu Ile Ile Met Leu Lys Asn Ala Gly Asp Lys Ser Glu Asp Lys
225                 230                 235                 240 aag aag agg aag agg ggg tcc tga                                       744
Lys Lys Arg Lys Arg Gly Ser
            245

<210> SEQ ID NO 2
<211> LENGTH: 247
<212> TYPE: PRT
<213> ORGANISM: Hordeum vulgare

<400> SEQUENCE: 2

Met Asp Ala Phe Tyr Ser Thr Ser Ser Ala Ala Ser Gly Trp Gly
1               5                   10                  15

His Asp Ser Leu Lys Asn Phe Arg Gln Ile Ser Pro Ala Val Gln Ser
            20                  25                  30

His Leu Lys Leu Val Tyr Leu Thr Leu Cys Phe Ala Leu Ala Ser Ser
        35                  40                  45

Ala Val Gly Ala Tyr Leu His Ile Ala Leu Asn Ile Gly Gly Met Leu
    50                  55                  60

Thr Met Leu Ala Cys Val Gly Thr Ile Ala Trp Met Phe Ser Val Pro
65                  70                  75                  80

Val Tyr Glu Glu Arg Lys Arg Phe Gly Leu Leu Met Gly Ala Ala Leu
                85                  90                  95

Leu Glu Gly Ala Ser Val Gly Pro Leu Ile Glu Leu Ala Ile Asp Phe
            100                 105                 110

Asp Pro Ser Ile Leu Val Thr Gly Phe Val Gly Thr Ala Ile Ala Phe
        115                 120                 125

Gly Cys Phe Ser Gly Ala Ala Ile Ile Ala Lys Arg Arg Glu Tyr Leu
    130                 135                 140

Tyr Leu Gly Gly Leu Leu Ser Ser Gly Leu Ser Ile Leu Leu Trp Leu
145                 150                 155                 160

Gln Phe Val Thr Ser Ile Phe Gly His Ser Ser Gly Ser Phe Met Phe
                165                 170                 175

Glu Val Tyr Phe Gly Leu Leu Ile Phe Leu Gly Tyr Met Val Tyr Asp
            180                 185                 190

Thr Gln Glu Ile Ile Glu Arg Ala His His Gly Asp Met Asp Tyr Ile
        195                 200                 205

Lys His Ala Leu Thr Leu Phe Thr Asp Phe Val Ala Val Leu Val Arg
    210                 215                 220

Val Leu Ile Ile Met Leu Lys Asn Ala Gly Asp Lys Ser Glu Asp Lys
225                 230                 235                 240

Lys Lys Arg Lys Arg Gly Ser
            245

<210> SEQ ID NO 3
<211> LENGTH: 1067
<212> TYPE: DNA
<213> ORGANISM: Arabidopsis thaliana
<220> FEATURE:
<221> NAME/KEY: CDS
<222> LOCATION: (1)..(741)
<223> OTHER INFORMATION: coding for BI1-protein
```

<400> SEQUENCE: 3

```
atg gat gcg ttc tct tcc ttc ttc gat tct caa cct ggt agc aga agc      48
Met Asp Ala Phe Ser Ser Phe Phe Asp Ser Gln Pro Gly Ser Arg Ser
 1               5                  10                  15 tgg agc tat gat tct ctt aaa aac ttc cgt cag att tct cca gcc gtt      96
Trp Ser Tyr Asp Ser Leu Lys Asn Phe Arg Gln Ile Ser Pro Ala Val
             20                  25                  30 cag aat cat ctt aaa cgg gtt tat ttg acc tta tgt tgt gct ctt gtg     144
Gln Asn His Leu Lys Arg Val Tyr Leu Thr Leu Cys Cys Ala Leu Val
         35                  40                  45 gcg tct gcc ttt gga gct tac ctc cat gtg ctc tgg aat atc ggc ggt     192
Ala Ser Ala Phe Gly Ala Tyr Leu His Val Leu Trp Asn Ile Gly Gly
     50                  55                  60 att ctt aca acg att gga tgt att gga act atg att tgg ctc ctt tca     240
Ile Leu Thr Thr Ile Gly Cys Ile Gly Thr Met Ile Trp Leu Leu Ser
 65                  70                  75                  80 tgt cct cct tat gaa cac caa aaa agg ctt tct ctt ctg ttt gtg tct     288
Cys Pro Pro Tyr Glu His Gln Lys Arg Leu Ser Leu Leu Phe Val Ser
                 85                  90                  95 gct gtt ctt gaa ggt gct tct gtt ggc ccc ttg atc aaa gtg gca att     336
Ala Val Leu Glu Gly Ala Ser Val Gly Pro Leu Ile Lys Val Ala Ile
            100                 105                 110 gat gtt gac cca agc atc ctt atc act gca ttt gtt gga act gcg ata     384
Asp Val Asp Pro Ser Ile Leu Ile Thr Ala Phe Val Gly Thr Ala Ile
        115                 120                 125 gcg ttt gtc tgt ttc tca gca gca gca atg tta gca aga cgc agg gag     432
Ala Phe Val Cys Phe Ser Ala Ala Ala Met Leu Ala Arg Arg Arg Glu
    130                 135                 140 tat ctc tac ctt gga gga ctg ctt tca tct ggc ttg tct atg cta atg     480
Tyr Leu Tyr Leu Gly Gly Leu Leu Ser Ser Gly Leu Ser Met Leu Met
145                 150                 155                 160 tgg ctc cag ttt gcc tct tca atc ttt ggt ggc tct gca tct atc ttt     528
Trp Leu Gln Phe Ala Ser Ser Ile Phe Gly Gly Ser Ala Ser Ile Phe
                165                 170                 175 aag ttt gag ttg tac ttt gga ctt ttg atc ttt gtg gga tac atg gtg     576
Lys Phe Glu Leu Tyr Phe Gly Leu Leu Ile Phe Val Gly Tyr Met Val
            180                 185                 190 gtg gac aca caa gag att ata gaa aag gca cac ctc ggt gac atg gac     624
Val Asp Thr Gln Glu Ile Ile Glu Lys Ala His Leu Gly Asp Met Asp
        195                 200                 205 tat gta aaa cat tcg ttg acc ctt ttc act gac ttt gta gct gtg ttt     672
Tyr Val Lys His Ser Leu Thr Leu Phe Thr Asp Phe Val Ala Val Phe
    210                 215                 220 gtt cgg att ctc atc ata atg ttg aag aac tca gca gat aaa gaa gag     720
Val Arg Ile Leu Ile Ile Met Leu Lys Asn Ser Ala Asp Lys Glu Glu
225                 230                 235                 240 aag aag aag aaa agg aga aac tgaggggatg taaagtaaat ttaactttat       771
Lys Lys Lys Lys Arg Arg Asn
                245 ggttgttatc gtgtgtggcc actttgaaga tattacttgt tagcactctc tattggtgac    831 cagacatgtt tccactaaaa aggatctgct tgtttcactt ctgcacaagt accatcttca    891 gattgtaaat gactcgagtg ttgttcttct tttcataaac ttttgttctt taagagtttg    951 gttctactga ttgcatctta ccaagctaag aataatgtag gaaatgata atcctgttta   1011 aattttctaa aatgtgtgca tttcagaaaa aaaaaaaaa aaaaaaaaa aaaaaa        1067

<210> SEQ ID NO 4
<211> LENGTH: 247
```

<212> TYPE: PRT
<213> ORGANISM: Arabidopsis thaliana

<400> SEQUENCE: 4

```
Met Asp Ala Phe Ser Ser Phe Asp Ser Gln Pro Gly Ser Arg Ser
  1               5                  10                  15

Trp Ser Tyr Asp Ser Leu Lys Asn Phe Arg Gln Ile Ser Pro Ala Val
                 20                  25                  30

Gln Asn His Leu Lys Arg Val Tyr Leu Thr Leu Cys Cys Ala Leu Val
             35                  40                  45

Ala Ser Ala Phe Gly Ala Tyr Leu His Val Leu Trp Asn Ile Gly Gly
         50                  55                  60

Ile Leu Thr Thr Ile Gly Cys Ile Gly Thr Met Ile Trp Leu Leu Ser
 65                  70                  75                  80

Cys Pro Pro Tyr Glu His Gln Lys Arg Leu Ser Leu Phe Val Ser
                 85                  90                  95

Ala Val Leu Glu Gly Ala Ser Val Gly Pro Leu Ile Lys Val Ala Ile
            100                 105                 110

Asp Val Asp Pro Ser Ile Leu Ile Thr Ala Phe Val Gly Thr Ala Ile
            115                 120                 125

Ala Phe Val Cys Phe Ser Ala Ala Ala Met Leu Ala Arg Arg Arg Glu
        130                 135                 140

Tyr Leu Tyr Leu Gly Gly Leu Leu Ser Ser Gly Leu Ser Met Leu Met
145                 150                 155                 160

Trp Leu Gln Phe Ala Ser Ser Ile Phe Gly Gly Ser Ala Ser Ile Phe
                165                 170                 175

Lys Phe Glu Leu Tyr Phe Gly Leu Leu Ile Phe Val Gly Tyr Met Val
                180                 185                 190

Val Asp Thr Gln Glu Ile Ile Glu Lys Ala His Leu Gly Asp Met Asp
                195                 200                 205

Tyr Val Lys His Ser Leu Thr Leu Phe Thr Asp Phe Val Ala Val Phe
            210                 215                 220

Val Arg Ile Leu Ile Ile Met Leu Lys Asn Ser Ala Asp Lys Glu Glu
225                 230                 235                 240

Lys Lys Lys Lys Arg Arg Asn
                245
```

<210> SEQ ID NO 5
<211> LENGTH: 1160
<212> TYPE: DNA
<213> ORGANISM: Nicotiana tabacum
<220> FEATURE:
<221> NAME/KEY: CDS
<222> LOCATION: (1)..(747)
<223> OTHER INFORMATION: coding for BI1-protein

<400> SEQUENCE: 5

```
atg gag tct tgc aca tcg ttc ttc aat tca cag tcg gcg tcg tct cgc      48
Met Glu Ser Cys Thr Ser Phe Phe Asn Ser Gln Ser Ala Ser Ser Arg
  1               5                  10                  15 aat cgc tgg agt tac gat tct ctt aag aac ttc cgc cag atc tct ccc      96
Asn Arg Trp Ser Tyr Asp Ser Leu Lys Asn Phe Arg Gln Ile Ser Pro
                 20                  25                  30 ttt gtt caa act cat ctc aaa aag gtc tac ctt tca tta tgt tgt gct     144
Phe Val Gln Thr His Leu Lys Lys Val Tyr Leu Ser Leu Cys Cys Ala
             35                  40                  45 tta gtt gct tcg gct gct gga gct tac ctt cac att ctt tgg aac att     192
Leu Val Ala Ser Ala Ala Gly Ala Tyr Leu His Ile Leu Trp Asn Ile
         50                  55                  60
```

```
ggt ggc tta ctt acg aca ttg gga tgt gtg gga agc ata gtg tgg ctg       240
Gly Gly Leu Leu Thr Thr Leu Gly Cys Val Gly Ser Ile Val Trp Leu
 65                  70                  75                  80 atg gcg aca cct ctg tat gaa gag caa aag agg ata gca ctt ctg atg       288
Met Ala Thr Pro Leu Tyr Glu Glu Gln Lys Arg Ile Ala Leu Leu Met
                 85                  90                  95 gca gct gca ctg ttt aaa gga gca tct att ggt cca ctg att gaa ttg       336
Ala Ala Ala Leu Phe Lys Gly Ala Ser Ile Gly Pro Leu Ile Glu Leu
            100                 105                 110 gct att gac ttt gac cca agc att gtg atc ggt gct ttt gtt ggt tgt       384
Ala Ile Asp Phe Asp Pro Ser Ile Val Ile Gly Ala Phe Val Gly Cys
        115                 120                 125 gct gtg gct ttt ggt tgc ttc tca gct gct gcc atg gtg gca agg cgc       432
Ala Val Ala Phe Gly Cys Phe Ser Ala Ala Ala Met Val Ala Arg Arg
    130                 135                 140 aga gag tac ttg tat ctt gga ggt ctt ctt tca tct ggt ctc tct atc       480
Arg Glu Tyr Leu Tyr Leu Gly Gly Leu Leu Ser Ser Gly Leu Ser Ile
145                 150                 155                 160 ctt ttc tgg ttg cac ttc gcg tcc tcc att ttt ggt ggt tct atg gcc       528
Leu Phe Trp Leu His Phe Ala Ser Ser Ile Phe Gly Gly Ser Met Ala
                165                 170                 175 ttg ttc aag ttc gag gtt tat ttt ggg ctc ttg gtg ttt gtg ggc tat       576
Leu Phe Lys Phe Glu Val Tyr Phe Gly Leu Leu Val Phe Val Gly Tyr
            180                 185                 190 atc att ttt gac acc caa gat ata att gag aag gca cac ctt ggg gat       624
Ile Ile Phe Asp Thr Gln Asp Ile Ile Glu Lys Ala His Leu Gly Asp
        195                 200                 205 ttg gac tac gtg aag cat gct ctg acc ctc ttt aca gat ttt gtt gct       672
Leu Asp Tyr Val Lys His Ala Leu Thr Leu Phe Thr Asp Phe Val Ala
    210                 215                 220 gtt ttt gtg cga ata tta atc ata atg ctg aag aat gca tcc gac aag       720
Val Phe Val Arg Ile Leu Ile Ile Met Leu Lys Asn Ala Ser Asp Lys
225                 230                 235                 240 gaa gag aag aag aag aag agg aga aac taatgcataa gcggttattc             767
Glu Glu Lys Lys Lys Lys Arg Arg Asn
                245 aaagactctg taactctaga atctggcatt ttcttgttca taaacttctg tagaccttcg     827 acaagtatgt tgttaatagt ttggtaacgc ctcagattaa gctgcgaggc tctgttatgc     887 cgcatgccaa tgtggttatg gtggtacata gatggttttg tttccgaagc ataccatcaa     947 ataacatgca tgtttacact atatcgataa cctacgagtg tactactcat ttctgctccc    1007 ttttgctgtg ttaggttgtt catgattgta tagttgattt tccgttatgt tagaccatct    1067 tctttcttga cgtttaattt ctcatattga tgggagaaat gaaaattcac accgtcgccc    1127 caacttgttt aagactgagg cgcaattgta gtt                                 1160
```

<210> SEQ ID NO 6
<211> LENGTH: 249
<212> TYPE: PRT
<213> ORGANISM: Nicotiana tabacum

<400> SEQUENCE: 6

```
Met Glu Ser Cys Thr Ser Phe Phe Asn Ser Gln Ser Ala Ser Ser Arg
 1               5                  10                  15

Asn Arg Trp Ser Tyr Asp Ser Leu Lys Asn Phe Arg Gln Ile Ser Pro
            20                  25                  30

Phe Val Gln Thr His Leu Lys Lys Val Tyr Leu Ser Leu Cys Cys Ala
        35                  40                  45
```

```
        Leu Val Ala Ser Ala Ala Gly Ala Tyr Leu His Ile Leu Trp Asn Ile
         50                  55                  60

Gly Gly Leu Leu Thr Thr Leu Gly Cys Val Gly Ser Ile Val Trp Leu
         65                  70                  75                  80

Met Ala Thr Pro Leu Tyr Glu Glu Gln Lys Arg Ile Ala Leu Leu Met
                         85                  90                  95

Ala Ala Ala Leu Phe Lys Gly Ala Ser Ile Gly Pro Leu Ile Glu Leu
                    100                 105                 110

Ala Ile Asp Phe Asp Pro Ser Ile Val Ile Gly Ala Phe Val Gly Cys
                115                 120                 125

Ala Val Ala Phe Gly Cys Phe Ser Ala Ala Met Val Ala Arg Arg
            130                 135                 140

Arg Glu Tyr Leu Tyr Leu Gly Gly Leu Leu Ser Ser Gly Leu Ser Ile
        145                 150                 155                 160

Leu Phe Trp Leu His Phe Ala Ser Ser Ile Phe Gly Gly Ser Met Ala
                        165                 170                 175

Leu Phe Lys Phe Glu Val Tyr Phe Gly Leu Leu Val Phe Val Gly Tyr
                    180                 185                 190

Ile Ile Phe Asp Thr Gln Asp Ile Ile Glu Lys Ala His Leu Gly Asp
                195                 200                 205

Leu Asp Tyr Val Lys His Ala Leu Thr Leu Phe Thr Asp Phe Val Ala
            210                 215                 220

Val Phe Val Arg Ile Leu Ile Ile Met Leu Lys Asn Ala Ser Asp Lys
        225                 230                 235                 240

Glu Glu Lys Lys Lys Lys Arg Arg Asn
                        245

<210> SEQ ID NO 7
<211> LENGTH: 1056
<212> TYPE: DNA
<213> ORGANISM: Oryza sativa
<220> FEATURE:
<221> NAME/KEY: CDS
<222> LOCATION: (1)..(747)
<223> OTHER INFORMATION: coding for BI1-protein

<400> SEQUENCE: 7 atg gac gcc ttc tac tcg acc tcg tcg gcg tac gga gcg gcg gcg agc        48
Met Asp Ala Phe Tyr Ser Thr Ser Ser Ala Tyr Gly Ala Ala Ala Ser
 1               5                  10                  15 ggc tgg ggc tac gac tcg ctg aag aac ttc cgc cag atc tcc ccc gcc        96
Gly Trp Gly Tyr Asp Ser Leu Lys Asn Phe Arg Gln Ile Ser Pro Ala
                20                  25                  30 gtc cag tcc cac ctc aag ctc gtt tac ctg aca cta tgc gtc gcc ctg       144
Val Gln Ser His Leu Lys Leu Val Tyr Leu Thr Leu Cys Val Ala Leu
            35                  40                  45 gct gcg tcg gcg gtg ggc gca tac ctg cac gtc gcc ttg aac atc ggc       192
Ala Ala Ser Ala Val Gly Ala Tyr Leu His Val Ala Leu Asn Ile Gly
        50                  55                  60 ggg atg ttg act atg ctc ggg tgc gtg ggg agc atc gcc tgg ttg ttc       240
Gly Met Leu Thr Met Leu Gly Cys Val Gly Ser Ile Ala Trp Leu Phe
 65                 70                  75                  80 tcg gtg cct gtc ttt gag gag agg aag agg ttt ggg att ctc ttg gcc       288
Ser Val Pro Val Phe Glu Glu Arg Lys Arg Phe Gly Ile Leu Leu Ala
                85                  90                  95 gct gcc ctg ctg gaa ggg gct tca gtt ggg cct ctg atc aag ctt gct       336
Ala Ala Leu Leu Glu Gly Ala Ser Val Gly Pro Leu Ile Lys Leu Ala
            100                 105                 110 gta gac ttt gac tca agc att ctc gta aca gca ttt gtt gga act gcc       384
```

```
Val Asp Phe Asp Ser Ser Ile Leu Val Thr Ala Phe Val Gly Thr Ala
        115                 120                 125 att gca ttt ggg tgc ttc act tgc gct gcc atc gtt gcc aag cgt agg      432
Ile Ala Phe Gly Cys Phe Thr Cys Ala Ala Ile Val Ala Lys Arg Arg
        130                 135                 140 gag tac ctc tac ctt ggt ggt ttg ctc tct tct ggc ctc tcc atc ctg      480
Glu Tyr Leu Tyr Leu Gly Gly Leu Leu Ser Ser Gly Leu Ser Ile Leu
145                 150                 155                 160 ctc tgg ctg cag ttt gcc gca tcc atc ttt ggc cac tcc acc ggc agc      528
Leu Trp Leu Gln Phe Ala Ala Ser Ile Phe Gly His Ser Thr Gly Ser
                165                 170                 175 ttc atg ttt gag gtt tac ttt ggc ctg ttg atc ttc ctg ggg tac atg      576
Phe Met Phe Glu Val Tyr Phe Gly Leu Leu Ile Phe Leu Gly Tyr Met
            180                 185                 190 gtg tat gac acg cag gag atc atc gag agg gct cac cac ggt gac atg      624
Val Tyr Asp Thr Gln Glu Ile Ile Glu Arg Ala His His Gly Asp Met
        195                 200                 205 gac tac atc aag cac gca ctc acc ctc ttc act gac ttc gtg gcc gtc      672
Asp Tyr Ile Lys His Ala Leu Thr Leu Phe Thr Asp Phe Val Ala Val
210                 215                 220 ctt gtc cgg atc ctc gtc atc atg ctc aag aac gcg tct gac aag tcg      720
Leu Val Arg Ile Leu Val Ile Met Leu Lys Asn Ala Ser Asp Lys Ser
225                 230                 235                 240 gag gag aag aag agg aag aag agg tct tgagagcttc tcttcccgct             767
Glu Glu Lys Lys Arg Lys Lys Arg Ser
                245 ttgcacataa gaaaaaacca ccgcggctat tgcctctacg tattatgaca gagccgcact     827 tcaactgggt tttatggtga atacaagttc ttttgcattt tgttgatacg gtgtgaatct    887 tctcaggttt gtcgtcgtag tagctttgca aatactagca tgctacatga cacggatctt    947 tctgtaatgg tggtcgcgtt gatcgaaacg tgaaaacaca tcttcatttg cgactaattt   1007 gtttgccttt tggtgattga tgatgatcct ttccccaaaa aaaaaaaa                 1056

<210> SEQ ID NO 8
<211> LENGTH: 249
<212> TYPE: PRT
<213> ORGANISM: Oryza sativa

<400> SEQUENCE: 8

Met Asp Ala Phe Tyr Ser Thr Ser Ser Ala Tyr Gly Ala Ala Ser
1               5                   10                  15

Gly Trp Gly Tyr Asp Ser Leu Lys Asn Phe Arg Gln Ile Ser Pro Ala
            20                  25                  30

Val Gln Ser His Leu Lys Leu Val Tyr Leu Thr Leu Cys Val Ala Leu
        35                  40                  45

Ala Ala Ser Ala Val Gly Ala Tyr Leu His Val Ala Leu Asn Ile Gly
    50                  55                  60

Gly Met Leu Thr Met Leu Gly Cys Val Gly Ser Ile Ala Trp Leu Phe
65                  70                  75                  80

Ser Val Pro Val Phe Glu Glu Arg Lys Arg Phe Gly Ile Leu Leu Ala
                85                  90                  95

Ala Ala Leu Leu Glu Gly Ala Ser Val Gly Pro Leu Ile Lys Leu Ala
            100                 105                 110

Val Asp Phe Asp Ser Ser Ile Leu Val Thr Ala Phe Val Gly Thr Ala
        115                 120                 125

Ile Ala Phe Gly Cys Phe Thr Cys Ala Ala Ile Val Ala Lys Arg Arg
    130                 135                 140
```

```
Glu Tyr Leu Tyr Leu Gly Gly Leu Leu Ser Ser Gly Leu Ser Ile Leu
145                 150                 155                 160

Leu Trp Leu Gln Phe Ala Ala Ser Ile Phe Gly His Ser Thr Gly Ser
                165                 170                 175

Phe Met Phe Glu Val Tyr Phe Gly Leu Leu Ile Phe Leu Gly Tyr Met
            180                 185                 190

Val Tyr Asp Thr Gln Glu Ile Ile Glu Arg Ala His His Gly Asp Met
        195                 200                 205

Asp Tyr Ile Lys His Ala Leu Thr Leu Phe Thr Asp Phe Val Ala Val
    210                 215                 220

Leu Val Arg Ile Leu Val Ile Met Leu Lys Asn Ala Ser Asp Lys Ser
225                 230                 235                 240

Glu Glu Lys Lys Arg Lys Lys Arg Ser
                245
```

<210> SEQ ID NO 9
<211> LENGTH: 973
<212> TYPE: DNA
<213> ORGANISM: Brassica napus
<220> FEATURE:
<221> NAME/KEY: CDS
<222> LOCATION: (1)..(741)
<223> OTHER INFORMATION: coding for BI1-protein

<400> SEQUENCE: 9

```
atg gat tca ttc tcg tcc ttc ttc gat tct caa cct ggt agc aga agc    48
Met Asp Ser Phe Ser Ser Phe Phe Asp Ser Gln Pro Gly Ser Arg Ser
  1               5                  10                  15 tgg agc tat gat tct ctc aaa aac ctc cgt cag att tct ccc tcc gtc    96
Trp Ser Tyr Asp Ser Leu Lys Asn Leu Arg Gln Ile Ser Pro Ser Val
             20                  25                  30 cag aat cat ctc aag agg gtt tat ctc act ctg tgt tgt gct ctc gtt   144
Gln Asn His Leu Lys Arg Val Tyr Leu Thr Leu Cys Cys Ala Leu Val
         35                  40                  45 gcg tct gcg ttt gga gct tac ctc cac gtg ctc tgg aac ata ggt ggt   192
Ala Ser Ala Phe Gly Ala Tyr Leu His Val Leu Trp Asn Ile Gly Gly
     50                  55                  60 att ctc act acc att gga tgc ttt gga agc atg att tgg ctg ctc tcc   240
Ile Leu Thr Thr Ile Gly Cys Phe Gly Ser Met Ile Trp Leu Leu Ser
 65                  70                  75                  80 tgt cct cct tat gaa caa caa aag agg ctt tcc ctt ctg ttt ctg tct   288
Cys Pro Pro Tyr Glu Gln Gln Lys Arg Leu Ser Leu Leu Phe Leu Ser
                 85                  90                  95 gct gtt ctc gaa ggt gct tca gtt ggt ccc ttg atc aaa gtg gca gtt   336
Ala Val Leu Glu Gly Ala Ser Val Gly Pro Leu Ile Lys Val Ala Val
            100                 105                 110 gat ttt gac cca agc atc ctc atc act gcg ttt gtc gga act gcg ata   384
Asp Phe Asp Pro Ser Ile Leu Ile Thr Ala Phe Val Gly Thr Ala Ile
        115                 120                 125 gcc ttt atc tgt ttc tca ggg gca gcg atg ttg gca aga cgc aga gag   432
Ala Phe Ile Cys Phe Ser Gly Ala Ala Met Leu Ala Arg Arg Arg Glu
    130                 135                 140 tac ctc tac ctc gga gga ctg ctt tca tct ggc ttg tcc atg ctt atg   480
Tyr Leu Tyr Leu Gly Gly Leu Leu Ser Ser Gly Leu Ser Met Leu Met
145                 150                 155                 160 tgg ctt cag ttt gcc tct tcc atc ttt ggt ggc tct gca tcc atc ttt   528
Trp Leu Gln Phe Ala Ser Ser Ile Phe Gly Gly Ser Ala Ser Ile Phe
                165                 170                 175 aag ttt gag ctc tac ttt gga ctc ttg atc ttt gtg gga tac atg gtg   576
Lys Phe Glu Leu Tyr Phe Gly Leu Leu Ile Phe Val Gly Tyr Met Val
            180                 185                 190
```

```
gtg gac act caa gat att ata gag aag gcc cac ctc ggt gac atg gat       624
Val Asp Thr Gln Asp Ile Ile Glu Lys Ala His Leu Gly Asp Met Asp
            195                 200                 205 tac gtg aaa cat tcg ttg acc ctt ttc acc gat ttt gta gct gtg ttt       672
Tyr Val Lys His Ser Leu Thr Leu Phe Thr Asp Phe Val Ala Val Phe
        210                 215                 220 gtt cgt gtt ctc atc att atg ctg aag aac tcg gca gat aaa gaa gat       720
Val Arg Val Leu Ile Ile Met Leu Lys Asn Ser Ala Asp Lys Glu Asp
225                 230                 235                 240 aaa aag aag agg agg agg aac tgagactaaa aagtgagaaa gaaagctaaa          771
Lys Lys Lys Arg Arg Arg Asn
                245 tagagtgggt gttatgtgtg tttcaaaaaa taaaaagag tgggtgttat aagtacagac      831 atgatagcgt tggtgttttt tacttgtttg gaacagtttt ggtaacaaca cacgttacgt     891 atttgtgtat tcctcttagt gactccagat tgtgaatgga tcagtatctt gaaactgtgt     951 tgaaaattat cagttgggag ct                                              973

<210> SEQ ID NO 10
<211> LENGTH: 247
<212> TYPE: PRT
<213> ORGANISM: Brassica napus

<400> SEQUENCE: 10

Met Asp Ser Phe Ser Ser Phe Phe Asp Ser Gln Pro Gly Ser Arg Ser
  1               5                  10                  15

Trp Ser Tyr Asp Ser Leu Lys Asn Leu Arg Gln Ile Ser Pro Ser Val
             20                  25                  30

Gln Asn His Leu Lys Arg Val Tyr Leu Thr Leu Cys Cys Ala Leu Val
         35                  40                  45

Ala Ser Ala Phe Gly Ala Tyr Leu His Val Leu Trp Asn Ile Gly Gly
     50                  55                  60

Ile Leu Thr Thr Ile Gly Cys Phe Gly Ser Met Ile Trp Leu Leu Ser
 65                  70                  75                  80

Cys Pro Pro Tyr Glu Gln Gln Lys Arg Leu Ser Leu Leu Phe Leu Ser
                 85                  90                  95

Ala Val Leu Glu Gly Ala Ser Val Gly Pro Leu Ile Lys Val Ala Val
            100                 105                 110

Asp Phe Asp Pro Ser Ile Leu Ile Thr Ala Phe Val Gly Thr Ala Ile
        115                 120                 125

Ala Phe Ile Cys Phe Ser Gly Ala Ala Met Leu Ala Arg Arg Arg Glu
    130                 135                 140

Tyr Leu Tyr Leu Gly Gly Leu Leu Ser Ser Gly Leu Ser Met Leu Met
145                 150                 155                 160

Trp Leu Gln Phe Ala Ser Ser Ile Phe Gly Gly Ser Ala Ser Ile Phe
                165                 170                 175

Lys Phe Glu Leu Tyr Phe Gly Leu Leu Ile Phe Val Gly Tyr Met Val
            180                 185                 190

Val Asp Thr Gln Asp Ile Ile Glu Lys Ala His Leu Gly Asp Met Asp
        195                 200                 205

Tyr Val Lys His Ser Leu Thr Leu Phe Thr Asp Phe Val Ala Val Phe
    210                 215                 220

Val Arg Val Leu Ile Ile Met Leu Lys Asn Ser Ala Asp Lys Glu Asp
225                 230                 235                 240

Lys Lys Lys Arg Arg Arg Asn
                245
```

<210> SEQ ID NO 11
<211> LENGTH: 747
<212> TYPE: DNA
<213> ORGANISM: Glycine max
<220> FEATURE:
<221> NAME/KEY: CDS
<222> LOCATION: (1)..(744)
<223> OTHER INFORMATION: coding for BI1-protein

<400> SEQUENCE: 11

```
cga ttg caa gca atg gac gcc ttc aat tcc ttc ttc gat tca aga aac      48
Arg Leu Gln Ala Met Asp Ala Phe Asn Ser Phe Phe Asp Ser Arg Asn
  1               5                  10                  15 cga tgg aat tac gat act ctc aaa aac ttc cgt cag att tct ccg gtc      96
Arg Trp Asn Tyr Asp Thr Leu Lys Asn Phe Arg Gln Ile Ser Pro Val
             20                  25                  30 gtg cag aat cac ctg aag cag gtt tat ttt act ctg tgt ttt gcc gtg     144
Val Gln Asn His Leu Lys Gln Val Tyr Phe Thr Leu Cys Phe Ala Val
         35                  40                  45 gtt gct gcg gct gtc ggg gct tac ctt cat gtc ctc ttg aac att ggg     192
Val Ala Ala Ala Val Gly Ala Tyr Leu His Val Leu Leu Asn Ile Gly
     50                  55                  60 ggt ttt ctt act aca gtg gca tgc atg gga agc agc ttt tgg tta ctc     240
Gly Phe Leu Thr Thr Val Ala Cys Met Gly Ser Ser Phe Trp Leu Leu
 65                  70                  75                  80 tcc aca cct cct ttt gaa gag agg aag agg gtg act ttg ttg atg gcc     288
Ser Thr Pro Pro Phe Glu Glu Arg Lys Arg Val Thr Leu Leu Met Ala
                 85                  90                  95 gca tca ctg ttt cag ggt tcc tct att gga ccc ttg att gat ttg gct     336
Ala Ser Leu Phe Gln Gly Ser Ser Ile Gly Pro Leu Ile Asp Leu Ala
            100                 105                 110 att cat atc gat cca agc ctt atc ttt agt gca ttt gtg gga aca gcc     384
Ile His Ile Asp Pro Ser Leu Ile Phe Ser Ala Phe Val Gly Thr Ala
        115                 120                 125 ttg gcc ttt gca tgc ttc tca gga gca gct ttg gtt gct agg cgt agg     432
Leu Ala Phe Ala Cys Phe Ser Gly Ala Ala Leu Val Ala Arg Arg Arg
    130                 135                 140 gag tac ctg tac ctt ggt ggc ttg gtt tct tct gga ttg tcc atc ctt     480
Glu Tyr Leu Tyr Leu Gly Gly Leu Val Ser Ser Gly Leu Ser Ile Leu
145                 150                 155                 160 ctc tgg ttg cac ttt gct tct tcc atc ttt gga ggc tca aca gct ctc     528
Leu Trp Leu His Phe Ala Ser Ser Ile Phe Gly Gly Ser Thr Ala Leu
                165                 170                 175 ttt aag ttt gag ttg tac ttt ggg ctt ttg gtg ttt gta ggt tac att     576
Phe Lys Phe Glu Leu Tyr Phe Gly Leu Leu Val Phe Val Gly Tyr Ile
            180                 185                 190 gta gta gac acc caa gaa ata gtt gag agg gca cac ttg ggc gat ctg     624
Val Val Asp Thr Gln Glu Ile Val Glu Arg Ala His Leu Gly Asp Leu
        195                 200                 205 gac tat gta aag cat gcc ttg acc ttg ttt acc gat ttg gtc gca gtt     672
Asp Tyr Val Lys His Ala Leu Thr Leu Phe Thr Asp Leu Val Ala Val
    210                 215                 220 ttt gtc cgg att ctt gtt att atg ttg aag aat tcg act gag agg aat     720
Phe Val Arg Ile Leu Val Ile Met Leu Lys Asn Ser Thr Glu Arg Asn
225                 230                 235                 240 gag aag aaa aag aag aga aga gat tga                                 747
Glu Lys Lys Lys Lys Arg Arg Asp
                245
```

<210> SEQ ID NO 12
<211> LENGTH: 248

-continued

```
<212> TYPE: PRT
<213> ORGANISM: Glycine max

<400> SEQUENCE: 12

Arg Leu Gln Ala Met Asp Ala Phe Asn Ser Phe Phe Asp Ser Arg Asn
 1               5                  10                  15

Arg Trp Asn Tyr Asp Thr Leu Lys Asn Phe Arg Gln Ile Ser Pro Val
             20                  25                  30

Val Gln Asn His Leu Lys Gln Val Tyr Phe Thr Leu Cys Phe Ala Val
         35                  40                  45

Val Ala Ala Ala Val Gly Ala Tyr Leu His Val Leu Leu Asn Ile Gly
     50                  55                  60

Gly Phe Leu Thr Thr Val Ala Cys Met Gly Ser Ser Phe Trp Leu Leu
 65                  70                  75                  80

Ser Thr Pro Pro Phe Glu Glu Arg Lys Arg Val Thr Leu Leu Met Ala
                 85                  90                  95

Ala Ser Leu Phe Gln Gly Ser Ser Ile Gly Pro Leu Ile Asp Leu Ala
            100                 105                 110

Ile His Ile Asp Pro Ser Leu Ile Phe Ser Ala Phe Val Gly Thr Ala
        115                 120                 125

Leu Ala Phe Ala Cys Phe Ser Gly Ala Ala Leu Val Ala Arg Arg Arg
    130                 135                 140

Glu Tyr Leu Tyr Leu Gly Gly Leu Val Ser Gly Leu Ser Ile Leu
145                 150                 155                 160

Leu Trp Leu His Phe Ala Ser Ser Ile Phe Gly Gly Ser Thr Ala Leu
                165                 170                 175

Phe Lys Phe Glu Leu Tyr Phe Gly Leu Leu Val Phe Val Gly Tyr Ile
            180                 185                 190

Val Val Asp Thr Gln Glu Ile Val Glu Arg Ala His Leu Gly Asp Leu
        195                 200                 205

Asp Tyr Val Lys His Ala Leu Thr Leu Phe Thr Asp Leu Val Ala Val
    210                 215                 220

Phe Val Arg Ile Leu Val Ile Met Leu Lys Asn Ser Thr Glu Arg Asn
225                 230                 235                 240

Glu Lys Lys Lys Lys Arg Arg Asp
                245

<210> SEQ ID NO 13
<211> LENGTH: 1510
<212> TYPE: DNA
<213> ORGANISM: Glycine max
<220> FEATURE:
<221> NAME/KEY: CDS
<222> LOCATION: (1)..(777)
<223> OTHER INFORMATION: coding for BI-1 protein
<220> FEATURE:
<221> NAME/KEY: misc_feature
<222> LOCATION: (1046)..(1095)
<223> OTHER INFORMATION: n is a, t, g, or t

<400> SEQUENCE: 13 atc acg aaa act ata cga ttc gat tcc ttg ttt tcg atg gac act ttc    48
Ile Thr Lys Thr Ile Arg Phe Asp Ser Leu Phe Ser Met Asp Thr Phe
 1               5                  10                  15 ttc aag tcc cca tct tct tct tct tcg aga agc cgc tgg agt tac gat    96
Phe Lys Ser Pro Ser Ser Ser Ser Ser Arg Ser Arg Trp Ser Tyr Asp
             20                  25                  30 act ctc aag aat ttc cgc gag atc tct ccg ctc gtt cag aat cac atc   144
Thr Leu Lys Asn Phe Arg Glu Ile Ser Pro Leu Val Gln Asn His Ile
         35                  40                  45
```

```
aaa ctg gtt tat ttt acg tta tgt tgc gct gtg gtg gct gct gct gtt      192
Lys Leu Val Tyr Phe Thr Leu Cys Cys Ala Val Val Ala Ala Ala Val
 50                  55                  60 gga gct ttc ctt cat gtt ctg tgg aac att ggc ggt ttt ctc acc acg      240
Gly Ala Phe Leu His Val Leu Trp Asn Ile Gly Gly Phe Leu Thr Thr
 65                  70                  75                  80 ttg gct tcc att ggg agc atg ttt tgg ttg cta tct aca ccc cct ttt      288
Leu Ala Ser Ile Gly Ser Met Phe Trp Leu Leu Ser Thr Pro Pro Phe
                 85                  90                  95 gaa gag caa aag agg ttg tct ctg ttg atg gct tcg gcc ctg ttt cag      336
Glu Glu Gln Lys Arg Leu Ser Leu Leu Met Ala Ser Ala Leu Phe Gln
            100                 105                 110 ggt gct tcc att gga cct ctg att gat ttg gct ttt gcc att gat cct      384
Gly Ala Ser Ile Gly Pro Leu Ile Asp Leu Ala Phe Ala Ile Asp Pro
            115                 120                 125 ggc ctt atc att ggc gca ttt gtg gca act tct ttg gct ttt gct tgc      432
Gly Leu Ile Ile Gly Ala Phe Val Ala Thr Ser Leu Ala Phe Ala Cys
130                 135                 140 ttt tct gca gta gcc tta gtt gca agg cga agg gag tac ctc tac ctt      480
Phe Ser Ala Val Ala Leu Val Ala Arg Arg Arg Glu Tyr Leu Tyr Leu
145                 150                 155                 160 ggt ggt ttg ctt tct tct tgg ctt tcc att ctt atg tgg ttg cac tct      528
Gly Gly Leu Leu Ser Ser Trp Leu Ser Ile Leu Met Trp Leu His Ser
                165                 170                 175 gat tcc tct ctc ttt ggg ggc tca att gca ctc ttc aag ttt gag ctg      576
Asp Ser Ser Leu Phe Gly Gly Ser Ile Ala Leu Phe Lys Phe Glu Leu
            180                 185                 190 tac ttt ggg ctt ttg gtg ttt gtg ggc tac gtt ata gta gac act caa      624
Tyr Phe Gly Leu Leu Val Phe Val Gly Tyr Val Ile Val Asp Thr Gln
            195                 200                 205 gaa att att gaa agg gct cac ttt ggt gac ctg gat tat gtg aag cat      672
Glu Ile Ile Glu Arg Ala His Phe Gly Asp Leu Asp Tyr Val Lys His
210                 215                 220 gca ttg aca ttg ttc act gat ttg gct gca atc ttt gtg cga att ctt      720
Ala Leu Thr Leu Phe Thr Asp Leu Ala Ala Ile Phe Val Arg Ile Leu
225                 230                 235                 240 att ata atg ttg aag aat tca tct gag aga aat gag aag aag aag aaa      768
Ile Ile Met Leu Lys Asn Ser Ser Glu Arg Asn Glu Lys Lys Lys Lys
                245                 250                 255 agg aga gat tagtaggctg accgaccgac tcgagctcag gcttctctac              817
Arg Arg Asp agtaatttag tttgtggaga atacataatt agctgtttag atgatgttgg tcccttgtgt    877
agttagttag ctatgtgttt gctgtaatgg taaatgtcag gatttctttt aaacatcttc    937
atatgtattt gccaatatca taatgtgtcg tataacatca taccttggtt taaaaaaaaa    997
aaaaaaaaaa aaaaaaaaaa aaaaaaaaaa aaaaaaaaaa aaaaaaaann nnnnnnnnn    1057 nnnnnnnnnn nnnnnnnnnn nnnnnnnnnn nnnnnnnngg tgtttgtggg ctacgttata   1117
gtagacactc aagtaatcat tgagagggct cactttggtg acctggatta tgttaagcat   1177
gcattgacac tgttcactga tttggctgca atctttgtgc gaattcttaa tataatgttg   1237
aataattcat ctaagagaaa tgagaagaag aggaggagag attaataggt tgaccgattg   1297
ctatgtgtag agtaatttgg tttgtagaga atacataatt agctgtttag aagttgttgg   1357
tccccttgtg tagttagtag ttagctatgt gtttgctgta atggtaaatg tcaggatttc   1417
ttttaaacat tttcatatgt atttgctaat aatcataata tatagtataa acatcattcc   1477
ttggtttaaa aaagaaaaa aaaaaaaaaa aaa                                 1510
```

<210> SEQ ID NO 14
<211> LENGTH: 259
<212> TYPE: PRT
<213> ORGANISM: Glycine max

<400> SEQUENCE: 14

```
Ile Thr Lys Thr Ile Arg Phe Asp Ser Leu Phe Ser Met Asp Thr Phe
  1               5                  10                  15

Phe Lys Ser Pro Ser Ser Ser Ser Arg Ser Arg Trp Ser Tyr Asp
             20                  25                  30

Thr Leu Lys Asn Phe Arg Glu Ile Ser Pro Leu Val Gln Asn His Ile
             35                  40                  45

Lys Leu Val Tyr Phe Thr Leu Cys Cys Ala Val Val Ala Ala Ala Val
 50                  55                  60

Gly Ala Phe Leu His Val Leu Trp Asn Ile Gly Gly Phe Leu Thr Thr
 65                  70                  75                  80

Leu Ala Ser Ile Gly Ser Met Phe Trp Leu Leu Ser Thr Pro Pro Phe
             85                  90                  95

Glu Glu Gln Lys Arg Leu Ser Leu Leu Met Ala Ser Ala Leu Phe Gln
            100                 105                 110

Gly Ala Ser Ile Gly Pro Leu Ile Asp Leu Ala Phe Ala Ile Asp Pro
            115                 120                 125

Gly Leu Ile Ile Gly Ala Phe Val Ala Thr Ser Leu Ala Phe Ala Cys
130                 135                 140

Phe Ser Ala Val Ala Leu Val Ala Arg Arg Arg Glu Tyr Leu Tyr Leu
145                 150                 155                 160

Gly Gly Leu Leu Ser Ser Trp Leu Ser Ile Leu Met Trp Leu His Ser
            165                 170                 175

Asp Ser Ser Leu Phe Gly Gly Ser Ile Ala Leu Phe Lys Phe Glu Leu
            180                 185                 190

Tyr Phe Gly Leu Leu Val Phe Val Gly Tyr Val Ile Val Asp Thr Gln
            195                 200                 205

Glu Ile Ile Glu Arg Ala His Phe Gly Asp Leu Asp Tyr Val Lys His
            210                 215                 220

Ala Leu Thr Leu Phe Thr Asp Leu Ala Ala Ile Phe Val Arg Ile Leu
225                 230                 235                 240

Ile Ile Met Leu Lys Asn Ser Ser Glu Arg Asn Glu Lys Lys Lys Lys
            245                 250                 255

Arg Arg Asp
```

<210> SEQ ID NO 15
<211> LENGTH: 651
<212> TYPE: DNA
<213> ORGANISM: Triticum aestivum
<220> FEATURE:
<221> NAME/KEY: CDS
<222> LOCATION: (1)..(651)
<223> OTHER INFORMATION: coding for BI-1 protein

<400> SEQUENCE: 15

```
gtc gca atg ccg ggt cga cga ttt cgt ctg acc tat gct ttg cct ggc    48
Val Ala Met Pro Gly Arg Arg Phe Arg Leu Thr Tyr Ala Leu Pro Gly
  1               5                  10                  15 ctc atc tgc cgt ggg tgc tta cct gca cat tgc cct gaa cat tgg cgg    96
Leu Ile Cys Arg Gly Cys Leu Pro Ala His Cys Pro Glu His Trp Arg
             20                  25                  30 gat gct gac aat gct cgc gtg tat cgg aac cat cgc ctg gat gtt ctc   144
Asp Ala Asp Asn Ala Arg Val Tyr Arg Asn His Arg Leu Asp Val Leu
```

```
                     35                  40                  45
ggt gcc agt cta cga gga gag gaa gag gtt tgg gct gct gat ggg tgc        192
Gly Ala Ser Leu Arg Gly Glu Glu Glu Val Trp Ala Ala Asp Gly Cys
 50                  55                  60 agc ctc ctg gaa ggg gct tca gtt gga cct ctg att gag ctt gcc ata        240
Ser Leu Leu Glu Gly Ala Ser Val Gly Pro Leu Ile Glu Leu Ala Ile
 65                  70                  75                  80 gac ttt gac cca agt atc ctc gtg aca ggg ttt gtc gga acc gcc atc        288
Asp Phe Asp Pro Ser Ile Leu Val Thr Gly Phe Val Gly Thr Ala Ile
                 85                  90                  95 gcc ttc ggg tgc ttc tct ggc gcc gcc atc atc gcc aag cgc agg gag        336
Ala Phe Gly Cys Phe Ser Gly Ala Ala Ile Ile Ala Lys Arg Arg Glu
            100                 105                 110 tac ctg tac ctc ggt ggt ctg ctc tcc tcc ggc ctg tcg atc ctg ctc        384
Tyr Leu Tyr Leu Gly Gly Leu Leu Ser Ser Gly Leu Ser Ile Leu Leu
        115                 120                 125 tgg ctg cag ttt gcc acg tcc atc ttt ggc cac tcc tct ggc agc ttc        432
Trp Leu Gln Phe Ala Thr Ser Ile Phe Gly His Ser Ser Gly Ser Phe
130                 135                 140 atg ttt gag gtt tac ttt ggc ctg ttg atc ttc ctg gga tac atg gtg        480
Met Phe Glu Val Tyr Phe Gly Leu Leu Ile Phe Leu Gly Tyr Met Val
145                 150                 155                 160 tac gac acg cag gag atc atc gag agg gcg cac cac ggc gac atg gat        528
Tyr Asp Thr Gln Glu Ile Ile Glu Arg Ala His His Gly Asp Met Asp
                165                 170                 175 tac atc aag cac gcg ctc acc ctc ttc acc gac ttc gtc gcc gtt ctc        576
Tyr Ile Lys His Ala Leu Thr Leu Phe Thr Asp Phe Val Ala Val Leu
            180                 185                 190 gtc cgc gtc ctc atc atc ttg ctc aag aac gca gcg gac aag gtc gga        624
Val Arg Val Leu Ile Ile Leu Leu Lys Asn Ala Ala Asp Lys Val Gly
        195                 200                 205 ggc caa gaa gag gag gaa gag aag tcc                                    651
Gly Gln Glu Glu Glu Glu Glu Lys Ser
    210                 215

<210> SEQ ID NO 16
<211> LENGTH: 217
<212> TYPE: PRT
<213> ORGANISM: Triticum aestivum

<400> SEQUENCE: 16

Val Ala Met Pro Gly Arg Arg Phe Arg Leu Thr Tyr Ala Leu Pro Gly
  1               5                  10                  15

Leu Ile Cys Arg Gly Cys Leu Pro Ala His Cys Pro Glu His Trp Arg
                 20                  25                  30

Asp Ala Asp Asn Ala Arg Val Tyr Arg Asn His Arg Leu Asp Val Leu
             35                  40                  45

Gly Ala Ser Leu Arg Gly Glu Glu Glu Val Trp Ala Ala Asp Gly Cys
 50                  55                  60

Ser Leu Leu Glu Gly Ala Ser Val Gly Pro Leu Ile Glu Leu Ala Ile
 65                  70                  75                  80

Asp Phe Asp Pro Ser Ile Leu Val Thr Gly Phe Val Gly Thr Ala Ile
                 85                  90                  95

Ala Phe Gly Cys Phe Ser Gly Ala Ala Ile Ile Ala Lys Arg Arg Glu
            100                 105                 110

Tyr Leu Tyr Leu Gly Gly Leu Leu Ser Ser Gly Leu Ser Ile Leu Leu
        115                 120                 125

Trp Leu Gln Phe Ala Thr Ser Ile Phe Gly His Ser Ser Gly Ser Phe
130                 135                 140
```

```
Met Phe Glu Val Tyr Phe Gly Leu Leu Ile Phe Leu Gly Tyr Met Val
145                 150                 155                 160

Tyr Asp Thr Gln Glu Ile Ile Glu Arg Ala His His Gly Asp Met Asp
                165                 170                 175

Tyr Ile Lys His Ala Leu Thr Leu Phe Thr Asp Phe Val Ala Val Leu
            180                 185                 190

Val Arg Val Leu Ile Ile Leu Leu Lys Asn Ala Ala Asp Lys Val Gly
        195                 200                 205

Gly Gln Glu Glu Glu Glu Glu Lys Ser
    210                 215

<210> SEQ ID NO 17
<211> LENGTH: 412
<212> TYPE: DNA
<213> ORGANISM: Zea mays
<220> FEATURE:
<221> NAME/KEY: CDS
<222> LOCATION: (3)..(410)
<223> OTHER INFORMATION: coding for BI1-protein

<400> SEQUENCE: 17 tt gtt att gac ttg gat tcg agg att ctc gtc act gcg ttc gtc ggg        47
   Val Ile Asp Leu Asp Ser Arg Ile Leu Val Thr Ala Phe Val Gly
   1               5                   10                  15 acc gca gtt gct ttt gca tgc ttc tct ggc gct gcc atc atc gcc aag       95
Thr Ala Val Ala Phe Ala Cys Phe Ser Gly Ala Ala Ile Ile Ala Lys
            20                  25                  30 cgc agg gaa tac ctg tac ctc ggc ggt ctg ctt tca tct ggc ctc tcc      143
Arg Arg Glu Tyr Leu Tyr Leu Gly Gly Leu Leu Ser Ser Gly Leu Ser
        35                  40                  45 att ctt ctc tgg ctg cag ttt gct act tca atc ttt ggc cac acc agc      191
Ile Leu Leu Trp Leu Gln Phe Ala Thr Ser Ile Phe Gly His Thr Ser
    50                  55                  60 gcg acc ttc atg ttt gag ctc tac ttt ggc ctc ctg gtt ttc ctg gga      239
Ala Thr Phe Met Phe Glu Leu Tyr Phe Gly Leu Leu Val Phe Leu Gly
65                  70                  75 tat atg gtg ttt gac acc cag gag atc atc gag agg gcg cac cgt ggg      287
Tyr Met Val Phe Asp Thr Gln Glu Ile Ile Glu Arg Ala His Arg Gly
 80                  85                  90                  95 gac atg gac tac atc aag cac gcg ctg act ctc ttc acc gac ttt gtt      335
Asp Met Asp Tyr Ile Lys His Ala Leu Thr Leu Phe Thr Asp Phe Val
                100                 105                 110 gcg gtt ctt gtt cga atc ctt gtc atc atg atg aag aat gca cag gag      383
Ala Val Leu Val Arg Ile Leu Val Ile Met Met Lys Asn Ala Gln Glu
            115                 120                 125 aaa tcc caa gac gag aag aag agg aag aa                               412
Lys Ser Gln Asp Glu Lys Lys Arg Lys
        130                 135

<210> SEQ ID NO 18
<211> LENGTH: 136
<212> TYPE: PRT
<213> ORGANISM: Zea mays

<400> SEQUENCE: 18

Val Ile Asp Leu Asp Ser Arg Ile Leu Val Thr Ala Phe Val Gly Thr
1               5                   10                  15

Ala Val Ala Phe Ala Cys Phe Ser Gly Ala Ala Ile Ile Ala Lys Arg
            20                  25                  30

Arg Glu Tyr Leu Tyr Leu Gly Gly Leu Leu Ser Ser Gly Leu Ser Ile
        35                  40                  45
```

```
Leu Leu Trp Leu Gln Phe Ala Thr Ser Ile Phe Gly His Thr Ser Ala
 50                  55                  60
Thr Phe Met Phe Glu Leu Tyr Phe Gly Leu Leu Val Phe Leu Gly Tyr
 65                  70                  75                  80
Met Val Phe Asp Thr Gln Glu Ile Ile Glu Arg Ala His Arg Gly Asp
                 85                  90                  95
Met Asp Tyr Ile Lys His Ala Leu Thr Leu Phe Thr Asp Phe Val Ala
                100                 105                 110
Val Leu Val Arg Ile Leu Val Ile Met Met Lys Asn Ala Gln Glu Lys
             115                 120                 125
Ser Gln Asp Glu Lys Lys Arg Lys
        130                 135

<210> SEQ ID NO 19
<211> LENGTH: 345
<212> TYPE: DNA
<213> ORGANISM: Triticum aestivum
<220> FEATURE:
<221> NAME/KEY: CDS
<222> LOCATION: (1)..(342)

<400> SEQUENCE: 19 gcc gcc atc atc gcc aag cgc agg gag tac ctg tac ctc ggt ggc ctg     48
Ala Ala Ile Ile Ala Lys Arg Arg Glu Tyr Leu Tyr Leu Gly Gly Leu
 1               5                  10                  15 ctc tcc tcc ggc ctg tcg atc ctg ctc tgg ctg cag ttt gcc acg tcc     96
Leu Ser Ser Gly Leu Ser Ile Leu Leu Trp Leu Gln Phe Ala Thr Ser
             20                  25                  30 atc ttt ggc cac tcc tct ggc agc ttc atg ttt gag gtt tac ttt ggc    144
Ile Phe Gly His Ser Ser Gly Ser Phe Met Phe Glu Val Tyr Phe Gly
         35                  40                  45 ctg ttg atc ttt ctg gga tac atg gtg tac gac acg cag gag atc atc    192
Leu Leu Ile Phe Leu Gly Tyr Met Val Tyr Asp Thr Gln Glu Ile Ile
     50                  55                  60 gag agg gcg cac cac ggc gac atg gac tac atc aag cac gcg ctc acc    240
Glu Arg Ala His His Gly Asp Met Asp Tyr Ile Lys His Ala Leu Thr
 65                  70                  75                  80 ctc ttc acc gac ttt gtc gcc gtc ctc gtc cgg atc ctc atc atc atg    288
Leu Phe Thr Asp Phe Val Ala Val Leu Val Arg Ile Leu Ile Ile Met
                 85                  90                  95 ctc aag aac gca ggc gac aag tcg gag gac aag aag aag agg aag agg    336
Leu Lys Asn Ala Gly Asp Lys Ser Glu Asp Lys Lys Lys Arg Lys Arg
                100                 105                 110 agg tcc tga                                                         345
Arg Ser

<210> SEQ ID NO 20
<211> LENGTH: 114
<212> TYPE: PRT
<213> ORGANISM: Triticum aestivum

<400> SEQUENCE: 20

Ala Ala Ile Ile Ala Lys Arg Arg Glu Tyr Leu Tyr Leu Gly Gly Leu
 1               5                  10                  15

Leu Ser Ser Gly Leu Ser Ile Leu Leu Trp Leu Gln Phe Ala Thr Ser
             20                  25                  30

Ile Phe Gly His Ser Ser Gly Ser Phe Met Phe Glu Val Tyr Phe Gly
         35                  40                  45

Leu Leu Ile Phe Leu Gly Tyr Met Val Tyr Asp Thr Gln Glu Ile Ile
     50                  55                  60
```

```
Glu Arg Ala His His Gly Asp Met Asp Tyr Ile Lys His Ala Leu Thr
 65                  70                  75                  80

Leu Phe Thr Asp Phe Val Ala Val Leu Val Arg Ile Leu Ile Ile Met
                 85                  90                  95

Leu Lys Asn Ala Gly Asp Lys Ser Glu Asp Lys Lys Arg Lys Arg
            100                 105                 110

Arg Ser

<210> SEQ ID NO 21
<211> LENGTH: 403
<212> TYPE: DNA
<213> ORGANISM: Zea mays
<220> FEATURE:
<221> NAME/KEY: CDS
<222> LOCATION: (1)..(402)
<223> OTHER INFORMATION: coding for BI1-protein

<400> SEQUENCE: 21 ggc agc atc gcc tgg ctc ttc tcg gtg ccc gtc tac gag gag agg aag       48
Gly Ser Ile Ala Trp Leu Phe Ser Val Pro Val Tyr Glu Glu Arg Lys
 1               5                  10                  15 agg tac tgg ctg ctg atg gcg gct gcc ctc ctg gaa ggg gcg tcg gtt       96
Arg Tyr Trp Leu Leu Met Ala Ala Ala Leu Leu Glu Gly Ala Ser Val
            20                  25                  30 gga ccc ctc atc aag ctc gcc gtg gaa ttt gac cca agc atc ctg gtg      144
Gly Pro Leu Ile Lys Leu Ala Val Glu Phe Asp Pro Ser Ile Leu Val
         35                  40                  45 aca gcg ttc gtg ggg act gcc att gcg ttc gcg tgc ttc tct tgc gcg      192
Thr Ala Phe Val Gly Thr Ala Ile Ala Phe Ala Cys Phe Ser Cys Ala
     50                  55                  60 gcc atg gtg gcc aag cgc agg gag tac ctc tac ctg ggc ggg ctg ctc      240
Ala Met Val Ala Lys Arg Arg Glu Tyr Leu Tyr Leu Gly Gly Leu Leu
 65                  70                  75                  80 tct tct ggc ctc tcc atc ctg ctc tgg ctg cag ttc gcc gcc tcc atc      288
Ser Ser Gly Leu Ser Ile Leu Leu Trp Leu Gln Phe Ala Ala Ser Ile
                 85                  90                  95 ttc ggc cac caa tcc act agc agc ttc atg ttt gag gtc tac ttt ggg      336
Phe Gly His Gln Ser Thr Ser Ser Phe Met Phe Glu Val Tyr Phe Gly
            100                 105                 110 ctg ctc atc ttc ctg ggc tac atg gtg tac gac acg cag gag gtc atc      384
Leu Leu Ile Phe Leu Gly Tyr Met Val Tyr Asp Thr Gln Glu Val Ile
         115                 120                 125 gag agg gcg cac cac ggc g                                            403
Glu Arg Ala His His Gly
     130

<210> SEQ ID NO 22
<211> LENGTH: 134
<212> TYPE: PRT
<213> ORGANISM: Zea mays

<400> SEQUENCE: 22

Gly Ser Ile Ala Trp Leu Phe Ser Val Pro Val Tyr Glu Glu Arg Lys
 1               5                  10                  15

Arg Tyr Trp Leu Leu Met Ala Ala Ala Leu Leu Glu Gly Ala Ser Val
            20                  25                  30

Gly Pro Leu Ile Lys Leu Ala Val Glu Phe Asp Pro Ser Ile Leu Val
         35                  40                  45

Thr Ala Phe Val Gly Thr Ala Ile Ala Phe Ala Cys Phe Ser Cys Ala
     50                  55                  60
```

```
Ala Met Val Ala Lys Arg Arg Glu Tyr Leu Tyr Leu Gly Gly Leu Leu
 65                  70                  75                  80

Ser Ser Gly Leu Ser Ile Leu Leu Trp Leu Gln Phe Ala Ala Ser Ile
             85                  90                  95

Phe Gly His Gln Ser Thr Ser Ser Phe Met Phe Glu Val Tyr Phe Gly
            100                 105                 110

Leu Leu Ile Phe Leu Gly Tyr Met Val Tyr Asp Thr Gln Glu Val Ile
        115                 120                 125

Glu Arg Ala His His Gly
        130

<210> SEQ ID NO 23
<211> LENGTH: 410
<212> TYPE: DNA
<213> ORGANISM: Zea mays
<220> FEATURE:
<221> NAME/KEY: CDS
<222> LOCATION: (3)..(410)
<223> OTHER INFORMATION: coding for BI1-protein

<400> SEQUENCE: 23 gc tgg aac atc ggc gtg agg ctg aca atg ctc ggt tgc atc ggc agc        47
   Trp Asn Ile Gly Val Arg Leu Thr Met Leu Gly Cys Ile Gly Ser
    1               5                  10                  15 atc gac tgg ctc ttc tcg gtg ccc gtc tac gag gag agg aag agg tat      95
Ile Asp Trp Leu Phe Ser Val Pro Val Tyr Glu Glu Arg Lys Arg Tyr
             20                  25                  30 ggg ctg ctg atg gcg gct gcc ctc ctg gaa ggc gct tcg gtc gga ccc      143
Gly Leu Leu Met Ala Ala Ala Leu Leu Glu Gly Ala Ser Val Gly Pro
         35                  40                  45 ctc gtc aag ctc gcc gtg gaa ttt gac cca agc atc ctg gtg acg gcg      191
Leu Val Lys Leu Ala Val Glu Phe Asp Pro Ser Ile Leu Val Thr Ala
     50                  55                  60 ttc gtg ggg act gcc atc gcg ttc gcg tgc ttc tcc ggc gcg gcc atg      239
Phe Val Gly Thr Ala Ile Ala Phe Ala Cys Phe Ser Gly Ala Ala Met
 65                  70                  75 gtg gcc agg cgc agg gag tac ctc tac ctg ggc ggg ctg ctc tcg tcg      287
Val Ala Arg Arg Arg Glu Tyr Leu Tyr Leu Gly Gly Leu Leu Ser Ser
 80                  85                  90                  95 ggg ctc tcc atc ctg ctc tgg ctg cag ctc gcc gcc tcc atc ttc ggc      335
Gly Leu Ser Ile Leu Leu Trp Leu Gln Leu Ala Ala Ser Ile Phe Gly
            100                 105                 110 cac tcc gca acc agc ttc atg ttc gag gtc tac ttc ggg ctc ctc atc      383
His Ser Ala Thr Ser Phe Met Phe Glu Val Tyr Phe Gly Leu Leu Ile
        115                 120                 125 ttc ctg ggc tac gtg gtg tac gac acg                                  410
Phe Leu Gly Tyr Val Val Tyr Asp Thr
    130                 135

<210> SEQ ID NO 24
<211> LENGTH: 136
<212> TYPE: PRT
<213> ORGANISM: Zea mays

<400> SEQUENCE: 24

Trp Asn Ile Gly Val Arg Leu Thr Met Leu Gly Cys Ile Gly Ser Ile
  1               5                  10                  15

Asp Trp Leu Phe Ser Val Pro Val Tyr Glu Glu Arg Lys Arg Tyr Gly
             20                  25                  30

Leu Leu Met Ala Ala Ala Leu Leu Glu Gly Ala Ser Val Gly Pro Leu
         35                  40                  45
```

```
Val Lys Leu Ala Val Glu Phe Asp Pro Ser Ile Leu Val Thr Ala Phe
 50                  55                  60

Val Gly Thr Ala Ile Ala Phe Ala Cys Phe Ser Gly Ala Ala Met Val
 65                  70                  75                  80

Ala Arg Arg Arg Glu Tyr Leu Tyr Leu Gly Gly Leu Leu Ser Ser Gly
                 85                  90                  95

Leu Ser Ile Leu Leu Trp Leu Gln Leu Ala Ala Ser Ile Phe Gly His
            100                 105                 110

Ser Ala Thr Ser Phe Met Phe Glu Val Tyr Phe Gly Leu Leu Ile Phe
            115                 120                 125

Leu Gly Tyr Val Val Tyr Asp Thr
            130                 135

<210> SEQ ID NO 25
<211> LENGTH: 463
<212> TYPE: DNA
<213> ORGANISM: Triticum aestivum
<220> FEATURE:
<221> NAME/KEY: CDS
<222> LOCATION: (1)..(462)
<223> OTHER INFORMATION: coding for BI1-protein

<400> SEQUENCE: 25 ttc tca ggt acg ttc cgc aat tcc cgg agc gac gat ttc gtg ctc tgc    48
Phe Ser Gly Thr Phe Arg Asn Ser Arg Ser Asp Asp Phe Val Leu Cys
 1               5                  10                  15 gaa ctt cag cga gag ctc ccc cga tgc cgg gac gca acc ttg acg gtc    96
Glu Leu Gln Arg Glu Leu Pro Arg Cys Arg Asp Ala Thr Leu Thr Val
             20                  25                  30 gta tac gtg atc cca ata gtg ggc cga ata aaa tct gcc gcg ggt gct   144
Val Tyr Val Ile Pro Ile Val Gly Arg Ile Lys Ser Ala Ala Gly Ala
         35                  40                  45 tac ctg cac att gcc ctg aac atc ggt ggg atg ctg aca atg ctt gcg   192
Tyr Leu His Ile Ala Leu Asn Ile Gly Gly Met Leu Thr Met Leu Ala
     50                  55                  60 tgt atc gga acc att gcc tgg atg ttc tct gtg cca gtc tat gag gag   240
Cys Ile Gly Thr Ile Ala Trp Met Phe Ser Val Pro Val Tyr Glu Glu
 65                  70                  75                  80 agg aag agg ttt ggg ctg ctg atg ggt gca gcc ctg gaa ggg gct       288
Arg Lys Arg Phe Gly Leu Leu Met Gly Ala Ala Leu Leu Glu Gly Ala
             85                  90                  95 tcg gtt gga cct ctg att gag ctt gcc ata gac ttt gac cca agc atc   336
Ser Val Gly Pro Leu Ile Glu Leu Ala Ile Asp Phe Asp Pro Ser Ile
            100                 105                 110 ctc gtg aca ggg ttt gtt gga acc gcc atc gcc ttt ggg tgc ttc tct   384
Leu Val Thr Gly Phe Val Gly Thr Ala Ile Ala Phe Gly Cys Phe Ser
            115                 120                 125 ggc gcc gcc atc atc gcc aag cgc agg gag tac ctg tac ctc gga ggc   432
Gly Ala Ala Ile Ile Ala Lys Arg Arg Glu Tyr Leu Tyr Leu Gly Gly
            130                 135                 140 ctg ctc tcc tcc ggc ctg acg atc ctg ctc t                         463
Leu Leu Ser Ser Gly Leu Thr Ile Leu Leu
145                 150

<210> SEQ ID NO 26
<211> LENGTH: 154
<212> TYPE: PRT
<213> ORGANISM: Triticum aestivum

<400> SEQUENCE: 26

Phe Ser Gly Thr Phe Arg Asn Ser Arg Ser Asp Asp Phe Val Leu Cys
 1               5                  10                  15
```

```
Glu Leu Gln Arg Glu Leu Pro Arg Cys Arg Asp Ala Thr Leu Thr Val
            20                  25                  30

Val Tyr Val Ile Pro Ile Val Gly Arg Ile Lys Ser Ala Ala Gly Ala
        35                  40                  45

Tyr Leu His Ile Ala Leu Asn Ile Gly Gly Met Leu Thr Met Leu Ala
    50                  55                  60

Cys Ile Gly Thr Ile Ala Trp Met Phe Ser Val Pro Val Tyr Glu Glu
65                  70                  75                  80

Arg Lys Arg Phe Gly Leu Leu Met Gly Ala Ala Leu Leu Glu Gly Ala
                85                  90                  95

Ser Val Gly Pro Leu Ile Glu Leu Ala Ile Asp Phe Asp Pro Ser Ile
            100                 105                 110

Leu Val Thr Gly Phe Val Gly Thr Ala Ile Ala Phe Gly Cys Phe Ser
        115                 120                 125

Gly Ala Ala Ile Ile Ala Lys Arg Arg Glu Tyr Leu Tyr Leu Gly Gly
    130                 135                 140

Leu Leu Ser Ser Gly Leu Thr Ile Leu Leu
145                 150
```

```
<210> SEQ ID NO 27
<211> LENGTH: 388
<212> TYPE: DNA
<213> ORGANISM: Zea mays
<220> FEATURE:
<221> NAME/KEY: CDS
<222> LOCATION: (3)..(386)
<223> OTHER INFORMATION: coding for BI1-protein

<400> SEQUENCE: 27
```

```
tc tgg aac atc ggc ggg acg ctg aca atg ctc ggt tgc gtc ggc agc        47
   Trp Asn Ile Gly Gly Thr Leu Thr Met Leu Gly Cys Val Gly Ser
   1               5                   10                  15 atc gcc tgg ctc ttc tcg gtg ccc gtc tac gag gag agg aag agg tat       95
Ile Ala Trp Leu Phe Ser Val Pro Val Tyr Glu Glu Arg Lys Arg Tyr
                20                  25                  30 ggg ctg ctg atg gcg gct gcc ctc ctg gaa ggc gct tcg gtc gga ccc      143
Gly Leu Leu Met Ala Ala Ala Leu Leu Glu Gly Ala Ser Val Gly Pro
            35                  40                  45 ctc gtc aag ctc gcc gtg gaa ttt gac cca agc atc ctg gtg acg gcg      191
Leu Val Lys Leu Ala Val Glu Phe Asp Pro Ser Ile Leu Val Thr Ala
        50                  55                  60 ttc gtg ggg act gcc atc gcg ttc gcg tgc ttc tcc ggc gcg cca tgg      239
Phe Val Gly Thr Ala Ile Ala Phe Ala Cys Phe Ser Gly Ala Pro Trp
65                  70                  75 tgg cag gcc agg gag tac ctc tac ctg ggc ggc tgc tct cgt cga ggc      287
Trp Gln Ala Arg Glu Tyr Leu Tyr Leu Gly Gly Cys Ser Arg Arg Gly
80                  85                  90                  95 tct cca tcc tgc tct ggc tgc agc tcg ccg cct cca tct tcg gca ctc      335
Ser Pro Ser Cys Ser Gly Cys Ser Ser Pro Pro Pro Ser Ser Ala Leu
            100                 105                 110 cgc aac agc ttc atg ttc gag gtc tac ttc ggg ctg ctc att ctt ctg      383
Arg Asn Ser Phe Met Phe Glu Val Tyr Phe Gly Leu Leu Ile Leu Leu
        115                 120                 125 ggc ta                                                                388
Gly
```

```
<210> SEQ ID NO 28
<211> LENGTH: 128
<212> TYPE: PRT
<213> ORGANISM: Zea mays
```

<400> SEQUENCE: 28

Trp Asn Ile Gly Gly Thr Leu Thr Met Leu Gly Cys Val Gly Ser Ile
 1               5                  10                  15

Ala Trp Leu Phe Ser Val Pro Val Tyr Glu Glu Arg Lys Arg Tyr Gly
             20                  25                  30

Leu Leu Met Ala Ala Ala Leu Leu Glu Gly Ala Ser Val Gly Pro Leu
         35                  40                  45

Val Lys Leu Ala Val Glu Phe Asp Pro Ser Ile Leu Val Thr Ala Phe
     50                  55                  60

Val Gly Thr Ala Ile Ala Phe Ala Cys Phe Ser Gly Ala Pro Trp Trp
 65                  70                  75                  80

Gln Ala Arg Glu Tyr Leu Tyr Leu Gly Gly Cys Ser Arg Arg Gly Ser
                 85                  90                  95

Pro Ser Cys Ser Gly Cys Ser Ser Pro Pro Ser Ser Ala Leu Arg
             100                 105                 110

Asn Ser Phe Met Phe Glu Val Tyr Phe Gly Leu Leu Ile Leu Leu Gly
             115                 120                 125

<210> SEQ ID NO 29
<211> LENGTH: 1737
<212> TYPE: DNA
<213> ORGANISM: Solanum tuberosum
<220> FEATURE:
<221> NAME/KEY: promoter
<222> LOCATION: (1)..(1737)
<223> OTHER INFORMATION: patatin promoter

<400> SEQUENCE: 29

```
aagcttatgt tgccatatag agtagtttgt gatggtatac ttcataaact ttaacttatg     60
ttaaatttgt aatgataaaa tttttattgt aaattaaaaa ttacttataa aattgggcat    120
tataacatat gaaagacaaa ttgtgttaca tattttactt ttgactttaa tatgaatatt    180
tcaatttaaa tcattgtttt attttctctt tcttttttaca ggtataaaag gtgaaaattg    240
aagcaagatt gattgcaagc tatgtgtcac cacgttattg atactttgga agaaattttt    300
acttatatgt ctttgtttag gagtaatatt tgatatgttt tagttagatt ttcttgtcat    360
ttatgcttta gtaatttttt agttattttt attatatgat catgggtgaa ttttgataca    420 aatattttg tcattaaata aattaattta tcacaacttg attactttca gtgacaaaaa    480
atgtattgtc gtagtaccct tttttgttga atatgaataa tttttttttat tttgtgacaa    540 ttgtaattgt cactacttat gataatattt agtgacatat atgtcgtcgg taaaagcaaa    600
cactttcagt gacaaaataa tagatttaat cacaaaatta ttaaccttt ttataataat    660 aaatttatcc ctaatttata catttaagga caaagtattt ttttttatata taaaaaatag    720 tctttagtga cgatcgtagt gttgagtcta gaaatcataa tgttgaatct agaaaaatct    780
catgcagtgt aaaataaacc tcaaaaagga cgttcagtcc atagagggg tgtatgtgac    840 accccaacct cagcaaaaga aaacctccct tcaacaagga catttgcggt gctaaacaat    900
ttcaagtctc atcacacata tatttattat ataatactaa taaagaatag aaaaggaaag    960
gtaaacatca ttaaatcgtc tttgtatatt tttagtgaca actgattgac gaaatctttt   1020
tcgtcacaca aaattttag tgacgaaaca tgatttatag atgatgaaat tatttgtccc   1080
tcataatcta atttgttgta gtgatcatta ctccttgtt tgttttatt gtcatgttag   1140 tccattaaaa aaaatatctc ctcttcttat gtacgtgaat ggttggaacg gatctattat   1200
ataatactaa taaagaatag aaaaaggaaa gtgagtgagg ttcgagggag agaatctgtt   1260
```

```
taatatcaga gtcgatcatg tgtcaatttt atcgatatga ccctaacttc aactgagttt    1320
aaccaattcc gataaggcga gaaatatcat agtattgagt ctagaaaaat ctcatgtagt    1380
gtggggtaaa cctcagcaag gacgttgagt ccatagaggg gggtgtatgt gacaccccaa    1440
cctcagcaaa agaaaacctc ccctcaagaa ggacatttgc ggtgctaaac aatttcaagt    1500
ctcatcacac atatatatat attatataat actaataaat aatagaaaaa ggaaaggtaa    1560
acatcactaa cgacagttgc ggtgcaaact gagtgaggta ataaacatca ctaactttta    1620
ttggttatgt caaactcaaa gtaaaatttc tcaacttgtt tacgtgccta tatataccat    1680
gcttgttata tgctcaaagc accaacaaaa tttaaaaaca ctttgaacat ttgcaaa      1737

<210> SEQ ID NO 30
<211> LENGTH: 1317
<212> TYPE: DNA
<213> ORGANISM: Triticum aestivum
<220> FEATURE:
<221> NAME/KEY: promoter
<222> LOCATION: (1)..(1317)
<223> OTHER INFORMATION: germin 9f-3.8 gene promoter

<400> SEQUENCE: 30
gaattcaagc tatcactctc gaaccaagca cattgatgta aggtatcatt ggattccaga      60
tgtcgtgagt tccaagttgc tgaaacttga gaagatccat accgacgaca atggttcaga     120
tatgatgacc aagatattgc gaaataagaa gctacaagca tgttgcaagg tagcgggcat     180
ggcggtgccc ccatcatgag tcggaggggg agatttgttg ggatatcctc ctcatgtggg     240
ttctgaggag atgaccattt gaggcctttt agccagccca aagaggtgca gaagcccact     300
acccattagg gttatgacct aggtcatttt ggactttgc acatgagtgg atggggatgc      360
tttaccctcc atccagcagc caccaccaag ggtgacgaaa atcagttcat cctccaagag     420
agaagaagag agaaaaccaa gagagcaagg gaagaagagg aagattgaag gaagaagaaa     480
agggagctcc tccccaaggt tgtgatggtc catatccact atcttgtctc cttcaaactt     540
cggttccacc atctttggta agattgttct aatccctagt tcttgagccc caaatcttgt     600
tgtgttcatc caagattcag aaatcttgat gtatgagatc ctcagtgct gtctagagaa      660 gaatttgttg tatcccacat ttgataatag tggaagagga tttgggtggc ttcggcccat     720
ggttttttcc ctcaagttga gggggttttcc acgtaaaatc tggtgtctct ttgttgatgc    780
ttggtgttgt ccagaaactt actcctacca caagacacta ggggccagtt cttttgggaa    840
attctcccag aattgaccct ctccccagct tctcccagaa ttgtcactcc attttttcttt  900 acaattccta gctagttaag gtctaattag ttaggaattg taaaaaaata tcaagtggca     960
attctgggag aagctgggga ggggtcaat tctggaagaa ttgcccaaaa gaactggccc     1020
taggctgagg agtgtcttgc ctgctgctta acattttctg cctccatata tgttgttgca    1080
tatgtttcct tccgtgctaa gcaacgatcc ttgagttagt acatgatgtg gtgctgagat    1140
tactttgttt tcgctgcagt tatcagttaa ccacaagtgc atttgcgtgc taattcccaa    1200
caatatgcca cccgcaactc atccaccata gctcagcagc aaccaccaat gccatagaca    1260
ctctcggtaa acaacctgta gcttatcagt ctagctaagc gtgctgcata gcaagca       1317

<210> SEQ ID NO 31
<211> LENGTH: 959
<212> TYPE: DNA
<213> ORGANISM: Arabidopsis thaliana
<220> FEATURE:
<221> NAME/KEY: promoter
```

```
<222> LOCATION: (1)..(959)
<223> OTHER INFORMATION: CAB-2 promoter

<400> SEQUENCE: 31
gaattcatgt gtgagggcaa ttagtgattg taaaaataaa attgtgttttt gtaaaaaact      60 tttactgtcg aaattatttta gggtgatgaa aaaatcagta aactacgaat gatagcttaa     120
agagtttcta tcaaagtgat tgaggaatag tttgttgcaa attaaacctc taacaaaatg     180
ttttctgttg tggtttttca tctctacaaa ttttgaattt tatgatgaat tagaaagata     240
gaatgagtta ctttagattt taaaaggttg ttcaagttta caaaacagat tactagaatc     300
atgattaaaa atttacaagc tacatattgt ctaaaccaat gatgttgaac ataccagatg     360
atagtttttc agtgtttgaa caatcaattg gatagttttt atgtttctgc aaaatatgca     420
aataatcagt gttttttgagt ctttgcattt tgatttaaaa gcaaaaacaa ctgagtttca     480
aggttaaatt aattacatta ttcatgagat ttatcaggtt agtggataaa ctgacaatgg     540
aatcaatgtt attgtaaatt ggtagtgatg ttggacttct aatgttactc tctatgatgt     600
ttcggtcatc ggtatcacac tatctttact tttatttaaa ggaaagatca cacaaataag     660
ttatctctat tcagaactat taagctgctt ccaaaagact tgcaacatgt ggtctcgaaa     720
tgctttggct gcaatgaaaa aatcatagca aaagctagtg gactagagac tgccacataa     780
gaatagtaaa cgttaaaacc aaaatctcaa aaatccaatg agtaaagaga tatagattac     840
ttcatagata acaaacgtta ctcgcaattt tcctatataa tccaacccta cctaaccatt     900
ttcaatcact ctcactcaca agttagtcac caaaaaaaaa aaaacacaa aaagtttca     959

<210> SEQ ID NO 32
<211> LENGTH: 445
<212> TYPE: DNA
<213> ORGANISM: Zea mays
<220> FEATURE:
<221> NAME/KEY: promoter
<222> LOCATION: (1)..(445)
<223> OTHER INFORMATION: PPCZm1 promoter

<400> SEQUENCE: 32
gaattccaaa aatagacacg gcaattttct tattcacaga aaaatataaa ctacaactaa      60
tccccaagtc cacagggatt agggatcaat ctgcaaaact aaaagtactt ttacagttgt     120
acttggcatg agtcatgtga ccatgagaga ggcgcacggt tcagcaaagc aacataaaat     180
tctccaaacg ggccccgcca cacgatca ccatcacccc cgggctcccg acccagtaca     240
aatagacacg cacactccca actccccacc catctccgcc gcgcacaccg cccaatcagc     300
caatctcctc ctcctcctcc gctctcagac gagcagcggt tgccatcact ctccacttcc     360
cacgcccgct gcgggctcgc aggcggcaga gaattgtctg tgccgccggg tgggaatttg     420
attcggtcgg attccgtgcg ccgcg                                          445

<210> SEQ ID NO 33
<211> LENGTH: 5455
<212> TYPE: DNA
<213> ORGANISM: Artificial sequence
<220> FEATURE:
<223> OTHER INFORMATION: Description of the artificial sequence:
      recombinant expression vector pUbiBI-1

<400> SEQUENCE: 33
ggggatcctc tagagtcgac ctgcaggcgg ccgcactagt gattaggatt ccaacgcgag      60
ccaggacaag cgaggaacct tgcgtgcgag gcgaggccgc ccgctccga ttcgattcga     120
```

```
cgcgcaggcg caggcgcagg gatggacgcc ttctactcga cctcgtcggc ggcggcgagc    180
ggctggggcc acgactccct caagaacttc cgccagatct cccccgccgt gcagtcccac    240
ctcaagctcg tttacctgac tctatgcttt gcactggcct catctgccgt gggtgcttac    300
ctacacattg ccctgaacat cggcgggatg ctgacaatgc tcgcttgtgt cggaactatc    360
gcctggatgt tctcggtgcc agtctatgag gagaggaaga ggtttgggct gctgatgggt    420
gcagccctcc tggaagggc ttcggttgga cctctgattg agcttgccat agactttgac    480
ccaagcatcc tcgtgacagg gtttgtcgga accgccatcg cctttgggtg cttctctggc    540
gccgccatca tcgccaagcg cagggagtac ctgtacctcg gtggcctgct ctcgtctggc    600
ctgtcgatcc tgctctggct gcagtttgtc acgtccatct ttggccactc ctctggcagc    660
ttcatgtttg aggtttactt tggcctgttg atcttcctgg ggtacatggt gtacgacacg    720
caggagatca tcgagagggc gcaccatggc gacatggact acatcaagca cgccctcacc    780
ctcttcaccg actttgttgc cgtcctcgtc cgagtcctca tcatcatgct caagaacgca    840
ggcgacaagt cggaggacaa gaagaagagg aagaggggt cctgaacgtw tctcccgcac    900
atgtagatac cgtcaccgcg tcgacctgca ggcatgcccg ctgaaatcac cagtctctct    960
ctacaaatct atctctctca taataatgtg tgagtagttc ccagataagg gaattagggt   1020
tcttataggg tttcgctcat gtgttgagca tataagaaac ccttagtatg tatttgtatt   1080
tgtaaaatac ttctatcaat aaaatttcta attcctaaaa ccaaaatcca gtgggtaccg   1140
agctcgaatt caagcttggc actgccgtc gttttacaac gtcgtgactg gaaaaccct    1200 ggcgttaccc aacttaatcg ccttgcagca catcccccttt cgccagctg gcgtaatagc   1260 gaagaggccc gcaccgatcg cccttcccaa cagttgcgca gcctgaatgg cgaatggcgc   1320
ctgatgcggt attttctcct tacgcatctg tgcggtattt cacaccgcat atggtgcact   1380
ctcagtacaa tctgctctga tgccgcatag ttaagccagc cccgacaccc gccaacaccc   1440
gctgacgcgc cctgacgggc ttgtctgctc ccggcatccg cttacagaca agctgtgacc   1500
gtctccggga gctgcatgtg tcagaggttt tcaccgtcat caccgaaacg cgcgagacga   1560
aagggcctcg tgatacgcct atttttatag gttaatgtca tgataataat ggtttcttag   1620
acgtcaggtg gcacttttcg gggaaatgtg cgcggaaccc ctatttgttt attttttctaa   1680 atacattcaa atatgtatcc gctcatgaga caataaccct gataaatgct tcaataatat   1740
tgaaaaagga agagtatgag tattcaacat ttccgtgtcg cccttattcc cttttttgcg   1800 gcatttgcc ttcctgtttt tgctcaccca gaaacgctgg tgaaagtaaa agatgctgaa   1860
gatcagttgg gtgcacgagt gggttacatc gaactggatc tcaacagcgg taagatcctt   1920
gagagttttc gccccgaaga acgttttcca atgatgagca cttttaaagt tctgctatgt   1980
ggcgcggtat tatcccgtat tgacgccggg caagagcaac tcggtcgccg catacactat   2040
tctcagaatg acttggttga gtactcacca gtcacagaaa agcatcttac ggatggcatg   2100
acagtaagag aattatgcag tgctgccata accatgagtg ataacactgc ggccaactta   2160
cttctgacaa cgatcggagg accgaaggag ctaaccgctt ttttgcacaa catgggggat   2220
catgtaactc gccttgatcg ttgggaaccg gagctgaatg aagccatacc aaacgacgag   2280
cgtgacacca cgatgcctgt agcaatggca acaacgttgc gcaaactatt aactggcgaa   2340
ctacttactc tagcttcccg gcaacaatta atagactgga tggaggcgga taaagttgca   2400
ggaccacttc tgcgctcggc ccttccggct ggctggttta ttgctgataa atctggagcc   2460
ggtgagcgtg ggtctcgcgg tatcattgca gcactggggc cagatggtaa gccctcccgt   2520
```

```
atcgtagtta tctacacgac ggggagtcag gcaactatgg atgaacgaaa tagacagatc    2580
gctgagatag gtgcctcact gattaagcat tggtaactgt cagaccaagt ttactcatat    2640
atactttaga ttgatttaaa acttcatttt taatttaaaa ggatctaggt gaagatcctt    2700
tttgataatc tcatgaccaa aatcccttaa cgtgagtttt cgttccactg agcgtcagac    2760
cccgtagaaa agatcaaagg atcttcttga gatccttttt ttctgcgcgt aatctgctgc    2820
ttgcaaacaa aaaaaccacc gctaccagcg gtggtttgtt tgccggatca agagctacca    2880 actcttttc cgaaggtaac tggcttcagc agagcgcaga taccaaatac tgttcttcta    2940
gtgtagccgt agttaggcca ccacttcaag aactctgtag caccgcctac atacctcgct    3000
ctgctaatcc tgttaccagt ggctgctgcc agtggcgata agtcgtgtct taccgggttg    3060
gactcaagac gatagttacc ggataaggcg cagcggtcgg gctgaacggg gggttcgtgc    3120
acacagccca gcttggagcg aacgacctac accgaactga gatacctaca gcgtgagctt    3180
tgagaaagcg ccacgcttcc cgaagggaga aaggcggaca ggtatccggt aagcggcagg    3240
gtcggaacag gagagcgcac gagggagctt ccaggggaa acgcctggta tctttatagt    3300
cctgtcgggt ttcgccacct ctgacttgag cgtcgatttt tgtgatgctc gtcaggggg    3360 cggagcctat ggaaaaacgc cagcaacgcg gccttttac ggttcctggc cttttgctgg    3420
ccttttgctc acatgttctt tcctgcgtta tccctgatt ctgtggataa ccgtattacc    3480
gcctttgagt gagctgatac cgctcgccgc agccgaacga ccgagcgcag cgagtcagtg    3540
agcgaggaag cggaagagcg cccaatacgc aaaccgcctc tccccgcgcg ttggccgatt    3600
cattaatgca gctggcacga caggtttccc gactggaaag cgggcagtga gcgcaacgca    3660
attaatgtga gttagctcac tcattaggca ccccaggctt tacactttat gcttccggct    3720
cgtatgttgt gtggaattgt gagcggataa caatttcaca caggaaacag ctatgaccat    3780
gattacgaat tcccatgcct cgaggatcta acatgcttag atacatgaag taacatgctg    3840
ctacggttta ataattcttg agttgatttt tactggtact tagatagatg tatatacatg    3900
cttagataca tgaagtaaca tgctcctaca gttcctttaa tcattattga gtacctatat    3960
attctaataa atcagtatgt tttaaattat tttgatttta ctggtactta gatagatgta    4020
tatatacatg ctcaaacatg cttagataca tgaagtaaca tgctgctacg gtttagtcat    4080
tattgagtgc ctataatttc taataaatca gtatgtttta aattattttg attttactgg    4140
tacttagata gatgtatata tacatgctca acatgcttag atacatgaa gtaatatgct    4200 actacggttt aattgttctt gagtacctat atattctaat aaatcagtat gttttaaatt    4260
atttcgattt tactggtact tagatagatg tatatataca tgcttagata catgaagtaa    4320
catgctacta cggtttaatt gttcttgaat acctatatat tctaataaat cagtatgttt    4380
taaattattt cgattttact ggtacttaga tagatgtata tacatgct cgaacatgct    4440 tagatacatg aagtaacatg ctacatatat attataataa atcagtatgt cttaaattat    4500 tttgattta ctggtactta gatagatgta tacatgct caaacatgct tagatacatg    4560
aagtaacatg ctactacggt ttaatcatta ttgagtacct atatattcta ataaatcagt    4620
atgttttcaa ttgttttgat tttactggta cttagatata tgtatatata catgctcgaa    4680
catgcttaga tacgtgaagt aacatgctac tatggttaat tgttcttgag tacctatata    4740
ttctaataaa tcagtatgtt ttaaattatt tcgattttac tggtacttag atagatgtat    4800
atatacatgc tcgaacatgc ttagatacat gaagtaacat gctactacgg tttaatcgtt    4860
cttgagtacc tatatattct aataaatcag tatgtcttaa attatcttga ttttactggt    4920
```

-continued

```
acttagatag atgtatatac atgcttagat acatgaagta acatgctact atgatttaat    4980
cgttcttgag tacctatata ttctaataaa tcagtatgtt tttaattatt ttgattttac    5040
tggtacttag atagatgtat atatacatgc tcgaacatgc ttagatacat gaagtaacat    5100
gctactacgg tttaatcatt cttgagtacc tatatattct aataaatcag tatgttttta    5160
attattttga tattactggt acttaacatg tttagataca tcatatagca tgcacatgct    5220
gctactgttt aatcattcgt gaatacctat atattctaat atatcagtat gtcttctaat    5280
tattatgatt ttgatgtact tgtatggtgg catatgctgc agctatgtgt agattttgaa    5340
tacccagtgt gatgagcatg catggcgcct tcatagttca tatgctgttt atttcctttg    5400
agactgttct tttttgttga tagtcaccct gttgtttggt gattcttatg caccc         5455
```

<210> SEQ ID NO 34
<211> LENGTH: 12633
<212> TYPE: DNA
<213> ORGANISM: Artificial Sequence
<220> FEATURE:
<223> OTHER INFORMATION: Description of the Artificial Sequence:
      recombinant expression vector pLo114UbiBI-1
<220> FEATURE:
<221> NAME/KEY: misc_feature
<222> LOCATION: (9590)..(9590)
<223> OTHER INFORMATION: n is a, c, g, or t
<220> FEATURE:
<221> NAME/KEY: misc_feature
<222> LOCATION: (9764)..(9764)
<223> OTHER INFORMATION: n is a, c, g, or t

<400> SEQUENCE: 34

```
aattcactgg ccgtcgtttt acaacgactc agagcttgac aggaggcccg atctagtaac      60
atagatgaca ccgcgcgcga taatttatcc tagtttgcgc gctatatttt gttttctatc     120
gcgtattaaa tgtataattg cgggactcta atcataaaaa cccatctcat aaataacgtc     180
atgcattaca tgttaattat tacatgctta acgtaattca acagaaatta tatgataatc     240
atcgcaagac cggcaacagg attcaatctt aagaaacttt attgccaaat gtttgaacga     300
tcggggatca tccgggtctg tggcgggaac tccacgaaaa tatccgaacg cagcaagatc     360
tagagcttgg gtcccgctca aagaactcg tcaagaaggc gatagaaggc gatgcgctgc     420
gaatcgggag cggcgatacc gtaaagcacg aggaagcggt cagcccattc gccgccaagc     480
tcttcagcaa tatcacgggt agccaacgct atgtcctgat agcggtccgc cacacccagc     540
cggccacagt cgatgaatcc agaaaagcgg ccattttcca ccatgatatt cggcaagcag     600
gcatcgccat gggtcacgac gagatcctcg ccgtcgggca tgcgcgcctt gagcctggcg     660
aacagttcgg ctggcgcgag cccctgatgc tcttcgtcca gatcatcctg atcgacaaga     720
ccggcttcca tccgagtacg tgctcgctcg atgcgatgtt tcgcttggtg gtcgaatggg     780
caggtagccg gatcaagcgt atgcagccgc cgcattgcat cagccatgat ggatactttc     840
tcggcaggag caaggtgaga tgacaggaga tcctgccccg gcacttcgcc caatagcagc     900
cagtcccttc ccgcttcagt gacaacgtcg agcacagctg cgcaaggaac gcccgtcgtg     960
gccagccacg atagccgcgc tgcctcgtcc tgcagttcat tcagggcacc ggacaggtcg    1020
gtcttgacaa aaagaaccgg gcgcccctgc gctgacagcc ggaacacggc ggcatcagag    1080
cagccgattg tctgttgtgc ccagtcatag ccgaatagcc tctccaccca gcggccgga     1140
gaacctgcgt gcaatccatc ttgttcaatc atgcgaaacg atccagatcc ggtgcagatt    1200
atttggattg agagtgaata tgagactcta attggatacc gaggggaatt tatgaacgt     1260
cagtggagca ttttgacaa gaaatatttg ctagctgata gtgaccttag gcgacttttg     1320
```

```
aacgcgcaat aatggtttct gacgtatgtg cttagctcat taaactccag aaacccgcgg   1380
ctgagtggct ccttcaacgt tgcggttctg tcagttccaa acgtaaaacg gcttgtcccg   1440
cgtcatcggc gggggtcata acgtgactcc cttaattctc cgctcatgat cagattgtcg   1500
tttcccgcct tcagtttaaa ctatcagtgt ttgacaggat cctgcttggt aataattgtc   1560
attagattgt ttttatgcat agatgcactc gaaatcagcc aattttagac aagtatcaaa   1620
cggatgttaa ttcagtacat taaagacgtc cgcaatgtgt tattaagttg tctaagcgtc   1680
aatttgttta caccacaata tatcctgcca ccagccagcc aacagctccc cgaccggcag   1740
ctcggcacaa aatcaccacg cgttaccacc acgccggccg gccgcatggt gttgaccgtg   1800
ttcgccggca ttgccgagtt cgagcgttcc ctaatcatcg accgcacccg gagcgggcgc   1860
gaggccgcca aggcccgagg cgtgaagttt ggcccccgcc ctaccctcac cccggcacag   1920
atcgcgcacg cccgcgagct gatcgaccag gaaggccgca ccgtgaaaga ggcggctgca   1980
ctgcttggcg tgcatcgctc gaccctgtac cgcgcacttg agcgcagcga ggaagtgacg   2040
cccaccgagg ccaggcggcg cggtgccttc cgtgaggacg cattgaccga ggccgacgcc   2100
ctggcggccg ccgagaatga acgccaagag gaacaagcat gaaaccgcac caggacggcc   2160
aggacgaacc gttttcatt accgaagaga tcgaggcgga gatgatcgcg gccgggtacg   2220
tgttcgagcc gcccgcgcac gtctcaaccg tgcggctgca tgaaatcctg gccggttgt   2280 ctgatgccaa gctggcggcc tggccggcca gcttggccgc tgaagaaacc gagcgccgcc   2340
gtctaaaaag gtgatgtgta tttgagtaaa acagcttgcg tcatgcggtc gctgcgtata   2400
tgatgcgatg agtaaataaa caaatacgca aggggaacgc atgaaggtta tcgctgtact   2460
taaccagaaa ggcgggtcag gcaagacgac catcgcaacc catctagccc gcgccctgca   2520
actcgccggg gccgatgttc tgttagtcga ttccgatccc cagggcagtg cccgcgattg   2580
ggcggccgtg cgggaagatc aaccgctaac cgttgtcggc atcgaccgcc cgacgattga   2640
ccgcgacgtg aaggccatcg gccggcgcga cttcgtagtg atcgacggag cgccccaggc   2700
ggcggacttg gctgtgtccg cgatcaaggc agccgacttc gtgctgattc cggtgcagcc   2760
aagcccttac gacatatggg ccaccgccga cctggtggag ctggttaagc agcgcattga   2820
ggtcacggat ggaaggctac aagcggcctt tgtcgtgtcg cgggcgatca aaggcacgcg   2880
catcggcggt gaggttgccg aggcgctggc cgggtacgag ctgcccattc ttgagtcccg   2940
tatcacgcag cgcgtgagct acccaggcac tgccgccgcc ggcacaaccg ttcttgaatc   3000
agaacccgag ggcgacgctg cccgcgaggt ccaggcgctg gccgctgaaa ttaaatcaaa   3060
actcatttga gttaatgagg taaagagaaa atgagcaaaa gcacaaacac gctaagtgcc   3120
ggccgtccga gcgcacgcag cagcaaggct gcaacgttgg ccagcctggc agacacgcca   3180
gccatgaagc gggtcaactt tcagttgccg cggaggatc acaccaagct gaagatgtac   3240
gcggtacgcc aaggcaagac cattaccgag ctgctatctg aatacatcgc gcagctacca   3300
gagtaaatga gcaaatgaat aaatgagtag atgaatttta gcggctaaag gaggcggcat   3360
ggaaaatcaa gaacaaccag gcaccgacgc cgtggaatgc cccatgtgtg gaggaacggg   3420
cggttggcca gcgtaagcg gctgggttgt ctgccggccc tgcaatggca ctggaacccc   3480
caagcccgag gaatcggcgt gagcggtcgc aaaccatccg gcccggtaca atcggcgcg   3540 gcgctgggtg atgacctggt ggagaagttg aaggccgcgc aggccgccca gcggcaacgc   3600
atcgaggcag aagcacgccc cggtgaatcg tggcaagcgg ccgctgatcg aatccgcaaa   3660
gaatcccggc aaccgccggc agccggtgcg ccgtcgatta ggaagccgcc caagggcgac   3720
```

```
gagcaaccag atttttttcgt tccgatgctc tatgacgtgg gcacccgcga tagtcgcagc   3780
atcatggacg tggccgtttt ccgtctgtcg aagcgtgacc gacgagctgg cgaggtgatc   3840
cgctacgagc ttccagacgg gcacgtagag gtttccgcag ggccggccgg catggccagt   3900
gtgtgggatt acgacctggt actgatggcg gtttcccatc taaccgaatc catgaaccga   3960
taccgggaag ggaagggaga caagcccggc cgcgtgttcc gtccacacgt tgcggacgta   4020
ctcaagttct gccggcgagc cgatggcgga aagcagaaag acgacctggt agaaacctgc   4080
attcggttaa acaccacgca cgttgccatg cagcgtacga agaaggccaa gaacggccgc   4140
ctggtgacgg tatccgaggg tgaagccttg attagccgct acaagatcgt aaagagcgaa   4200
accgggcggc cggagtacat cgagatcgag ctagctgatt ggatgtaccg cgagatcaca   4260
gaaggcaaga acccggacgt gctgacggtt caccccgatt acttttttgat cgatcccggc   4320 atcggccgtt ttctctaccg cctgcacgcg cgcgccgcag gcaaggcaga agccagatgg   4380
ttgttcaaga cgatctacga acgcagtggc agcgccggag agttcaagaa gttctgtttc   4440
accgtgcgca agctgatcgg gtcaaatgac ctgccggagt acgatttgaa ggaggaggcg   4500
gggcaggctg gcccgatcct agtcatgcgc taccgcaacc tgatcgaggg cgaagcatcc   4560
gccggttcct aatgtacgga gcagatgcta gggcaaattg ccctagcagg ggaaaaaggt   4620
cgaaaaggtc tctttcctgt ggatagcacg tacattggga acccaaagcc gtacattggg   4680
aaccggaacc cgtacattgg gaacccaaag ccgtacattg ggaaccggtc acacatgtaa   4740
gtgactgata taaagagaaa aaaggcgat ttttccgcct aaaactcttt aaaacttatt   4800
aaaactctta aaacccgcct ggcctgtgca taactgtctg gccagcgcac agccgaagag   4860
ctgcaaaaag cgcctaccct tcggtcgctg cgctccctac gccccgccgc ttcgcgtcgg   4920
cctatcgcgg ccgctggccg ctcaaaaatg gctggcctac ggccaggcaa tctaccaggg   4980
cgcggacaag ccgcgccgtc gccactcgac cgccggcgcc cacatcaagg cacccctgcct   5040 cgcgcgtttc ggtgatgacg gtgaaaacct ctgacacatg cagctcccgg agacggtcac   5100
agcttgtctg taagcggatg ccgggagcag acaagcccgt cagggcgcgt cagcgggtgt   5160
tggcgggtgt cggggcgcag ccatgaccca gtcacgtagc gatagcggag tgtatactgg   5220
cttaactatg cggcatcaga gcagattgta ctgagagtgc accatatgcg gtgtgaaata   5280
ccgcacagat gcgtaaggag aaaataccgc atcaggcgct cttccgcttc ctcgctcact   5340
gactcgctgc gctcggtcgt tcggctgcgg cgagcggtat cagctcactc aaaggcggta   5400
atacggttat ccacagaatc aggggataac gcaggaaaga acatgtgagc aaaaggccag   5460
caaaaggcca ggaaccgtaa aaaggccgcg ttgctggcgt ttttccatag gctccgcccc   5520
cctgacgagc atcacaaaaa tcgacgctca agtcagaggt ggcgaaaccc gacaggacta   5580
taaagatacc aggcgtttcc ccctggaagc tccctcgtgc gctctcctgt tccgaccctg   5640
ccgcttaccg gatacctgtc cgcctttctc ccttcgggaa gcgtggcgct ttctcatagc   5700
tcacgctgta ggtatctcag ttcggtgtag gtcgttcgct ccaagctggg ctgtgtgcac   5760
gaaccccccg ttcagcccga ccgctgcgcc ttatccggta actatcgtct gagtccaac    5820 ccggtaagac acgacttatc gccactggca gcagccactg gtaacaggat tagcagagcg   5880
aggtatgtag gcggtgctac agagttcttg aagtggtggc ctaactacgg ctacactaga   5940
aggacagtat ttggtatctg cgctctgctg aagccagtta ccttcggaaa aagagttggt   6000
agctcttgat ccggcaaaca aaccaccgct ggtagcggtg ttttttttgt ttgcaagcag   6060
cagattacgc gcagaaaaaa aggatctcaa gaagatcctt tgatcttttc tacggggtct   6120
```

```
gacgctcagt ggaacgaaaa ctcacgttaa gggattttgg tcatgcatga tatatctccc    6180
aatttgtgta gggcttatta tgcacgctta aaaataataa aagcagactt gacctgatag    6240
tttggctgtg agcaattatg tgcttagtgc atctaacgct tgagttaagc cgcgccgcga    6300
agcggcgtcg gcttaacga  atttctagct agacattatt tgccgactac cttggtgatc    6360 tcgccttttca cgtagtggac aaattcttcc aactgatctg cgcgcgaggc caagcgatct    6420
tcttcttgtc caagataagc ctgtctagct tcaagtatga cgggctgata ctgggccggc    6480
aggcgctcca ttgcccagtc ggcagcgaca tccttcggcg cgattttgcc ggttactgcg    6540
ctgtaccaaa tgcgggacaa cgtaagcact acatttcgct catcgccagc ccagtcgggc    6600
ggcgagttcc atagcgttaa ggtttcattt agcgcctcaa atagatcctg ttcaggaacc    6660
ggatcaaaga gttcctccgc cgctggacct accaaggcaa cgctatgttc tcttgctttt    6720
gtcagcaaga tagccagatc aatgtcgatc gtggctggct cgaagatacc tgcaagaatg    6780
tcattgcgct gccattctcc aaattgcagt tcgcgcttag ctggataacg ccacggaatg    6840
atgtcgtcgt gcacaacaat ggtgacttct acagcgcgga gaatctcgct ctctccaggg    6900
gaagccgaag tttccaaaag gtcgttgatc aaagctcgcc gcgttgtttc atcaagcctt    6960
acggtcaccg taaccagcaa atcaatatca ctgtgtggct tcaggccgcc atccactgcg    7020
gagccgtaca aatgtacggc cagcaacgtc ggttcgagat ggcgctcgat gacgccaact    7080
acctctgata gttgagtcga tacttcggcg atcaccgctt cccccatgat gtttaacttt    7140
gttttagggc gactgccctg ctgcgtaaca tcgttgctgc tccataacat caaacatcga    7200
cccacggcgt aacgcgcttg ctgcttggat gcccgaggca tagactgtac cccaaaaaaa    7260
cagtcataac aagccatgaa aaccgccact gcggggttc  catggacata caaatggacg    7320
aacggataaa ccttttcacg cccttttaaa tatccgatta ttctaataaa cgctcttttc    7380
tcttaggttt acccgccaat atatcctgtc aaacactgat agtttaaact gaaggcggga    7440
aacgacaatc agatctagta ggaaacagct atgaccatga ttacgccaag cttgcatgcc    7500
tgcaggtcga ctctagagga tcgatccccg ggtaggtcag tcccttatgt tacgtcctgt    7560
agaaacccca acccgtgaaa tcaaaaaact cgacggcctg tgggcattca gtctggatcg    7620
cgaaaactgt ggaattggtc agcgttggtg ggaaagcgcg ttacaagaaa gccgggcaat    7680
tgctgtgcca ggcagtttta acgatcagtt cgccgatgca gatattcgta attatgcggg    7740
caacgtctgg tatcagcgcg aagtctttat accgaaaggt tgggcaggcc agcgtatcgt    7800
gctgcgtttc gatgcggtca ctcattacgg caaagtgtgg gtcaataatc aggaagtgat    7860
ggagcatcag gcggctata  cgccatttga agccgatgtc acgccgtatg ttattgccgg    7920
gaaaagtgta cgtaagtttc tgcttctacc tttgatatat atataataat tatcattaat    7980
tagtagtaat ataatatttc aaatattttt ttcaaaataa aagaatgtag tatatagcaa    8040
ttgcttttct gtagtttata agtgtgtata ttttaattta taacttttct aatatatgac    8100
caaaatttgt tgatgtgcag gtatcaccgt ttgtgtgaac aacgaactga actggcagac    8160
tatcccgccg ggaatggtga ttaccgacga aaacggcaag aaaaagcagt cttacttcca    8220 tgatttctt  aactatgccg gaatccatcg cagcgtaatg ctctacacca cgccgaacac    8280
ctgggtggac gatatcaccg tggtgacgca tgtcgcgcaa gactgtaacc acgcgtctgt    8340
tgactggcag gtggtggcca atggtgatgt cagcgttgaa ctgcgtgatg cggatcaaca    8400
ggtggttgca actggacaag gcactagcgg gactttgcaa gtggtgaatc cgcacctctg    8460
gcaaccgggt gaaggttatc tctatgaact gtgcgtcaca gccaaaagcc agacagagtg    8520
```

```
tgatatctac ccgcttcgcg tcggcatccg gtcagtggca gtgaagggcg aacagttcct   8580
gattaaccac aaaccgttct actttactgg ctttggtcgt catgaagatg cggacttgcg   8640
tggcaaagga ttcgataacg tgctgatggt gcacgaccac gcattaatgg actggattgg   8700
ggccaactcc taccgtacct cgcattaccc ttacgctgaa gagatgctcg actgggcaga   8760
tgaacatggc atcgtggtga ttgatgaaac tgctgctgtc ggctttaacc tctctttagg   8820
cattggtttc gaagcgggca acaagccgaa agaactgtac agcgaagagg cagtcaacgg   8880
ggaaactcag caagcgcact acaggcgat taaagagctg atagcgcgtg acaaaaacca   8940
cccaagcgtg gtgatgtgga gtattgccaa cgaaccggat acccgtccgc aaggtgcacg   9000
ggaatatttc gcgccactgg cggaagcaac gcgtaaactc gacccgacgc gtccgatcac   9060
ctgcgtcaat gtaatgttct gcgacgctca caccgatacc atcagcgatc tctttgatgt   9120
gctgtgcctg aaccgttatt acggatggta tgtccaaagc ggcgatttgg aaacggcaga   9180
gaaggtactg gaaaaagaac ttctggcctg gcaggagaaa ctgcatcagc cgattatcat   9240
caccgaatac ggcgtggata cgttagccgg gctgcactca atgtacaccg acatgtggag   9300
tgaagagtat cagtgtgcat ggctggatat gtatcaccgc gtcttgatc gcgtcagcgc   9360 cgtcgtcggt gaacaggtat ggaatttcgc cgattttgcg acctcgcaag gcatattgcg   9420
cgttggcggt aacaagaaag ggatcttcac tcgcgaccgc aaaccgaagt cggcggcttt   9480
tctgctgcaa aaacgctgga ctggcatgaa cttcggtgaa aaaccgcagc agggaggcaa   9540
acaatgagag ctcgaatttc cccgatcggt caaacatttg gcaataaagn ttcttaagat   9600
tgaatcctgt tgccggtctt gcgatgatta tcatataatt tctgttgaat tacgttaagc   9660
atgtaataat taacatgtaa tgcatgacgt tatttatgag atgggttttt atgattagag   9720
tcccgcaatt atacatttaa tacgcgatag aaaacaaaat atancgcgca aactaggata   9780
aattatcgcg cgcggtgtca tctatgttac tagatcggga attcccatgc ctcgaggatc   9840
taacatgctt agatacatga agtaacatgc tgctacggtt taataattct tgagttgatt   9900
tttactggta cttagataga tgtatataca tgcttagata catgaagtaa catgctccta   9960
cagttccttt aatcattatt gagtacctat atattctaat aaatcagtat gttttaaatt  10020
attttgattt tactggtact tagatagatg tatatataca tgctcaaaca tgcttagata  10080
catgaagtaa catgctgcta cggtttagtc attattgagt gcctataatt tctaataaat  10140
cagtatgttt taaattattt tgattttact ggtacttaga tagatgtata tacatgct   10200 caaacatgct tagatacatg aagtaatatg ctactacggt ttaattgttc ttgagtaccet  10260 atatattcta ataaatcagt atgttttaaa ttatttcgat tttactggta cttagataga  10320
tgtatatata catgcttaga tacatgaagt aacatgctac tacggtttaa ttgttcttga  10380
atacctatat attctaataa atcagtatgt tttaaattat ttcgatttta ctggtactta  10440
gatagatgta tatacatg ctcgaacatg cttagataca tgaagtaaca tgctacatat  10500
atattataat aaatcagtat gtcttaaatt attttgattt tactggtact tagatagatg  10560
tatatacatg ctcaaacatg cttagataca tgaagtaaca tgctactacg gtttaatcat  10620
tattgagtac ctatatattc taataaatca gtatgttttc aattgttttg atttactgg  10680 tacttagata tatgtatata tacatgctcg aacatgctta gatacgtgaa gtaacatgct  10740
actatggtta attgttcttg agtacctata tattctaata atcagtatg ttttaaatta  10800 tttcgatttt actggtactt agatagatgt atatacat gctcgaacat gcttagatac  10860
atgaagtaac atgctactac ggtttaatcg ttcttgagta cctatatatt ctaataaatc  10920
```

```
agtatgtctt aaattatctt gattttactg gtacttagat agatgtatat acatgcttag    10980
atacatgaag taacatgcta ctatgattta atcgttcttg agtacctata tattctaata    11040
aatcagtatg tttttaatta ttttgatttt actggtactt agatagatgt atatatacat    11100
gctcgaacat gcttagatac atgaagtaac atgctactac ggtttaatca ttcttgagta    11160
cctatatatt ctaataaatc agtatgtttt taattatttt gatattactg gtacttaaca    11220
tgtttagata catcatatag catgcacatg ctgctactgt ttaatcattc gtgaatacct    11280
atatattcta atatatcagt atgtcttcta attattatga ttttgatgta cttgtatggt    11340
ggcatatgct gcagctatgt gtagattttg aatacccagt gtgatgagca tgcatggcgc    11400
cttcatagtt catatgctgt ttatttcctt tgagactgtt cttttttgtt gatagtcacc    11460
ctgttgtttg gtgattctta tgcacccggg gatcctctag agtcgacctg caggcggccg    11520
cactagtgat taggattcca acgcgagcca ggacaagcga ggaaccttgc gtgcgaggcg    11580
aggccgcccc gctccgattc gattcgacgc gcaggcgcag gcgcagggat ggacgccttc    11640
tactcgacct cgtcggcggc ggcgagcggc tggggccacg actccctcaa gaacttccgc    11700
cagatctccc ccgccgtgca gtcccacctc aagctcgttt acctgactct atgctttgca    11760
ctggcctcat ctgccgtggg tgcttaccta cacattgccc tgaacatcgg cgggatgctg    11820
acaatgctcg cttgtgtcgg aactatcgcc tggatgttct cggtgccagt ctatgaggag    11880
aggaagaggt ttgggctgct gatgggtgca gccctcctgg aagggcttc ggttggacct     11940 ctgattgagc ttgccataga ctttgaccca agcatcctcg tgacagggtt tgtcggaacc    12000
gccatcgcct ttgggtgctt ctctggcgcc gccatcatcg ccaagcgcag ggagtacctg    12060
tacctcggtg gcctgctctc gtctggcctg tcgatcctgc tctggctgca gtttgtcacg    12120
tccatctttg gccactcctc tggcagcttc atgtttgagg tttacttggg cctgttgatc    12180
ttcctggggt acatggtgta cgacacgcag gagatcatcg agagggcgca ccatggcgac    12240
atggactaca tcaagcacgc cctcacccte ttcaccgact tgttgccgt cctcgtccga     12300 gtcctcatca tcatgctcaa gaacgcaggc gacaagtcgg aggacaagaa gaagaggaag    12360 aggggggtcct gaacgtwtct cccgcacatg tagataccgt caccgcgtcg acctgcaggc    12420
atgcccgctg aaatcaccag tctctctcta caaatctatc tctctcataa taatgtgtga    12480
gtagttccca gataagggaa ttagggttct tatagggttt cgctcatgtg ttgagcatat    12540
aagaaaccct tagtatgtat ttgtatttgt aaaatacttc tatcaataaa atttctaatt    12600
cctaaaacca aaatccagtg ggtaccgagc tcg                                 12633
```

<210> SEQ ID NO 35
<211> LENGTH: 5598
<212> TYPE: DNA
<213> ORGANISM: Artificial sequence
<220> FEATURE:
<223> OTHER INFORMATION: Description of the artificial sequence: recombinant expression vector pOXoBI-1

<400> SEQUENCE: 35

```
ggggatcctc tagagtcgac ctgcaggcgg ccgcactagt gattaggatt ccaacgcgag      60
ccaggacaag cgaggaacct tgcgtgcgag gcgaggccgc cccgctccga ttcgattcga     120
cgcgcaggcg caggcgcagg gatggacgcc ttctactcga cctcgtcggc ggcggcgagc    180
ggctggggcc acgactccct caagaacttc cgccagatct cccccgccgt gcagtcccac    240
ctcaagctcg tttacctgac tctatgcttt gcactggcct catctgccgt gggtgcttac    300
```

```
ctacacattg ccctgaacat cggcgggatg ctgacaatgc tcgcttgtgt cggaactatc    360
gcctggatgt tctcggtgcc agtctatgag gagaggaaga ggtttgggct gctgatgggt    420
gcagccctcc tggaagggc ttcggttgga cctctgattg agcttgccat agactttgac    480
ccaagcatcc tcgtgacagg gtttgtcgga accgccatcg cctttgggtg cttctctggc    540
gccgccatca tcgccaagcg cagggagtac ctgtacctcg gtggcctgct ctcgtctggc    600
ctgtcgatcc tgctctggct gcagtttgtc acgtccatct ttggccactc ctctggcagc    660
ttcatgtttg aggtttactt tggcctgttg atcttcctgg ggtacatggt gtacgacacg    720
caggagatca tcgagagggc gcaccatggc gacatggact acatcaagca cgccctcacc    780
ctcttcaccg actttgttgc cgtcctcgtc cgagtcctca tcatcatgct caagaacgca    840
ggcgacaagt cggaggacaa gaagaagagg aagaggggt cctgaacgtw tctcccgcac    900
atgtagatac cgtcaccgcg tcgacctgca ggcatgcccg ctgaaatcac cagtctctct    960
ctacaaatct atctctctca taataatgtg tgagtagttc ccagataagg gaattagggt   1020
tcttatagg tttcgctcat gtgttgagca tataagaaac ccttagtatg tatttgtatt   1080
tgtaaaatac ttctatcaat aaaatttcta attcctaaaa ccaaaatcca gtgggtaccg   1140
agctcgaatt caagcttggc actggccgtc gttttacaac gtcgtgactg ggaaaaccct   1200
ggcgttaccc aacttaatcg ccttgcagca catcccccctt cgccagctg gcgtaatagc   1260
gaagaggccc gcaccgatcg cccttcccaa cagttgcgca gcctgaatgg cgaatggcgc   1320
ctgatgcggt attttctcct tacgcatctg tgcggtattt cacaccgcat atggtgcact   1380
ctcagtacaa tctgctctga tgccgcatag ttaagccagc cccgacaccc gccaacaccc   1440
gctgacgcgc cctgacgggc ttgtctgctc ccggcatccg cttacagaca agctgtgacc   1500
gtctccggga gctgcatgtg tcagaggttt tcaccgtcat caccgaaacg cgcgagacga   1560
aagggcctcg tgatacgcct atttttatag gttaatgtca tgataataat ggtttcttag   1620
acgtcaggtg gcacttttcg gggaaatgtg cgcggaaccc ctatttgttt attttttctaa   1680
atacattcaa atatgtatcc gctcatgaga caataaccct gataaatgct tcaataatat   1740
tgaaaaagga agagtatgag tattcaacat ttccgtgtcg cccttattcc cttttttgcg   1800
gcatttgcc ttcctgtttt tgctcaccca gaaacgctgg tgaaagtaaa agatgctgaa   1860
gatcagttgg gtgcacgagt gggttacatc gaactggatc tcaacagcgg taagatcctt   1920
gagagttttc gccccgaaga acgttttcca atgatgagca cttttaaagt tctgctatgt   1980
ggcgcggtat tatcccgtat tgacgccggg caagagcaac tcggtcgccg catacactat   2040
tctcagaatg acttggttga gtactcacca gtcacagaaa agcatcttac ggatggcatg   2100
acagtaagag aattatgcag tgctgccata accatgagtg ataacactgc ggccaactta   2160
cttctgacaa cgatcggagg accgaaggag ctaaccgctt ttttgcacaa catggggat   2220
catgtaactc gccttgatcg ttgggaaccg gagctgaatg aagccatacc aaacgacgag   2280
cgtgacacca cgatgcctgt agcaatggca acaacgttgc gcaaactatt aactggcgaa   2340
ctacttactc tagcttcccg gcaacaatta atagactgga tggaggcgga taaagttgca   2400
ggaccacttc tgcgctcggc ccttccggct ggctggttta ttgctgataa atctggagcc   2460
ggtgagcgtg ggtctcgcgg tatcattgca gcactgggc cagatggtaa gccctcccgt   2520
atcgtagtta tctacacgac ggggagtcag gcaactatgg atgaacgaaa tagacagatc   2580
gctgagatag gtgcctcact gattaagcat tggtaactgt cagaccaagt ttactcatat   2640
atactttaga ttgatttaaa acttcatttt taatttaaaa ggatctaggt gaagatcctt   2700
```

```
tttgataatc tcatgaccaa aatcccttaa cgtgagtttt cgttccactg agcgtcagac   2760
cccgtagaaa agatcaaagg atcttcttga gatccttttt ttctgcgcgt aatctgctgc   2820
ttgcaaacaa aaaaaccacc gctaccagcg gtggtttgtt tgccggatca agagctacca   2880
actctttttc cgaaggtaac tggcttcagc agagcgcaga taccaaatac tgttcttcta   2940
gtgtagccgt agttaggcca ccacttcaag aactctgtag caccgcctac atacctcgct   3000
ctgctaatcc tgttaccagt ggctgctgcc agtggcgata gtcgtgtct taccgggttg   3060 gactcaagac gatagttacc ggataaggcg cagcggtcgg gctgaacggg gggttcgtgc   3120
acacagccca gcttggagcg aacgacctac accgaactga gatacctaca gcgtgagctt   3180
tgagaaagcg ccacgcttcc cgaagggaga aaggcggaca ggtatccggt aagcggcagg   3240
gtcggaacag gagagcgcac gagggagctt ccaggggaa acgcctggta tctttatagt   3300
cctgtcgggt ttcgccacct ctgacttgag cgtcgatttt tgtgatgctc gtcagggggg   3360
cggagcctat ggaaaaacgc cagcaacgcg gcctttttac ggttcctggc cttttgctgg   3420
ccttttgctc acatgttctt tcctgcgtta tcccctgatt ctgtggataa ccgtattacc   3480
gcctttgagt gagctgatac cgctcgccgc agccgaacga ccgagcgcag cgagtcagtg   3540
agcgaggaag cggaagagcg cccaatacgc aaaccgcctc tccccgcgcg ttggccgatt   3600
cattaatgca gctggcacga caggtttccc gactggaaag cgggcagtga gcgcaacgca   3660
attaatgtga gttagctcac tcattaggca ccccaggctt tacactttat gcttccggct   3720
cgtatgttgt gtggaattgt gagcggataa caatttcaca caggaaacag ctatgaccat   3780
gattacgaat tcccatgcct cgagcagaaa gatataatat gtaaaaaaat gggtctatat   3840
atatggaagg tttcaggaag acaaaggttc tagaaacttc caaaaaaaat ccagaatata   3900
ttttggaaga ataccctct tgggttggcc ccggcgcagc ccctagtggg ccaaaaagcc   3960
acgatctaat cccggtctaa ttggtctaat agtttagact tctaattaga cgggctctta   4020
tgccggtcta attggtctaa ttagattaaa atcctaatta aatatgaacg caactaggct   4080
tcccctctct ctagttttct cggagctctt tttcatggac cttgaagtat tgccggatca   4140
ctacttcgga actcgtggat acttcagagt gcacatctac tttgaatctt gattggtaga   4200
tcatctcgga gaaattctca cagttgggag gtataaccag ttgccgaaat tgccatgctt   4260
cactcacagc caggatcagc ccatgtccca aggcaaccct tgtagctaca tgccgaggcc   4320
tgactacttg gggcctcgcg ccctgcattt ttgcatgttc atgtgacacg ttaaatgttg   4380
agagaaatag attactaaat atcacccatt tcgttattct agatgagtat cctacaatat   4440
gtataccgaa aaatgtattt taaactgtgg taggtgagaa agatctatta aaaagaactc   4500
tacgtatact ccccccctccc aatccccatc caggtttgta agacactttc gtcttttttt   4560
gccgaatttt aaccgtaaat ttgactagta aaaataagtt atactgaatg taataaatat   4620
cgtacattcg gatgttggag acagggagag ctggctggt gcgctggatg gatcacggtc   4680
agaaagtctg acttgcaacg ccacaggccc gttgattgcc actgacaacc aagttttcgt   4740
tgtttcgctg gtgccatatt ttccgcgatc gaatatttaa actgcgagga gaaaggcaag   4800
cagggcgcca tatcagcact tgatcactca ctgatcgatc agtagtagcc accttctctg   4860
cgccgacgtg ttatatatta ttggcaacaa gtcatcgatt gagaacagaa acaaaacaag   4920
aagagaacta tttgagagag agtagttacg ccgcagcgag tagcctccca tttctgacga   4980
tcatgccata cgataaaccg gccggcggcg agaccagtta gcaaggttga aatgccaaca   5040
catgtcgcgc tcatttctcg gcttttttcat tttgcatgtc gtcatgcagg ccctggacac   5100
```

-continued

```
tgacatttct ctcttttgct gttgaatgaa gaccctaacc tttcaccatc agcacgcccc    5160
tcaacttgat aagcctagac gaaacccata tgcatgattg atgagtaatg gtgtgcacga    5220
atattatgaa cccgtttcca agagcaatac tccattgaga tacacctcct ccttgtatct    5280
gttcgttggt cccatttcca tagcagccgg cagtggcctt gactctgact gccacgcaag    5340
taatatatct ttaataaact cgctgccttg cttcgtgtgt ccatttgcaa atgcatgcag    5400
tgacgacatg cacatgcata gcttaattag ctccatgcat ccactgcttc cattaatccc    5460
ctatataaag gactccatat gcctcaccat tcactcatcc accacagctt agcagcagca    5520
acaaccagtg ccatagacac tctccatcaa caaactctag ctgatcaatc ctagctaagc    5580
ttattacata gcaagccc                                                  5598
```

<210> SEQ ID NO 36
<211> LENGTH: 12776
<212> TYPE: DNA
<213> ORGANISM: Artificial sequence
<220> FEATURE:
<223> OTHER INFORMATION: Description of the artificial sequence:
      recombinant expression vector pLo114OXoBI-1
<220> FEATURE:
<221> NAME/KEY: misc_feature
<222> LOCATION: (9590)..(9590)
<223> OTHER INFORMATION: n is a, c, g, or t
<220> FEATURE:
<221> NAME/KEY: misc_feature
<222> LOCATION: (9764)..(9764)
<223> OTHER INFORMATION: n is a, c, g, or t

<400> SEQUENCE: 36

```
aattcactgg ccgtcgtttt acaacgactc agagcttgac aggaggcccg atctagtaac      60
atagatgaca ccgcgcgcga taatttatcc tagtttgcgc gctatatttt gttttctatc     120
gcgtattaaa tgtataattg cgggactcta atcataaaaa cccatctcat aaataacgtc     180
atgcattaca tgttaattat tacatgctta acgtaattca acagaaatta tatgataatc     240
atcgcaagac cggcaacagg attcaatctt aagaaacttt attgccaaat gtttgaacga     300
tcggggatca tccgggtctg tggcgggaac tccacgaaaa tatccgaacg cagcaagatc     360
tagagcttgg gtcccgctca aagaactcg tcaagaaggc gatagaaggc gatgcgctgc     420
gaatcgggag cggcgatacc gtaaagcacg aggaagcggt cagcccattc gccgccaagc     480
tcttcagcaa tatcacgggt agccaacgct atgtcctgat agcggtccgc cacacccagc     540
cggccacagt cgatgaatcc agaaaagcgg ccattttcca ccatgatatt cggcaagcag     600
gcatcgccat gggtcacgac gagatcctcg ccgtcgggca tgcgcgcctt gagcctggcg     660
aacagttcgg ctggcgcgag cccctgatgc tcttcgtcca gatcatcctg atcgacaaga     720
ccggcttcca tccgagtacg tgctcgctcg atgcgatgtt tcgcttggtg gtcgaatggg     780
caggtagccg gatcaagcgt atgcagccgc cgcattgcat cagccatgat ggatactttc     840
tcggcaggag caaggtgaga tgacaggaga tcctgccccg gcacttcgcc caatagcagc     900
cagtcccttc ccgcttcagt gacaacgtcg agcacagctg cgcaaggaac gcccgtcgtg     960
gccagccacg atagccgcgc tgcctcgtcc tgcagttcat tcagggcacc ggacaggtcg    1020
gtcttgacaa aagaaccggg cgcccctgc gctgacagcc ggaacacggc ggcatcagag    1080
cagccgattg tctgttgtgc ccagtcatag ccgaatagcc tctccaccca gcggccgga    1140 gaacctgcgt gcaatccatc ttgttcaatc atgcgaaacg atccagatcc ggtgcagatt    1200
atttggattg agagtgaata tgagactcta attggatacc gaggggaatt tatgaacgt    1260 cagtggagca ttttttgacaa gaaatatttg ctagctgata gtgaccttag gcgacttttg    1320
```

| | |
|---|---|
| aacgcgcaat aatggtttct gacgtatgtg cttagctcat aaaactccag aaacccgcgg | 1380 |
| ctgagtggct ccttcaacgt tgcggttctg tcagttccaa acgtaaaacg gcttgtcccg | 1440 |
| cgtcatcggc gggggtcata acgtgactcc cttaattctc cgctcatgat cagattgtcg | 1500 |
| tttcccgcct tcagttttaaa ctatcagtgt ttgacaggat cctgcttggt aataattgtc | 1560 |
| attagattgt ttttatgcat agatgcactc gaaatcagcc aattttagac aagtatcaaa | 1620 |
| cggatgttaa ttcagtacat taaagacgtc cgcaatgtgt tattaagttg tctaagcgtc | 1680 |
| aatttgttta caccacaata tatcctgcca ccagccagcc aacagctccc cgaccggcag | 1740 |
| ctcggcacaa aatcaccacg cgttaccacc acgccggccg gccgcatggt gttgaccgtg | 1800 |
| ttcgccggca ttgccgagtt cgagcgttcc ctaatcatcg accgcacccg gagcgggcgc | 1860 |
| gaggccgcca aggcccgagg cgtgaagttt ggccccccgcc ctaccctcac cccggcacag | 1920 |
| atcgcgcacg cccgcgagct gatcgaccag gaaggccgca ccgtgaaaga ggcggctgca | 1980 |
| ctgcttggcg tgcatcgctc gaccctgtac cgcgcacttg agcgcagcga ggaagtgacg | 2040 |
| cccaccgagg ccaggcggcg cggtgccttc cgtgaggacg cattgaccga ggccgacgcc | 2100 |
| ctggcggccg ccgagaatga acgccaagag gaacaagcat gaaaccgcac caggacggcc | 2160 |
| aggacgaacc gttttttcatt accgaagaga tcgaggcgga gatgatcgcg gccgggtacg | 2220 |
| tgttcgagcc gcccgcgcac gtctcaaccg tgcggctgca tgaaatcctg gccggttgt | 2280 |
| ctgatgccaa gctggcggcc tggccggcca gcttggccgc tgaagaaacc gagcgccgcc | 2340 |
| gtctaaaaag gtgatgtgta tttgagtaaa acagcttgcg tcatgcggtc gctgcgtata | 2400 |
| tgatgcgatg agtaaataaa caaatacgca aggggaacgc atgaaggtta cgctgtact | 2460 |
| taaccagaaa ggcgggtcag gcaagacgac catcgcaacc catctagccc cgcccctgca | 2520 |
| actcgccggg gccgatgttc tgttagtcga ttccgatccc cagggcagtg cccgcgattg | 2580 |
| ggcggccgtg cgggaagatc aaccgctaac cgttgtcggc atcgaccgcc cgacgattga | 2640 |
| ccgcgacgtg aaggccatcg gccggcgcga cttcgtagtg atcgacggag cgccccaggc | 2700 |
| ggcggacttg gctgtgtccg cgatcaaggc agccgacttc gtgctgattc cggtgcagcc | 2760 |
| aagcccttac gacatatggg ccaccgccga cctggtggag ctggttaagc agcgcattga | 2820 |
| ggtcacggat ggaaggctac aagcggcctt tgtcgtgtcg cgggcgatca aaggcacgcg | 2880 |
| catcggcggt gaggttgccg aggcgctggc cgggtacgag ctgcccattc ttgagtcccg | 2940 |
| tatcacgcag cgcgtgagct acccaggcac tgccgccgcc ggcacaaccg ttcttgaatc | 3000 |
| agaacccgag ggcgacgctg cccgcgaggt ccaggcgctg gccgctgaaa ttaaatcaaa | 3060 |
| actcatttga gttaatgagg taaagagaaa atgagcaaaa gcacaaacac gctaagtgcc | 3120 |
| ggccgtccga gcgcacgcag cagcaaggct gcaacgttgg ccagcctggc agacacgcca | 3180 |
| gccatgaagc gggtcaactt tcagttgccg gcggaggatc acaccaagct gaagatgtac | 3240 |
| gcggtacgcc aaggcaagac cattaccgag ctgctatctg aatacatcgc gcagctacca | 3300 |
| gagtaaatga gcaaatgaat aaatgagtag atgaatttta gcggctaaag gaggcggcat | 3360 |
| ggaaaatcaa gaacaaccag gcaccgacgc cgtggaatgc cccatgtgtg gaggaacggg | 3420 |
| cggttggcca ggcgtaagcg gctgggttgt ctgccggccc tgcaatggca ctggaacccc | 3480 |
| caagcccgag gaatcggcgt gagcggtcgc aaaccatccg gcccggtaca atcggcgcg | 3540 |
| gcgctgggtg atgacctggt ggagaagttg aaggccgcgc aggccgccca gcggcaacgc | 3600 |
| atcgaggcag aagcacgccc cggtgaatcg tggcaagcgg ccgctgatcg aatccgcaaa | 3660 |
| gaatcccggc aaccgccggc agccggtgcg ccgtcgatta ggaagccgcc caagggcgac | 3720 |

```
gagcaaccag attttttcgt tccgatgctc tatgacgtgg gcacccgcga tagtcgcagc    3780
atcatggacg tggccgtttt ccgtctgtcg aagcgtgacc gacgagctgg cgaggtgatc    3840
cgctacgagc ttccagacgg gcacgtagag gtttccgcag ggccggccgg catggccagt    3900
gtgtgggatt acgacctggt actgatggcg gtttcccatc taaccgaatc catgaaccga    3960
taccgggaag ggaagggaga caagcccggc cgcgtgttcc gtccacacgt tgcggacgta    4020
ctcaagttct gccggcgagc cgatggcgga aagcagaaag acgacctggt agaaacctgc    4080
attcggttaa acaccacgca cgttgccatg cagcgtacga agaaggccaa gaacggccgc    4140
ctggtgacgg tatccgaggg tgaagccttg attagccgct acaagatcgt aaagagcgaa    4200
accgggcggc cggagtacat cgagatcgag ctagctgatt ggatgtaccg cgagatcaca    4260
gaaggcaaga acccggacgt gctgacggtt caccccgatt acttttttga tcgatcccgg c    4320 atcggccgtt ttctctaccg cctggcacgc cgcgccgcag gcaaggcaga agccagatgg    4380
ttgttcaaga cgatctacga acgcagtggc agcgccgaga gttcaagaa gttctgtttc    4440 accgtgcgca agctgatcgg gtcaaatgac ctgccggagt acgatttgaa ggaggaggcg    4500
gggcaggctg gcccgatcct agtcatgcgc taccgcaacc tgatcgaggg cgaagcatcc    4560
gccggttcct aatgtacgga gcagatgcta gggcaaattg ccctagcagg ggaaaaggt    4620 cgaaaaggtc tctttcctgt ggatagcacg tacattggga acccaaagcc gtacattggg    4680
aaccggaacc cgtacattgg gaacccaaag ccgtacattg gaaccggtc acacatgtaa    4740 gtgactgata taaagagaa aaaaggcgat ttttccgcct aaaactcttt aaaacttatt    4800
aaaactctta aaaccgcct ggcctgtgca taactgtctg gccagcgcac agccgaagag    4860
ctgcaaaaag cgcctaccct tcggtcgctg cgctccctac gccccgccgc ttcgcgtcgg    4920
cctatcgcgg ccgctggccg ctcaaaaatg gctggcctac ggccaggcaa tctaccaggg    4980
cgcggacaag ccgcgccgtc gccactcgac cgccggcgcc cacatcaagg caccctgcct    5040
cgcgcgtttc ggtgatgacg gtgaaaacct ctgacacatg cagctcccgg agacggtcac    5100
agcttgtctg taagcggatg ccgggagcag acaagcccgt cagggcgcgt cagcgggtgt    5160
tggcgggtgt cggggcgcag ccatgaccca gtcacgtagc gatagcggag tgtatactgg    5220
cttaactatg cggcatcaga gcagattgta ctgagagtgc accatatgcg gtgtgaaata    5280
ccgcacagat gcgtaaggag aaaataccgc atcaggcgct cttccgcttc ctcgctcact    5340
gactcgctgc gctcggtcgt tcggctgcgg cgagcggtat cagctcactc aaaggcggta    5400
atacggttat ccacagaatc aggggataac gcaggaaaga acatgtgagc aaaaggccag    5460
caaaaggcca ggaaccgtaa aaaggccgcg ttgctggcgt ttttccatag gctccgcccc    5520
cctgacgagc atcacaaaaa tcgacgctca agtcagaggt ggcgaaaccc gacaggacta    5580
taaagatacc aggcgtttcc ccctggaagc tccctcgtgc gctctcctgt tccgaccctg    5640
ccgcttaccg gatacctgtc cgcctttctc ccttcgggaa gcgtggcgct ttctcatagc    5700
tcacgctgta ggtatctcag ttcggtgtag tcgttcgct ccaagctggg ctgtgtgcac    5760
gaaccccccg ttcagcccga ccgctgcgcc ttatccggta actatcgtct tgagtccaac    5820
ccggtaagac acgacttatc gccactggca gcagccactg gtaacaggat tagcagagcg    5880
aggtatgtag gcggtgctac agagttcttg aagtggtggc ctaactacgg ctacactaga    5940
aggacagtat ttggtatctg cgctctgctg aagccagtta ccttcggaaa aagagttggt    6000
agctcttgat ccggcaaaca aaccaccgct ggtagcggtg ttttttttgt ttgcaagcag    6060
cagattacgc gcagaaaaaa aggatctcaa gaagatcctt tgatctttc tacggggtct    6120
```

```
gacgctcagt ggaacgaaaa ctcacgttaa gggattttgg tcatgcatga tatatctccc    6180
aatttgtgta gggcttatta tgcacgctta aaaataataa aagcagactt gacctgatag    6240
tttggctgtg agcaattatg tgcttagtgc atctaacgct tgagttaagc cgcgccgcga    6300
agcggcgtcg gcttaacga atttctagct agacattatt tgccgactac cttggtgatc    6360
tcgcctttca cgtagtggac aaattcttcc aactgatctg cgcgcgaggc caagcgatct    6420
tcttcttgtc caagataagc ctgtctagct tcaagtatga cgggctgata ctgggccggc    6480
aggcgctcca ttgcccagtc ggcagcgaca tccttcggcg cgattttgcc ggttactgcg    6540
ctgtaccaaa tgcgggacaa cgtaagcact acatttcgct catcgccagc ccagtcgggc    6600
ggcgagttcc atagcgttaa ggtttcattt agcgcctcaa atagatcctg ttcaggaacc    6660
ggatcaaaga gttcctccgc cgctggacct accaaggcaa cgctatgttc tcttgctttt    6720
gtcagcaaga tagccagatc aatgtcgatc gtggctggct cgaagatacc tgcaagaatg    6780
tcattgcgct gccattctcc aaattgcagt tcgcgcttag ctggataacg ccacggaatg    6840
atgtcgtcgt gcacaacaat ggtgacttct acagcgcgga gaatctcgct ctctccaggg    6900
gaagccgaag tttccaaaag gtcgttgatc aaagctcgcc gcgttgtttc atcaagcctt    6960
acggtcaccg taaccagcaa atcaatatca ctgtgtggct tcaggccgcc atccactgcg    7020
gagccgtaca aatgtacggc cagcaacgtc ggttcgagat ggcgctcgat gacgccaact    7080
acctctgata gttgagtcga tacttcggcg atcaccgctt cccccatgat gtttaacttt    7140
gttttagggc gactgccctg ctgcgtaaca tcgttgctgc tccataacat caaacatcga    7200
cccacggcgt aacgcgcttg ctgcttggat gcccgaggca tagactgtac cccaaaaaaa    7260
cagtcataac aagccatgaa aaccgccact gcggggttc catggacata caaatggacg    7320
aacggataaa ccttttcacg ccctttaaa tatccgatta ttctaataaa cgctctttc    7380 tcttaggttt acccgccaat atatcctgtc aaacactgat agtttaaact gaaggcggga    7440
aacgacaatc agatctagta ggaaacagct atgaccatga ttacgccaag cttgcatgcc    7500
tgcaggtcga ctctagagga tcgatccccg ggtaggtcag tcccttatgt tacgtcctgt    7560
agaaacccca acccgtgaaa tcaaaaaact cgacggcctg tgggcattca gtctggatcg    7620
cgaaaactgt ggaattggtc agcgttggtg ggaaagcgcg ttacaagaaa gccgggcaat    7680
tgctgtgcca ggcagtttta acgatcagtt cgccgatgca gatattcgta attatgcggg    7740
caacgtctgg tatcagcgcg aagtctttat accgaaaggt tgggcaggcc agcgtatcgt    7800
gctgcgtttc gatgcggtca ctcattacgg caaagtgtgg gtcaataatc aggaagtgat    7860
ggagcatcag gcggctata cgccatttga agccgatgtc acgccgtatg ttattgccgg    7920
gaaaagtgta cgtaagtttc tgcttctacc tttgatatat atataataat tatcattaat    7980
tagtagtaat ataatatttc aaatattttt ttcaaaataa aagaatgtag tatatagcaa    8040 ttgctttttct gtagtttata agtgtgtata ttttaattta taactttct aatatatgac    8100 caaaatttgt tgatgtgcag gtatcaccgt ttgtgtgaac aacgaactga actggcagac    8160
tatcccgccg ggaatggtga ttaccgacga aaacggcaag aaaaagcagt cttacttcca    8220
tgatttcttt aactatgccg gaatccatcg cagcgtaatg ctctacacca cgccgaacac    8280
ctgggtggac gatatcaccg tggtgacgca tgtcgcgcaa gactgtaacc acgcgtctgt    8340
tgactggcag gtggtggcca atggtgatgt cagcgttgaa ctgcgtgatg cggatcaaca    8400
ggtggttgca actggacaag gcactagcgg gactttgcaa gtggtgaatc cgcacctctg    8460
gcaaccgggt gaaggttatc tctatgaact gtgcgtcaca gccaaaagcc agacagagtg    8520
```

```
tgatatctac ccgcttcgcg tcggcatccg gtcagtggca gtgaagggcg aacagttcct      8580
gattaaccac aaaccgttct actttactgg ctttggtcgt catgaagatg cggacttgcg      8640
tggcaaagga ttcgataacg tgctgatggt gcacgaccac gcattaatgg actggattgg      8700
ggccaactcc taccgtacct cgcattaccc ttacgctgaa gagatgctcg actgggcaga      8760
tgaacatggc atcgtggtga ttgatgaaac tgctgctgtc ggctttaacc tctctttagg      8820
cattggtttc gaagcgggca acaagccgaa agaactgtac agcgaagagg cagtcaacgg      8880
ggaaactcag caagcgcact acaggcgat taaagagctg atagcgcgtg acaaaaacca      8940
cccaagcgtg gtgatgtgga gtattgccaa cgaaccggat acccgtccgc aaggtgcacg      9000
ggaatatttc gcgccactgg cggaagcaac gcgtaaactc gacccgacgc gtccgatcac      9060
ctgcgtcaat gtaatgttct gcgacgctca caccgatacc atcagcgatc tctttgatgt      9120
gctgtgcctg aaccgttatt acggatggta tgtccaaagc ggcgatttgg aaacggcaga      9180
gaaggtactg gaaaaagaac ttctggcctg gcaggagaaa ctgcatcagc cgattatcat      9240
caccgaatac ggcgtggata cgttagccgg gctgcactca atgtacaccg acatgtggag      9300
tgaagagtat cagtgtgcat ggctggatat gtatcaccgc gtctttgatc gcgtcagcgc      9360
cgtcgtcggt gaacaggtat ggaatttcgc cgattttgcg acctcgcaag gcatattgcg      9420
cgttggcggt aacaagaaag ggatcttcac tcgcgaccgc aaaccgaagt cggcggcttt      9480
tctgctgcaa aaacgctgga ctggcatgaa cttcggtgaa aaaccgcagc agggaggcaa      9540
acaatgagag ctcgaatttc cccgatcggt caaacatttg gcaataaagn ttcttaagat      9600
tgaatcctgt tgccggtctt gcgatgatta tcatataatt tctgttgaat tacgttaagc      9660
atgtaataat taacatgtaa tgcatgacgt tatttatgag atgggttttt atgattagag      9720
tcccgcaatt atacatttaa tacgcgatag aaaacaaaat atancgcgca aactaggata      9780
aattatcgcg cgcggtgtca tctatgttac tagatcggga attcccatgc ctcgagcaga      9840
aagatataat atgtaaaaaa atgggtctat atatatggaa ggtttcagga agacaaaggt      9900
tctagaaact tccaaaaaaa atccagaata tattttggaa gaaataccct cttgggttgg      9960
ccccggcgca gccccctagtg ggccaaaaag ccacgatcta atcccggtct aattggtcta     10020
atagtttaga cttctaatta gacgggctct tatgccggtc taattggtct aattagatta     10080
aaatcctaat taaatatgaa cgcaactagg cttcccctct ctctagtttt ctcggagctc     10140
tttttcatgg accttgaagt attgccggat cactacttcg gaactcgtgg atacttcaga     10200
gtgcacatct actttgaatc ttgattggta gatcatctcg gagaaattct cacagttggg     10260
aggtataacc agttgccgaa attgccatgc ttcactcaca gccaggatca gcccatgtcc     10320
caaggcaacc cttgtagcta catgccgagg cctgactact tggggcctcg cgccctgcat     10380
ttttgcatgt tcatgtgaca cgttaaatgt tgagagaaat agattactaa atatcaccca     10440
tttcgttatt ctagatgagt atcctacaat atgtataccg aaaaatgtat tttaaactgt     10500
ggtaggtgag aaagatctat taaaaagaac tctacgtata ctccccccte ccaatcccca     10560 tccaggtttg taagacactt tcgtcttttt ttgccgaatt ttaaccgtaa atttgactag     10620
taaaaataag ttatactgaa tgtaataaat atcgtacatt cggatgttgg agacagggag     10680
aggctggctg gtgcgctgga tggatcacgg tcagaaagtc tgacttgcaa cgccacaggc     10740
ccgttgattg ccactgacaa ccaagttttc gttgtttcgc tggtgccata ttttccgcga     10800
tcgaatattt aaactgcgag gagaaaggca agcaggcgc catatcagca cttgatcact     10860
cactgatcga tcagtagtag ccaccttctc tgcgccgacg tgttatatat tattggcaac     10920
```

```
aagtcatcga ttgagaacag aaacaaaaca agaagagaac tatttgagag agagtagtta   10980
cgccgcagcg agtagcctcc catttctgac gatcatgcca tacgataaac cggccggcgg   11040
cgagaccagt tagcaaggtt gaaatgccaa cacatgtcgc gctcatttct cggctttttc   11100
attttgcatg tcgtcatgca ggccctggac actgacattt ctctcttttg ctgttgaatg   11160
aagaccctaa cctttcacca tcagcacgcc cctcaacttg ataagcctag acgaaaccca   11220
tatgcatgat tgatgagtaa tggtgtgcac gaatattatg aacccgtttc caagagcaat   11280
actccattga gatacacctc ctccttgtat ctgttcgttg gtcccatttc catagcagcc   11340
ggcagtggcc ttgactctga ctgccacgca agtaatatat ctttaataaa ctcgctgcct   11400
tgcttcgtgt gtccatttgc aaatgcatgc agtgacgaca tgcacatgca tagcttaatt   11460
agctccatgc atccactgct tccattaatc ccctatataa aggactccat atgcctcacc   11520
attcactcat ccaccacagc ttagcagcag caacaaccag tgccatagac actctccatc   11580
aacaaactct agctgatcaa tcctagctaa gcttattaca tagcaagccc ggggatcctc   11640
tagagtcgac ctgcaggcgg ccgcactagt gattaggatt ccaacgcgag ccaggacaag   11700
cgaggaacct tgcgtgcgag gcgaggccgc cccgctccga ttcgattcga cgcgcaggcg   11760
caggcgcagg gatggacgcc ttctactcga cctcgtcggc ggcggcgagc ggctggggcc   11820
acgactccct caagaacttc cgccagatct ccccgccgt gcagtcccac ctcaagctcg   11880
tttacctgac tctatgcttt gcactggcct catctgccgt gggtgcttac ctacacattg   11940
ccctgaacat cggcgggatg ctgacaatgc tcgcttgtgt cggaactatc gcctggatgt   12000
tctcggtgcc agtctatgag gagaggaaga ggtttgggct gctgatgggt gcagccctcc   12060
tggaaggggc ttcggttgga cctctgattg agcttgccat agactttgac ccaagcatcc   12120
tcgtgacagg gtttgtcgga accgccatcg cctttgggtg cttctctggc gccgccatca   12180
tcgccaagcg cagggagtac ctgtacctcg gtggcctgct ctcgtctggc ctgtcgatcc   12240
tgctctggct gcagtttgtc acgtccatct ttggccactc ctctggcagc ttcatgtttg   12300
aggtttactt tggcctgttg atcttcctgg ggtacatggt gtacgacacg caggagatca   12360
tcgagagggc gcaccatggc gacatggact acatcaagca cgccctcacc ctcttcaccg   12420
actttgttgc cgtcctcgtc cgagtcctca tcatcatgct caagaacgca ggcgacaagt   12480
cggaggacaa gaagaagagg aagaggggggt cctgaacgtw tctcccgcac atgtagatac   12540
cgtcaccgcg tcgacctgca ggcatgcccg ctgaaatcac cagtctctct ctacaaatct   12600
atctctctca taataatgtg tgagtagttc ccagataagg gaattagggt tcttataggg   12660
tttcgctcat gtgttgagca tataagaaac ccttagtatg tatttgtatt tgtaaaatac   12720
ttctatcaat aaaatttcta attcctaaaa ccaaaatcca gtgggtaccg agctcg        12776
```

<210> SEQ ID NO 37
<211> LENGTH: 744
<212> TYPE: DNA
<213> ORGANISM: Triticum aestivum
<220> FEATURE:
<221> NAME/KEY: CDS
<222> LOCATION: (1)..(741)
<223> OTHER INFORMATION: coding for TaBI-1

<400> SEQUENCE: 37

```
atg gac gcc ttc tac tcg acc tcg tcg gcg gcg gcg agc ggc tgg ggc        48
Met Asp Ala Phe Tyr Ser Thr Ser Ser Ala Ala Ala Ser Gly Trp Gly
 1               5                  10                  15 tac gac tcc ctc aag aac ttc cgc gag atc tcc ccc gcc gtg cag tcc        96
```

```
                                                                     144
cac ctc aag ctc gtt tac ctg acc cta tgc ttt gcc ctg gcc tca tct
His Leu Lys Leu Val Tyr Leu Thr Leu Cys Phe Ala Leu Ala Ser Ser
         35                  40                  45

192
gcc gtg ggt gct tac ctg cac att gcc ctg aac atc ggt ggg atg ctg
Ala Val Gly Ala Tyr Leu His Ile Ala Leu Asn Ile Gly Gly Met Leu
 50                  55                  60

240
aca atg ctc gcg tgt gtt gga acc atc gcc tgg atg ttc tct gtg cca
Thr Met Leu Ala Cys Val Gly Thr Ile Ala Trp Met Phe Ser Val Pro
65                  70                  75                  80

288
gtc tat gag gag agg aag agg ttt ggg ctg ctg atg ggt gca gcc ctc
Val Tyr Glu Glu Arg Lys Arg Phe Gly Leu Leu Met Gly Ala Ala Leu
             85                  90                  95

336
ctg gaa ggg gct tcg gtt gga cct ctg att gag ctt gcc ata gac ttt
Leu Glu Gly Ala Ser Val Gly Pro Leu Ile Glu Leu Ala Ile Asp Phe
                100                 105                 110

384
gac cca agt atc ctc gtg aca ggg ttt gtc gga acc gcc atc gcc ttc
Asp Pro Ser Ile Leu Val Thr Gly Phe Val Gly Thr Ala Ile Ala Phe
            115                 120                 125

432
ggg tgc ttc tct ggc gcc gcc atc atc gcc aag cgc agg gag tac ctg
Gly Cys Phe Ser Gly Ala Ala Ile Ile Ala Lys Arg Arg Glu Tyr Leu
    130                 135                 140

480
tac ctc ggt ggt ctg ctc tcc tcc ggc ctg tcg atc ctg ctc tgg ctg
Tyr Leu Gly Gly Leu Leu Ser Ser Gly Leu Ser Ile Leu Leu Trp Leu
145                 150                 155                 160

528
cag ttt gcc acg tcc atc ttt ggc cac tcc tct ggc agc ttc atg ttt
Gln Phe Ala Thr Ser Ile Phe Gly His Ser Ser Gly Ser Phe Met Phe
                165                 170                 175

576
gag gtt tac ttt ggc ctg ttg atc ttc ctg gga tac atg gtg tac gac
Glu Val Tyr Phe Gly Leu Leu Ile Phe Leu Gly Tyr Met Val Tyr Asp
            180                 185                 190

624
acg cag gag atc atc gag agg gcg cac cac ggc gac atg gat tac atc
Thr Gln Glu Ile Ile Glu Arg Ala His His Gly Asp Met Asp Tyr Ile
    195                 200                 205

672
aag cac gcg ctc acc ctc ttc acc gac ttc gtc gcc gtt ctc gtc cgc
Lys His Ala Leu Thr Leu Phe Thr Asp Phe Val Ala Val Leu Val Arg
210                 215                 220

720
gtc ctc atc atc atg ctc aag aac gca ggc gac aag tcg gag gac aag
Val Leu Ile Ile Met Leu Lys Asn Ala Gly Asp Lys Ser Glu Asp Lys
                225                 230                 235                 240

744
aag aag agg aag agg ggg tcc tga
Lys Lys Arg Lys Arg Gly Ser
                245

<210> SEQ ID NO 38
<211> LENGTH: 247
<212> TYPE: PRT
<213> ORGANISM: Triticum aestivum

<400> SEQUENCE: 38

Met Asp Ala Phe Tyr Ser Thr Ser Ser Ala Ala Ala Ser Gly Trp Gly
 1               5                  10                  15

Tyr Asp Ser Leu Lys Asn Phe Arg Glu Ile Ser Pro Ala Val Gln Ser
             20                  25                  30

His Leu Lys Leu Val Tyr Leu Thr Leu Cys Phe Ala Leu Ala Ser Ser
         35                  40                  45

Ala Val Gly Ala Tyr Leu His Ile Ala Leu Asn Ile Gly Gly Met Leu
     50                  55                  60

Thr Met Leu Ala Cys Val Gly Thr Ile Ala Trp Met Phe Ser Val Pro
```

```
                 65                  70                  75                  80
Val Tyr Glu Glu Arg Lys Arg Phe Gly Leu Leu Met Gly Ala Ala Leu
                     85                  90                  95

Leu Glu Gly Ala Ser Val Gly Pro Leu Ile Glu Leu Ala Ile Asp Phe
                100                 105                 110

Asp Pro Ser Ile Leu Val Thr Gly Phe Val Gly Thr Ala Ile Ala Phe
            115                 120                 125

Gly Cys Phe Ser Gly Ala Ala Ile Ile Ala Lys Arg Arg Glu Tyr Leu
        130                 135                 140

Tyr Leu Gly Gly Leu Leu Ser Ser Gly Leu Ser Ile Leu Leu Trp Leu
145                 150                 155                 160

Gln Phe Ala Thr Ser Ile Phe Gly His Ser Ser Gly Ser Phe Met Phe
                165                 170                 175

Glu Val Tyr Phe Gly Leu Leu Ile Phe Leu Gly Tyr Met Val Tyr Asp
                180                 185                 190

Thr Gln Glu Ile Ile Glu Arg Ala His His Gly Asp Met Asp Tyr Ile
            195                 200                 205

Lys His Ala Leu Thr Leu Phe Thr Asp Phe Val Ala Val Leu Val Arg
        210                 215                 220

Val Leu Ile Ile Met Leu Lys Asn Ala Gly Asp Lys Ser Glu Asp Lys
225                 230                 235                 240

Lys Lys Arg Lys Arg Gly Ser
                245

<210> SEQ ID NO 39
<211> LENGTH: 1293
<212> TYPE: DNA
<213> ORGANISM: Hordeum vulgare
<220> FEATURE:
<221> NAME/KEY: CDS
<222> LOCATION: (173)..(1126)
<223> OTHER INFORMATION: coding for Hordeum vulgare subsp. vulgare
      syntaxin (Ror2)

<400> SEQUENCE: 39
gtaactaacc ccttcttcct cccttgtcca ctccgcttct ccccatccaa gaaacagcgc        60
caacagctcc acccatcgag gagaatcaag aaaccgcgcc ggcgtggtga tcaaggacat       120
ccatcgatcg atcgaccgac cctgccttgc ctgagtcaac ccggcggcag cc atg aac       178
                                                          Met Asn
                                                            1 aac ctc ttc tcg agc tcg tgg aag cgg gcg ggc gcg ggg ggc gac ggg        226
Asn Leu Phe Ser Ser Ser Trp Lys Arg Ala Gly Ala Gly Gly Asp Gly
          5                  10                  15 gac ctg gag tcg ggc ggc ggc gtg gag atg acg gcg ccg ccg ggc            274
Asp Leu Glu Ser Gly Gly Gly Val Glu Met Thr Ala Pro Pro Gly
     20                  25                  30 gcc gcg gcg ggg gcg agc ctg gac cgc ttc ttc gag gac gtg gag tcg        322
Ala Ala Ala Gly Ala Ser Leu Asp Arg Phe Phe Glu Asp Val Glu Ser
 35                  40                  45                  50 atc aag gac gac ctg cgg gag ctg gag cgg atc cag cgc tcc ctc cac        370
Ile Lys Asp Asp Leu Arg Glu Leu Glu Arg Ile Gln Arg Ser Leu His
                 55                  60                  65 gac ggc aac gag tcg ggc aag tcg ctc cac gac gcg tcg gcg gtg cgc        418
Asp Gly Asn Glu Ser Gly Lys Ser Leu His Asp Ala Ser Ala Val Arg
             70                  75                  80 gcg ctc cgc tcc cgc atg gac gcc gac gtg gcc gcc gcc atc aag aag        466
Ala Leu Arg Ser Arg Met Asp Ala Asp Val Ala Ala Ala Ile Lys Lys
         85                  90                  95
```

```
gcc aag gtg gtg aag ttg cgg ctc gag tcg ctc gac cgc gcc aac gcc      514
Ala Lys Val Val Lys Leu Arg Leu Glu Ser Leu Asp Arg Ala Asn Ala
    100                 105                 110 gcc aac cgg tcc gtg gcc ggg tgc ggg ccg ggg tcg tcc acg gac cgc      562
Ala Asn Arg Ser Val Ala Gly Cys Gly Pro Gly Ser Ser Thr Asp Arg
115                 120                 125                 130 acc cgc acc tcc gtc gtg gcc ggg ctg cgc aag aag ctg cgg gat gcc      610
Thr Arg Thr Ser Val Val Ala Gly Leu Arg Lys Lys Leu Arg Asp Ala
                135                 140                 145 atg gag tcc ttc tcc tcc ctc cgc tcc cgc atc acc tcc gag tac cgg      658
Met Glu Ser Phe Ser Ser Leu Arg Ser Arg Ile Thr Ser Glu Tyr Arg
            150                 155                 160 gaa acc gtg gcc cgc cgc tac ttc acg gtg acg ggg tcc cag ccc gac      706
Glu Thr Val Ala Arg Arg Tyr Phe Thr Val Thr Gly Ser Gln Pro Asp
        165                 170                 175 gag gcc acg ctg gac acg ctg gcg gag acg ggg gag ggg gag cgg ctc      754
Glu Ala Thr Leu Asp Thr Leu Ala Glu Thr Gly Glu Gly Glu Arg Leu
    180                 185                 190 ctg cag cgc gcc atc gcg gag cag cag ggg aga ggg gag gtg ctg ggc      802
Leu Gln Arg Ala Ile Ala Glu Gln Gln Gly Arg Gly Glu Val Leu Gly
195                 200                 205                 210 gtg gtg gcg gag atc cag gag cgg cac ggc gcc gtg gcg gac ctg gag      850
Val Val Ala Glu Ile Gln Glu Arg His Gly Ala Val Ala Asp Leu Glu
                215                 220                 225 cgg tcc ctg ctg gag ctg cag cag gtg ttc aac gac atg gcc gtg ctg      898
Arg Ser Leu Leu Glu Leu Gln Gln Val Phe Asn Asp Met Ala Val Leu
            230                 235                 240 gtg gcg gcg cag ggg gag cag ctg gac gac atc gag ggc cac gtc ggg      946
Val Ala Ala Gln Gly Glu Gln Leu Asp Asp Ile Glu Gly His Val Gly
        245                 250                 255 cgg gcg agg tcg ttc gtc gac cgc ggg cgc gag cag ctg cag gtg gca      994
Arg Ala Arg Ser Phe Val Asp Arg Gly Arg Glu Gln Leu Gln Val Ala
    260                 265                 270 cgc aag cac cag aag agc tcc cgc aag tgg acc ttc atc ggc atc ggc     1042
Arg Lys His Gln Lys Ser Ser Arg Lys Trp Thr Phe Ile Gly Ile Gly
275                 280                 285                 290 atc ctg ctc gtc gtc atc ctc atc atc gtc atc ccc atc gtg ctc aag     1090
Ile Leu Leu Val Val Ile Leu Ile Ile Val Ile Pro Ile Val Leu Lys
                295                 300                 305 aac acc aac aag agc aac aac aac aac agc cag cag tagtggtagg          1136
Asn Thr Asn Lys Ser Asn Asn Asn Asn Ser Gln Gln
            310                 315 aacagcctgt ggatctgttg tctgtctctg atgatcctgg tcctggattg cttcctggtt   1196
gttgttgttg attgtctttt gtggaatttt ttgcgattgt aattactcca tccatgtggt   1256
tcgttgagcc actcgattat tatttcatga ctatata                            1293

<210> SEQ ID NO 40
<211> LENGTH: 318
<212> TYPE: PRT
<213> ORGANISM: Hordeum vulgare

<400> SEQUENCE: 40

Met Asn Asn Leu Phe Ser Ser Ser Trp Lys Arg Ala Gly Ala Gly Gly
1               5                   10                  15

Asp Gly Asp Leu Glu Ser Gly Gly Gly Val Glu Met Thr Ala Pro
            20                  25                  30

Pro Gly Ala Ala Ala Gly Ala Ser Leu Asp Arg Phe Phe Glu Asp Val
        35                  40                  45

Glu Ser Ile Lys Asp Asp Leu Arg Glu Leu Glu Arg Ile Gln Arg Ser
```

```
                50                  55                  60
Leu His Asp Gly Asn Glu Ser Gly Lys Ser Leu His Asp Ala Ser Ala
 65                  70                  75                  80

Val Arg Ala Leu Arg Ser Arg Met Asp Ala Asp Val Ala Ala Ala Ile
                 85                  90                  95

Lys Lys Ala Lys Val Val Lys Leu Arg Leu Glu Ser Leu Asp Arg Ala
            100                 105                 110

Asn Ala Ala Asn Arg Ser Val Ala Gly Cys Gly Pro Gly Ser Ser Thr
            115                 120                 125

Asp Arg Thr Arg Thr Ser Val Val Ala Gly Leu Arg Lys Lys Leu Arg
        130                 135                 140

Asp Ala Met Glu Ser Phe Ser Ser Leu Arg Ser Arg Ile Thr Ser Glu
145                 150                 155                 160

Tyr Arg Glu Thr Val Ala Arg Arg Tyr Phe Thr Val Thr Gly Ser Gln
                165                 170                 175

Pro Asp Glu Ala Thr Leu Asp Thr Leu Ala Glu Thr Gly Glu Gly Glu
            180                 185                 190

Arg Leu Leu Gln Arg Ala Ile Ala Glu Gln Gln Gly Arg Gly Glu Val
        195                 200                 205

Leu Gly Val Val Ala Glu Ile Gln Glu Arg His Gly Ala Val Ala Asp
    210                 215                 220

Leu Glu Arg Ser Leu Leu Glu Leu Gln Gln Val Phe Asn Asp Met Ala
225                 230                 235                 240

Val Leu Val Ala Ala Gln Gly Glu Gln Leu Asp Asp Ile Glu Gly His
                245                 250                 255

Val Gly Arg Ala Arg Ser Phe Val Asp Arg Gly Arg Glu Gln Leu Gln
            260                 265                 270

Val Ala Arg Lys His Gln Lys Ser Ser Arg Lys Trp Thr Phe Ile Gly
        275                 280                 285

Ile Gly Ile Leu Leu Val Val Ile Leu Ile Ile Val Ile Pro Ile Val
    290                 295                 300

Leu Lys Asn Thr Asn Lys Ser Asn Asn Asn Asn Ser Gln Gln
305                 310                 315

<210> SEQ ID NO 41
<211> LENGTH: 948
<212> TYPE: DNA
<213> ORGANISM: Arabidopsis thaliana
<220> FEATURE:
<221> NAME/KEY: CDS
<222> LOCATION: (1)..(945)
<223> OTHER INFORMATION: coding for Arabidopsis thaliana syntaxin 121
      (SYP121) / syntaxin-related protein (SYR1)
      (At3g11820)

<400> SEQUENCE: 41 atg gcg aat ccc gcg gga tca acc ggt ggt gtg aac ctc gac aag ttc    48
Met Ala Asn Pro Ala Gly Ser Thr Gly Gly Val Asn Leu Asp Lys Phe
  1               5                  10                  15 ttc gaa gat gtt gaa tct gtg aaa gaa gag cta aag gag cta gat cgg    96
Phe Glu Asp Val Glu Ser Val Lys Glu Glu Leu Lys Glu Leu Asp Arg
                 20                  25                  30 ctc aac gaa aca ctc tct tca tgt cac gag cag agc aag acg ctt cac   144
Leu Asn Glu Thr Leu Ser Ser Cys His Glu Gln Ser Lys Thr Leu His
             35                  40                  45 aat gct aaa gcc gtt aaa gat ctc cgg tct aaa atg gac ggt gac gtt   192
Asn Ala Lys Ala Val Lys Asp Leu Arg Ser Lys Met Asp Gly Asp Val
         50                  55                  60
```

```
gga gtc gcg ttg aag aag gcg aag atg att aaa gtt aaa ctc gag gcg    240
Gly Val Ala Leu Lys Lys Ala Lys Met Ile Lys Val Lys Leu Glu Ala
 65                  70                  75                  80 cta gat cgt gcc aat gct gct aat cgg agt ctc cct ggc tgt gga cct    288
Leu Asp Arg Ala Asn Ala Ala Asn Arg Ser Leu Pro Gly Cys Gly Pro
                 85                  90                  95 ggt tct tcc tcc gat cga acc agg acc tct gtc ctc aat ggt ctc agg    336
Gly Ser Ser Ser Asp Arg Thr Arg Thr Ser Val Leu Asn Gly Leu Arg
            100                 105                 110 aag aaa ttg atg gac tct atg gat agt ttc aac cga ttg agg gag ctt    384
Lys Lys Leu Met Asp Ser Met Asp Ser Phe Asn Arg Leu Arg Glu Leu
        115                 120                 125 atc tcg tcc gag tat aga gaa act gta cag agg agg tac ttc acc gtc    432
Ile Ser Ser Glu Tyr Arg Glu Thr Val Gln Arg Arg Tyr Phe Thr Val
    130                 135                 140 acc ggc gag aat ccg gat gaa cga acc cta gat cga ctg att tcc act    480
Thr Gly Glu Asn Pro Asp Glu Arg Thr Leu Asp Arg Leu Ile Ser Thr
145                 150                 155                 160 gga gag agt gag aga ttc ttg cag aaa gca ata caa gaa caa gga aga    528
Gly Glu Ser Glu Arg Phe Leu Gln Lys Ala Ile Gln Glu Gln Gly Arg
                165                 170                 175 gga agg gtg tta gac acc att aac gag att caa gaa agg cat gat gcg    576
Gly Arg Val Leu Asp Thr Ile Asn Glu Ile Gln Glu Arg His Asp Ala
            180                 185                 190 gtt aaa gac att gag aag aat ctc agg gag ctt cac cag gtg ttt cta    624
Val Lys Asp Ile Glu Lys Asn Leu Arg Glu Leu His Gln Val Phe Leu
        195                 200                 205 gac atg gcc gtg ctg gta gag cac cag gga gct cag ctt gat gac atc    672
Asp Met Ala Val Leu Val Glu His Gln Gly Ala Gln Leu Asp Asp Ile
    210                 215                 220 gag agt cat gtg ggt cga gct agc tcc ttt atc aga ggc gga act gac    720
Glu Ser His Val Gly Arg Ala Ser Ser Phe Ile Arg Gly Gly Thr Asp
225                 230                 235                 240 cag cta caa acc gct cgg gtt tac cag aag aac acg cga aaa tgg aca    768
Gln Leu Gln Thr Ala Arg Val Tyr Gln Lys Asn Thr Arg Lys Trp Thr
                245                 250                 255 tgt att gcc att att att ctc atc atc atc ata act gtt gtg gtt ctt    816
Cys Ile Ala Ile Ile Ile Leu Ile Ile Ile Ile Thr Val Val Val Leu
            260                 265                 270 gct gtt tta aaa ccg tgg aac aac agc agt ggc ggc ggc ggt ggt        864
Ala Val Leu Lys Pro Trp Asn Asn Ser Ser Gly Gly Gly Gly Gly Gly
        275                 280                 285 ggt ggt ggg ggt acc act gga gga agt caa cca aat tca ggg aca cca    912
Gly Gly Gly Gly Thr Thr Gly Gly Ser Gln Pro Asn Ser Gly Thr Pro
    290                 295                 300 cca aat cct cct cag gca agg cgt cta ttg cgt tga                    948
Pro Asn Pro Pro Gln Ala Arg Arg Leu Leu Arg
305                 310                 315

<210> SEQ ID NO 42
<211> LENGTH: 315
<212> TYPE: PRT
<213> ORGANISM: Arabidopsis thaliana

<400> SEQUENCE: 42

Met Ala Asn Pro Ala Gly Ser Thr Gly Gly Val Asn Leu Asp Lys Phe
 1               5                  10                  15

Phe Glu Asp Val Glu Ser Val Lys Glu Glu Leu Lys Glu Leu Asp Arg
                20                  25                  30

Leu Asn Glu Thr Leu Ser Ser Cys His Glu Gln Ser Lys Thr Leu His
        35                  40                  45
```

```
Asn Ala Lys Ala Val Lys Asp Leu Arg Ser Lys Met Asp Gly Asp Val
         50                  55                  60

Gly Val Ala Leu Lys Lys Ala Lys Met Ile Lys Val Lys Leu Glu Ala
 65                  70                  75                  80

Leu Asp Arg Ala Asn Ala Ala Asn Arg Ser Leu Pro Gly Cys Gly Pro
                 85                  90                  95

Gly Ser Ser Ser Asp Arg Thr Arg Thr Ser Val Leu Asn Gly Leu Arg
                100                 105                 110

Lys Lys Leu Met Asp Ser Met Asp Ser Phe Asn Arg Leu Arg Glu Leu
            115                 120                 125

Ile Ser Ser Glu Tyr Arg Glu Thr Val Gln Arg Arg Tyr Phe Thr Val
130                 135                 140

Thr Gly Glu Asn Pro Asp Glu Arg Thr Leu Asp Arg Leu Ile Ser Thr
145                 150                 155                 160

Gly Glu Ser Glu Arg Phe Leu Gln Lys Ala Ile Gln Glu Gln Gly Arg
                165                 170                 175

Gly Arg Val Leu Asp Thr Ile Asn Glu Ile Gln Glu Arg His Asp Ala
                180                 185                 190

Val Lys Asp Ile Glu Lys Asn Leu Arg Glu Leu His Gln Val Phe Leu
            195                 200                 205

Asp Met Ala Val Leu Val Glu His Gln Gly Ala Gln Leu Asp Asp Ile
210                 215                 220

Glu Ser His Val Gly Arg Ala Ser Ser Phe Ile Arg Gly Gly Thr Asp
225                 230                 235                 240

Gln Leu Gln Thr Ala Arg Val Tyr Gln Lys Asn Thr Arg Lys Trp Thr
                245                 250                 255

Cys Ile Ala Ile Ile Leu Ile Ile Ile Ile Thr Val Val Leu
                260                 265                 270

Ala Val Leu Lys Pro Trp Asn Asn Ser Ser Gly Gly Gly Gly Gly
            275                 280                 285

Gly Gly Gly Gly Thr Thr Gly Gly Ser Gln Pro Asn Ser Gly Thr Pro
290                 295                 300

Pro Asn Pro Pro Gln Ala Arg Arg Leu Leu Arg
305                 310                 315

<210> SEQ ID NO 43
<211> LENGTH: 1275
<212> TYPE: DNA
<213> ORGANISM: Hordeum vulgare
<220> FEATURE:
<221> NAME/KEY: CDS
<222> LOCATION: (80)..(1006)
<223> OTHER INFORMATION: coding for Hordeum vulgare subsp. vulgare
      SNAP-34

<400> SEQUENCE: 43
ggcccctcca ccccacccca cccagtcgct gcggatactt gattctgcta ctcggccagc      60
gatcgatctc gcctccgcc atg agc gcc acc agg ccc tcc ttc ttc ccc tcc     112
                     Met Ser Ala Thr Arg Pro Ser Phe Phe Pro Ser
                      1               5                  10 aac aac aac agg aac aag ccc gcc acc cgg aac ccc ttc gac tcc gac     160
Asn Asn Asn Arg Asn Lys Pro Ala Thr Arg Asn Pro Phe Asp Ser Asp
             15                  20                  25 tcg gac gac gac ggc ggc atg gcc cgg cgc ggc ccg gcg cgg gcc tcg     208
Ser Asp Asp Asp Gly Gly Met Ala Arg Arg Gly Pro Ala Arg Ala Ser
         30                  35                  40 tcc gtc ccg acc ccc gcc gcg ggg ccg gcc agg gcc tcg tcg gcc ccg     256
```

```
                Ser Val Pro Thr Pro Ala Ala Gly Pro Ala Arg Ala Ser Ser Ala Pro
                         45                  50                  55 atc ccc gcc gac gag gcg gac cag cgg ggc gcc ctg ttc ggc gcg ggc      304
Ile Pro Ala Asp Glu Ala Asp Gln Arg Gly Ala Leu Phe Gly Ala Gly
 60                  65                  70                  75 ccc gcg ccg tcc ggc ttc gcg tcc tcc tcc gcg gcc gcc agg ggc          352
Pro Ala Pro Ser Gly Phe Ala Ser Ser Ser Ala Ala Ala Arg Gly
             80                  85                  90 cgg tac agg aac gac ttc cgc gac tcg ggc ggt gtg gag gcg cag tcc      400
Arg Tyr Arg Asn Asp Phe Arg Asp Ser Gly Gly Val Glu Ala Gln Ser
 95                 100                 105 gtg cag gag ctc gag ggc tac gcg gcc tac aag gcc gag gag acc acg      448
Val Gln Glu Leu Glu Gly Tyr Ala Ala Tyr Lys Ala Glu Glu Thr Thr
        110                 115                 120 cgc cgg gtc gac ggc tgc ctc cgg gtc gcc gag gag atg cgg gac acc      496
Arg Arg Val Asp Gly Cys Leu Arg Val Ala Glu Glu Met Arg Asp Thr
125                 130                 135 gcg tca aag acc ctg ctc cag gtg cac cag cag ggc cag cag atc agg      544
Ala Ser Lys Thr Leu Leu Gln Val His Gln Gln Gly Gln Gln Ile Arg
140                 145                 150                 155 cgc acc cac gcc atg gcc gtc gac atc gac cag gat ctc tcc agg ggg      592
Arg Thr His Ala Met Ala Val Asp Ile Asp Gln Asp Leu Ser Arg Gly
                160                 165                 170 gaa aag cta cta ggt gat ctt ggt ggt ttg ttt tcc aag aag tgg aag      640
Glu Lys Leu Leu Gly Asp Leu Gly Gly Leu Phe Ser Lys Lys Trp Lys
            175                 180                 185 cca aag aag aac ggc gca atc agg ggc cct atg ctg acc aga gac gat      688
Pro Lys Lys Asn Gly Ala Ile Arg Gly Pro Met Leu Thr Arg Asp Asp
        190                 195                 200 tcc ttc ata cgc aag ggc agc cat atg gag cag agg cat aaa ctg ggg      736
Ser Phe Ile Arg Lys Gly Ser His Met Glu Gln Arg His Lys Leu Gly
205                 210                 215 ctg tca gat cgt ccg cat cga tcc aat gca cgc cag ttc cta tct gaa      784
Leu Ser Asp Arg Pro His Arg Ser Asn Ala Arg Gln Phe Leu Ser Glu
220                 225                 230                 235 ccc aca tca ggc ctt gag aaa gtc gag gtg gag aag gca aag cag gat      832
Pro Thr Ser Gly Leu Glu Lys Val Glu Val Glu Lys Ala Lys Gln Asp
                240                 245                 250 gat ggc ctg tct gac ctt agc gac ata ctg aca gag ttg aaa gga atg      880
Asp Gly Leu Ser Asp Leu Ser Asp Ile Leu Thr Glu Leu Lys Gly Met
            255                 260                 265 gcc att gac atg gga act gag att gag ggg caa aca aag gat ctt ggt      928
Ala Ile Asp Met Gly Thr Glu Ile Glu Gly Gln Thr Lys Asp Leu Gly
        270                 275                 280 cat gcg gag aag gac ttt gac gaa ctt aac tac agg gtc aag ggg gca      976
His Ala Glu Lys Asp Phe Asp Glu Leu Asn Tyr Arg Val Lys Gly Ala
285                 290                 295 aac gct cga aca cgt cgc ctg ctt ggc aga taggcaagaa gcatatgttg       1026
Asn Ala Arg Thr Arg Arg Leu Leu Gly Arg
300                 305 ttcaccagag gattctgtga cactccttat cttctgcatt tgctttcgtg ggctgttaat    1086
tcagatcatt ttgtgcataa aactctggtt aggaaggtct gttggggagt tgtatcaggg    1146
tttattgtgt atatacgcta gacgggcggt tcgttttcta tgttgcagtt gtactacatt    1206
tgctatggac agtagatacg tttgtattcg gttttcttgt tttgcaatcg ctatgctgca    1266
ggaaagcac                                                           1275

<210> SEQ ID NO 44
<211> LENGTH: 309
```

<210> TYPE: PRT
<213> ORGANISM: Hordeum vulgare

<400> SEQUENCE: 44

Met Ser Ala Thr Arg Pro Ser Phe Phe Pro Ser Asn Asn Arg Asn
1               5                   10                  15

Lys Pro Ala Thr Arg Asn Pro Phe Asp Ser Asp Ser Asp Asp Gly
            20                  25                  30

Gly Met Ala Arg Arg Gly Pro Ala Arg Ala Ser Ser Val Pro Thr Pro
        35                  40                  45

Ala Ala Gly Pro Ala Arg Ala Ser Ser Ala Pro Ile Pro Ala Asp Glu
50                  55                  60

Ala Asp Gln Arg Gly Ala Leu Phe Gly Ala Gly Pro Ala Pro Ser Gly
65                  70                  75                  80

Phe Ala Ser Ser Ser Ala Ala Arg Gly Arg Tyr Arg Asn Asp
                85                  90                  95

Phe Arg Asp Ser Gly Gly Val Glu Ala Gln Ser Val Gln Glu Leu Glu
                100                 105                 110

Gly Tyr Ala Ala Tyr Lys Ala Glu Glu Thr Thr Arg Arg Val Asp Gly
            115                 120                 125

Cys Leu Arg Val Ala Glu Glu Met Arg Asp Thr Ala Ser Lys Thr Leu
        130                 135                 140

Leu Gln Val His Gln Asn Gly Gln Gln Ile Arg Arg Thr His Ala Met
145                 150                 155                 160

Ala Val Asp Ile Asp Gln Asp Leu Ser Arg Gly Glu Lys Leu Leu Gly
                165                 170                 175

Asp Leu Gly Gly Leu Phe Ser Lys Lys Trp Lys Pro Lys Lys Asn Gly
            180                 185                 190

Ala Ile Arg Gly Pro Met Leu Thr Arg Asp Asp Ser Phe Ile Arg Lys
        195                 200                 205

Gly Ser His Met Glu Gln Arg His Lys Leu Gly Leu Ser Asp Arg Pro
210                 215                 220

His Arg Ser Asn Ala Arg Gln Phe Leu Ser Glu Pro Thr Ser Gly Leu
225                 230                 235                 240

Glu Lys Val Glu Val Glu Lys Ala Lys Gln Asp Asp Gly Leu Ser Asp
                245                 250                 255

Leu Ser Asp Ile Leu Thr Glu Leu Lys Gly Met Ala Ile Asp Met Gly
            260                 265                 270

Thr Glu Ile Glu Gly Gln Thr Lys Asp Leu His Ala Glu Lys Asp
        275                 280                 285

Phe Asp Glu Leu Asn Tyr Arg Val Lys Gly Ala Asn Ala Arg Thr Arg
290                 295                 300

Arg Leu Leu Gly Arg
305

<210> SEQ ID NO 45
<211> LENGTH: 1398
<212> TYPE: DNA
<213> ORGANISM: Glycine max
<220> FEATURE:
<221> NAME/KEY: CDS
<222> LOCATION: (212)..(946)
<220> FEATURE:
<221> NAME/KEY: misc_feature
<222> LOCATION: (1367)..(1367)
<223> OTHER INFORMATION: n is a, c, g, or t
<220> FEATURE:
<221> NAME/KEY: misc_feature
<222> LOCATION: (1368)..(1368)

```
<223> OTHER INFORMATION: n is a, c, g, or t
<220> FEATURE:
<221> NAME/KEY: misc_feature
<222> LOCATION: (1369)..(1369)
<223> OTHER INFORMATION: n is a, c, g, or t
<220> FEATURE:
<221> NAME/KEY: misc_feature
<222> LOCATION: (1370)..(1370)
<223> OTHER INFORMATION: n is a, c, g, or t
<220> FEATURE:
<221> NAME/KEY: misc_feature
<222> LOCATION: (1371)..(1371)
<223> OTHER INFORMATION: n is a, c, g, or t
<220> FEATURE:
<221> NAME/KEY: misc_feature
<222> LOCATION: (1372)..(1372)
<223> OTHER INFORMATION: n is a, c, g, or t
<220> FEATURE:
<221> NAME/KEY: misc_feature
<222> LOCATION: (1373)..(1373)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1375)..(1375)
<223> OTHER INFORMATION: n is a, c, g, or t
<220> FEATURE:
<221> NAME/KEY: misc_feature
<222> LOCATION: (1376)..(1376)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1378)..(1378)
<223> OTHER INFORMATION: n is a, c, g, or t
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1381)..(1381)
<223> OTHER INFORMATION: n is a, c, g, or t
<220> FEATURE:
<221> NAME/KEY: misc_feature
<222> LOCATION: (1382)..(1382)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t
<220> FEATURE:
<221> NAME/KEY: misc_feature
<222> LOCATION: (1384)..(1384)
<223> OTHER INFORMATION: n is a, c, g, or t

<400> SEQUENCE: 45
ggaatttccg tggcgaccca tcggacgctc gtccgacgca tcaacactac ggccgactgg      60
aggcgacttg aatgaaaggg aggtaatctt aagtggaacc gtttgcaaaa ttacccgttc     120
ctcgtacctc gaatgcagtc taaacttggg gtcgctgaag tcacagccat atacgacact     180
agacatattt gtgtgtctcc gattgcaagc a atg gac tcc ttc aat tcc ttc        232
                                   Met Asp Ser Phe Asn Ser Phe
                                    1               5 ttc gat tca aca aac cga tgg aat tac gat act ctc aaa aac ttc cgt       280
Phe Asp Ser Thr Asn Arg Trp Asn Tyr Asp Thr Leu Lys Asn Phe Arg
```

```
                          10              15                  20
caa att tct ccg gtc gtt cag aat cac ctc aag cag gtt tat ttt act      328
Gln Ile Ser Pro Val Val Gln Asn His Leu Lys Gln Val Tyr Phe Thr
         25                  30                  35 ctg tgt ttc gcc gtg gtt gct gcg gct gtt ggg gct tac ctt cat gtc      376
Leu Cys Phe Ala Val Val Ala Ala Ala Val Gly Ala Tyr Leu His Val
 40                  45                  50                  55 ctc ttg aac att ggg ggt ttt ctt act aca gtg gca tgc gtg gga agc      424
Leu Leu Asn Ile Gly Gly Phe Leu Thr Thr Val Ala Cys Val Gly Ser
                 60                  65                  70 agt gtt tgg tta ctc tcg aca cct cct ttt gaa gag agg aaa aga gtg      472
Ser Val Trp Leu Leu Ser Thr Pro Pro Phe Glu Glu Arg Lys Arg Val
             75                  80                  85 act ttg ttg atg gcc gca tca ctg ttt cag ggt gcc tct att gga ccc      520
Thr Leu Leu Met Ala Ala Ser Leu Phe Gln Gly Ala Ser Ile Gly Pro
         90                  95                 100 ttg ata gat ttg gct att caa atc gat cca agc ctt atc ttt agt gca      568
Leu Ile Asp Leu Ala Ile Gln Ile Asp Pro Ser Leu Ile Phe Ser Ala
    105                 110                 115 ttt gtg gga aca tcc ttg gcc ttt gca tgc ttc tca gga gca gct ttg      616
Phe Val Gly Thr Ser Leu Ala Phe Ala Cys Phe Ser Gly Ala Ala Leu
120                 125                 130                 135 gtt gct agg cgt agg gag tac ctg tac ctt ggt ggc ttg gtt tct tct      664
Val Ala Arg Arg Arg Glu Tyr Leu Tyr Leu Gly Gly Leu Val Ser Ser
                140                 145                 150 gga ttg tcc atc ctt ctc tgg ttg cac ttt gct tct tcc atc ttt gga      712
Gly Leu Ser Ile Leu Leu Trp Leu His Phe Ala Ser Ser Ile Phe Gly
            155                 160                 165 ggc tca aca gct ctc ttt aag ttt gag ttg tac ttt ggg cta ttg gtg      760
Gly Ser Thr Ala Leu Phe Lys Phe Glu Leu Tyr Phe Gly Leu Leu Val
        170                 175                 180 ttt gta ggt tac att gta gta gac acc caa gaa ata gtt gag agg gca      808
Phe Val Gly Tyr Ile Val Val Asp Thr Gln Glu Ile Val Glu Arg Ala
    185                 190                 195 cac ttg ggc gat ctg gac tat gta aag cat gcc ttg acc ttg ttt acc      856
His Leu Gly Asp Leu Asp Tyr Val Lys His Ala Leu Thr Leu Phe Thr
200                 205                 210                 215 gat ttg gtc gca gtt ttt gtc cgg att ctt gtt att atg ttg aag aat      904
Asp Leu Val Ala Val Phe Val Arg Ile Leu Val Ile Met Leu Lys Asn
                220                 225                 230 tcg act gag agg aat gag aag aaa aag aag aga aga gat tga ttttcttacc  956
Ser Thr Glu Arg Asn Glu Lys Lys Lys Lys Arg Arg Asp
            235                 240 aatctgctcg attaacactt cacctcgctt ggtctgtaat acataaaaac agccgtctat   1016
acagtgtttt ccacttttta agcttgctcc tcctactgtg cagttaagtc gtttgtttac   1076
caatagtaca tgttgacatg ttttgagctc tctaataaga gaaatgttta cattacattt   1136
gttttaaaga tgaaaagggg agtggggaag aagtcgatgg tgaaggtccc taataaattc   1196
ttactcccaa gactcagaat ttttcttggg gaggaagtgg aattcaggga aacacttttt   1256
tttcacacat tattgagtat atttttatact agactcgcca aatcacgaat ttcattatct   1316
atttagcttc ttttttttcc ccctgtaaaa aaaaaaaaaa aaaaaaaaaa nnnnnnnnnn   1376
nnnnnnnnaa aaaaaaaaaa aa                                            1398

<210> SEQ ID NO 46
<211> LENGTH: 244
<212> TYPE: PRT
<213> ORGANISM: Glycine max
```

<400> SEQUENCE: 46

```
Met Asp Ser Phe Asn Ser Phe Asp Ser Thr Asn Arg Trp Asn Tyr
 1               5                  10                  15

Asp Thr Leu Lys Asn Phe Arg Gln Ile Ser Pro Val Val Gln Asn His
                20                  25                  30

Leu Lys Gln Val Tyr Phe Thr Leu Cys Phe Ala Val Ala Ala Ala
            35                  40                  45

Val Gly Ala Tyr Leu His Val Leu Leu Asn Ile Gly Gly Phe Leu Thr
        50                  55                  60

Thr Val Ala Cys Val Gly Ser Ser Val Trp Leu Leu Ser Thr Pro Pro
 65                  70                  75                  80

Phe Glu Glu Arg Lys Arg Val Thr Leu Leu Met Ala Ala Ser Leu Phe
                85                  90                  95

Gln Gly Ala Ser Ile Gly Pro Leu Ile Asp Leu Ala Ile Gln Ile Asp
            100                 105                 110

Pro Ser Leu Ile Phe Ser Ala Phe Val Gly Thr Ser Leu Ala Phe Ala
        115                 120                 125

Cys Phe Ser Gly Ala Ala Leu Val Ala Arg Arg Glu Tyr Leu Tyr
    130                 135                 140

Leu Gly Gly Leu Val Ser Ser Gly Leu Ser Ile Leu Leu Trp Leu His
145                 150                 155                 160

Phe Ala Ser Ser Ile Phe Gly Gly Ser Thr Ala Leu Phe Lys Phe Glu
                165                 170                 175

Leu Tyr Phe Gly Leu Leu Val Phe Val Gly Tyr Ile Val Val Asp Thr
            180                 185                 190

Gln Glu Ile Val Glu Arg Ala His Leu Gly Asp Leu Asp Tyr Val Lys
        195                 200                 205

His Ala Leu Thr Leu Phe Thr Asp Leu Val Ala Val Phe Val Arg Ile
    210                 215                 220

Leu Val Ile Met Leu Lys Asn Ser Thr Glu Arg Asn Glu Lys Lys Lys
225                 230                 235                 240

Lys Arg Arg Asp
```

<210> SEQ ID NO 47
<211> LENGTH: 20
<212> TYPE: DNA
<213> ORGANISM: Artificial sequence
<220> FEATURE:
<223> OTHER INFORMATION: GFP-Primer 1

<400> SEQUENCE: 47
atggtgagca agggcgagga                                          20

<210> SEQ ID NO 48
<211> LENGTH: 43
<212> TYPE: DNA
<213> ORGANISM: Artificial sequence
<220> FEATURE:
<223> OTHER INFORMATION: GFP-Primer 2

<400> SEQUENCE: 48
ttgaacaacg atgtgcaaga ctccttgtac agctcgtcca tgc                43

<210> SEQ ID NO 49
<211> LENGTH: 6
<212> TYPE: PRT
<213> ORGANISM: Artificial sequence
<220> FEATURE:
<223> OTHER INFORMATION: BI1 consensus motif

```
<220> FEATURE:
<221> NAME/KEY: MISC_FEATURE
<222> LOCATION: (2)..(2)
<223> OTHER INFORMATION: Xaa is Leu or Ile
<220> FEATURE:
<221> NAME/KEY: MISC_FEATURE
<222> LOCATION: (4)..(4)
<223> OTHER INFORMATION: Xaa is any amino acid

<400> SEQUENCE: 49

His Xaa Lys Xaa Val Tyr
 1               5

<210> SEQ ID NO 50
<211> LENGTH: 7
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Tyr or Phe
<220> FEATURE:
<221> NAME/KEY: MISC_FEATURE
<222> LOCATION: (6)..(6)
<223> OTHER INFORMATION: Xaa is any amino acid

<400> SEQUENCE: 50

Ala Xaa Gly Ala Xaa Xaa His
 1               5

<210> SEQ ID NO 51
<211> LENGTH: 4
<212> TYPE: PRT
<213> ORGANISM: Artificial sequence
<220> FEATURE:
<223> OTHER INFORMATION: BI1 consensus motif

<400> SEQUENCE: 51

Asn Ile Gly Gly
 1

<210> SEQ ID NO 52
<211> LENGTH: 8
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (2)..(2)
<223> OTHER INFORMATION: Xaa is Val or Pro
<220> FEATURE:
<221> NAME/KEY: MISC_FEATURE
<222> LOCATION: (3)..(3)
<223> OTHER INFORMATION: Xaa is Tyr or Phe
<220> FEATURE:
<221> NAME/KEY: MISC_FEATURE
<222> LOCATION: (5)..(5)
<223> OTHER INFORMATION: Xaa is Glu or Gln
<220> FEATURE:
<221> NAME/KEY: MISC_FEATURE
<222> LOCATION: (6)..(6)
<223> OTHER INFORMATION: Xaa is Arg or Gln

<400> SEQUENCE: 52

Pro Xaa Xaa Glu Xaa Xaa Lys Arg
 1               5
```

<210> SEQ ID NO 53
<211> LENGTH: 8
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (1)..(1)
<223> OTHER INFORMATION: Xaa is Glu or Gln
<220> FEATURE:
<221> NAME/KEY: MISC_FEATURE
<222> LOCATION: (3)..(3)
<223> OTHER INFORMATION: Xaa is Ala or Ser
<220> FEATURE:
<221> NAME/KEY: MISC_FEATURE
<222> LOCATION: (5)..(5)
<223> OTHER INFORMATION: Xaa is Val or Ile

<400> SEQUENCE: 53

Xaa Gly Xaa Ser Xaa Gly Pro Leu
 1               5

<210> SEQ ID NO 54
<211> LENGTH: 5
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (3)..(3)
<223> OTHER INFORMATION: Xaa is Ser or Gly
<220> FEATURE:
<221> NAME/KEY: MISC_FEATURE
<222> LOCATION: (4)..(4)
<223> OTHER INFORMATION: Xaa is Leu or Ile
<220> FEATURE:
<221> NAME/KEY: MISC_FEATURE
<222> LOCATION: (5)..(5)
<223> OTHER INFORMATION: Xaa is Ile or Leu

<400> SEQUENCE: 54

Asp Pro Xaa Xaa Xaa
 1               5

<210> SEQ ID NO 55
<211> LENGTH: 11
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (2)..(2)
<223> OTHER INFORMATION: Xaa is Gly or Ala
<220> FEATURE:
<221> NAME/KEY: MISC_FEATURE
<222> LOCATION: (4)..(4)
<223> OTHER INFORMATION: Xaa is Ala or Ser
<220> FEATURE:
<221> NAME/KEY: MISC_FEATURE
<222> LOCATION: (5)..(5)
<223> OTHER INFORMATION: Xaa is Leu or Ile
<220> FEATURE:
<221> NAME/KEY: MISC_FEATURE
<222> LOCATION: (8)..(8)
<223> OTHER INFORMATION: Xaa is Ala or Gly
<220> FEATURE:
<221> NAME/KEY: MISC_FEATURE
<222> LOCATION: (11)..(11)
<223> OTHER INFORMATION: Xaa is Ser or Thr

<400> SEQUENCE: 55

```
Val Xaa Thr Xaa Xaa Ala Phe Xaa Cys Phe Xaa
 1               5                  10

<210> SEQ ID NO 56
<211> LENGTH: 6
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (3)..(3)
<223> OTHER INFORMATION: Xaa is Tyr or Phe

<400> SEQUENCE: 56

Tyr Leu Xaa Leu Gly Gly
 1               5

<210> SEQ ID NO 57
<211> LENGTH: 7
<212> TYPE: PRT
<213> ORGANISM: Artificial sequence
<220> FEATURE:
<223> OTHER INFORMATION: BI1 consensus motif

<400> SEQUENCE: 57

Glu Tyr Leu Tyr Leu Gly Gly
 1               5

<210> SEQ ID NO 58
<211> LENGTH: 11
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (2)..(2)
<223> OTHER INFORMATION: Xaa is Leu or Val
<220> FEATURE:
<221> NAME/KEY: MISC_FEATURE
<222> LOCATION: (5)..(5)
<223> OTHER INFORMATION: Xaa is Gly or Trp
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
<222> LOCATION: (8)..(8)
<223> OTHER INFORMATION: Xaa is Ile or Met
<220> FEATURE:
<221> NAME/KEY: MISC_FEATURE
<222> LOCATION: (10)..(10)
<223> OTHER INFORMATION: Xaa is Leu or Met

<400> SEQUENCE: 58

Leu Xaa Ser Ser Xaa Leu Xaa Xaa Leu Xaa Trp
 1               5                  10

<210> SEQ ID NO 59
<211> LENGTH: 7
<212> TYPE: PRT
<213> ORGANISM: Artificial sequence
<220> FEATURE:
<223> OTHER INFORMATION: BI1 consensus motif
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
```

<222> LOCATION: (5)..(5)
<223> OTHER INFORMATION: Xaa is Ile or Val
<220> FEATURE:
<221> NAME/KEY: MISC_FEATURE
<222> LOCATION: (6)..(6)
<223> OTHER INFORMATION: Xaa is Ile or Val

<400> SEQUENCE: 59

Asp Thr Gly Xaa Xaa Xaa Glu
 1               5

<210> SEQ ID NO 60
<211> LENGTH: 237
<212> TYPE: PRT
<213> ORGANISM: Homo sapiens

<400> SEQUENCE: 60

Met Asn Ile Phe Asp Arg Lys Ile Asn Phe Asp Ala Leu Leu Lys Phe
 1               5                  10                  15

Ser His Ile Thr Pro Ser Thr Gln Gln His Leu Lys Lys Val Tyr Ala
             20                  25                  30

Ser Phe Ala Leu Cys Met Phe Val Ala Ala Gly Ala Tyr Val His
         35                  40                  45

Met Val Thr His Phe Ile Gln Ala Gly Leu Leu Ser Ala Leu Gly Ser
     50                  55                  60

Leu Ile Leu Met Ile Trp Leu Met Ala Thr Pro His Ser His Glu Thr
 65                  70                  75                  80

Glu Gln Lys Arg Leu Gly Leu Leu Ala Gly Phe Ala Phe Leu Thr Gly
                 85                  90                  95

Val Gly Leu Gly Pro Ala Leu Glu Phe Cys Ile Ala Val Asn Pro Ser
            100                 105                 110

Ile Leu Pro Thr Ala Phe Met Gly Thr Ala Met Ile Phe Thr Cys Phe
        115                 120                 125

Thr Leu Ser Ala Leu Tyr Ala Arg Arg Ser Tyr Leu Phe Leu Gly
    130                 135                 140

Gly Ile Leu Met Ser Ala Leu Ser Leu Leu Leu Ser Ser Leu Gly
145                 150                 155                 160

Asn Val Phe Phe Gly Ser Ile Trp Leu Phe Gln Ala Asn Leu Tyr Val
                165                 170                 175

Gly Leu Val Val Met Cys Gly Phe Val Leu Phe Asp Thr Gln Leu Ile
            180                 185                 190

Ile Glu Lys Ala Glu His Gly Asp Gln Asp Tyr Ile Trp His Cys Ile
        195                 200                 205

Asp Leu Phe Leu Asp Phe Ile Thr Val Phe Arg Lys Leu Met Met Ile
    210                 215                 220

Leu Ala Met Asn Glu Lys Asp Lys Lys Glu Lys Lys
225                 230                 235

<210> SEQ ID NO 61
<211> LENGTH: 244
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(239)
<223> OTHER INFORMATION: Xaa at positions 2, 3, 5-13, 15, 22, 24, 28,
      31, 35, 38, 42, 45, 49, 56, 57, 62, 65, 73, 76, 78, 87, 88, 106,
      168, 169, 171, 202, 222, 234, 237 and 239 can be any amino acid

<400> SEQUENCE: 61

```
Phe Xaa Xaa Ser Xaa Xaa Xaa Xaa Xaa Xaa Xaa Trp Xaa Tyr
 1           5                  10                  15

Asp Ser Leu Lys Asn Xaa Arg Xaa Ile Ser Pro Xaa Val Gln Xaa His
             20                  25                  30

Leu Lys Xaa Val Tyr Xaa Thr Leu Cys Xaa Ala Leu Xaa Ala Ser Ala
             35                  40                  45

Xaa Gly Ala Tyr Leu His Val Xaa Xaa Asn Ile Gly Gly Xaa Leu Thr
 50                  55                  60

Xaa Leu Gly Cys Ile Gly Ser Ile Xaa Trp Leu Xaa Ser Xaa Pro Val
 65                  70                  75                  80

Tyr Glu Glu Arg Lys Arg Xaa Xaa Leu Leu Met Ala Ala Ala Leu Leu
             85                  90                  95

Glu Gly Ala Ser Val Gly Pro Leu Ile Xaa Leu Ala Ile Asp Phe Asp
            100                 105                 110

Pro Ser Ile Leu Val Thr Ala Phe Val Gly Thr Ala Ile Ala Phe Ala
            115                 120                 125

Cys Phe Ser Gly Ala Ala Ile Val Ala Lys Arg Arg Glu Tyr Leu Tyr
            130                 135                 140

Leu Gly Gly Leu Leu Ser Ser Gly Leu Ser Ile Leu Leu Trp Leu Gln
145                 150                 155                 160

Phe Ala Ser Ser Ile Phe Gly Xaa Xaa Ser Xaa Ala Ser Phe Met Phe
                165                 170                 175

Glu Val Tyr Phe Gly Leu Leu Ile Phe Leu Gly Tyr Met Val Tyr Asp
            180                 185                 190

Thr Gln Glu Ile Ile Glu Arg Ala His Xaa Gly Asp Met Asp Tyr Ile
            195                 200                 205

Lys His Ala Leu Thr Leu Phe Thr Asp Phe Val Ala Val Xaa Val Arg
            210                 215                 220

Ile Leu Ile Ile Met Leu Lys Asn Ala Xaa Asp Lys Xaa Glu Xaa Lys
225                 230                 235                 240

Lys Lys Arg Arg
```

METHODS FOR INCREASING THE RESISTANCE IN PLANTS TO BIOTROPIC FUNGI

RELATED APPLICATIONS

This application is a national stage application (under 35 U.S.C. §371) of PCT/EP2007/061436, filed Oct. 24, 2007, which claims benefit of European application 06122870.6, filed Oct. 24, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00101. The size of the text file is 161 KB, and the text file was created on Feb. 27, 2012.

FIELD OF THE INVENTION

The present invention relates to methods for generating or increasing resistance to at least one biotrophic pathogen in a plant or a part of a plant by increasing the protein quantity or function of at least one Bax inhibitor-1 (BI-1) protein in at least one part of the plant. Moreover, the invention relates to polypeptide sequences and nucleic acid sequences which code for a BI-1 protein, and to expression cassettes, vectors and organisms which comprise such sequences or such a protein, in particular to recombinant plants, to cultures, parts or recombinant propagation material derived there from, and to the use of same for the production of foodstuffs, feeding stuffs, seed, pharmaceuticals or fine chemicals.

BACKGROUND OF THE INVENTION

The cultivation of agricultural crop plants serves mainly for the production of foodstuffs for humans and feedingstuffs for animals. The last 25 years have seen pronounced yield increases in crop production. This was the result of a good combination of altered production techniques, newly developed varieties, fertilization and, last but not least, increased crop protection. In the light of an ever increasing world population, safeguarding food production gains increasingly in importance. It has been estimated that 7 billion people will inhabit Earth in 2010. To feed all these people, without the proportion of malnourished people increasing, food production would have to be increased by 60% (Entrup N. L. et al., Lehrbuch des Pflanzenbaues [Textbook of crop production], Thomas Mann Verlag, Gelsenkirchen, 2000). Efficient crop protection is a decisive factor in this context. Monocultures in particular, which are the rule nowadays, are highly susceptible to an epidemic-like spreading of diseases. The result are markedly reduced yields. To date, the pathogenic organisms have been controlled mainly by using pesticides. Nowadays, in contrast, the possibility of directly modifying the genetic disposition of a plant or pathogen is open to man.

Fungi are distributed worldwide so they may form a heterogeneous group with a range of species. They are eukaryotes, do not contain chlorophyll and are therefore heterotrophic. Hence, they rely on external carbon sources which they tap as parasites, saprophytes or symbionts. Saprophytes live exclusively on dead plant material. Parasitic fungi feed on live tissue and must have concluded their development before the plant has died. Facultative parasites can feed both on live and on dead tissue. Symbionts, such as mycorrhiza, live in close association with the plants. Fungi have one or more nuclei per cell and are homokaryotic or heterokaryotic. Fungi have a firm cell wall during at least one stage in their life history. This cell wall usually consists of chitin or, in some cases such as the Oomycota, of cellulose. The vegetative part of the fungus (thallus) is usually haploid, in rare cases diploid. The thallus of lower fungi (Myxomycota, inter alia) consists of ameboidal cells or plasmodia (naked, polynuclear protoplasma). Eumycota have budding cells, as in the case of yeasts (for example *Saccharomyces cerevisiae*), or form a mycelium which consists of threadlike hyphae. As the result of hyphal aggregation, specific organs for propagation (fruiting bodies) or for surviving unfavorable environmental conditions (sclerotia) may be formed. Propagation and multiplication is usually by way of spores; asexually by means of conidia, uredospores, sporarigiospores, chlamydospores and zoospores, and sexually with oospores, ascospores, zygospores and basidiospores.

Approximately 100 000 different fungal species are known to date. Among these, however, only 5% are plant pathogens. The Basidiomycota are a division of the true fungi which are characterized by the development of a particular structure, the basidium, on which the basidiospores mature. The Basidiomycota also include the generally known mushrooms. The Basidiomycota are predominantly heterothallic and self-sterile. Mating occurs by somatogamy. During somatogamy, two compatible, haploid, mononuclear mycelia or sporidia coalesce. The resulting dikaryotic mycelium constitutes the dominant phase of the life cycle over a prolonged period. The only two phytopathogenic genera of the Basidiomycota are the smuts (Ustilages) and the rusts (Uredinales). Smuts only attack angiosperms and use to be of great economical importance. Nowadays they are controlled successfully by suitable active substances and tight seed control. The rusts are still somewhat more important nowadays. They are biotrophic and can have a complicated development cycle with up to five different spores stages (spermatium, aecidiospore, uredospore, teleutospore and basidiospore). Rusts which develop all spore stages are referred to as macrocyctic rusts. If some stages are absent, these rusts are referred to as being macrocyclic. "Imperfect rusts" lack the basidiospores. Some rusts change their hosts during their development. These are referred to as heteroecious. Host alternation can be linked to nuclear-phase alternation. In contrast, autoecious rusts complete all of their development on one host. A traditional example of a macrocyclic heteroecious rust is black rust of cereals, *Puccinia graminis. P. graminis*, in its dikaryotic stage, attacks predominantly wheat. The haplont is pathogenic to barberry (Börner H., Pflanzenkrankheiten and Pflanzenschutz [Plant disease and plant protection], Ulmer Verlag Stuttgart, 1997; Sitte P. et al., Strasburger—Lehrbuch der Botanik [Textbook of Botany], Gustav Fischer Verlag, Stuttgart, 1998; Entrup N. L. et al., Lehrbuch des Pflanzenbaues [Textbook of crop production], Thomas Mann Verlag, Gelsenkirchen, 2000).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. The attachment of the spores requires either an active metabolism, which is the case in *Colletotrichum graminicola*, or it is passive, as is the case with *Magnaporthe grisea*. In the latter case, moisture leads to the secretion of a "mucilage adhesive", by means of which the spore attaches (Howard R. J. et al., Annu. Rev. Microbiol. 50, 491 (1996)). Spore germination is induced either by unspecific inductors such as water, nutrients, ethylene or, more rarely, as is the case in *Phyllosticta ampelicida*, by hydrophobic surfaces (Kuo K. et al., Fungal Genet. Biol. 20, 18 (1996)). Some fungi develop two germ tubes, as is the case in powdery mildew cereals, *Blumeria graminis*, while other fungi develop only one germ tube (Green J. R. et al., The powdery mildews, a comprehensive treatise; The formation and function of infection and feeding structures, APS Press, 2002). Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. These pressure organs are referred to as appressoria and allow the fungus to build up a high pressure above a discrete point. It is estimated that appressorium of *M. grisea* reaches a pressure of 80 bar (Howard R. J. et al., Annu. Rev. Microbial. 50, 491 (1996)). Most rusts, in contrast, penetrate the plant via the stomata. The soya rust *Phakopsora pachyrhizi* directly penetrates the plant epidermis and therefore resembles powdery mildew of cereals, *B. graminis*, in its penetration behavior (Koch E. et al., Phytopath. p. 106, 302 (1983); Tucker S. L. et al., Annu. Rev. Phytopathol. 39, 385 (2001); Green J. R. et al., The powdery mildews, a comprehensive treatise; The formation and function of infection and feeding structures, APS Press, 2002).

Phytopathogenic fungi do not always colonize all of the plant; in contrast, sometimes it is only specific areas or tissues which are colonized. Following the successful invasion of the plant, phytopathogenic fungi follow different nutritional strategies. Pertotrophic or necrotrophic pathogens kill the host cells by means of extracellular enzymes or toxins and feed by degrading the dead cells. Some genera with pertotrophic nutrition are the *Fusaria* sp., *Alternaria* sp. and *Cochliobolus*. Most fungi use this feeding strategy. The biotrophic phytopathogenic fungi, such as mildew and many rusts, depend, for their nutrition, on the metabolism of live cells. An intermediate position is occupied by the hemi-biotrophic pathogenic fungi, which include the genera *Phythophtora* and *Peronospora*. Most of these are biotrophs at the beginning of their development and only change over to a pertotrophic lifestyle during the later stages of their development (Prell H. H., Interaktionen von Pflanzen and phyto-pathogenen Pilzen [Interactions between plants and phyto-pathogenic fungi], Gustav Fischer Verlag, Jena, 1996). The plants have developed defense mechanisms to avoid infection. Another intermediate position is occupied for example by soybean rust, which penetrates the epidermis directly, whereupon the penetrated cell becomes necrotic; after the penetration, the fungus changes over to an obligatory-biotrophic lifestyle. The subgroup of the biotrophic fungal pathogens which follows essentially such an infection strategy will, for the purposes of the present description, be referred to as being "heminecrotrophic".

It must be emphasized that plants, during their development, are exposed to constant attack by a large number of phytopathogenic organisms. Nevertheless, colonization of the plant by phytopathogenic organisms is the exception rather than the rule. Before a pathogen can attack the plant, it has to overcome a series of barriers. Frequently, the pathogen has developed specific pathogenicity factors which are adapted to the plant, known as virulence factors, in order to overcome these barriers. In such a case, the plant becomes a host plant for the pathogen, i.e. the latter is virulent on the plant. There is a basic compatibility between the plant and the pathogen. This means that the physiological and biochemical prerequisites which are required for the colonization are already in existence or have been produced (Prell H. H., Interaktionen von Pflanzen und phytopathogenen Pilzen [Interactions between plants and phytopathogenic fungi], Gustav Fischer Verlag, Jena, 1996). In the case of compatible interaction, the pathogen develops at the expense of the plant, thus causing the formation of disease symptoms such as wilting, necroses and chloroses. However, if basic compatibility exists, the plant can still defend itself against the pathogen when a resistance mutation has taken place in the plant. The resistance of the plant, thus acquired, is referred to as host resistance. It is only directed against a certain individual pathogen and can be overcome readily by the latter. The pathogens in question are mostly, but not always, biotrophic pathogens. Host resistance can be subdivided into non-race-specific horizontal resistances which, in most cases, involves several genes, and race-specific vertical resistance. The latter is only effective against certain, individual races of a pathogen, while the plant defends itself a priori against most pathogens. This phenomenon is referred to as basic incompatibility or non-host resistance. In contrast to host resistance, non-host resistance is based on a series of causes and not on individual genes. Firstly, the pathogen may lack the necessary pathogenicity factors, or else the plant is capable of recognizing, and successfully defending itself, against the pathogen. Another term which is important in particular for agriculture is tolerance. A plant is tolerant to a pathogen when it can be attacked, but the attack does not lead to the development of disease systems and yield reduction (Prell H. H., Interaktionen von Pflanzen und phytopathogenen Pilzen [Interactions between plants and phytopathogenen fungi], Gustav Fischer Verlag, Jena, 1996). For the purposes of the description of the present invention, generating, or increasing, a resistance is to comprise an increase or generation of any type of resistance, but also of tolerance, i.e. in particular all cases of an increased tolerance or resistance which lead to reduced yield losses as caused by the pathogen.

In connection with resistance responses of plants, the term resistance factors includes structures, substances and processes which prevent or inhibit attack of the plant by potential pathogens. If the resistance factors are already constitutively present in the plant, they are referred to as pre-formed resistance factors. Induced resistance factors are only formed when a recognition response between the plant and the potential pathogen has taken place. Recognition can be described as a signal/sensor response (elicitor/receptor model, Keen N. T. et al., Phytopathology 62, 768 (1972)). The signal are plant substances or substances produced by the pathogen, known as elicitors, which bind to a sensor or receptor which is specific for the elicitor in question. This binding triggers one or more effectors, which may be, for example, signal transduction chains and induce the resistance response. A whole series of substances act as elicitors. These include proteins, glycoproteins, glucans and lipids (Garcia Brugger et al., MPMI 19, 711 (2006)). Plant cell wall degradation products which are released by enzymes of the pathogen or else by wounding of the plant may also induce a resistance response. In this context, an avirulence factor of the pathogen and the corresponding resistance gene of the plant is frequently mentioned ("Gene-for-gene hypothesis", nor, J. Agric. Res. 74, 241 (1947)). The pathogen can prevent recognition by the plant by means of structural modifications of the elicitor, masking of the recognition sequence or by competition with another substance for the binding sites on the elicitor or receptor.

Preformed resistance factors form the first defense against colonization by pathogenic organisms. These factors can be morphological factors or else substances of the secondary plant metabolism (phytoanticipins). Morphological factors which prevent colonization are hairy leaves, stomatal density and shape, and the nature of the cuticle and of the cell wall.

Recognition, of the pathogen, by the plant may also lead to the induction of resistance factors, i.e. morphological and physiological resistance responses. Many of these responses are the result of a signal cascade. Signal molecules such as $Ca^{2+}$, NO, reactive oxygen compounds and phytohormones such as ethylene and jasmonate are involved in the cascades and contribute to the crosslinking of the signal pathways. Resistance responses in which morphological structures in the plant cell are modified are the formation of cell wall appositions (papillae), cork and abscission layers, thyllae and the impregnation of the cell wall. The beginning of penetration by a pathogenic fungus can trigger the formation of papillae. Lignin, callose, suberin and hydroxyproline-rich proteins are deposited at the inner cell wall opposite the potential penetration site and are crosslinked with one another. Callose can be stained by the intercalation of aniline blue. In addition, the papilla formed accumulates phenols, reactive oxygen species and hydrolases (Hückelhoven R. et al., Plant Physiol. 119, 1251 (1999); Assaad F. F. et al., Mol. Biol. of the Cell, 15, 5118 (2004)). The development of papillae leads to a substantially thickened cell wall and may prevent penetration of the pathogenic fungus. Physiological processes which contribute to induced resistance are depolarization of the cell membrane, the oxidative burst, the hypersensitive reaction, the formation of phytoalexins and the expression of pathogenesis-related proteins (PR proteins). One of the first responses to contact with an elicitor is the depolarization of the cell membrane. This results in a pronounced efflux of $Cl^-$ and $K^+$ ions, linked with pronounced water loss. It is assumed that depolarization triggers an increased $Ca^{2+}$ concentration, which is an important signal molecule (Ward J. M. et al., Plant Cell 7, 833 (1995)) and plays a role in the hypersensitive reaction (HR) (Wendehenne a et al., Plant Cell 14, 1937 (2002)). HR in plants is a form of programmed cell death. It allows the plant to stop the fungus even after penetration of the latter by denying it a source of nutrients. The course of HR appears to depend on the combination of plant and pathogen. However, protein biosynthesis, an intact cytoskeleton and salicylic acid appear to be necessary for inducing HR (Heath M., Plant Mol. Biol. 44, 321 (2000)).

A very rapid response to the pathogen is the oxidative burst, the formation of reactive oxygen species, such as the superoxide anion $O_2^-$, the hydroxyl radical OH and hydrogen peroxide. These compounds are formed by various oxidases. The hydroxyl radical acts locally, while $H_2O_2$ can diffuse via the membranes. Both oxidize polyunsaturated fatty acids and can thus destroy membranes (Grant J. J. et al., Plant Physiol. 124, 21 (2000)). $H_2O_2$ is also suspected of performing a function in gene regulation. In addition, the compounds support the defense responses by crosslinking the cell wall components, by increasing lignification and by exerting a toxic effect on pathogens (Garcia-Brugger A. et al., MPMI 19, 711 (2006)). Last but not least, the pathogen attack leads to the expression of genes which code for PR proteins and for phytoalexins. PR proteins are a heterogeneous group of proteins which have a toxic effect on penetrating fungi. The term phytoalexins refers to low-molecular-weight antimicrobially active substances whose synthesis is triggered by biotic or abiotic stress (Prell H. H., Interaktionen von Pflanzen and phytopathogenen Pilzen [Interactions between plants and phytopathogenic fungi], Gustav Fischer Verlag, Jena, 1996; van Loon L. C. et al., Physiol. Mol. Plant Physiol. 55, 85 (1999)). The responses described proceed partly not only when the pathogen interact with a host plant, but also when it reacts with a non-host-plant. Decisive for pathogen defense is the quality of the recognition and the quantity and speed of the resistance response (Thordal-Christensen H., Current Opinion in Plant Biology 6, 351 (2003)).

A plant disease which has become increasingly important in recent times is soybean rust. The disease is caused by the pathogenic rusts *Phakopsora pachyrhizi* (Sydow) and *Phakopsora meibomiae* (Arthur). They belong to the class Basidiomycota, order Uredinales, family Phakopsoraceae. The two species are very closely related with one another. The intergenic sequences of their rRNA genes show 80% similarity (Frederick R. D. et al., Phytopathology 92, 217 (2002)). The species are distinguished by morphological characteristics of the teliospores (Ono Y. et al., Mycol. Res. 96, 825 (1992)). Both rusts infect a wide spectrum of host plants. *P. pachyrhizi*, also referred to as Asian soybean rust, is the more aggressive pathogen on soybeans (*Glycine max*), and is therefore, at least currently, of great importance for agriculture. *P. pachyrhizi* is capable of infecting 31 species from 17 families of the Leguminosae under natural conditions and is capable of growing on further 60 species under controlled conditions (Sinclair et al. (eds.), Proceedings of the soybean rust workshop (1995), National Soybean Research Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* was originally discovered in Japan in 1902. From there,*P. pachyrhizi* spread over large parts of Asia and over India and Australia and, finally, reached Africa in 1996. In 2001, the fungus arrived in South America and reached America for the first time in 2004 (Sconyers E.L. et al., at ers.usda.gov/Features/SoyBeanRust/ (2005)). In South America in particular, *P. pachyrhizi* caused big yield losses of up to 80%. It is estimated that 1.5 million tons of the Brazilian soybean harvest 2005/2006 alone have succumbed to infection with soybean rust. *P. pachyrhizi* is a hemicyclic rust which forms three types of spores. The formation of teliospores was observed in Asia towards the end of the vegetation period (Yeh C.C. et al., Phytopathology 71, 1111 (1981)). The formation of basidiospores, in contrast, is only known under laboratory conditions. The most important spore form are the uredospores, which are formed over the entire vegetation period and which serve to spread the disease. These spores are formed in large amounts and are capable of spreading over wide distances with the aid of wind and rain. *P. pachyrhizi* is an obligate biotroph. If a uredospore arrives on a suitable host, it germinates with a single germ tube. At the end of this germ tube, an appressorium develops and rapidly reaches the size of the spore. With the appressorium, the fungus is capable of building up a large pressure and of penetrating the epidermal cells directly with the aid of a penetration hypha. The penetration hypha of *P. pachyrhizi* grows through the epidermal cell and, once it reaches the intercellular space in the leaf, forms the first septum. It now continues to grow in the leaf as a primary hypha. As early as 24-48 h after the infection, the first haustorial mother cell is divided by a septum, and a sacciform haustorium is formed in a mesophyll cell of the leaf. The cell wall of the mesophyll cell is penetrated, but the plasmalemma is only folded, so that the cell remains alive and can act as a nutrient source. The nutrients travel from the membrane of the live host cell via the extrahaustorial matrix to the haustorium. The epidermal cell which has been penetrated at the beginning turns necrotic shortly after penetration. This manner of infection of a biotrophic pathogen, as is used by *P. pachyrhizi*, will therefore be referred to as "heminecrotrophic" for the purposes of the description of the present invention. The first uredospores are found only 11-12 days after the infection, and the cycle can start afresh (Koch E. et al., Phytopath. p. 106, 302 (1983)).

The crop plant soybean *Glycine max* (L.) Merr. belongs to the family Leguminosae, subfamily Papilionoideae, tribe Phaseoleae, genus *Glycine Willd.* and subgenus *soja* (Moench). Soybean is planted in more than 35 countries. Some of the most important production areas are located in the United States, China, Korea, Argentina and Brazil. It is considered to be one of the oldest crop plants and was domesticated for the first time in China between the 11$^{th}$ and 17$^{th}$ century (Hymowitz T., Econ. Bot. 24, 408 (1970)). It was introduced into the United States in 1765; the United States are currently one of the largest soya production areas. Wild soybean species can be found in China, Korea, Japan, Taiwan and the former USSR. Morphological, cytological and molecular evidence suggests that *G. soja* is the ancestor of the cultivated form *G. max*. Being a subtropical plant, soybeans prefer a mean annual temperature of 5.9-27° C.; they are not frost resistant (OECD, Consensus document on the biology of *Gycine max* (L.) Merr. (Soybean); Series on harmonization of regulatory oversight in biotechnology No. 15, ENV/JM/MONO(2000)9). Soybeans are currently an important oil and protein source. This extensive use of soya in food production underlines the importance of efficient control of soybean rust.

Soybean plants are infected by *P. pachyrhizi* by windborne uredospores. The first discernible symptoms are small yellow to reddish-brown lesions on the upper surface of the leaf, which later spread further until all of the leaf finally turns chlorotic and dies. Upon advanced infection, the lesions are found on all of the plant. The first uredia have a diameter of 100-200 µm and are found on the underside of the leaf 10-14 days after the infection; they can produce spores for three to six weeks. Telia are formed subepidermally and mostly occur on the periphery of the lesions. The spores are first yellow to brown and later turn black. The first symptoms are frequently first observed on the older leaves. The rapid development of the disease correlates with the beginning of flowering (R1+) and finally destroys all of the foliage. The fact that most of the photosynthetically active area is destroyed and that water and nutrients are extracted by the fungus leads to reduced productivity of the plant (Sconyers E.L. et al., at ers.usda.gov/Features/SoyBeanRust/ (2005)).

In order to germinate, *P. pachyrhizi* requires moisture in the form of dew or the like on the upper surface of the leaf. The fungus is encouraged in particular by frequent rain and temperatures of between 15 and 29° C. (Sconyers E.L. et al., at ers.usda.gov/Features/SoyBeanRust/ (2005)). Frequently, the disease starts at discrete locations and subsequently spreads rapidly over the entire field. The fungus is autoecious, i.e. it requires no host alternation for its development, and it can persist readily on its numerous alternative host plants. In the United States, kudzu vine (*Pueraria lobata*), which originates in Japan, is considered to be a potential host plant on which *P. pachyrhizi* can overwinter and provide fresh inoculum in the next spring.

*P. pachyrhizi* can currently be controlled in the field only by means of fungicides. Soybean plants with resistance to the entire spectrum of the isolates are not available. When searching for resistant plants, four dominant genes Rpp1-4, which mediate resistance of soya to *P. pachyrhizi*, were discovered; however, this resistance is only isolate-specific (Hartwig E. E. et al., Crop Science, 23, 237 (1983); Hartwig E. E., Crop Science 26, 1135 (1986)). Since the resistance was only based on individual genes, it was lost rapidly. Only the Rpp4-mediated resistance has as yet only been broken down under greenhouse conditions (Posada-Buitrago M. L. et al., Fungal Genetics and Biology 42, 949 (2005). The utilization of potential resistance sources from representatives of the perennial subgenus soja is limited (Hartman G. I. et al., Plant Disease 76, 396 (1992)). So far, all crosses have only led to sterile progeny (Singh R. et al., Wendl. Theor. Appl. Genet 74, 391 (1987).

The efficient control of soybean rust with fungicides requires low application into the foliage of the plants, since infection occurs first on the lower leaves. A double treatment has proved to be effective. A disadvantage of the fungicides used is that, as the result of their specific mechanism of action, resistances may develop readily. A potential alternative to the use of fungicides is the use of glyphosate-resistant soybean plants. In a greenhouse experiment, soybean plants were treated with the herbicide three days before inoculation, and a reduction of rust-caused lesions by 46-70% was observed (Feng C. C. P. et al., PNAS 102, 17290 (2005)). Whether this effect will also be retained in field trials remains to be seen.

In recent years, *P. pachyrhizi* has gained in importance as pest in soybean production. There was therefore a demand in the prior art for developing methods of controlling the fungus. Right now, plant breeding cannot be expected to contribute since the available resistance sources are not accessible. Treatment with fungicides has a limited efficiency and is only effective when the disease is yet to break out. This is why in particular the pathosystem soya/*P. pachyrhizi* is the method of choice for a recombinant approach. For an approach to be successful, it is initially important to have detailed knowledge of the course of infection and the response of the plant, in particular during the first stages of the infection. Potential candidate genes which confer resistance must be identified, and their effect in the interaction between plant and pathogen must be characterized. The stable transformation of plants is very time-consuming and costly, which is why transient transformation, which makes possible a characterization of the plant/pathogen interaction at the cell level, is preferred. The method of choice here is the transient transformation of leaves with the gene gun. In plants, non-host-resistance is particularly effective and durable and based on the fact that quantity and speed of the resistance response is increased in comparison with the compatibility response. Thus, the characterization of decisive genes in non-host-resistance can serve to identify potential candidate genes for the generation of resistant plants. Thus, to also study the response of a non-host-plant to soya rust, the system barley (Hordeum vulgare)/*P. pachyrhizi* was chosen since barley is a model plant which has been described in detail. Moreover, the pathosystem barley/with *Blumeria graminis* f.sp. *hordei* (Bgh) and with *Blumeria graminis* f.sp. *tritici* (Bgt), which is incompatible, has been studied in great detail. Although Bgh and *P. pachyrhizi* differ in some respects, they share at least phenotypically some steps at the beginning of the infection process. Thus, the analysis in barley can provide information on the mechanisms of the non-host-resistance to *P. pachyrhizi* in comparison with the host resistance of barley. Thus, candidate genes were tested in transiently transformed barley leaves for their effect in the resistance to *P. pachyrhizi*. The transient transformation with the gene gun provides a method of studying, in the pathosystem barley/*P. pachyrhizi*, a series of genes which may be involved in the resistance response.

Programmed cell death (PCD) is an important process in the development and stress response of plants and animals. Some morphological and biochemical changes in the cell, such as chromatin condensation, shrinking of the cytoplasm and DNA fragmentation, appear to be shared by plants and animals (Lam E. et al., Nature 411, 848 (2001)). A clear distinction between PCD and HR, which is caused by biotic or abiotic stress, is not possible (Heath M., Plant Mol. Biol. 44, 321 (2000)). One activator of PCD in animals is BAX. BAX develops channels in the outer mitochondrial membrane and causes the release of cytochrome c. This triggers a caspase cascade, and thus the proteolysis of proteins which the cell needs to survive (Green D. R. et al, Science 281, 1309 (1998). The overexpression of BAX in tobacco (*N. tabacum*, Lacomme C. et al., Proc. Nat. Acad. Sci. USA 96, 7956 (1999)) and *Arabidopsis thaliana* (Kawai-Yamada M. et al., Plant Cell 16, 21 (2004)) causes PCD and thus suggests similar mechanisms in plants and animals. However, no BAX homologs have been identified in plants. However, a BAX-antagonistic regulator of PCD, the Bax inhibitor-1 (BI-1), is conserved in plants, animals and other organisms such as yeast. Similar proteins have been identified since in *A. thaliana, H. vulgare, Brassica napus, Brassica oleracea, Oryza sativa* and *N. tabacum* (Hückelhoven R., Apoptosis 9, 299 (2004)). In experiments with BI-1/GFP fusion proteins, a localization of BI-1 in the membrane of the endoplasmic reticulum (ER) and the nuclear membrane has been observed (Eichmann R. et al., Mol. Plant Microbe Interact. 17, 484 (2004)). The protein has a size of 25-27 kDa and has 6-7 transmembrane domains. The C-terminal end, which is probably located in the cytoplasm (Bolduc N. et al., Planta 216, 377 (2003)), is essential for the function of BI-1 (Kawai-Yamada et al., Plant Cell 16, 21 (2004)). It is possible that the transmembrane domains form an ion channel (Bolduc N. et al., Planta 216, 377 (2003)). Thus, BI-1 might have a function in regulating the cytosolic $Ca^{2+}$ level and/or the redox state of the cell as the result of the ER's storage function for $Ca^{2+}$ (Xu Q. et al., Mol. Cell 18, 1084 (1998); Balduc N. et al., FEBS Lett 532, 111 (2003); Hückelhoven R. et al., Proc. Natl. Aced Sci. USA 29, 5555 (2003); Matsumura H. et al., Plant J. 33, 425 (2003)). In animal cells, there is no direct physical interaction between BI-1 and Bax. However, BI00-1 interacts with other PCD regulators (Xu Q. et al., Mol. Cell 18, 1084 (1998)). It is probable that BI-1, in plants, also interacts with other PCD regulators, thus influencing the resistance responses. In *Arabidopsis*, BI-1 is capable of suppressing BAX and the $H_2O_2$ have induced PCD (Baek et al., Plant Mol. Biol. 56, 15 (2004); Kawai-Yamada M. et al., Plant Cell 16, 21 (2004)). Therefore, it probably regulates the processes at a level lower than the oxidative stress response (Kawai-Yamada M. et al., Plant Cell 16, 21 (2004)).

The expression of BI-1 is induced by biotic and abiotic stress such as attack by pathogens or wounding, but also in aging tissues (Balduc N. et al., FEBS Lett. 532, 111 (2003); Hückelhoven R., Apoptosis 9, 299 (2004)). In *Arabidopsis*, the mRNA levels of BI-1 are increased after heat shock (Watanabe N. et al., Plant J. 45, 884 (2006)). BI-1 expression is induced in tomato (*Lycopersicum esculentum*) by $H_2O_2$, and in *Arabidopsis* by $H_2O_2$ and salicylic acid (Hückelhoven R., Apoptosis 9, 299 (2004); Kawai-Yamada M. et al., Plant Cell 16, 21 (2004)). This suggests that BI-1 has a function in pathogen defense, because this is where both substances play an important role (Prell H. H., Interaktionen von Pflanzen and phytopathogenen Pilzen [Interactions between plants and phytopathogenic fungi], Gustav Fischer Verlag, Jena, 1996).

Accordingly, the infection of barley with Bgh or Bgt triggers an increased expression of BI-1 (Hückelhoven R. et al., Plant Mol. Biol. 47, 739 (2001); Eichmann R. et al., Mol. Plant Microbe Interact. 17, 484 (2004)). In rice, the expression is biphasic after infection with *M. grisea*. It is first slightly increased, but is reduced 12 hours after the infection only to rise again (Matsumura H. et al., Plant J. 33, 425 (2003)), The increased expression of BI-1 in *Arabidopsis* cells after treatment with fumonisin B1 (Watanabe N. et al., Plant J. 45, 884 (2006)), and the reduction of the BI-1 expression after the treatment of rice cells with *M. grisea* elicitor extract, demonstrates that the expression patterns can differ greatly, depending on the inducing factor and on the plant. The expression patterns suggest a role of BI-1 in the regulation of the stress-induced PCD or HR and in the resistance response to pathogens. The influence on the HR can increase the resistance of a plant, especially if the pathogens are pertotrophic or hemibiotrophic fungi. Overexpression of BI-1 in carrots (*Daucus carota* ssp. *sativa*) leads to resistance of the plants to *Botrytis cinerea* Omani J. et al., Mol. Plant Physiol. in press). In tomatoes, the expression of the PCD inhibitor p35 protects against *Alternaria alternata, Colletotrichum coccodes* and *Pseudomonas syringae* (Lincoln J. E. et al., Proc. Nat. Acad. Sci. USA 99, 15217 (2002)).

Against this background, there was a continuous demand in the prior art for crop plants with an increased resistance to pathogens. Only few approaches exist which confer, to plants, a resistance to a broader spectrum of pathogens, especially fungal pathogens. Systemic acquired resistance (SAR)—a defense mechanism in various plant/pathogen interactions—can be conferred by application of endogenous messenger substances such as jasmonate (JA) or salicylic acid (SA) (Ward J. M., et al., Plant Cell 3, 1085 (1991); Uknes et al., 4(6), 645 (1992)). Similar effects can also be brought about by synthetic compounds such as 2,6-dichloroisonicotinic acid (DCINA) or benzo(1,2,3)thiadiazole-7-thiocarboxylic acid S-methyl ester (BTH; Bion®) (Friedrich et al., Plant J. 10(1), 61 (1996); Lawton et al., Plant J. 10, 71 (1996)). Also, expression of "pathogenesis-related" (PR) proteins, which has been upregulated in the context of SAR, may partly bring about resistance to pathogens.

In barley, the Mlo locus has been described as a negative regulator of pathogen defense. The loss, or loss of function, of the Mlo gene brings about an increased, race-unspecific resistance to a large number of mildew isolates (Büschges R. et al., Cell 88, 695 1997); Jorgensen J. H., Euphytica 26, 55 (1997); Lyngkjaer M. F. et al., Plant Pathol 44, 786 (1995)).

The Mlo gene has been described (Büschges R. et al., Cell 88, 695 (1997); WO 98/04586; Schulze-Lefert P. et al., Trends Plant Sci. 5, 343 (2000)). Various Mlo homologs from other cereal species have been isolated. Methods using these genes for obtaining pathogen resistance have been described (WO 98/04586; WO 00/01722; WO 99/47552). The disadvantage is that Mlo-deficient plants also initiate the above-mentioned defense mechanism in the absence of a pathogen, which manifests itself in the spontaneous dying of plant cells (Wolter M. et al., Mol. Gen. Genet. 239, 122 (1993)). As the result, mlo-resistant plants suffer a yield loss of up to 5% (Jörgensen J.H. Euphytica 63, 141 (1992)). The spontaneous dying of the leaf cells furthermore brings about a disadvantageous hypersusceptibility to necrotrophic and hemibiotrophic pathogens such as *Magnaporthe grisea* (*M. grisea*) or *Cochliobolus sativus* (*Bipolaris sorokiniana*) (Jarosch B. et al., Mol Plant Microbe Interact. 12, 508 (1999); Kumar J. et al., Phytopathology 91, 127 (2001)).

Apoptosis, also referred to as programmed cell death, is an essential mechanism for maintaining tissue homoeostasis, and, as such, counteracts cell division as a negatively-regulating mechanism. In the multi-celled organism, apoptosis is a natural component of ontogenesis, and involved, inter alia, in organ development and the removal of senescent, infected or mutated cells. As the result of apoptosis, undesired cells are eliminated in an efficient manner. Interference with, or inhibition of, apoptosis contributes to the pathogenesis of a variety of diseases, among which carcinogenesis. The main effectors of apoptosis are aspartate-specific cysteine proteases, which are known by the name of caspases. They can generally be activated by at least two apoptotic signal pathways: firstly by the activation of the TNF (tumor necrosis factor) receptor family; secondly, the mitochondria play a central role. Activation of the mitochondrial apoptosis signal pathway is regulated by proteins of the Bcl-2 family. This protein family consists of antiapoptotic and proapoptotic proteins such as, for example, Bax. In the case of an apoptotic stimulus, the Bax protein undergoes an allosteric conformation change, which leads to the anchoring of the protein in the external mitochondrial membrane, and to its oligomerization. As the result of these oligomers, proapoptotic molecules are released from the mitochondria into the cytosol and bring about an apoptotic signal cascade and, ultimately, the degradation of specific cellular substrates, resulting in cell death. The Bax inhibitor-1 (BI1) was isolated via its property of inhibiting the proapoptotic effect of BAX (Xu Q. et al., Mol Cell 1(3), 337 (1998)). BI1 is a highly conserved protein. It is found predominantly as an integral constituent of intracellular membranes. BI1 interacts with bcl-2 and bcl-xl. The overexpression of BI1 in mammalian cells suppresses the proapoptotic effect of BAX, etoposid and staurosporin, but not of Fas antigen (Roth W. et al., Nat. Med. 8, 216 (2002)). The inhibition of BI1 by antisense RNA, in contrast, induces apoptosis (Xu Q. et al., Mol Cell 1(3), 337 (1998)). The first plant homologs of BI1 have been isolated from rice and *Arabidopsis* (Kawai et al., FEBS Lett 464, 143 (1999); Sanchez et al., Plant J. 21, 393 (2000)). These plant proteins suppress the BAX-induced cell death in yeast. The amino acid sequence homology with human BI1 is approximately 45%. In recombinant plants, the *Arabidopsis* homolog AtBI1 is capable of suppressing the proapoptotic effect of murine BAX (Kawai-Yamada M. et al., Proc. Natl. Acad. Sci. USA 98(21), 12295 (2001)). The rice (*Oryza sativa*) BI1 homolog OsBI1 is expressed in all plant tissues (Kawai et al., FEBS Lett 464, 143(1999)). Furthermore described are BI1 genes from barley (*Hordeum vulgare*; GenBank Acc.-No.: AJ290421), rice (GenBank Acc.-No.: AB025926), *Arabidopsis* (GenBank Acc.-No.: AB025927), tobacco (GenBank Acc.-No.: AF390556) and oilseed rape (GenBank Acc.-No.: AF390555, Bolduc N. et al., Planta 216, 377-386 (2003)). The expression of BI1 in barley is upregulated as the result of infection with mildew (Hückelhoven R. et al., Plant Mol. Biol. 47(6), 739 (2001)).

WO 00/26391 describes the overexpression, in plants, of the antiapoptotic genes Ced-9 from *C. elegans*, sfIAP from *Spodoptera frugiperda*, bcl-2 from humans and bcl-xl from chicken for increasing the resistance to necrotrophic or hemibiotrophic fungi. Plant BI1 homologs are not disclosed. Expression is under the control of constitutive promoters. Furthermore described is the expression of a BI1 protein from *Arabidopsis* under the strong constitutive 35S CaMV promoter in rice cells and a hereby-induced resistance to celldeath-inducing substances from *Magnaporthe grisea* (Matsumura H. et al., Plant J. 33, 425 (2003)).

Originally, the prior art described that constitutive expression of an inhibitor of the programmed cell death in plants can bring about resistance to necrotrophic fungi.

However, the person skilled in the art was faced in particular with the problem of providing methods for the pathogen defense in plants, in particular against biotrophic pathogens.

Surprisingly, the problem is solved by the inventive methods, peptide sequences, nucleic acid sequences, expression cassettes, vectors and organisms defined in the main claims, using a BI1 protein. The dependent claims define specific, especially preferred use forms of the present invention.

The roll of BI-1 has been tested in three independent experiments in the transient transformation system. In the control, 53% (averaged over the experiments) of the transformed cells which interacted with *P. pachyrhizi* were penetrated, while only 37% of the BI-1 transformed cells were penetrated (FIG. 8; Table FIG. 10). The data are based on three independent experiments. Barley leaves were transformed with the reporter gene construct pGY1-GFP and the blank vector in order to act as controls. The penetration rate in the BI-1 transformed cells differs significantly from the WT ($P<0.05$). After the evaluation, the cells which have been transiently transformed with BI-1 therefore surprisingly show a significantly increased penetration resistance to *P. pachyrhizi* ($P<0.05$; FIG. 8; Table FIG. 10). A noteworthy aspect of the observation under the microscope was that the BI-1-forming cells had a markedly more vital appearance than cells, which expressed GFP or ADF3.

Thus, even the transient overexpression of the cell death inhibitor BI-1 in barley revealed, surprisingly, the trend to an increased resistance of the plant cells to penetration by soybean rust. To confirm this, the interaction between transgenic barley plants cv. "Golden Promise" (GP) which contain a GFP-BI-1 overexpression construct was studied under the microscope in comparison with the wild type (WT) of this variety. To generate the transgenic plants, a GFP-BI-1 fusion under the control of the constitutive CaMV 35S promoter was used, thus ensuring sufficient expression of the protein.

In preliminary experiments, leaves of the WT cv. "Golden Promise" and of the transgenic barley line (cv. "Golden Promise") #6(1)E8L1(T1)' were inoculated with *P. pachyrhizi* and, 24 hours after the inoculation, fixed in destaining solution. After destaining was complete, the leaves were stained with aniline blue. Aniline blue intercalates into the structure of callose and thus preferentially stains papillae where callose undergoes accumulation and crosslinking with other polymeric substances. Cells which, as the result of a hypersensitive response (HR), have undergone a similar process as apoptosis in mammalian cells, will, after staining with aniline blue, also show a light fluorescence. The number of spores, the germinated spores with germ tubes which had already formed an appressorium and, as cell response, the appressoria with underlying papillae and the HR were counted on the inoculated barley leaves. Larger spore agglomerations where an assignation of the appressoria to the spores was no longer possible were not included. As far as possible, at least 100 spores with appressoria were counted per leaf. Even in this experiment, a significantly increased formation of papillae and a significantly decreased HR of the cells was observed in the transgenic line ($P<0.01$; Table FIG. 11A/B, FIG. 12).

Both Bgh (Hückelhoven R., FEMS Microbiol. Letters 245, 9(2005)) and *P. pachyrhizi* (Koch E. et al., Phytopath, p. 106, 302 (1983)) are biotrophic pathogens. An HR of the infected cells can therefore stop the development of the fungi since it deprives them from their food source. If the HR is prevented, the cells may become more sensitive to infection by biotrophic pathogens. Despite this, barley cells which have been transiently transformed with a BI-1 overexpression construct surprisingly show an increased resistance to penetration by *P. pachyrhizi*. This is surprising because an increased sensitivity to the biotrophic fungus would have been expected However, the HR is not the only resistance reaction in the resistance of barley and wheat to the incompatible pathogen *P. pachyrhizi*, and perhaps not the decisive one Thus, the defense of wheat against *P. pachyrhizi* is papille formation (Hoppe H. H. et al., Pro. Intern. Congress of SABRAO (Bangkok 1985) 1986). Barley responds with papilla formation and with HR of the infected cells, depending on the variety. Moreover, barley with the mlo5 allele responds with papilla increased papilla formation. The defense of barley to Bgt is also affected by papilla formation, but mostly by an HR of infected cells (Hückelhoven R. et al., Mol. Plant Pathol. 2, 199 (2001). In contrast to *P. pachyrhizi*, the transient overexpression of BI-1 in barley leads to an increased penetration rate of the cells by Bgt (Eichmann R. et al., Mol. Plant Microbe Interact. 17, 484 (2004)). Likewise, barley plants with the mlo5 allele, which confers broad resistance to Bgh demonstrate, in the case of transient overexpression of BI-1, greater sensitivity of the cells to penetration by Bgh (Hückelhoven R. et al., Proc. Natl. Acad. Sci. USA, 29, 5555 (2003). Although the resistance of barley with the mlo5 allele is based not on an HR of the infected cells, but on a more efficient accumulation of antimicrobial compounds, $H_2O_2$ and an increased formation of papillae, the inhibition of the HR also appears to affect the other resistance responses (Hückelhoven R. et al., Plant Physiol. 119, 1251 (1999)). Without causing limitation by theory, these observations of a reduced penetration resistance as the result of inhibition of HR suggests that crosslinked regulation of the resistance responses. The suspicion that the resistance responses are subject to crosslinked regulation is supported by the microscopic analysis of transgenic barley plants which have been inoculated with *P. pachyrhizi*. These barley plants contain a BI-1 overexpression construct and respond to infection with increased papilla formation. While only 16-26% of the infected cells show HR on the leaves of the transgenic plants, HR was observed in approximately 50% of the infected cells on the WT leaves. Consequently, in the barley variety "Golden Promise", the HR of the cells also appears to be an important resistance mechanism against *P. pachyrhizi*, which is a biotroph, although *P. pachyrhizi* does not utilize the epidermal cells as a food source, at least not in soybean, but only forms haustoria in the mesophyll (Koch E. et al., Phytopath, p. 106, 302 (1983)). In general, however, the fungus did not reach this stage on the non-host plant barley. Inhibition of the HR makes it possible for Bgt to penetrate the cells, and the fungus can establish itself successfully (Eichmann R. et al., Mol. Plant Microbe Interact. 17, 484 (2004)). Further fungus-specific factors appear to be necessary for this process. It appears that these specific factors of Bgt are capable of suppressing either the alternative resistance response of the plant cell or the recognition by the latter. These factors are probably absent in *P. pachyrhizi*. Thus, the plant cell is perhaps capable of recognizing *P. pachyrhizi* and, since BI-1 suppresses the HR, capable of inducing an alternative resistance response, papilla formation. Recognition of *P. pachyrhizi* by the plant is supported by the observation of increased papilla formation in barley with the mlo5 allele. However, the reason why the plant is capable of recognizing the pathogen *P. pachyrhizi*, which is specialized to host plants of a completely different order, remains unexplained (Sinclair J. B. et al. (eds.), Proceedings of the soybean rust workshop (1995), National Soybean Research Laboratory, Publication No. 1 (1996)). The "recognition feature" of *P. pachyrhizi* might be an unspecific elicitor ('pathogenesis-associated molecular patterns' PAMP) such as the INF1 from *P. infestans*, which triggers an HR in *Nicotiana* sp. (Kamoun S. et al., Plant Cell 10, 1413 (1998)). PAMPs are recognized by the plant as foreign molecules and trigger a resistance response. Not all leaves of the transgenic plant show increased papilla formation, although the BI-1 gene construct has been identified in them by means of PCR. This might be the consequence of an unfavorable insertion type of the construct, which prevents an effective expression of BI-1 and/or leads to antagonistic effects by other genes. Since the identification was performed at the DNA level, no comments can be made on the expression of BI-1. It must also be borne in mind that even minor damage to the seeds or the leaves can have a decisive effect, or prevent, the development of the plant. Thus, some seeds of the line #6(2)E15L7P2 (T2) did not germinate.

SUMMARY OF THE INVENTION

Consequently, a first subject matter of the invention relates to a method of generating or increasing a resistance in the plant, or a part of a plant, to a pathogen which is preferably a biotroph. The method comprises a step in which the amount of a Bax inhibitor-1 (BI-1) protein or its function in the plant or at least a part of a plant is increased. A part of a plant is understood as meaning the entire plant, one or more of its organs, a tissue or at least a cell. The method furthermore comprises the step of selecting a plant or a part of a plant in which the BI1 protein or its function has been increased in such a way that it shows increased resistance in comparison with a starting plant, in which the increase in the amount of function of the BI1 protein in comparison with the starting plant or its part is increased.

BRIEF DESCRIPTION OF THE DRAWINGS

FIG. 1*a*-1*c*: Alignment of protein sequences of various BI-1 proteins from plants. AtBI-1 (SEQ ID NO: 4 ): Arabidopsis; BnBI-1 (SEQ ID NO: 10 ): Brassica napus (oil seed rape); GmBI2 (SEQ ID NO: 12 ): Glycine max (soybean; variant 1); GmBI3 (SEQ ID NO: 14): Glycine max (soybean; variant 2); HVBI-1 (SEQ ID NO: 2): Hordeum vulgare (barley); NtBI-1 (SEQ ID NO: 6): Nicotiana tabacum (tobacco); OsBI-1 (SEQ ID NO: 8): Oryza sativa (rice); TaBI11 (SEQ ID NO: 20): Triticum aestivum (wheat, variant 1); TaBI18 (SEQ ID NO: 26): Triticum aestivum (wheat, variant 2); TaBI5 new (SEQ ID NO: 16): Triticum aestivum (wheat, variant 3); ZmBI4 (SEQ ID NO: 22): Zea mays (maize; variant 1); ZmBI6 (SEQ ID NO: 24): Zea mays (maize; variant 2); ZmBI33 (SEQ ID NO: 28): Zea mays (maize; variant 3); ZmBI8 (SEQ ID NO: 18): Zea mays (maize; variant 4); Consensus (SEQ ID NO: 61): consensus sequence derived from the alignment.

FIG. 6: Alignment of the protein sequences of BI-1 proteins from barley (Hordeum vulgare, GenBank Acc.-No.: CAC37797), rice (Oryza sativa, GenBank Acc.-No.: Q9MBD8), Arabidopsis thaliana (GenBank Acc.-No.:

Q9LD45) and humans (Homo sapiens, GenBank Acc.-No.: AAB87479). Amino acids shown against the black background are identical in all species. Amino acids shown against a gray background are only identical in plants. Bars indicate the predicted seven transmembrane domains in HvBI 1. "H. vul.": SEQ ID NO: 2; "O . sat.": SEQ ID NO: 8; "A. tha.": SEQ ID NO: 4; "H. sap.": SEQ ID NO: 60.

Figure 2:
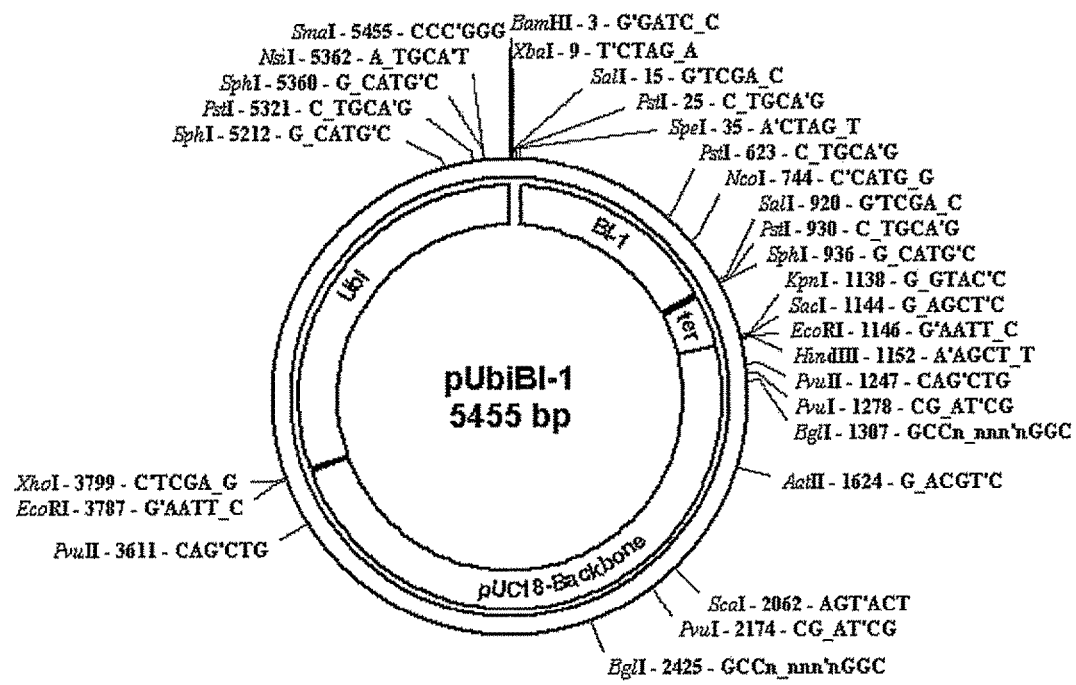
FIG. 2: Vector map for the vector pUbiBI-1 (Ubi: ubiquitin promoter; BI-1 nucleic acid sequence coding for barley BI1 protein; ter: transcription terminator). Also indicated is the localization of the cleavage sites of various restriction enzymes.
Figure 3:
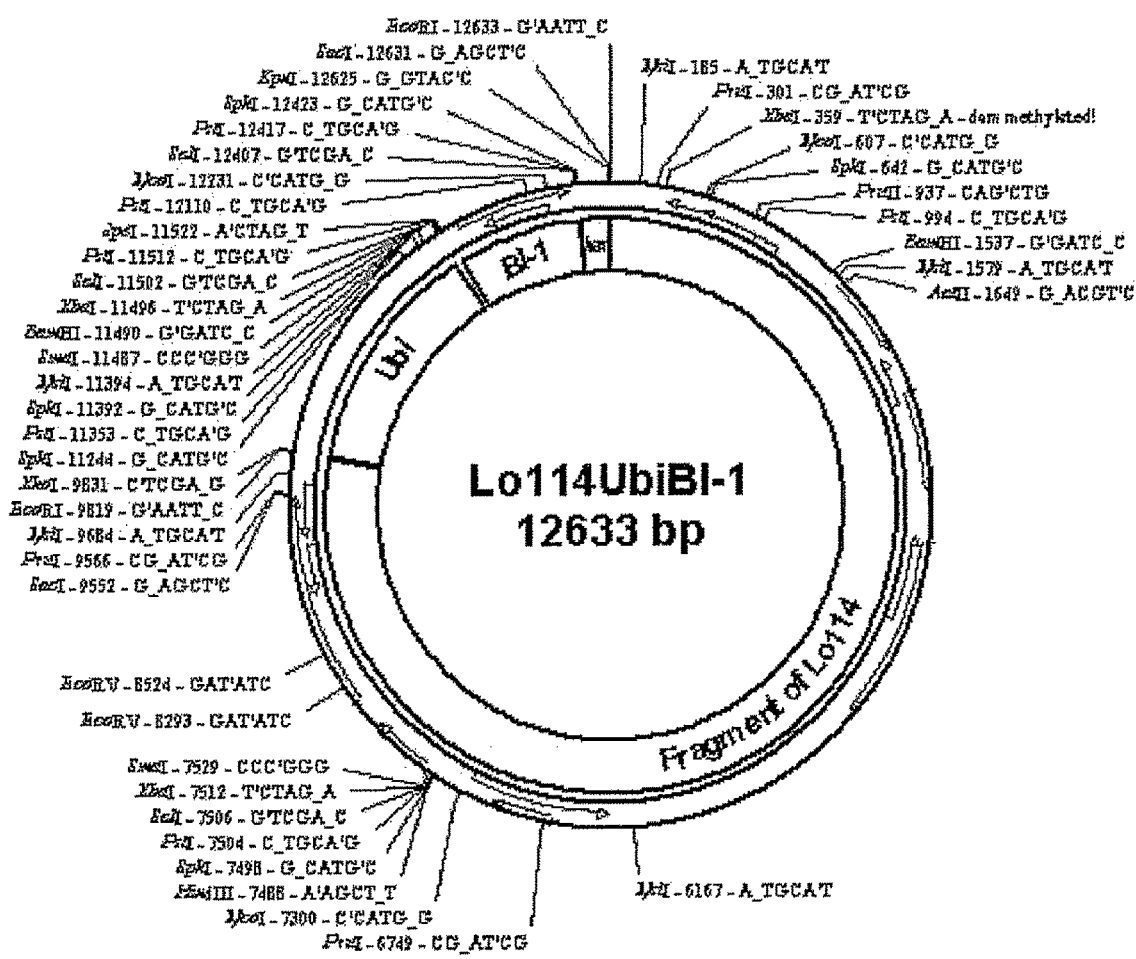
FIG. 3: Vector map for the vector pLO114UbiBI-1 (Ubi: ubiquitin promoter; BI-1 nucleic acid sequence coding for barley BI1 protein; ter: transcription terminator). Also indicated is the localization of the cleavage sites of various restriction enzymes.
Figure 4:
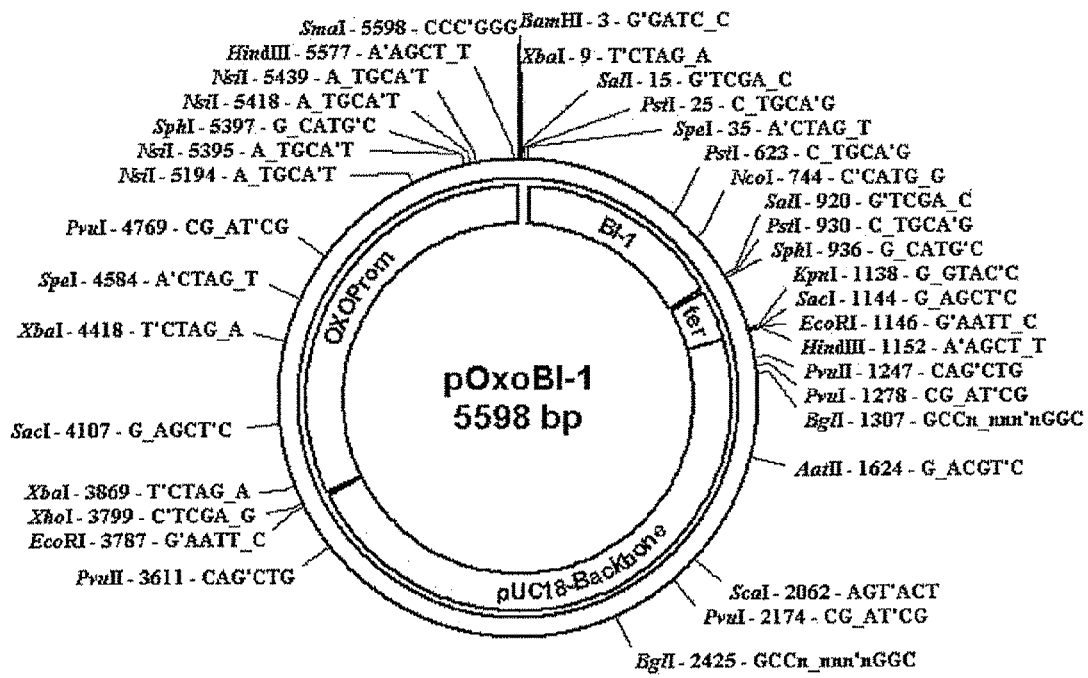
FIG. 4: Vector map for the vector pOxoBI-1 (Oxo: TaGermin 9f-2.8 promoter; BI-1 nucleic acid sequence coding for barley BI1 protein; ter: transcription terminator). Also indicated is the localization of the cleavage sites of various restriction enzymes.
Figure 5:
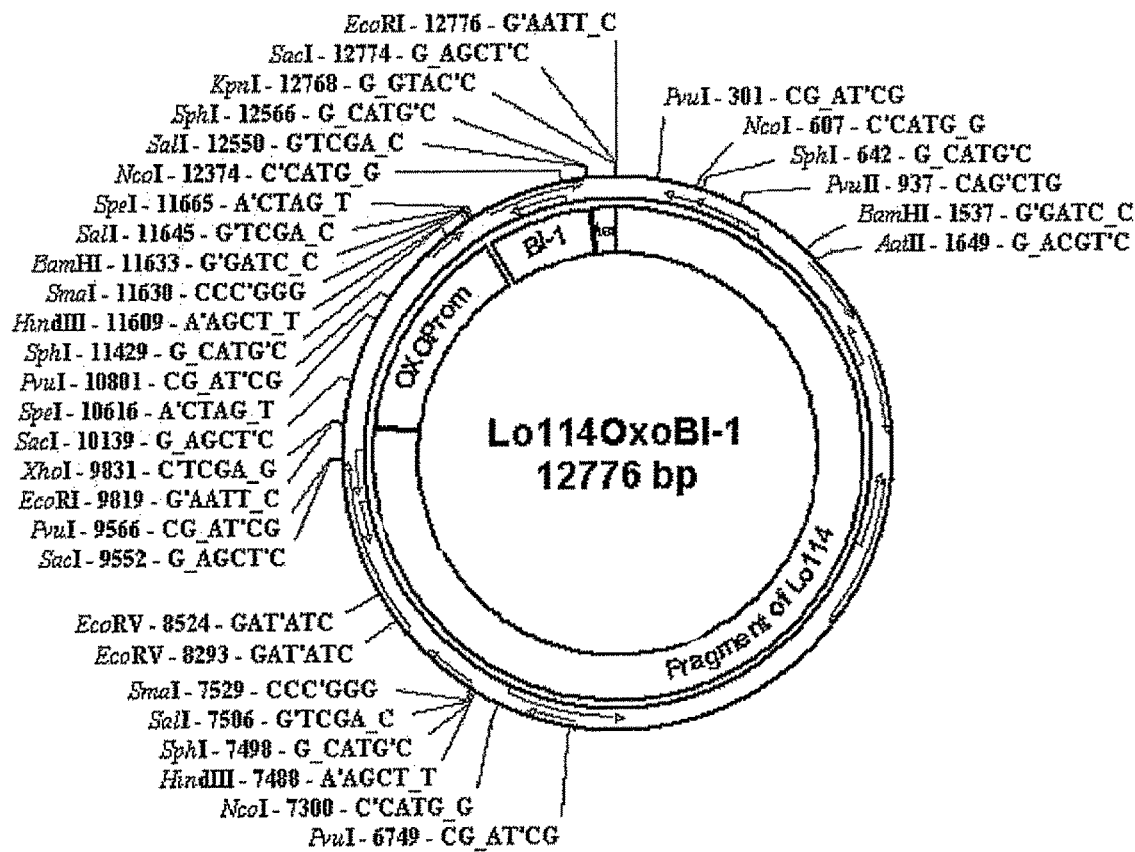
FIG. 5: Vector map for the vector pLO114OxoBI-1 (Oxo: TaGermin 9f-2.8 promoter; BI-1 nucleic acid sequence coding for barley BI1 protein; ter: transcription terminator). Also indicated is the localization of the cleavage sites of various restriction enzymes.
Figure 7:
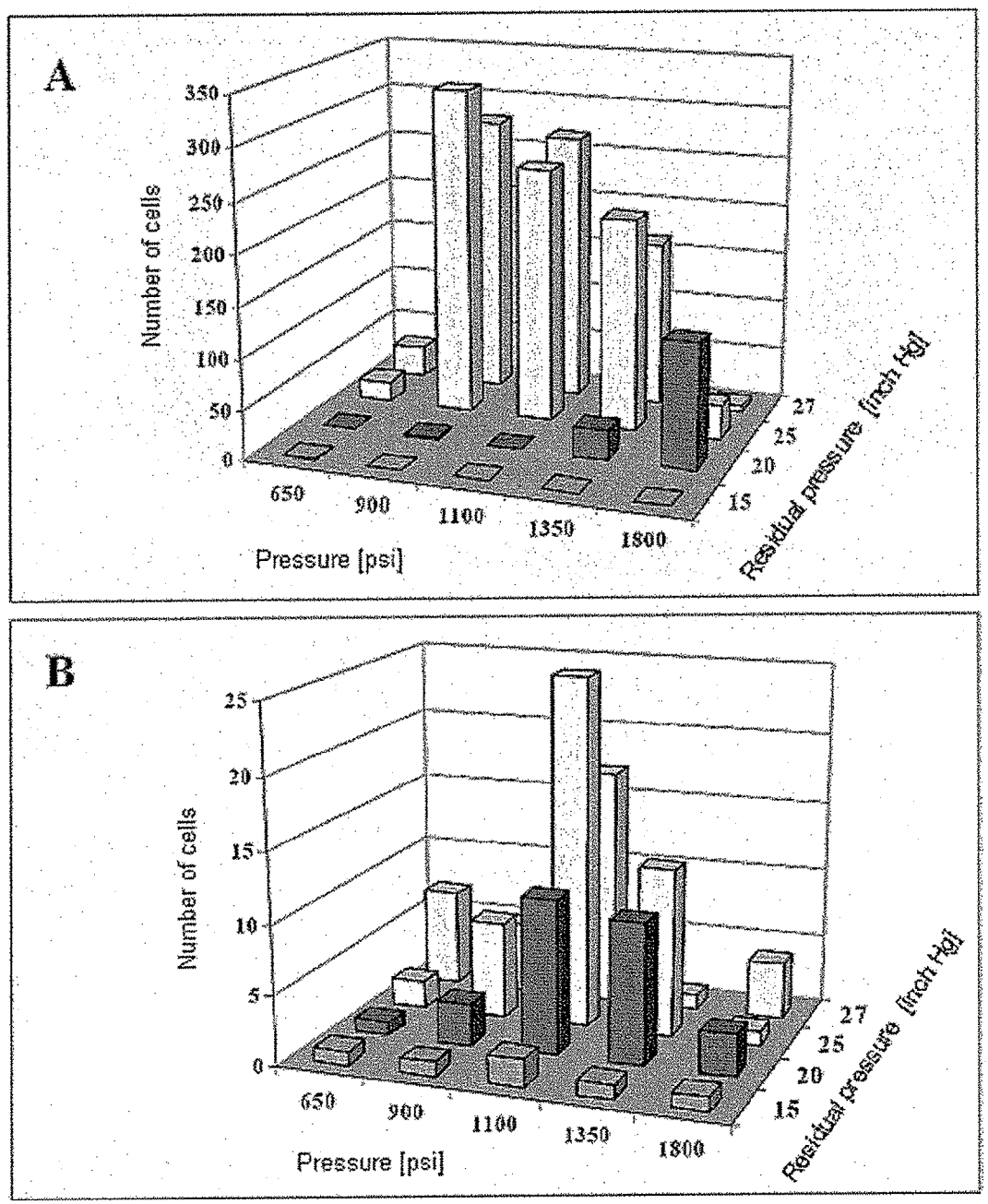

FIG. 7: Diagram of the transformation rate as a function of the conditions during the transformation of soybean leaves (A) and barley leaves (B) with the gene gun. For the transformation, in each case 1.6 µg of DNA were used per bombardment; particles of diameter 0.6 µm were used for barley leaves and with 1µm diameter for soybean. The number of transformed cells was determined 24 hours after the transformation.

Figure 8:
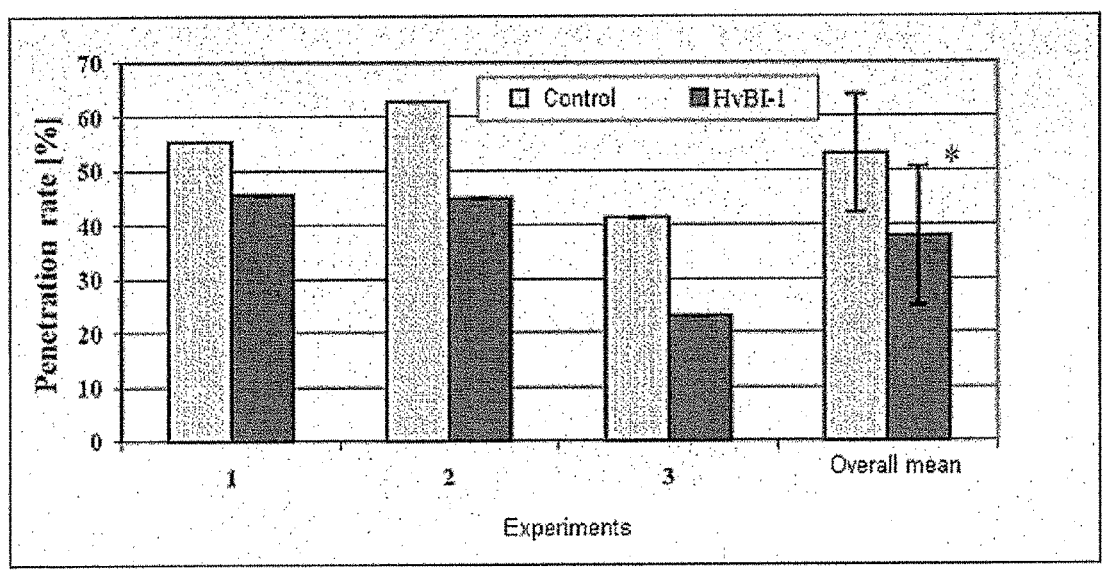
Figure 9:
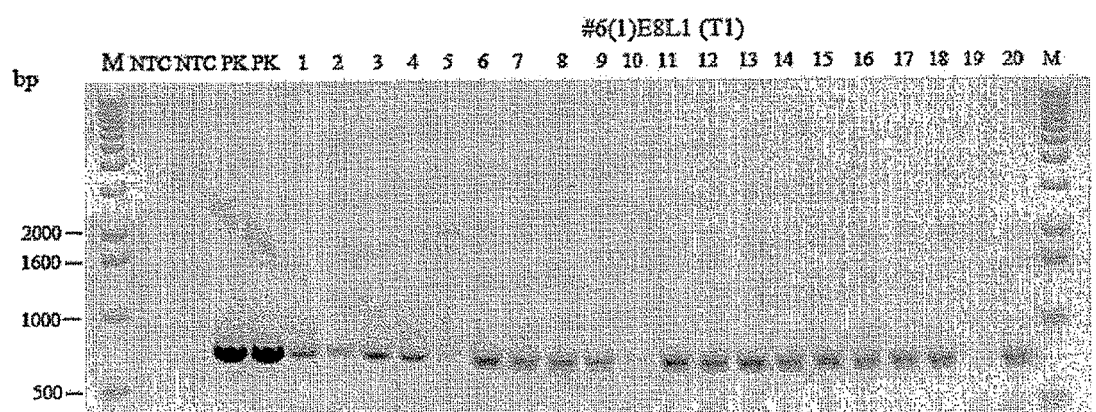
Figure 12:
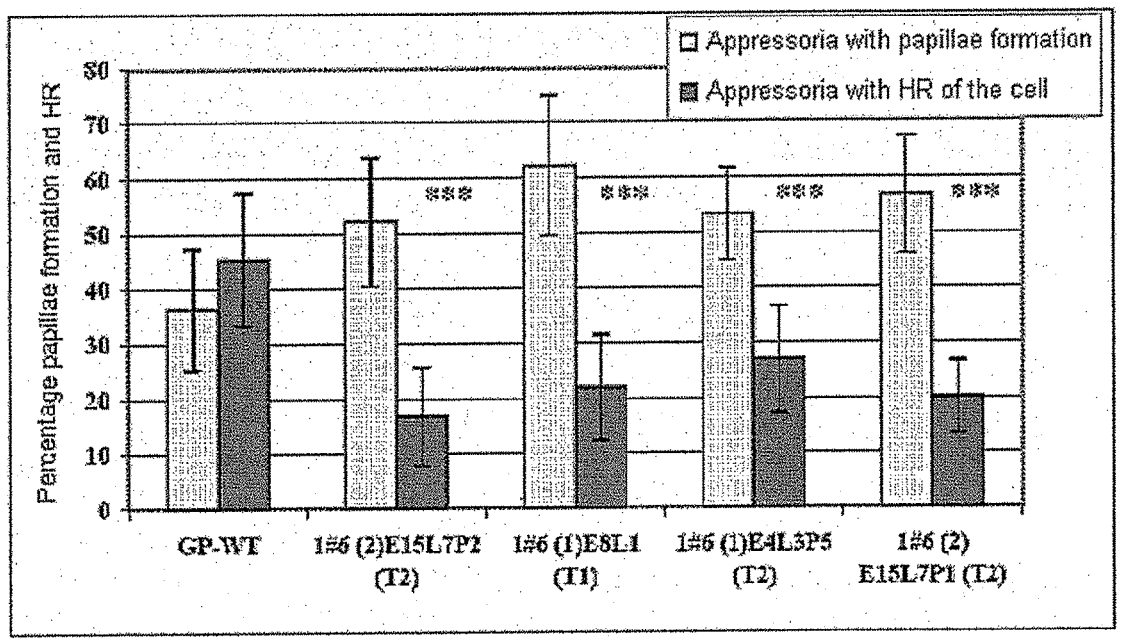

FIG. 8: Diagram of the penetration rate of *P. pachyrhizi* in barley cells which have been transformed transiently with a BI 1 overexpression construct in comparison with the control. The data are based on three independent experiments. By way of control, barley leaves were transformed with the reporter gene construct pGY1 GFP and with the blank vector. In the BI 1 transformed cells, the penetration rate differs significantly from the WT ($P<0.05$).

FIG. 9: PCR for detecting the GFP BI 1 construct in the transgenic barley lines #6(1)E4L3P5 (T2), 1#6(2)E15L7P1 (T2), #6(2)E15L7P2 (T2) and #6(1)E8L1(T1) ('Golden Promise'). The PCR was carried out with genomic DNA of the plants with the GFP-specific primers. In positive transgenic plants, the entire GFP, which is 740 bp in size is amplified. The negative control used was genomic DNA from the WT 'Golden Promise' (WT) or water (NTC). The GFP of plasmid pGY1 GFP was amplified as the positive control (PC).

FIG. 10: Data obtained for the penetration rate of *P. pachyrhizi* in barley cells which have been transformed transiently with a BI 1 overexpression construct. The data shown are those of FIG. 8 (see also examples hereinbelow).

FIG. 11 A/B: Counted spores and cell responses in the interaction between soybean rust and transgenic barley lines with the GFP BI 1 overexpression construct #6(1)E4L3P5 (T2), 1#6(2)E15L7P1(T2), #6(2)E15L7P2(T2) and #6(1)E8L1(T1) CV. 'Golden Promise'. The WT acted as the control. Leaves of 7-day old plants were inoculated with soybean rust, fixed after 24 hours and stained with aniline blue for counting.

FIG. 12: Relative fraction of papillae formation and HR following inoculation with *P. pachyrhizi* in barley leaves of the transgenic lines (CV. 'Golden Promise') #6(1)E4L3P5 (T2), 1#6(2)E15L7P1 (T2), #6(2)E15L7P2 (T2) and #6(1)E8L1(T1) in comparison with the WT. The primary leaves were removed seven days after sowing the barley seeds inoculated with *P. pachyrhizi* and evaluated 24 hours after the inoculation. The data shown are the mean values of the WT and of the individual lines. The error bars represent the standard deviation. A Student's t-test reveals that the relative papillae formation and HR in the transgenic lines are significantly different from the WT, $P<0.001$.

DETAILED DESCRIPTION OF THE INVENTION

In a preferred embodiment, the resistance is a resistance to at least one biotrophic pathogen, preferably a biotrophic fungus, and especially preferably a heminecrotrophic fungus as defined herein. In preferred embodiments of the present invention, the biotrophic fungus is selected from the group Basidiomycota, preferably the Uredinales (rusts), especially preferably the Melompsoraceae, and in particular the genus *Phacopsora*. In especially preferred embodiments, the pathogen is *Phacopsora pachyrhizi* and/or *P. meibomiae* (together also referred to as "soybean rust" or "soya rust"). Preference being given to the former. When the pathogen is selected from the group of the biotrophic pathogens or fungi, it is preferred in some embodiments that the pathogen is other than powdery mildew or downy mildew.

In preferred embodiments, the step of increasing the amount or function of the BI1 protein is accomplished by biotechnological methods. The term "biotechnological" methods comprises, inter alia, the recombinant expression of the protein in a cell, preferably in operable linkage with, and driven by, a heterologous promoter. The abovementioned increase, however, can also be accomplished for example by substituting only the endogenous promoter or, for example, the silencing of factors which generally inhibit the expression of the endogenous BI1 protein. Accordingly, the term "biological method" comprises all methods which are open to modern molecular biology, in particular the methods of recombinant gene technology, which are known to the skilled worker and which will be discussed in greater detail in the course of the description.

The plant in which the resistance is generated is preferably selected from the group of the monocotyledonous plants, in particular comprising wheat, oats, millet, barley, rye, maize, rice, sorghum, triticale, spelt or sugar cane; or from the group of the dicotyledonous plants, in particular comprising *Arabidopsis*, cotton, buckwheat, potato, cabbages, cress, linseed, oil seed rape, tomato, aubergine, bell peppers, sunflower, tobacco, Tagetes, lettuce, Calendula, melon, pumpkin/squash, courgette, sugarbeet, ornamentals, trees and legumes. Since soybean rust attacks more than 70 leguminous species, the plant is especially preferably selected, among the legumes, at least in cases where the pathogen is a heminecrotrophic pathogen or a rust or soybean rust pathogen.

Consequently, the plant is selected especially preferably among the legumes, comprising plants of the genus *Phaseolus* (comprising French bean, dwarf bean, climbing bean (*Phaseolus. vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (Cicer), lentils (*Lens*) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L) R. Wilczek), bambara groundnut (*Vigna subterrane* (L.) Verdc.), rice bean (*Vigna umbellata* (Thunb.) Ohwi & H. Ohashi), *Vigna vexillata* (L.) *A. Rich., Vigna unguiculata* (L.) Walp., in the three subspecies asparagus bean, cowpea, catjang bean)); pigeonpea (*Cajanus cajan* (L) Millsp.), the genus *Macrotyloma* (comprising geocarpa groundnut (*Macrotyloma geocarpum* (Harms) Maréchal &. Baudet), horse bean (*Macrotyloma unifiorum* (Lam.) Verdc.)); goa bean (*Psophocarpus tetragonolobus* (L.) DC.), African yam bean (*Sphenostylis*

*stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and the genus *Canavalia* (comprising jack bean (*Canavalia ensiformis* (L) DC.), sword bean (*Canavalia gladiata* (Jacq.) DC.)).

In any of the embodiments of the present invention which are disclosed herein, it is especially preferred that the amount or function of the BI1 protein is increased at least in the epidermis, preferably essentially in a tissue-specific manner in the epidermis; in particular, it is preferred that the amount or function of the BI1 protein is specifically increased in the epidermis and/or essentially not increased in the mesophyll.

By epidermis, the skilled worker means the predominant epidermal tissue of primary aerial plant parts, for example of the shoot, the leaves, flowers, fruits and seeds. The epidermal cells secrete outwardly a water-repellent layer, the cuticle. The roots are surrounded by the rhizodermis, which, in many ways, resembles the epidermis, but also shows pronounced differences. While the outermost layer of the apical meristem gives rise to the epidermis, the formation of the rhizodermis is much less clear. Depending on the species, it can be considered, in phylogenetic terms, either as part of the calyptra or as part of the primary cortex. The epidermis has a number of functions: it protects the plant against desiccation and regulates the transpiration rate. It protects the plant against a wide range of chemical and physical external influences, against being fed upon by animals and against attack by parasites. It is involved in gas exchange, in the secretion of certain metabolites and in the absorption of water. It comprises receptors for light and mechanical stimuli. it thus acts as a signal transformer between the environment and the plant. In accordance with its various functions, the epidermis comprises a number of differently differentiated cells. To this must be added species-specific variants and different organizations of the epidermides in the individual parts of a plant. Essentially, it consists of three categories of cells: the "actual" epidermal cells, the cells of the stomata and of the trichomes (Greek: trichoma, hair), epidermal appendages of varying shape, structure and function.

The "actual", i.e. the least specialized, epidermal cells account for the bulk of the cells of the epidermal tissue. In topview, they appear either polygonal (slab or plate shaped) or elongated. The walls between them are often wavy or sinuate. It is not known what induces this shape during development; existing hypotheses only offer unsatisfactory explanations herefor. Elongated epidermal cells can be found in organs or parts of organs that are elongated themselves, thus, for example, in stems, petioles, leaf veins and on the leaves of most monocots. The upper surface and undersurface of laminae can be covered in epidermides with different structures, it being possible for the shape of the cells, the wall thickness and the distribution and number of specialized cells (stomata and/or trichomes) per unit area to vary. A high degree of variation is also found within individual families, for example in the Crassulaceae. In most cases, the epidermis consists of a single layer, though multi-layered water-storing epidermides have been found among species from a plurality of families (Moraceae: most Ficus species; *Piperaceae: Peperonia, Begoniaceae, Malvaceae* and the like). Epidermal cells however secrete a cuticle on the outside which covers all epidermal surfaces as an uninterrupted film. It may either be smooth or structured by bulges, rods, folds and furrows. However, the folding of the cuticle, which can be observed when viewing the surface, is not always caused by cuticular rods. Indeed, there are cases where cuticular folding is merely the expression of the underlying bulges of the cell wall. Epidermal appendages of various form, structure and function are referred to as trichomes and, in the present context, likewise come under the term "epidermis". They occur in the form of protective hairs, supportive hairs and gland hairs in the form of scales, different papillae and, in the case of roots, as absorbent hairs. They are formed exclusively by epidermal cells. Frequently, a trichome is formed by only one such a cell, however, occasionally, more than one cell is involved in its formation.

The term "epidermis" likewise comprises papillae. Papillae are bulges of the epidermal surface. The textbook example are the papillae on flower surfaces of pansy (*Viola tricolor*) and the upper surfaces of the leaves of many species from tropical rain forests. They impart a velvet-like consistency to the surface. Some epidermal cells can form water stores. A typical example are the water vesicles at the surfaces of many *Mesembryanthemum* species and other succulents. In some plants, for example in the case of campanula (*Campanula persicifolia*), the outer walls of the epidermis are thickened like a lens.

The bulk of all tissues is the parenchyma. The parenchymatic tissues include the mesophyll which, in leaves, can be differentiated into palisade parenchyma and spongy parenchyma.

Accordingly the skilled worker understands, by mesophyll, a parenchymatic tissue. Parenchymatic cells are always alive, in most cases isodiametric, rarely elongated. The pith of the shoots, the storage tissues of the fruits, seeds, the root and other underground organs are: also parenchymas, as is the mesophyll.

In the leaves of most ferns and phanerogams, especially in the case of the dicots and many monocots, the mesophyll is subdivided into palisade parenchyma and spongy parenchyma. A "typical" leaf is of dorsiventral organization. In most cases, the palisade parenchyma is at the upper surface of the leaf immediately underneath the epidermis. The sponge parenchyma fills the underlying space. It is interspersed by a voluminous intercellular system whose gas space is in direct contact with the external space via the stomata.

The palisade parenchyma consists of elongated cylindrical cells. In some species, the cells are irregular, occasionally bifurcate (Y-shaped: arm palisade parenchyma). Such variants are found in ferns, conifers and a few angiosperms (for example in Ranunculaceae and Caprifoliaceae species [example: elder]). Besides the widest-spread organization form which has just been described, the following variants have been found:

palisade parenchyma on the abaxial leaf surface. Particularly noticeable in scaly leaves. Example: arbor vitae (Thuja), and on the leaves of wild garlic (*Allium ursinum*).

palisade parenchyma on both leaf surfaces (adaxial and abaxial). Frequently in plants which grow in dry habitats (xerophytes). Example: prickly lettuce (*Lactuca serriola*);

ring-shaped closed palisade parenchyma: In cylindrically organized leaves and in conifers' needles.

The variability of the cells of the spongy parenchyma, and the organization of the spongy parenchyma itself, are even more varied than that of the palisade parenchyma. It is most frequently referred to as aerenchyma since it comprises a multiplicity of interconnected intercellular spaces.

The mesophyll may comprise what is known as the assimilation tissue, but the terms mesophyll and assimilation tissue are not to be used synonymously. There are chloroplast-free leaves whose organization differs only to a minor extent from comparable green leaves. As a consequence, they comprise mesophyll, but assimilation does not take place; conversely, assimilation also takes place in, for example, sections of the shoot.

In the present description, the epidermis is characterized in biochemical terms. In a preferred embodiment, the epidermis can be characterized by the activity of one or more of the following promoters:

WIR5 (=GstA1); acc. X56012; Dudler & Schweizer,
GLP4, acc. AJ310534; Wei Y., Zhang Z., Andersen C. H., Schmelzer E., Gregersen Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999); Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Warm J., Lucca P., Hahn T., Potrykus I. and Fütterer J., PMB 40, 249 (1999);
Chitinase ChtC2-Promotor from potato (Ancillo et al., Planta. 217(4), 566, (2003));
AtProT3 Promotor (Grallath et al., Plant Physiology. 137 (1), 117 (2005))
SHN-Promotors from Arabidopsis (AP2/EREBP transcription factors involved in cutin and wax production) (Aarón et al., Plant Cell. 16(9), 2463 (2004));
GSTA1 from wheat (Dudler et al., WP2005306368 and Altpeter at al., Plant Molecular Biology. 57(2), 271 (2005)).

In preferred embodiments, the epidermis is characterized by the fact that all the abovementioned promoters are active in the tissue or the cell. In other preferred embodiments, the epidermis is characterized by the fact that only some of the promoters are active, for example preferably 2, 3, 5 or most preferably 7 or more, but at least from only one of those detailed above.

In a preferred embodiment, the mesophyll is characterized in biochemical terms. The mesophyll can be characterized by the activity of one or more of the following promoters:

PPCZm1 (=PEPC); Kausch A. P., Owen T. P., Zachwieja S. J., Flynn A. R. and Sheen J., Plant Mol. Biol. 45, 1 (2001);
OsrbcS, Kyozuka at al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1 b, acc. X74940; Bryngelsson et al., Mol. Plant Microbe Interact. 7(2), 267 (1994); HvB1,3gluc; acc. AF479647;
HvPrxS, acc. AJ276227; Kristensen et al., Molecular Plant Pathology, 2(6), 311 (2001);
HvPAL, acc. X97313; Wei Y., Zhang Z., Andersen C. H., Schmelzer E., Gregersen Collinge D. B., Smedegaard-Petersen V. and Thordal-Christensen H. Plant Molecular Biology 36, 101 (1998).

In preferred embodiments, the mesophyll is characterized by the fact that all the abovementioned promoters are active in the tissue or the cell. In another embodiment, the mesophyll comprises the fact that only some of the promoters are active, for example preferably 2, 3, 5 or especially preferably 7 or more, but at least from only one of those detailed above.

In preferred embodiments, all of the abovementioned promoters are active in a plant used or produced in accordance with the invention or in the epidermis and in the mesophyll in a plant according to the invention. In one embodiment, only some of the abovementioned promoters are active, for example preferably 2, 5, or especially preferably 7 or more; however, at least one of the promoters detailed above is active in each case.

In preferred embodiments, the increase in the protein quantity or function of the BI1 protein takes place in a constitutive or tissue-specific manner. In especially preferred embodiments, an essentially tissue-specific increase in the protein quantity or protein function takes place in an essentially epidermis-specific manner, for example by recombinant expression of a nucleic acid. sequence coding for said BI1 protein under the control of an epidermis-specific promoter. In particular, the increase in the expression or function of the BI1 protein takes place in .the epidermis, where, however, the expression of the BI-1 protein in the mesophyll remains essentially unchanged, or it is reduced, and where other tissues are unaffected.

As described in the present text, in one embodiment, the expression or function of the protein according to the invention or of the BI-1 characterized in the present text is increased at least in the epidermis of a plant An increase in expression can be achieved as described hereinbelow. By increased expression or function, the present text means both the activation or enhancement of the expression or function of the endogenous protein including a de novo expression, but also an increase in or enhancement as the result of the expression of a transgenic protein or factor.

In an especially preferred embodiment, the increase in the protein quantity or function of at least one plant BI1 protein can be combined with an mlo-resistant phenotype or with the inhibition or reduction, in comparison with a control plant, of the expression of MLO, RacB and/or NaOx in the plant or a part thereof, for example in a tissue, but especially advantageously at least in the epidermis or a considerable number of the epidermal cells, and/or with the increase in the expression or function of PEN2 and/or PEN1 in the plant, for example constitutively, or a part thereof, for example in a tissue, but especially advantageously at least in the epidermis or in a considerable number of epidermal cells, with the proviso that the expression of a plant BI1 protein in the leaf epidermis remains essentially unchanged or is reduced.

The Mlo locus has been described in barley as negative regulator of pathogen defense. The loss, or loss of function, of the Mlo gene brings about an increased, race-unspecific resistance to a number of mildew isolates (Büschges R. et al., Cell 88, 695 (1997); Jorgensen J. H., Euphytica 26, 55 (1977); Lyngkjaer M. F. et al., Plant Pathol. 44, 786 (1995)). An mlo-resistant phenotype can be obtained as described in the prior art. Methods using these genes for obtaining a pathogen resistance are described, inter alia, in WO 98/04586; WO 00/01722; WO 99/47552.

In one embodiment of the present invention, the activity, expression or function of MLO, RacB and/or NaOx in the plant or a part thereof, for example in a tissue, but especially advantageously at least in the epidermis or a substantial number of epidermal cells, can advantageously be inhibited or reduced in comparison with a control plant or a part thereof. By reducing the activity or function of MLO, RacB and/or NaOx in the plant or a part thereof, for example in a tissue, but especially advantageously at least in the epidermis or a substantial number of epidermal cells, it is preferred to increase the resistance, or withstanding power, to biotrophic pathogens in plants produced in accordance with the invention. The activity or function of MLO, RacB and/or NaOx can be reduced or inhibited analogously to what has been described for MLO in WO 98/04586;. WO 00/01722; WO 99/47552 and the other publications mentioned hereinbelow, whose content is herewith expressly incorporated into the present description, in particular for describing the activity and inhibition of MLO. The description of the abovementioned publications describes processes, methods and especially preferred embodiments for reducing or inhibiting the activity or function of MLO; the examples detail specifically how this can be performed.

The reduction of the activity or function, if appropriate the expression, of RacB is described in detail in WO 2003/20939, which is herewith expressly incorporated into the present description.

The description of the abovementioned publication describes processes and methods for reducing or inhibiting the activity or function of proteins; the examples detail specifically how this can be performed. It is especially preferred to carry out the reduction or inhibition of the activity or function of RacB as described in the embodiments and the examples which are especially preferred in WO 2003/20939 and in the organisms specified therein as being especially preferred, in particular in a plant or a part thereof, for example in a tissue, but especially advantageously at least in the epidermis or a substantial number of epidermal cells. The reduction of the activity or function, if appropriate the expression, of RacB is described in detail in WO 2003/20939. In WO 2003/20939, the skilled worker can find the sequences which code for RacB proteins and can also identify RacB by means of the method provided in WO 2003/20939.

The reduction of the activity or function, if appropriate of the expression, of NaOX is described in detail in WO 2004/09820 (=PCT/EP/03/07589) which is herewith expressly incorporated into the present description. The description of the abovementioned publication describes processes and methods for reducing or inhibiting the activity or function of NaOx; the examples detail specifically how this can be performed. It is especially preferred to carry out the reduction or inhibition of the activity or function of NaOx as described in the embodiments and the examples which are especially preferred in WO 2004/09820 (=PCT/EP/03/07589) and in the organisms specified therein as being especially preferred, in particular in a plant or a part thereof, for example in a tissue, but especially advantageously at least in the epidermis or a substantial number of epidermal cells. In WO 2004/09820 (=PCT/EP/03/07589), the skilled worker can find the sequences which code for NaOx proteins and can also identify NaOx by means of the method provided in WO 2004/09820 (=PCT/EP/03/07589).

In one embodiment of the present invention, the activity, expression or function of PEN1, PEN2 and/or SNAP34 can advantageously be increased in the plant, for example constitutively, or in a part thereof, for example in a tissue, but especially advantageously at least in the epidermis or a substantial number of epidermal cells. The increase in activity, which also comprises a de novo expression, of PEN1, PEN2 and/or SNAP34 in the plant, for example constitutively, or in a part thereof, for example in a tissue, but especially advantageously at least in the epidermis or a substantial number of epidermal cells will preferably increase the resistance or withstanding power to biotrophic pathogens in the plants produced in accordance with the invention. The increase in the activity or function, if appropriate the expression, of PEN2 is described in detail in WO 03/074688, which is herewith expressly incorporated into the present description. The description of the abovementioned publication describes processes and methods for reducing or inhibiting the activity or function of PEN2; the examples detail specifically how this can be performed. The reduction or inhibition of the activity or function of PEN2 is especially preferably carried out in accordance with the embodiments and examples which are especially preferred in WO 03/074688 and in the organisms detailed therein as being especially preferred, in particular in plants, for example constitutively, or in a part thereof, for example in a tissue, but especially advantageously at least in the epidermis or a considerable part of the epidermal cells. In WO 03074688, the skilled worker will find the sequences which code for PEN2 proteins and can also identify PEN2 by means of the method provided in WO 03/074688.

The expression of PEN1 and SNAP34 can be increased analogously to the methods described in WO 03/074688. Owing to his general expert knowledge and the prior art with which he is familiar, the skilled worker can isolate and overexpress PEN1 and SNAP34 nucleic acid sequences and protein sequences. SEQ ID No: 39 describes the nucleic acid sequence which codes for PEN1 from barley; the protein sequence is described in SEQ ID No: 40. SEQ ID No: 41 describes the nucleic acid sequences which codes for PEN1 from *Arabidopsis thaliana;* the protein sequence is described in SEQ ID No:42. PEN1 from *Arabidopis thaliana* is published under the accession numbers NM 202559 and NM 112015. The homolog from barley is disclosed in accession numbers AY246907 and AY246906 as ROR2. They are members of the fairly large family of the syntaxin proteins. Thus, the skilled worker can use simple homology comparisons for identifying further syntaxin proteins which are expressed as potential resistance genes in the method according to the invention.

SEQ ID No: 43 describes the nucleic acid sequence which codes for SNAP34 from barley; the protein sequence is described in SEQ ID No: 44. The SNAP-34 homolog from barley is also published as AY 247208 (SNAP-34). Homologs whose function is unknown and which might play a role in the resistance are published as AY 247209. (SNAP-28) and AY 247210 (SNAP-25). The following *Arabidopsis* genes show a higher degree of homology with barley SNAP34 than barley SNAP-28 or SNAP-25 to SNAP-34 and can thus advantageously be co-overexpressed as potential resistance-mediating genes:

AAM 62553—*Arabidopsis* SNAP25a
NP 200929—*Arabidopsis.* SNAP33b
NP 172842—*Arabidopsis* SNAP30
NP 196405—*Arabidopsis* SNAP29

Accordingly, the invention also relates to a plant in which a polypeptide whch is encoded by a nucleic acid molecule comprising the sequences shown in SEQ ID No: 39, 41 or 43 or one of the sequences shown in the abovementioned database publications or which comprises one of the amino acid sequences shown in the abovementioned database publications or in SEQ ID No: 40, 42 or 44, or which is a functional equivalent thereof or which has at least 50%, preferably 70%, more preferably 80%, even more preferably 90%, 95% or more homology with the abovementioned sequences at the coding nucleic acid molecule level or, preferably, at the amino acid level is overexpressed at least furthermore in the epidermis, or relates to a plant in which the above-characterized polypeptide is activated, or its activity or function increased, constitutively or in a part, for example in a tissue, but especially advantageously at least in the epidermis or a substantial number of epidermal cells.

A reduction of the expression or activity of a protein can be brought about by the methods with which the skilled worker is familiar, for example mutagenesis, for example EMS, if appropriate TILLING, iRNA; ribozyme, silencing, knockout, and the like. Reduction methods are described in particular in WO 2003/20939, whose methods can readily be adapted to the sequences described herein, which is why the content of WO 2003/20939 is explicitly incorporated herein.

The lowering or reduction of the expression of a protein, the activity or the function can be performed in many ways.

"Lowering", "to lower", "reduction" or "to reduce" is to be understood in the broad sense in connection with the present invention and comprises the partial or essentially complete prevention or blocking of the functionality or a protein, as the result of different cell-biological mechanisms.

A reduction for the purposes of the invention also comprise a quantitative reduction of a protein down to an essentially complete absence of the protein (i.e. lacking detectability of activity or function or lacking immunological detectability of the protein). In this context, the expression of a certain protein or the activity, or function, in a cell or an organism is preferably reduced by more than 50%, especially preferably by more than 80%, very especially. preferably by more than 90%.

The methods of dsRNAi, cosuppression by means of sense RNA and "VIGS" ("virus induced gene silencing") are also referred to as "post-transcriptional gene silencing" (PTGS). PTGS methods, like the reduction of the function or activity with dominant-negative variants, are especially advantageous because the requirements to homology between the endogenous gene to be suppressed and the recombinantly expressed sense or dsRNA nucleic acid sequence (or between the endogenous gene and its dominant-negative variant, respectively) are lower than, for example in the case of a traditional antisense approach. Such homology criteria are mentioned in the description of the dsRNAi method and can generally be applied to PIGS methods or dominant-negative approaches.

"Introduction" comprises, within the context of the present invention, all methods which are capable of introducing a compound, directly or indirectly, into the epidermis or a substantial part of the epidermal cells, compartment or tissues of same, or which are suitable for generating it therein. This comprises direct and indirect methods. The introduction can lead to a transient presence of a compound (for example a dsRNA) or else to a stable presence. Introducing, comprises, for example, methods such as transfection, transduction or transformation.

In expression constructs of the present invention, a nucleic acid molecule disclosed herein, whose expression (transcription and, if appropriate, translation) generates a corresponding amino acid molecule, is preferably in operation linkage with at least one genetic controller (for example a promoter) which ensures expression in an organism, preferably in plants, preferably an epidermis-specific expression. If the expression construct is to be introduced directly into the plant, plant-specific genetic control elements (for example promoters) are preferred, where, as can be seen from what has been said above, the epidermis-specific activity of the promoter is mandatory in most use forms, as described herein above.

Operable linkage is understood as meaning, for example, the sequential arrangement of a promoter and the nucleic acid sequence to be expressed and, if appropriate, further regulatory elements such as, for example, a terminator, in such a way that each of the regulatory elements can fulfil its function in the recombinant expression of the nucleic acid sequence, depending on the arrangement of the nucleic acid sequences to make sense RNA or antisense RNA. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another. The distance between the promoter sequence and the nucleic acid sequence to be expressed recombinantly is preferably less than 200 base pairs, especially preferably less than 100 base pairs, very especially preferably less than 50 base pairs.

The generation of an operable linkage can be accomplished by means of current recombination and cloning techniques, as is the generation of an expression cassette. Such techniques are described, for example, in Maniatis T., Fritsch E. F. and Sambrook J., Molecular Cloning: A Laboratory Manual, Cold Spring Harbor Laboratory, Cold. Spring Harbor (N.Y.) (1989), in Silhavy T. J., Berman M. L. and Enquist L W., Experiments with Gene Fusions, Cold Spring Harbor Laboratory, Cold Spring Harbor (N.Y.) (1984), in Ausubel F. M. et al., Current Protocols in Molecular Biology, Greene Publishing Assoc. and Wiley Interscience (1987) and in Gelvin et al. in Plant Molecular Biology Manual (1990). However, it is also possible to position, between the two sequences, further sequences which have, for example, the function of a linker with certain restriction enzyme cleavage sites, or of a signal peptide. The insertion of sequences may also lead to the expression of fusion proteins. Preferably, the expression cassette, consisting of a linkage of promoter and nucleic acid sequence to be expressed, can exist as integrated into a vector and can be inserted into a plant genome by, for example, transformation. The control elements preferably mediate an epidermis-specific expression.

For the purposes of the present invention, "approximately" in connection with numbers or sizes means a range of numbers or sizes around the numerical value or the size. In general, the term "approximately" means a range of in each case 10% above and below the value detailed.

For the purposes of the present invention, "plant" means all genera and species of higher and lower plants of the plant kingdom. The term includes the mature plants, seed, fruits and seedlings, and parts, propagation material, plant organs, tissue, protoplasts, callus and other cultures, for example cell cultures, derived therefrom, and any other types of associations of plants cells to the functional or structural units. Mature plants means plants at any developmental stage beyond the seedling stage. Seedling means a young, immature plant in an early developmental stage.

"Plant" comprises all annual and perennial, monocotyledonous and dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Ciahorium, Helianthus, Lactuca, Bromus, Asparagus, Antirrhinum, Het-* erocallis, Nemesis, Pelargonium, Panieum, Pennisetum, Ranunculus, Senecio, Salpiglossis, Cucumis, Browaalia, Glycine, Pisum, Phaseolus, Lawn, Oryza, Zea, Avena, Hordeum, Secale, Triticum, Sorghum, Picea and Populus.

The term "plant" preferably comprises the monocotyledonous and dicotyledonous crop plants. Preferred within the scope of the invention are plants which are employed as foodstuffs or feedingstuffs, very especially preferred are agriculturally important monocotyledonous and dicotyledonous genera and species, as detailed in the claims.

"Pathogen resistance" means the reduction or diminishing of disease symptoms of a plant as the result of attack by at least one pathogen. The symptoms can be manifold in nature, but preferably comprise those which directly or indirectly lead to a negative effect on plant quality, yield quantity, the suitability for use as foodstuff or feedingstuff, or else which make sowing, planting, harvesting or processing of the crop more difficult. For the purposes of the present invention, "pathogen tolerance" is, in particular, to be considered as being comprised by "pathogen resistance".

"Confering", "existing", "generating" or "increasing" (of) a resistance means that the defense mechanisms of a particular plant species or variety displays increased resistance to one or more pathogens, as the result of the application of the method according to the invention, in comparison with the wild type of the plant ("starting plant") to which this method according to the invention has not been applied, under otherwise essentially identical conditions (such as, for example, climatic conditions, culture conditions, type of stress, pathogen species and the like). in this context, the increased resistance preferably manifests itself in a reduced manifestation of the disease symptoms, where disease symptoms—in addition to the abovementioned adverse effects—also comprises for example the penetration efficiency of a pathogen into the plant or plant cells, or the proliferation efficiency in or on same. in this context, the disease symptoms are preferably reduced by at least 5%, 10% or at least 20%, especially preferably by at least 40% or 60%, very especially preferably by at least 70% or 80%, most preferably by at least 90% or 95%.

"Selection" means, with regard to plants where—as opposed to, or in comparison with, the starting plant—resistance to at least one pathogen exists or is increased, all those methods which are suitable for recognizing an existing or increasing pathogen resistance. This can be for example symptoms of the pathogen infection (for example development of necroses in the case of fungal infection), but may also comprise the above-described symptoms, which affect the quality of the plant, the quantity of the yield, the suitability for use as feedstuff or foodstuff, and the like.

For the purposes of the invention, "pathogen" means by way of example, but not by limitation, viruses or viroids, bacteria, fungi, animal pests such as, for example, insects or nematodes. Fungi, in particular biotrophic or heminecrotrophic fungi as defined herein, are especially preferred. However, it can be assumed that the mesophyll-specific expression of a BI1 protein also brings about a resistance to other pathogens since a resistance to stress factors in total is being generated.

Pathogens which may be mentioned by way of example, but not by limitation, are the following:

1. Fungal Pathogens of Fungus-Like Pathogens:

Fungal pathogens or fungus-like pathogens (such as, for example, Chromista) preferably belong to the group comprising Plasmodiophoramycota, Oomycota, Ascomycota, Chytridiomycetes, Zygomycetes, Basidiomycota and Deuteromycetes (Fungi imperfecti). Pathogens which may be mentioned by way of example, but not by limitation, are those detailed in Tables 1 to 4, and the diseases which are associated with them.

TABLE 1

Diseases caused by biotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 2

Diseases caused by necrotrophic and/or hemibiotrophic fungi and Oomycetes

| Disease | Pathogen |
|---|---|
| Plume blotch | *Septoria (Stagonospora) nodorum* |
| Leaf blotch | *Septoria tritici* |
| Ear fusarioses | *Fusarium* spp. |
| Eyespot | *Pseudocercosporella herpotrichoides* |
| Smut | *Ustilago* spp. |
| Late blight | *Phytophthora infestans* |
| Bunt | *Tilletia caries* |
| Take-all | *Gaeumannomyces graminis* |
| Anthrocnose leaf blight | *Colletotrichum graminicola* (teleomorph: *Glomerella* |
| Anthracnose stalk rot | *graminicola Politis*); *Glomerella tucumanensis* (anamorph: *Glomerella falcatum* Went) |
| *Aspergillus* ear and kernel rot | *Aspergillus flavus* |
| Banded leaf and sheath spot ("Wurzeltöter") | *Rhizoctonia solani* Kuhn = *Rhizoctonia microsclerotia* J. Matz (telomorph: *Thanatephorus cucumeris*) |
| Black bundle disease | *Acremonium strictum* W. Gams = *alosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |

TABLE 2-continued

Diseases caused by necrotrophic and/or hemibiotrophic fungi and Oomycetes

| Disease | Pathogen |
|---|---|
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata, C. eragrostidis,* = *C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* ear and stalk rot | *Diplodia frumenti* (teleomorph: *Botryosphaeria festucae*) |
| *Diplodia* ear and stalk rot, seed rot and seedling blight | *Diplodia maydis* = *Stenocarpella maydis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Dry ear rot (cob, kernel and stalk rot) | *Nigrospora oryzae* (teleomorph: *Khuskia oryzae*) |
| Ear rots (minor) | *Alternaria alternata* = *A. tenuis, Aspergillus glaucus, A. niger, Aspergillus* spp., *Botrytis cinerea* (teleomorph: *Botryotinia fuckeliana*), *Cunninghamella* sp., *Curvularia pallescens, Doratomyces stemonitis* = *Cephalotrichum stemonitis, Fusarium culmorum, Gonatobotrys simplex, Pithomyces maydicus, Rhizopus microsporus Tiegh., R. stolonifer* = *R. nigricans, Scopulariopsis brumptii* |
| Ergot (horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis, C. zeae-maydis* |
| *Helminthosporium* root rot | *Exserohilum pedicellatum* = *Helminthosporium pedicellatum* (teleomorph: *Setosphaeria pedicellata*) |
| *Hormodendrum* ear rot (*Cladosporium* rot) | *Cladosporium cladosporioides* = *Hormodendrum cladosporioides, C. herbarum* (teleomorph: *Mycosphaerella tassiana*) |
| Leaf spots, minor | *Alternaria alternata, Ascochyta maydis, A. tritici, A. zeicola, Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum, Exserohilum prolatum* = *Drechslera prolata* (teleomorph: *Setosphaeria prolata*) *Graphium penicillioides, Leptosphaeria maydis, Leptothyrium zeae, Ophiosphaerella herpotricha,* (anamorph: *Scolecosporiella* sp.), |

TABLE 2-continued

Diseases caused by necrotrophic and/or hemibiotrophic fungi and Oomycetes

| Disease | Pathogen |
|---|---|
|  | *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Penicillium* ear rot (blue eye, blue mold) | *Penicillium* spp., *P. chrysogenum*, *P. expansum*, *P. oxalicum* |
| *Phaeocytostroma* stalk and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk and root rot | *Phoma terrestris* = *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot (sclerotial rot) | *Rhizoctonia zeae* (teleomorph: *Waitea circinata*) |
| *Rhizoctonia* root and stalk rot | *Rhizoctonia solani*, *Rhizoctonia zeae* |
| Root rots (minor) | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M ruber* |
| Smut, common | *Ustilago zeae* = *U. maydis* |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots (minor) | *Cercospora sorghi*, *Fusarium episphaeria*, *F. merismoides*, *F. oxysporum* Schlechtend, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. und weitere Pilze |
| Tar spot | *Phyllachora maydis* |
| *Trichoderma* ear rot and root rot | *Trichoderma viride* = *T. lignorum* teleomorph: *Hypocrea* sp. |
| White ear rot, root and stalk rot | *Stenocarpella maydis* = *Diplodia zeae* |

TABLE 2-continued

Diseases caused by necrotrophic and/or hemibiotrophic fungi and Oomycetes

| Disease | Pathogen |
|---|---|
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

TABLE 4

Diseases caused by fungi and Oomycetes with unclear classification regarding biotrophic, hemibiotrophic or necrotrophic behavior

| Disease | Pathogen |
|---|---|
| *Hyalothyridium* leaf spot | *Hyalothyridium maydis* |
| Late wilt | *Cephalosporium maydis* |

The following are especially preferred:

Plasmodiophoromycota such as *Plasmodiophora brassicae* (clubroot of crucifers), *Spongospora subterranea*, *Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora hamuli* (downy mildew of hops), *Plasmopara* (downy mildew in grapevines) (*P. viticola*) and sunflower (*P. halstedli*), *Sclerophthora macrospora* (downy mildew in cereals and grasses), Pythium (for example damping-off of Beta beet caused by *P. debaryanum*), Phytophthora infestans (late blight in potato and in tomato and the like), *Albugo* spec.

Ascomycota such as Microdochium nivale (snow mold of rye and wheat), *Fusarium graminearum*, *Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (Nectria canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea*, *Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnate* (*typhula* blight on barley, rye, wheat), *Ustilago maydis* (blister smut on maize.), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondite* (leaf rust on wheat), *Puccinia disperse* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, among which in particular heminecrotrophic pathogens, i.e. *Phakopsora pachyrhizi* and/or those pathogens which have essentially a similar infection mechanism as *Phakopsora pachyrhizi*, as described herein. Particularly preferred are pathogens from the group Uredinales (rusts), among which in particular the Melompsoraceae. Especially preferred are *Phakopsora pachyrhizi* and/or *Phakopsora meibomiae*.

2. Bacterial Pathogens:

The pathogens and, the diseases associated with them which are mentioned in Table 5 may be mentioned by way of example but not by limitation.

TABLE 5

Bacterial diseases

| Disease | Pathogen |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv. *andnebraskense* |
| Holcus spot | *Pseudomonas syringae* pv. *syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

3. Viral Pathogens:

"Viral pathogen" includes all plant viruses such as, for example, tobacco or cucumber mosaic virus, ringspot virus, necrosis virus, maize dwarf mosaic virus and the like.

The pathogens and diseases associated with them which are mentioned in Table 6 may be mentioned by way of example, but not by limitation.

TABLE 6

Viral diseases

| Disease | Pathogen |
|---|---|
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |
| Corn chlorotic vein banding (Brazilian maize mosaic) | Corn chlorotic vein banding virus (CCVBV) |
| Corn lethal necrosis | Virus complex of Maize chlorotic mottle virus (MCMV) and Maize dwarf mosaic virus (MDMV) A or B or Wheat streak mosaic virus (WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| Maize rayado fino (fine striping disease) | Maize rayado fino virus (MRFV) |
| Maize red leaf and red stripe | Mollicute |
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |
| Maize sterile stunt | Maize sterile stunt virus (strains of barley yellow striate virus) |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (auch: sugarcane mosaic virus (SCMV) Stämme H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

4. Animal Pests 4.1 Pathogenic Insects:

The follovving may be mentioned by way of example, but not by limitation: insects such as, for example, beetles, caterpillars, lice or mites.

Preferred insects are those of the genera Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc. Especially preferred are coleopteran and lepidopte an insects such as, for example, the European corn borer (ECB), *Diabrotica barberi*, *Diabrotica undecimpunctata*, *Diabrotica virgifera*, *Agrotis ipsilon*, *Crymodes devastator*, *Feltia ducens*, *Agrotis gladiaria*, *Melanotus* spp., *Aeolus mellillus*, *Aeolus mancus*, *Horistonotus uhlerii*, *Sphenophorus maidis*, *Sphenophorus zeae*, *Sphenophorus parvulus*, *Sphenophorus callosus*, *Phyllogphaga* spp., *Anuraphis maidiradicis*, *Delia platura*, *Colaspis brunnea*, *Stenolophus lecontei* and *Clivinia impressifrons*.

Other examples are: barley leaf beetle (*Oulema melanopus*), frit fly (*Oscinella frit*), wireworms (*Agrotis lineatus*) and aphids (such as, for example, the oat grain aphid *Rhopalosiphum padi,* the blackberry aphid Sitobion avenae).

4.2 Nematodes:

The pathogens and the diseases associated with them mentioned in Table 7 may be mentioned by way of example, but not by limitation.

TABLE 7

Parasitic nematodes

| Damage | Pathogenic nematode |
| --- | --- |
| Awl | *Dolichodorus* spp., *D. heterocephalus* |
| Bulb and stem nematode disease; bulb eelworm | *Ditylenchus dipsaci* |
| Burrowing | *Radopholus similis* |
| Cyst nematode disease | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. ornata* |
| Root-knot disease | *Meloidogyne* spp., *M. chitwoodi, M. incognita, M. javanica* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

Very especially preferred are *Globodera rostochiensis* and *G. pallida* (cyst eelworm on potato, tomato and other Solanaceae), *Heterodera schachtii* (beet eelvvorm on sugar and fodder beet, oilseed rape, cabbage and the like), *Heterodera avenae* (oat cyst nematode on oat and other cereal species), *Ditylenchus dipsaci* (stem or bulb eelworm, stem eelworm of rye, oats, maize, clover, tobacco, beet), *Anguilla tritici* (grain nematode, cockle disease of wheat (spelt, rye), *Meloidogyne hapla* (root-knot nematode of carrot, cucumber, lettuce, tomato, potato, sugar beet, lucerne).

Examples of preferred fungal or viral pathogens for the individual varieties are:

1. Barley:
Fungal, bacterial and viral pathogens: *Puccinia graminis* f.sp. *hordei* barley yellow dwarf virus (BYDV),
Pathogenic insects/nematodes: *Ostrinia nubilalis* (European corn borer); *Agrotis Ipsilon; Schizaphis graminum; Blissus leucopterus leucopterus; Acrosternum hilare; Euschistus servus; Deliaplatura; Mayetiola destructor; Petrobia latens.*

2. Soybean:
Fungal, bacterial or viral pathogens: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffussa, Fusarium semitectum, Phialophora gregata,* soybean mosaic virus, soybean rust, *Glomerella glycines,* tobacco ring spot virus, tobacco streak virus, *Phakopsorapachyrhizi, Pythium aphanidermatum, Pythium ultimum, Pythium debaryanum,* tomato spotted wilt virus, *Heterodera glycines Fusarium solani*; particularly soybean rust.
Pathogenic insects/nematodes: *Pseudoplusia includens; Anticarsia gemmatalis; Plathypena scabra; Ostrinia nubilalis; Agrotis ipsilon; Spodoptera exigua; Heliothis virescens; Helicoverpa zea; Epilachna varivestis; Myzus persicae; Empoasca fabae; Acrosternum hilare; Melanoplus femurrubrum; Melanoplus differentialis; Hylemya platura; Sericothrips variabilis; Thrips tabaci; Tetranychus turkestani; Tetranychus urticae;*

3. Oil Seed Rape:
Fungal, bacterial or viral pathogens: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternate.*

4. Alfalfa:
Fungal, bacterial or viral pathogens: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae.*

5. Wheat:
Fungal, bacterial or viral pathogens: *Pseudomonas syringae* p.v. *atrofaciens, Urocystis agropyri, Xanthomonas campestris* p.v. *translucens, Pseudomonas syringae* p.v. *syringae, Alternaria alternate, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia. recondita* f.sp. *tritici, Puccinia striiformis, Pyrenophora tritici-repentis, Septoria (Stagonospora) nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* barley tellow dwarf virus, brome mosaic virus, soil borne wheat mosaic virus, wheat streak mosaic virus, wheat spindle streak virus, American wheat striate virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* high plains virus, European wheat striate virus, *Puccinia graminis* f.sp. *tritici* (wheat stem rust), *Blumeria (Erysiphe) graminis* f.sp. *tritici* (wheat powdery mildew).
Pathogenic insects/nematodes: *Pseudaletia unipunctata; Spodoptera, frugiperda; Elasmopalpus lignosellus; Agrotis orthogonia; Elasmopalpus Zignosellus; Oulema melanopus; Hypera punctata; Diabrotica undecimpunctata howardi;* Russian wheat aphid; *Schizaphis graminum; Macrosiphum avenae; Melanoplus femurrubrum; Melanoplus differentialis; Melanoplus sanguinipes; Mayetiola destructor; Sitodiplosis mosellana; Meromyza americana; Hylemya coarctata; Frankliniella fusca; Cephus cinctus; Aceria tulipae;*

6. Sunflower:
Fungal, bacterial or viral pathogens: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *Carotovora, Cephalosporium acremonium, Phytophthora cryptogea, Albugo tragopogonis.*
Pathogenic insects/nematodes: *Suleima helianthana; Homoeosoma electellum;* zygogramma exclamationis; *Bothyrus gibbosus; Neolasioptera murtfeldtiana;*

7. Maize:

Fungal, bacterial or viral pathogens: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* 0, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxallicum, Nigrospora oryzae, Cladosporium herbarum, Curvularia lunata, Curvularia inaequalis, Curvularia pallescens, Clavibacter michiganese* subsp. *nebraskense, Trichoderma viride,* maize dwarf mosaic virus A & B, wheat streak mosaic virus, maize chlorotic dwarf virus, *Claviceps sorghi, Pseudonomas avenae, Erwinia chrysantherni* p.v. *Zea, Erwinia corotovora, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zeae, Cephalosporium maydis, Caphalosporium acremonium,* maize chlorotic mottle virus, high plains virus, maize mosaic virus, maize rayado fino virus, maize streak virus (MSV), maize stripe virus, maize rough dwarf virus.

Pathogenic insects/nematodes: *Ostrinia nubilalis; Agrotis ipsilon; Helicoverpa zea; Spodoptera frugiperda; Diatraea grandiosella; Elasmopalpus lignosellus; Diatraea saccharalis; Diabrotica virgifera; Diabrotica, longicornis barberi; Diabrotica undecimpunctata howardi; Melanotus* spp.; *Cyclocephala borealis; Cyclocephala immaculate; Popillia japonica; Chaetocnema pulicaria; Sphenophorus maidis; Rhopalosiphum maidis; Anuraphis maidiradicis; Blissus leucopterus leucopterus; Melanoplus femurrubrum; Melanoplus sanguinipes; Hylemva platura; Agromyza. parvicornis; Anaphothrips obscrurus; Solenopsis milesta; Tetranychus urticae.*

8. Sorghum:

Fungal, bacterial or viral pathogens: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium monilifonne, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* sugarcane mosaic H, maize dwarf mosaic virus A & 8, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola.*

Pathogenic insects/nematodes: *Chilo partellus; Spodoptera frugiperda; Helicoverpa zea; Elasmopalpus lignosellus; Feltia subterranea; Phvllophaga crinita; Eleodes, Conoderus und Aeolus* spp.; *Oulema melanopus; Chaetocnema pulicaria; Sphenophorus maidis; Rhopalosiphum maidis; Siphaflava; Blissus leucopterus eucopterus; Contarinia sorghicola; Tetranychus cinnabarinus; Tetranychus urticae.*

9. Cotton:

Pathogenic insects/nematodes: *Heliothis virescens; Helicoverpa zea; Spodoptera exigua; Pectinophora gossypiella; Anthonomus grandis grandis; Aphis gossypii; Pseudatomoscelis seriatus; Trialeurodes abutilonea; Lygus lineolaris; Melanoplus femurrubrum; Melanoplus differentialis; Thrips tabaci* (onion thrips); *Franklinkiella fusca; Tetranychus cinnabarinus; Tetranychus urticae.*

10. Rice:

Pathogenic insects/nematodes: *Diatraea saccharalis; Spodoptera frugiperda; Helicoverpa zea; Colaspis brunnea; Lissorhoptrus oryzophilus; Sitophilus oryzae; Nephotettix nigropictus; Blissus leucopterus leucopterus; Acrosternum hilare.*

11. Oilseed rape:

Pathogenic insects/nematodes: *Brevicoryne brassicae; Phyilotrea cruciferae; Mamestra conjgurata; Plutella xylostella; Delia* ssp.

The processes and methods according to the invention firstly relate by preference to soya, plant parts, cells and/or seed thereof. Thereof. Equally, the processes and methods according to the invention relate by preference to soybean rust.

For the purposes of the invention, "BI1 protein" means polypeptides which have at least one sequence with at least 50%, preferably at least 80%, especially preferably at least 90%, very especially preferably at least 95% and especially preferably 100% homology with a BI1 consensus motif selected from the group consisting of

| | | |
|---|---|---|
| a) | H(L/I)KXVY | (SEQ ID NO: 49) |
| b) | AXGA(Y/F)XH | (SEQ ID NO: 50) |
| c) | NIGG | (SEQ ID NO: 51) |
| d) | P(V/P)(Y/F)E(E/Q)(R/Q)KR | (SEQ ID NO: 52) |
| e) | (E/Q)G(A/S)S(V/I)GPL | (SEQ ID NO: 53) |
| f) | DP(S/G)(L/I)(I/L) | (SEQ ID NO: 54) |
| g) | V(G/A)T(A/S)(L/I)AF(A/G)CF(S/T) | (SEQ ID NO: 55) |
| h) | YL(Y/F)LGG, | (SEQ ID NO: 56) |
| | preferably EYLYLGG | (SEQ ID NO: 57) |
| i) | L(L/V)SS(G/W)L(S/T)(I/M)L(L/M)W | (SEQ ID NO: 58) |
| j) | DTGX(I/V)(I/V)E. | (SEQ ID NO: 59) |

Especially preferred in this context is the BI consensus motif f) YL(Y/F)LGG (SEQ ID NO: 56), very especially preferred is (EYLYLGG, SEQ ID NO: 57). This motif is characteristic for plant BI1 proteins. Sequences with homology to at least 2 or 3 of these motifs (a to j) are especially preferably found in a BI1 protein, very especially preferably at least 4 or 5, most preferably all motifs a to j. Further BI1-typical sequence motifs can be derived by the skilled worker without difficulty from the sequence alignment of BI1 proteins as shown in FIG. 1 or 6.

Especially preferred for the use in the methods disclosed herein are BI1 proteins which are encoded by a polypeptide which comprises at least one sequence selected from the group consisting of:

a) the sequences as shown in SEQ ID NO: 2, 4, 6, 8, 10,12, 14, 16, 18, 20, 22, 24, 26, 28, 30, 32, 38 or 46;

b) sequences with at least 50%, more preferably 60%, 70%, 80%, 85% or 90%, especially preferably 95, 97 or 99% or more identity with one of the sequences as shown in SEQ ID NO: 2, 4, 6, 8, 10, 12, 14, 16, 18, 20, 22, 24, 26, 28, 30, 32, 38 or 46; and c) sequences which comprise at least one part-sequence of at least 10 contiguous amino acid residues of one of the sequences as shown in SEQ ID NO: 2, 4, 6, 8, 10, 12, 14, 16, 18, 20, 22, 24, 26, 28, 30, 32, 38 or 46, and/or which comprise at least a part-sequence of at least 20 contiguous amino acid residues, where the part-sequence has at 80%, preferably 85% or 90%, especially preferably 95, 97 or 99% or more identity with the corresponding part-sequence from one of the sequences as shown in SEQ ID NO: 2, 4, 6, 8, 10, 12, 14, 16, 18, 20, 22, 24, 26, 28, 30, 32, 38 or 46.

Comprised in accordance with the invention by the term BI protein are in particular natural or artificial mutations of the BI1 polypeptides as shown in SEQ ID NO: 2, 4, 6, 8, 10, 38 and in particular 46, and homologous or similar polypeptides from other organisms, preferably plants, which furthermore have essentially identical properties. Mutations comprise substitutions, additions, deletions, inversions or insertions of one or more amino acid residues.

Also comprised are thus use forms utilizing BI1 proteins from nonplant organisms such as for example humans (GenBank Acc.-No.: P55061), rat (GenBank Acc.-No.: P55062) or *Drosophila* (GenBank Acc.-No.: Q9VSH3). Motifs which are conserved between plant and nonplant BI1 proteins can be identified readily by sequence alignments (cf. alignment in Bolduc N. et al., Planta 216, 377 (2003); FIGS. 1 and 6), Thus, the present invention also comprises for example those polypeptides which are obtained by modification of a polypeptide as shown in SEQ ID NO: 2, 4, 6, 8, 10, 38 and 46.

The sequences from other plants which are homologous to the BI1 sequences disclosed within the scope of the present invention can be found for example by a) database search in libraries of organisms whose genomic or cDNA sequence is known in full or in part, using the BI1 sequences provided as search sequence, or b) screening gene libraries or cDNA libraries using the BI1 sequences provided as probe.

Screening cDNA libraries or genomic libraries (for example using one of the nucleic acid sequences described under SEQ ID NO: 1, 3, 5, 7, 9, 11, 13, 15, 17, 19, 21, 23, 25, 27, 29, 31, 37 and 45 or parts of these as probe) is a method of identifying homologous or similar or identical sequences, which method is known to the skilled worker. In this context, the probes derived from the nucleic acid sequences as shown in SEQ ID NO: 1, 3, 5, 7, 9, 11, 13, 15, 17, 19, 21, 23, 25, 27, 29, 31, 37 and 45 have a length of at least 20 bp, preferably at least 50 bp, especially preferably at least 100 bp, very especially preferably at least 200 bp, most preferably at least 400 bp. A DNA strand which is complementary to the sequences described under SEQ ID NO: 1, 3, 5, 7, 9, 11, 13, 15, 17, 19, 21, 23, 25, 27, 29, 31, 37 and 45 may also be employed for screening the libraries.

Homology between two nucleic acid sequences is understood as meaning, in the present context, the identity of the nucleic acid sequence over in each case the entire sequence length which, in turn, is calculated by alignment with the aid of the program algorithm GAP (Wisconsin Package Version 10.0, University of Wisconsin, Genetics Computer Group (GCG), Madison, USA; Altschul at al., Nucleic Acids Res. 25, 3389 (1997)) setting the following parameters:

| Gap weight: 50 | Length weight: 3 |
|---|---|
| Average match: 10 | Average mismatch: 0 |

For example a sequence which has at least 80% homology with sequence SEQ ID NO: 1 at the nucleic acid level is understood as me$_a$ning a sequence which, upon alignment with the sequence SEQ ID NO: 1 by the above program algorithm with the above parameter set, has at least 80% homology.

Homology between two polypeptides is understood as meaning the identity of the amino acid sequence over in each case the entire sequence length which is calculated by alignment with the aid of the program algorithm GAP (Wisconsin Package Version 10.0, University of. Wisconsin, Genetics Computer Group (GCG), Madison, USA), setting the following parameters:

| Gap weight: 8 | Length weight: 2 |
|---|---|
| Average match: 2,912 | Average mismatch: −2,003 |

For example a sequence which has at least 80% homology with sequence SEQ ID NO: 2 at the protein level is understood as meaning a sequence which, upon comparison with the sequence SEQ ID NO: 2 by the above program algorithm with the above parameter set, has at least 80% homology.

BI1 proteins also comprise those polypeptides which are encoded by nucleic acid sequences which hybridize under standard conditions with one of the BI1 nucleic acid sequences described by SEQ ID NO: 1, 3, 5, 7, 9, 11, 13, 15, 17, 19, 21, 23, 25, 27, 29, 31, 37 and 45, the nucleic acid sequence which is complementary thereto or parts of the above, and which have essentially identical properties as the proteins described under SEQ ID NO: 2, 4, 6, 8, 10, 38 and 46.

"Standard hybridization conditions" is to be understood in the broad sense and means stringent or else less stringent hybridization conditions. Such hybridization conditions are described, inter alia, by Sambrook J., Fritsch E. F., Maniatis T. et al., in Molecular Cloning (A Laboratory Manual), 2nd Edition, Cold Spring Harbor Laboratory Press, 1989, pages 9.31-9.57) or in Current Protocols in Molecular Biology, John Wiley & Sons, N.Y. (1989), 6.3.1-6.3.6. For example, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C.

"Essential properties" means, with regard to a BI protein, one or more of the following properties:

a) Conferring or increasing the pathogen resistance to at least one pathogen while increasing the protein quantity or function of said BI protein in at least one tissue of the plant, preferably at least in the epidermis of the plant.
b) Nonappearance of a spontaneously induced cell death when increasing the protein quantity or the function of said BI protein.
c) The property of significantly inhibiting the BAX-induced apoptosis in the case of transient cotransfection of Bax with said BI1 protein, for example in HEK293 cells. Suitable methods have been described (Bolduc N. et al, Planta 216, 377 (2003)).
d) The presence of five to seven putative transmembrane domains within said BI1 protein.
e) Preferential localization in cell membranes, in particular the nuclear membrane, the ER membrane and/or the thylakoid membrane.

In this context, the quantitative manifestation of said properties of a BI1 protein may deviate up or down in comparison with the value obtained for the BI1 protein as shown in SEQ ID NO: 2, 4, 6, 8, 10, 38 or 46.

For the purposes of the present invention, the term "increasing the BI1 protein quantity or function" is to be understood in the broad sense and may be based on different cell-biological mechanisms.

"Protein quantity" means the amount of a BI1 protein in the organism, tissue, cell or cell compartment detailed.

"Increasing the protein quantity" means the quantitative increase of the amount of a BI1 protein in the organism, tissue, cell or cell compartment detailed, for example by means of one of the methods described hereinbelow, in comparison with the wild type of the same genus and species, to which this method has not been applied, but on the otherwise identical conditions (such as, for example, culture conditions, age of the plants and the like). In this context, the increase amounts to at least 10%, preferably at least 30% or at least 50%, especially preferably at least 70% or 100%, very especially preferably at least 200% or 500%, most preferably at least 1000%. The protein quantity can be determined by means of a variety of methods with which the skilled worker is familiar. Examples which may be mentioned, but not by limitation, are the micro-biuret method (Goa J., Scand J. Clin. Lab. Invest. 5, 218 (1953)), the Folin-Ciocalteu method (Lowry O. H. et al., J Biol Chem 193, 265 (1951)) or the measurement of the adsorption of CBB G-250 (Bradford M. M., Analyt. Biochem. 72, 248 (1976)). Furthermore, a quantification can be accomplished via immunological methods such as, for example, Western blot The generation of suitable BI1 antibodies and the procedure of BI1 Western blots is described (Bolduc N. et al., FEBS Lett 532, 111 (2002)). An indirect quantification can be accomplished via Northern blots, where, as a rule, the mRNA quantity correlates well with the resulting protein quantity. Suitable methods have been described (Bolduc N. et al., Planta 216, 377 (2003); Matsumura H. et al., Plant J. 33, 425 (2003)).

"Function" preferably means the property of a BI1 protein of reducing the spontaneously induced cell death and/or the property of inhibiting the apoptosis-inducing effect of Bax. Such functions are among the essential properties of a BI1 protein.

Within the scope of the present invention, "increasing" the function means, for example, the quantitative increase of the inhibitor effect on the Bax-induced apoptotic cell death, which can be determined quantitatively by methods with which the skilled worker is familiar (see herein above). In this context, the increase amounts to at least 10%, preferably at least 30% or at least 50%, especially preferably at least 70% or 100%, very especially preferably at least 200% or 500%, most preferably at least 1000%. Methods of increasing the function comprise, beside the above-described method of increasing the protein quantity (which, as a rule, also increases the function) furthermore—by way of example, but not by limitation—in particular the introduction of mutations into a BI1 protein or the inhibition of a putative BI1 inhibitor, and the like.

The BI1 protein quantity can be increased for example, but not by limitation, by one of the following methods:

a) recombinant expression or overexpression of a BI1 protein by introducing a recombinant expression cassette comprising a nucleic acid sequence coding for a BI1 protein under the control of a tissue-specific promoter, where said promoter has activity preferably essentially specifically in the leaf epidermis and/or no activity in the mesophyll.
b) modification (for example substitution) of the regulatory regions (for example the promoter region) of an endogenous BI1 gene, for example substitution for a tissue-specific promoter by means of homologous recombination, where said promoter has activity preferably essentially specifically in the leaf epidermis and/or no activity in the mesophyll.
c) insertion of a nucleic acid sequence, coding for a BI1 protein, into the plant genome downstream of a tissue-specific promoter by means of homologous recombination, where said promoter has activity preferably essentially specifically in the leaf epidermis and/or no activity in the mesophyll.
d) increasing the expression of an endogenous BI1 protein by introducing a transcription factor (for example artificial transcription factor from the class of the zinc finger proteins) which is suitable for inducing the expression of said BI1 protein. Preferred is the introduction of a recombinant expression cassette comprising a nucleic acid sequence coding for said transcription factor under the control of a tissue-specific promoter, where said promoter has activity preferably essentially specifically in the leaf epidermis and/or no activity in the mesophyll.

For the purposes of the present invention, the. term "to introduce/introduction" generally comprises all methods which are suitable for transferring the compound to be introduced, either directly or indirectly, into a plant or into a cell, compartment, tissue, organ or seed thereof, or generating it therein. This comprises direct and indirect methods. The introduction can lead to a transient presence of said compound or else to a stable or inducible presence. "Introducing" comprises for example methods such as transfection, transduction or transformation.

In the recombinant expression cassettes which are employed within the scope of the present invention, a nucleic acid molecule (for example coding for a BI1 protein) is in operable linkage with at least one tissue-specific promoter, where said promoter has activity preferably essentially specifically in the leaf epidermis and/or no activity in the mesophyll, and where the promoter is heterologous with regard to the nucleic acid sequence to be expressed, i.e. does not naturally occur in combination with same. The recombinant expression cassettes according to the invention may optionally comprise further genetic control elements.

Operable linkage is to be understood as meaning, for example, the sequential arrangement of said promoter with the nucleic acid sequence to be expressed and, if appropriate, further regulatory elements such as, for example, a terminator in such a way that each of the regulatory elements can fulfil its function when the nucleic acid sequence is expressed recombinantly. To this end, direct linkage in the chemical sense is not necessarily required. Genetic control sequences such as, for example, enhancer sequences, can also exert their function on the target sequence from positions which are further away, or indeed from other DNA molecules.

Preferred arrangements are those in which the nucleic acid sequence to be expressed recombinantly is positioned downstream of the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. Operable linkage, and a recombinant expression cassette, can be generated by means of customary recombination and cloning techniques as are described above. However, further sequences which, for example, act as a linker with specific cleavage sites for restriction enzymes, or as a signal peptide, may also be positioned between the two sequences. The insertion of sequences may also lead to the expression of fusion proteins.

Preferably, the expression cassette, consisting of a linkage of promoter and nucleic acid sequence to be expressed, can exist in a vector-integrated form and be inserted into a plant genome, for example by transformation.

However, a recombinant expression cassette also denotes those constructions in which the promoter is positioned upstream of an endogenous BI1 gene, for example by means of homologous recombination, thus controlling the expression of the BI1 protein. Analogously, the nucleic acid sequence to be expressed (for example coding for a BI1 protein) can be placed downstream of an endogenous promoter in such a way that the same effect is manifested. Both approaches lead to inventive recombinant expression cassettes.

By "tissue-specific promoter with activity essentially specifically in the leaf epidermis" there are generally to be understood, for the purposes of the present invention, those promoters which are suitable of ensuring or increasing recombinant expression of a nucleic acid sequence in at least one plant tissue with the proviso that
a) the expression is manifested at least in the epidermis and preferably not in the mesophyll, or remains essentially unchanged in the mesophyll, where tissues other than the two tissues mentioned are not been taken into consideration, and
b) the recombinant expression under the control of said promoter in said plant tissue amounts to at least five times, preferably at least ten times, especially preferably at least hundred times, the expression of a comparative plant.

Genetic control sequences furthermore also encompass the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, N.Y. (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie et al., Nucl. Acids Res. 15, 8693 (1987)) and the like. Furthermore they may promote tissue specificity (Raster J. et al., Plant J 15, 435 (1998)).

The recombinant expression cassette may advantageously comprise one or more of what. are known as enhancer sequences, linked operably to the promoter, which make possible an increased recombinant expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

Polyadenylation signals which are suitable as control sequences are plant polyadenylation signals, preferably those which essentially correspond to T-DNA polyadenylation signals from *Agrobacterium tumefaciens*, in particular the OCS (octopin synthase) terminator and the NOS (nopalin synthase) terminator.

Control sequences are furthermore to be understood as those which make possible homologous recombination or insertion into the genome of a host organism or which permit removal from the genome. In the case of homologous recombination, for example the natural promoter of a BI1 gene may be exchanged for one of the preferred tissue-specific promoters. Methods such as the cre/lox technology permit a tissue-specific, if appropriate inducible, removal of the recombinant expression cassette from the genome of the host organism (Sauer B., Methods. 14(4), 381 (1998)). In this method, specific flanking sequences (lox sequences), which later allow removal by means of cre recombinase, are attached to the target gene.

A recombinant expression cassette and the vectors derived from it may comprise further functional elements. The term functional element is to be understood in the broad sense and refers to all those elements which have an effect on the generation, amplification or function of the recombinant expression cassettes, vectors or recombinant organisms according to the invention. The following may be mentioned by way of example, but not by limitation:
a) Selection markers which confer a resistance to a metabolism inhibitor such as 2-deoxyglucose-6-phosphate (WO 98/45456), antibiotics or biocides, preferably herbicides, such as, for example, kanamycin, G 418, bleomycin or hygromycin, or else phosphinothricin and the like. Especially preferred selection markers are those which confer resistance to herbicides. Examples which may be mentioned are DNA sequences which code for phosphinothricin acetyltransferases (PAT) and which inactivate glutamin synthase inhibitors (bar and pat genes), 5-enolpyruvylshikimate-3-phosphate synthase genes (EPSP synthase genes), which confer resistance to Glyphosat® (N-(phosphonomethyl)glycine), the gox gene, which encodes Glyphosat®-degrading enzymes (Glyphosate oxidoreductase), the deh gene (encoding a dehalogenase which inactivates Dalapon®), and bxn genes, which encode bromoxynil-degrading nitrilase enzymes, the ansa gene, which confers resistance to the antibiotic spectinomycin, the streptomycin phosphotransferase (SPT) gene, which allows resistance to streptomycin, the neomycin phosphotransferase (NPTII) gene, which confers resistance to kanamycin or geneticidin, the hygromycin phosphotransferase (HPT) gene, which mediates resistance to hygromycin, the acetolactate synthase gene (ALS), which confers resistance to sulfonylurea herbicides (for example mutated ALS variants with, for example, the S4 and/or Hra mutation), and the acetolactate synthase gene (ALS), which confers resistance to imidazolinone herbicides.
b) Reporter genes which code for readily quantifiable proteins and, via their color or enzyme. activity, make possible an assessment of the transformation efficacy, the site of expression or the time of expression. Very especially preferred in this context are genes coding for reporter proteins (Schenborn E., Groskreutz D., Mol. Biotechnol. 13(1), 29 (1999)) such as the green fluorescent protein (GFP) (Sheen et al,. Plant Journal 8(5), 777 (1995); Heseloff et al., Proc. Natl. Acad. Sci. USA 94(6), 2122 (1997); Reichel et al., Proc. Natl. Acad. Sci. USA 93(12), 5888 (1996); Tian et al., Plant Cell Rep. 16, 267 (1997); WO 97/41228; Chui W. L. et al., Curr. Biol. 6, 325 (1996); Leffel S. M. et al., Biotechniques 23(5), 912 (1997)), chloramphenicol transferase, a luciferase (Ow et al., Science 234, 856 (1986); Millar et al., Plant Mol. Biol. Rep. 10, 324 (1992)), the aequorin gene (Prasher et al., Biochem. Biophys. Res. Commun. 126(3), 1259 (1985)), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates; Dellaporta et al. in Chromosome Structure and Function: Impact of New Concepts, 18th Stadler Genetics Symposium, 11 (1988)), with β-glucuronidase being very especially preferred (Jefferson et al., EMBO J. 6, 3901 (1987)).

c) Origins of replication, which ensure amplification of the recombinant expression cassettes or vectors according to the invention in for example, *E. coli*. Examples which may be mentioned are ORI (origin of DNA replication), the pBR322 ori or the P15A ori (Sambrook et al., Molecular Cloning. A Laboratory Manual, 2nd ed. Cold Spring Harbor Laboratory Press, Cold Spring Harbor, N.Y., 1989).

d) Elements which are necessary for *Agrobacterium*-mediated plant transformation, such as, for example, the right or left border of the T-DNA or the vir region.

To select cells which have successfully undergone homologous recombination, or else to select transformed cells, it is, as a rule, necessary additionally to introduce a selectable marker which confers resistance to a biocide (for example herbicide), a metabolism inhibitor such as 2-deoxyglucose-6-phosphate (WO 98/45456) or an antibiotic to the cells which have successfully undergone recombination. The selection marker permits the selection of the transformed cells from untransformed ones (McCormick et al., Plant Cell Reports 5, 81 (1986)).

The introduction of a recombinant expression cassette according to the invention into an organism or cells, tissues, organs, parts or seeds thereof (preferably into plants or plant cells, tissue, organs, parts or seeds) can be effected advantageously using vectors which comprise the recombinant expression cassettes. The recombinant expression cassette can be introduced into the, vector (for example a plasmid) via a suitable restriction cleavage site. The plasmid formed is first introduced into *E. coli*. Correctly transformed *E. coli* are selected, grown, and the recombinant plasmid is obtained by the methods familiar to the skilled worker. Restriction analysis and sequencing may serve to verify the cloning step.

Examples of vectors may be plasmids, cosmids, phages, viruses or else agrobacteria. In an advantageous embodiment, the expression cassette is introduced by means of plasmid vectors. Preferred vectors are those which make possible stable integration of the recombinant expression cassette into the host genome.

The generation of a transformed organism (or of a transformed cell or tissue) requires introducing the DNA, RNA or protein in question into the relevant host cell.

A plurality of methods are available for this procedure, which is referred to as transformation (or transduction or transfection) (Keown et al., Methods Enzymol. 185, 527 (1990); Jenes B. et al., Techniques for Gene Transfer, in: Transgenic Plants, Vol. 1, Engineering and Utilization, edited by Kung S. D. and Wu R, Academic Press, p. 128-143 (1993), and in Potrykus, Annu. Rev. Plant Physiol. Plant Molec. Biol. 42, 205 (1991)).

For example, the DNA or RNA can be introduced directly by microinjection or by bombardment with DNA-coated microparticles. Also, the cell can be permeabilized chemically, for example using polyethylene glycol, so that DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Suitable methods have been described (for example by Bilang et al., Gene 100, 247 (1991); Scheid et al, Mol. Gen. Genet. 228, 104 (1991); Guerche et al., Plant Science 52, 111 (1987); Neuhause et al., Theor. Appl. Genet. 75, 30 (1987); Klein et al., Nature 327, 70 (1987); Howell et al., Science 208, 1265 (1980); Horsch et al., Science 227, 1229 (1985); DeBlock et al., Plant Physiol 91, 694 (1989)).

In plants, the above-described methods of transforming and regenerating plants from plant tissues or plant cells are exploited for transient or stable transformation. Suitable methods are especially protoplast transformation by polyethylene-glycol-induced DNA uptake, the biolistic method with the gene gun, what is known as the particle bombardment method, electroporation, incubation of dry embryos in DNA-containing solution, and microinjection.

In addition to these "direct" transformation techniques, transformation can also be effected by bacterial infection by means of Agrobacterium tumefaciens or *Agrobacterium rhizogenes*. The *Agrobacterium*-mediated transformation is best suited to dicotyledonous plant cells. The methods are described, for example, by Horsch R. B. et al., Science 225, 1229 (1985).

When agrobacteria are used, the expression cassette must be integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region.

Binary vectors are preferably used. Binary vectors are capable of replication both in *E. coli* and in *Agrobacterium*. As a rule, they comprise a selection marker gene and a linker or polylinker flanked by the right and left T-DNA border sequence. They can be transferred directly into *Agrobacterium* (Holsters et al., Mol. Gen. Genet. 163, 181 (1978)). The selection marker gene permits a selection of transformed agrobacteria and is, for example, the nptII gene, which confers resistance to kanamycin. The *agrobacterium* which acts as host organism in this case should already contain a plasmid with the vir region. The latter is required for transferring the T-DNA to the plant cell. An *agrobacterium* transformed in this way can be used for transforming plant cells. The use of T-DNA for transforming plant cells has been studied and described intensively (EP 120 516; Hoekema in The Binary Plant Vector System, Offsetdrukkerij Kanters B. V., Alblasserdam, Chapter V; An et al., EMBO J. 4, 277 (1985)). Various binary vectors are known, some of which are commercially available such as, for example, pBI101.2 or pBIN19 (Bevan et al., Nucl. Acids Res. 12, 8711 (1984); Clontech Laboratories, Inc. USA). Further promoters which are suitable for expression in plants have been described (Rogers et al., Methods Enzymol. 153, 253 (1987); Schardl et al., Gene 61, 1(1987); Berger et al., Proc. Natl. Acad. Sci. USA 86, 8402 (1989)).

Direct transformation techniques are suitable for any organism and cell type. The plasmid used need not meet any particular requirements in the case of the injection or electroporation of DNA or RNA into plant cells. Simple plasmids such as those of the pUC series may be used. If complete plants are to be regenerated from the transformed cells, it is necessary for an additional selectable marker gene to be located on the plasmid.

Stably transformed cells, i.e. those which comprise the introduced DNA integrated into the DNA of the host cell, can be selected from untransformed cells when a selectable marker is part of. the DNA introduced. Examples of genes which can act as markers are all those which are capable of conferring resistance to antibiotics or herbicides (such as kanamycin, G 418, bleomycin, hygromycin or phosphinothricin) (see above). Transformed cells which express such marker genes are capable of surviving in the presence of concentrations of a corresponding antibiotic or herbicide which kill an untransformed wild type. Examples of suitable selection markers are mentioned above. As soon as a transformed plant cell has been generated, a complete plant can be obtained by using methods known to the skilled worker. Starting material in this context is, for example, callus cultures. The development of shoot and root and can be induced in the known manner in these as yet undifferentiated cell biomasses. The plantlets obtained can be grown on and bred. The skilled worker is familiar with methods of regenerating plant parts of entire plants starting from plant cells. For example, methods described by Fennell et al., Plant Cell Rep. 11, 567 (1992); Stoeger et al., Plant Cell Rep. 14, 273 (1995); Jahne et al., Theor. Appl. Genet. 89, 525 (1994) are used in this context. The plants obtained can be bred and/or hybridized in the customary manner. Two or more generations should be grown in order to ensure that the genomic integration is stable and hereditary.

The method according to the invention can advantageously be combined with further methods which bring about pathogen resistance (for example to insects, fungi, bacteria, nematodes and the like), stress resistance or another improvement of the plant properties. Examples are mentioned, inter &la, by Dunwell J. M., J. Exp. Bot. 51 (Spec No), 487 (2000).

With regard to, for example a nucleic acid sequence, an expression cassette or a vector comprising said nucleic acid sequence or an organism transformed with said nucleic acid sequence, expression cassette or vector, the term "recombinant" means all those constructs which are the result of recombinant methods and in which either
a) the BI1 nucleic acid sequence or
b) a genetic control sequence, for example promoter, which is operably linked with the BI1 nucleic acid sequence, or
c) (a) and (b)
are not located in their natural genetic environment or have been modified by recombinant methods, an example of the modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1000 bp, very especially preferably at least 5000 bp, in length. A naturally occurring expression cassette—for example the naturally occurring combination of the BI1 promoter with the corresponding BI1 gene—becomes a recombinant expression cassette when it is modified by non-natural, synthetic "artificial" methods such as, for example, mutagenization. Such methods have been described (U.S. Pat. No. 5,565,350; WO 00/15815; also see above).

The invention also relates to recombinant organisms transformed with at least one of the nucleic acid sequences according to the invention, expression cassette according to the invention or vector according to the invention, and to cells, cell cultures, tissues, parts—such as, for example, leaves, roots and the like in the case of plant organisms—or propagation material derived from such organisms. The term organism is to be understood in the broad sense and refers to prokaiyotic and eukaryotic organisms, preferably bacteria, yeasts, fungi, animal organisms and plant organisms. Host or starting organisms which are preferred as recombinant organisms are mainly plants in accordance with the above definition.

The invention furthermore relates to the use of the recombinant organisms according to the invention and of the cells, cell cultures, parts—such as for example, roots, leaves and the like in the case of recombinant plant organisms—derived from them, and to recombinant propagation material such as seeds or fruits, for the production of foodstuffs or feedingstuffs, pharmaceuticals or fine chemicals.

Furthermore is a nucleic acid molecule which is antisense to the nucleic acid according to the invention, a monoclonal antibody which binds specifically to the polypeptide according to the invention, and a fungicide which comprises the nucleic acid according to the invention, the vector according to the invention, in particular an infectious, for example viral, vector according to the invention, the polypeptide according to the invention in a form which is suitable for application to plants, for example in encapsulated form or in an infectious organism which is preferably suitable for transferring nucleic acids or for expressing genes in a cell, such as an agrobacterium or a virus.

In one embodiment, the invention relates to the use of a BI-1 encoding nucleic acid molecule or of a BI-1 protein for the generation of a pathogen-resistant plant, preferably for the generation of a fungus-resistant plant or for the generation of a fungicide which brings this about, or for controlling or treating plants which are attacked, or liable to be attacked, by pathogens.

Sequences
1. SEQ ID NO: 1: Nucleic acid sequence coding for a BI1 protein from barley (Hordeum vulgare).
2. SEQ ID NO: 2: Amino acid sequence coding for a BI1 protein from barley (Hordeum vulgare).
3. SEQ ID NO: 3: Nucleic acid sequence coding for a BI1 protein from *Arabidopsis thaliana*.
4. SEQ ID NO: 4: Amino acid sequence coding for a BI1 protein from *Arabidopsis thaliana*.
5. SEQ ID NO 5: Nucleic acid sequence coding for a BI1 protein from tobacco.
6. SEQ ID NO: 6: Amino acid sequence coding for a BI1 protein from tobacco.
7. Nucleic acid sequence coding for a BI1 protein from rice.
8. Amino acid sequence coding for a BI1 protein from rice.
9. SEQ ID NO: 9: Nucleic acid sequence coding for a BI1 protein from oil seed rape.
10. SEQ ID NO: 10: Amino acid sequence coding for a BI1 protein from oil seed rape.
11. SEQ ID NO: 11: Nucleic acid sequence coding for part of a BI1 protein from soybean.
12. SEQ ID NO: 12: Amino acid sequence coding for part of a BI1 protein from soybean.
13. SEQ ID NO: 13: Nucleic acid sequence coding for part of a BI1 protein from soybean.

14. SEQ ID NO: 14: Amino acid sequence coding for part of a BI1 protein from soybean.
15. SEQ ID NO: 15: Nucleic acid sequence coding for part of a BI1 protein from wheat.
16. SEQ ID NO: 16: Amino acid sequence coding for part of a BI1 protein from wheat.
17. SEQ ID NO: 17: Nucleic acid sequence coding for part of a BI1 protein from maize.
18. SEQ ID NO: 18: Amino acid sequence coding for part of a BI1 protein from maize.
19. SEQ ID NO: 19: Nucleic acid sequence coding for part of a BI1 protein from wheat.
20. SEQ ID NO: 20: Amino acid sequence coding for part of a BI1 protein from wheat.
21. SEQ ID NO: 21: Nucleic acid sequence coding for part of a BI1 protein from maize.
22. SEQ ID NO: 22: Amino acid sequence coding for part of a BI1 protein from maize.
23. SEQ ID NO: 23: Nucleic acid sequence coding for part of a BI1 protein from maize.
24. SEQ ID NO: 24: Amino acid sequence coding for part of a BI1 protein from maize.
25. SEQ ID NO: 25: Nucleic acid sequence coding for part of a BI1 protein from wheat.
26. SEQ ID NO: 26: Amino acid sequence coding for part of a BI1 protein from wheat.
27. SEQ ID NO: 27: Nucleic acid sequence coding for part of a BI1 protein from maize.
28. SEQ ID NO: 28: Amino acid sequence coding for part of a BI1 protein from maize.
29. SEQ ID NO 29: Nucleic acid sequence coding for the patatin promote from potato.
30. SEQ ID NO: 30: Nucleic acid sequence coding for the Germin 9f-3.8 promoter from wheat.
31. SEQ ID NO: 31: Nucleic acid sequence coding for the *Arabidopsis* CAB-2 promoter
32. SEQ ID NO: 32: Nucleic acid sequence coding for the PPCZm1 promoter from maize.
33. SEQ ID NO: 33: Nucleic acid sequence coding for the recombinant expression vector pUbiBI-1
34. SEQ ID NO: 34: Nucleic acid sequence coding for the recombinant expression vector pLo114UbiBI-1
35. SEQ ID NO: 35: Nucleic acid sequence coding for the recombinant expression vector pOXoBI-1
36. SEQ ID NO: 36: Nucleic acid sequence coding for the recombinant expression vector pLo114OXoBI-1
37. SEQ ID NO: 37: Nucleic acid sequence coding for BI-1 protein from wheat
38. SEQ ID NO: 38: Amino acid sequence coding for BI-1 protein from wheat
39. SEQ ID NO: 39: Nucleic acid sequence for PEN1 (=ROR2) from barley
40. SEQ ID NO: 40: Amino acid sequence coding for PEN1 (=ROR2) from barley
41. SEQ ID NO: 41: Nucleic acid sequence for PEN1 (=ROR2) from *Arabidopsis thaliana*
42. SEQ ID NO: 42: Amino acid sequence coding for PEN1 (=ROR2) from *Arabidopsis thaliana*
43. SEQ ID NO: 43: Nucleic acid sequence coding for SNAP34 from barley
44. SEQ ID NO: 44: Amino acid sequence coding for SNAP34 from barley
45. SEQ ID NO: 45: Nucleic acid sequence coding for. BI-1 from soya
46. SEQ ID NO: 46: Amino acid sequence coding for BI-1 from soya
47. SEQ ID NO: 47: GFP primer 1 (see herein below)
48. SEQ ID NO: 48: GFP primer 2 (see herein below)

EXAMPLES

General Methods:

The chemical synthesis of oligonucleotides can be effected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 1

Inoculation with *P. pachyrhizi*

Suitable spore material (Uredospores) of the pathogen *Phakopsora pachyrhizi* was obtained from BASF Aktiengesellschaft. To this end, spores of soybean plants which had been inoculated 2-3 weeks earlier were used directly or shaken onto aluminum foil and stored in the dark at room temperature on a desiccant (TROPAGel, Tropack, Lahnau).

To prepare a spore suspension, the spores were washed from the leaves with Tween/$H_2O$ (0.1%). The spores were counted using a Thoma hematocytometer under the light microscope. To carry out the inoculation, the leaves were fixed on 1% $H_2O$ agar using a metal ring. Various methods were finally used for the inoculation. For the spray inoculation, the spore suspension was placed into a spray bottle operated with pressurized air and were distributed uniformly on the plants until the upper surface of the leaf was thoroughly moistened. To obtain a higher spore density, leaves which had previously been sprayed with Tween/$H_2O$ were additionally dry-inoculated in a ‘precipitation column’. To this end, the column is placed over the plates with the moistened leaves. The young spores of infected soybean plants are blown into the column via an inlet flap As the result of the draft, the spores are fluidized, finely distributed, and fall down onto the leaves.

To obtain higher inoculation densities without spore aggregation, the leaves were, as an alternative, covered with a layer of a spore suspension and, after 15 minutes, removed from the suspension (layering method). After this time, sufficient adhesion of the precipitated spores was, already ensured. The inoculated leaves were incubated in a chamber with on average 25° C. and an atmospheric humidity of 71.2%.

To assess the course of the infection under the microscope, leaf samples were taken 0 hours post inoculation (hpi), 6 hpi, 24 hpi and 48 hpi, and stained by different methods.

a) Coomassie Staining

To carry out the Coomassie staining, the infected leaf material was harvested and destained overnight at room temperature. For the microscopy, the leaf material was covered in Coomassie solution, and the solution was rinsed off after 5 minutes using a little water. The sample was viewed under the microscope immediately thereafter.

b) Calcofluor Staining To prepare the Calcofluor staining solution, 0.03% of Calcofluor White (Sigma-Aldrich) was dissolved in 50 mM Tris/HCl pH 8.0 nd 0.01% Tween 20. To stain the extracellular fungal structures, the infected leaf was immersed in the staining solution for 30 seconds and then washed with water for 10 seconds. The stained fungal structures fluoresce pale blue under UV excitation.

c) Aniline Blue Staining

The leaf material was transferred into Falcon tubes or dishes with destaining solution and incubated overnight at RT. Thereafter, the destaining solution was removed and the leaves were washed 2× with water. For the staining, the leaves were covered for 1.5-2 h in aniline blue staining solution and subsequently viewed directly under the microscope.

d) Wheat Germ Agglutinin Alexa Fluor 488 Staining (WGA Staining)

For the WGA staining of *P. pachyrhizi*, inoculated barley leaves were placed into 10% (w|v) KOH for 30-45 minutes at RT. Inoculated soybean leaves were dissected into 1 cm$^2$ sections and boiled for 5 minutes in 10% (w|v) KOH. Thereafter, the barley and the soybean leaves were washed 5 times for 3-5 minutes with 1× PBS buffer. For the staining, the leaf material was placed into WGA staining solution and allowed to infiltrate for 10 minutes under a residual pressure of 100 mbar. Thereafter, the material was viewed directly under the microscope or stored in the staining solution at 4° C. in the dark.

Example 2

Transient Biolistic Transformation of Plant Cells

For the transient overexpresssion of the Bax inhibitor (for constructs and other methods, see patent WO 2004/081217) by biolistic transformation, 30-100 mg of gold particles were weighed, resuspended in 1 ml of 70% strength EtOH and shaken for 3-5 minutes. After incubation for 1 hour at room temperature, pelletization was effected by centrifugation (1 min, 10 000 rpm, Eppendorf microcentrifuge). Thereafter, the particles were washed 3× with sterile water and subsequently taken up in sterile 50% (v/v) glycerol and stored at 4° C. When 30 mg of gold particles were weighed in, the solution contained approximately 25 mg/ml gold. Prior to use the particles were again shaken in order to distribute them thoroughly and sonicated for 15 seconds in a sonicator.

In general, enough gold particles for at least three bombardments were prepared. Up to the precipitation step, the mixture was shaken vigorously for a few seconds on a vortex mixer after each step. For the DNA precipitation into gold particles for 3 bombardments, one 12.5 μl of the thoroughly shaken gold particle glycerol solution were removed and treated with the desired DNA (pGY1-BI-1, pGY1-GFP, pGY1, see WO 2004/081217). 1.6 μg/μl DNA were employed per bombardment on the plasmid. Thereafter, 12.5 μl of 2.5 M CaCl$_2$ solution and 5 μl of 0.1 M spermidine solution were added. The mixture was shaken for 3 minutes, treated with 70 μl of 70% (v/v) ethanol and carefully inverted. After addition of 70 μl of 100% ethanol, the mixture was again mixed thoroughly by inverting and incubated at −20° C. for up to 1 hour. The particles were pelleted by centrifugation (1 min, 11000 rpm, Eppendorf microcentrifuge, Weaseling-Berzdorf), resuspended in 18 μl of 100% ethanol and distributed as uniformly as possible on the macrocarriers (Bio-Rad, Munich), which had previously been washed with 100% ethanol and dried, within a radius of approx. 1 cm. The macrocarriers were then incubated at room temperature until all of the ethanol had evaporated.

The transient biolistic transformation of barley and soya leaves was performed using the Biolistic Particle Delivery System PDS-1000/He system (Bio-Rad, Munich). The material used for the transformation was preferably barley leaves of 7-day old barley plants (cv. 'Hanna') or the first two leaves (two-leaf stage) of soybean plants (cv. 'Oxford'). The leaves to be transformed were placed on 1% (w|v) water agar and fixed using a metal ring.

In order to determine the optimum ratio between pressure applied and residual pressure in the vacuum chamber for the transformation, various pressure/residual-pressure combinations were tested. Residual pressures of 15-27 inches Hg and rupture disks rated at 650-1800 psi were used After the bombardment, the chamber was ventilated, the carrier together with the leaves was removed, and the leaves were incubated for at least 24 hours at room temperature before being viewed under the microscope or stained.

Gold particles were used for the ballistic transformation of the leaves. It emerged that bombardment with particles 0.6 μm in diameter was best suited to barley since they caused less tissue injury. In the case of the transient transformation of soybeans, the highest transformation rate was obtained with the 1 μm particles.

For the transient transformation to be successful, the ratios between the pressure for accelerating the particles, the residual pressure in the vacuum chamber and the distance between sample and particles must be adapted to each other. To achieve this, various conditions were tested for barley leaves and soybean leaves. In the case of soybean, a pressure of 900 psi with a residual pressure in the vacuum chamber of 25 inches Hg and a sample distance of 9 cm has proven successful (FIG. 7A). In the case of barley leaves, the highest cell numbers were obtained with a pressure of 1100 psi, a residual pressure in the vacuum chamber of 25 inches Hg and a distance between leaves and particles of 9 cm (FIG. 7B).

To study the effects of BI-1 on the interaction between *P. pachyrhizi* and barley, use was made of the transient biolistic transformation. The primary leaves of seven-day old barley plants (cv. 'Hanna') were bombarded with overexpression constructs of BI-1 (pGY1-BI-1, Hückelhoven R. et al., 2001). These plasmids contain a Camv 35S promoter, which ensures constitutive expression of the genes. A CaMV 35S/GFP construct as reporter gene was bombarded into the cells together with the expression plasmids (Schweizer P. et al., MPMI 12, 647 (1999)). The blank vector pGY-1 together with the GFP/reporter gene construct was used as the control. The inoculation with *P. pachyrhizi* was effected 24 hours after the transformation by precipitation from a spore suspension (layering method, 2-3×10$^4$ spores/ml). After incubation for 18 hours, the interactions were evaluated under the microscope following Calcofluor staining of the extracellular fungal structures. The structures counted were GFP-forming cells which had been penetrated by the fungus and GFP-forming cells which had been attacked by the fungus, but could either successfully defend themselves against it (or where the fungus has died prior to penetration). In addition, the total number of GFP-forming cells was counted. To carry out the evaluation, the relative penetration rates were calculated on the basis of the total number of transformed cells which interacted with soybean rust.

In the control, 53% of the transformed cells which interacted with *P. pachyrhizi* were penetrated (averaged over the experiments), while only 37% of the BI-1-transformed cells were penetrated (see Table FIG. 10 and FIG. 8). According to the evaluation, the penetration resistance of the cells which had been transformed transiently with BI-1 is significantly increased over *P. pachyrhizi*. Viewing under the microscope revealed that the BI-1-forming cells had a markedly more vital appearance than cells which only expressed GFP.

Example 3

Stable Transformation of Barley, and Detection of the GFP:BI-1 Transgene

To study the effect of BI-1 on interaction of barley with *Phakopsora pachyrhizi* in greater detail, stably transformed barley plants which overexpressed a GFP:BI-1 fusion protein were generated. The *agrobacterium*-mediated stable transformation used for this purpose is a technique which has been established for years and whose methods have already been published in a number of review articles (Cheng Z. et al., Plant Mol. Biol. 60, 583(2004); Taylor et al., DNA & Cell Biology. 21(12), 963 (2002); Rakoczy-Trojanowska, Cellular & Molecular Biology Letters. 7(3), 849 (2002); Grabowska A., Acta Physiologiae Plantarum. 26(4), 451 (2004); Chesnokov V., Sel'skokhozyaistvennaya Biologiya. 1, 26 (2004). Even the transformation of monocotyledonous species such as, for example, barley, which was still difficult in the 1990s, is now a standard technique (Travella S. et al., Plant Cell Reports 23(12), 780 (2005); Murray F. et at, Plant Cell Reports 22(6), 397 (2004)).

Since it was not known of the resulting transgenic plants whether they were homozygous lines, the presence of the overexpression construct had first to be detected. To this end, the genomic DNA was isolated from one leaf of all of the plants. This was done using the DNeasy 96 Plant Kit (Quiagen, Hilden; following the manufacturer's instructions). The overexpression construct GFP-BI-1 was detected with GFP-specific primers by means of PCR for the presence of the construct. The Phusion Hot Start (Finnzymes, Espoo) was used for the in-vitro amplification of DNA by PCR (Mullis & Faloona, 1987).

```
Primer 1:
                                        (SEQ ID NO: 47)
5'-ATGGTGAGCAAGGGCGAGGA-3'

Primer 2:
                                        (SEQ ID NO: 48)
5'-TTGAACAACGATGTGCAAGACTCCTTGTACAGCTCGTCCATGC-3')
```

PCR approach for detecting the GFP:BI-1 transgene:

| | |
|---|---|
| DMSO | 0.6 µl |
| Buffer (5x) (F-519 GC) | 4 µl |
| DNA | 3 µl |
| dNTP mix (10 mM each) | 0.4 µl |
| Primer 1 (20 pmol) | 1 µl |
| Primer 2 (20 pmol) | 1 µl |
| Hot Start Phusion F 540L | 0.2 µl |
| Water | 9.8 µl |

The PCR was carried out a therrnocycler with heatable lid (Tgradient; Biometra, Göttingen
PCR Programme:

| | | | | |
|---|---|---|---|---|
| 1. | Initial denaturation | 98° C. | 30 sec | |
| 2. | Denaturation | 98° C. | 10 sec | 35 cycles of steps 2-4 |
| 3. | Annealing | 58° C. | 30 sec | |
| 4. | Elongation | 72° C. | 30 sec | |

-continued

| | | | | |
|---|---|---|---|---|
| 5. | Elongation | 72° C. | 5 min | |
| 6. | Storage | 4° C. | | |

Using standard methods, the DNA was separated and analyzed by gel electrophoresis in a 1% agarose gel ([w/v], INVITROGEN, Karlsruhe; in 1× TAE buffer) (Sambrook et al., Molecular Cloning: A Laboratory Manual, Cold Spring Harbor Laboratory, Cold Spring Harbor (N.Y.) 1989).

In a total of six plants out of the transgenic lines #6(2)E15L7P2 (T2) and #6(1)E8L1(T1), it was not possible to detect the 740 by GFP fragment, and thus the construct. The data of these plants [plants 5, 10 and 19 of line #6(1)E8L1(T1) and plant 3, 11 and 12 of line #6(2)E15L7P2 (T2)] were therefore not taken into consideration in the calculations which follow (see FIG. 9).

Example 4

Interaction of *P. pachyrhizi* with Transgenic Bax Inhibitor-1 Overexpressing Barley To verify the resistance-increasing effect as the result of transient overexpression of BI-1, the interaction between *P. pachyrhizi* and transgenic barley plants cv. 'Golden Promise' (GP), which contain a GFP-BI-1 overexpression construct was studied under the microscope in comparison with the wild type (WT) of this variety. To generate the transgenic plants, a GFP-BI-1 fusion under the control of the constitutive CaMV 35S promoter was used, thus ensuring a sufficient expression of the protein.

In each case 20 plants of the wild type and of four transgenic lines #6(1)E4L3P5 (T2), 1#6(2)E15L7P1 (T2), #6(2)E15L7P2 (T2) and #6(1)E8L1(T1) were grown. Only 14 plants germinated from the seeds of line #6(2)E15L7P2 (T2). Since there was only a limited amount of seed available, the experiments were carried out with a smaller number of plants of this line. Seven days after sowing, the primary leaf was removed, inoculated with the *P. pachyrhizi* with the aid of the precipitation column and fixed in destaining solution 24 hours after the inoculation. After destaining of the leaves was complete, they were stained with aniline blue. Aniline blue intercollates into the structure of callose and thus preferentially stains papillae where callose accumulates and crosslinks with other polymeric substances. Cells which have, as the result of a hypersensitivity response (HR), undergone a process which resembles apoptosis in mammalian cells, also show a light fluorescence after staining with aniline blue. The number of spores, the germinated spores with germ tube which had already formed an appressorium and, as cell response, the appressoria with the papillae which lie underneath, and the HR, were counted on the inoculated barley leaves. Larger spore accumulations where an allocation of the appressoria to the spores was no longer possible, were not included in the count. As far as possible, at least 100 spores with appressoria were counted per leaf (see Table in FIG. 11).

The analysis of the leaves under the microscope revealed the formation of papillae, which was frequently markedly increased in the transgenic lines. In contrast, an appearance of HR in the infected cells was observed less frequently in the transgenic plants. In the wild type, an average of 36% of the infected cells developed papillae as defence response, 45% of the cells responded with an HR. In contrast, the formation of papillae in the transgenic lines amounted to between 50 and 60%. The HR, which amounted to 16-26%, was also markedly less pronounced in comparison with the wild type (FIG. 12). According to examination with the so-called "Student test" (t-Test), the relative formation of papillae in the transgenic lines is significantly increased over the WT and the HR is significantly reduced (P<0.001). According to the observations in these experiments, BI-1 prevents the programmed cell death and promotes papillae formation, by the cells, as alternative defence.

Example 5

Interaction of *P. pachyrhizi* with Transgenic Bax-Inhibitor-1-Overexpressing Soya Soya plants which overexpress NtBI-1 were generated by methods known per se and were inoculated with *P. pachyrhizi* as described above. The NtBI-1-transformed soya plants showed a markedly reduced soya rust infection in comparison with the wild-type soya plants—the reduction amounted on average to in the region of over 30%.

Likewise, soya plants transformed with NTBI-1 and with SELDA were generated and inoculated with *P. pachyrhizi* as described above. The NtBI-1+SELDA-transformed soya plants likewise showed a markedly reduced soya rust infection in comparison with the wild-type soya plants—the reduction here amounted on average to in the region of over 15%.

We claim:

1. A method of generating or increasing resistance to at least one biotrophic fungus of the genus *Phakopsora* in a plant, plant part, plant tissue, or plant cell, comprising:
   a) increasing protein quantity or function of at least one Bax inhibitor-1 (BI1) protein in a plant or part thereof in comparison with a control plant or part thereof by:
      i) stably transforming a plant cell with a recombinant expression cassette comprising a nucleic acid sequence encoding the BI1 protein operably linked to a heterologous tissue-specific promoter,
      ii) regenerating a plant from said plant cell, and
      iii) expressing the nucleic acid sequence encoding the BI1 protein in at least one part or tissue of said plant,
   b) selecting a plant or part thereof having resistance to at least one biotrophic fungus of the genus *Phakopsora* generated or increased in comparison with a control plant or part thereof,
   wherein the plant is a soybean plant and the BI1 protein comprises an amino acid sequence having at least 90% sequence identity with the amino acid sequence of SEQ ID NO: 6.

2. The method of claim 1, wherein the at least one biotrophic fungus is *Phakopsora pachyrhizi* or *Phakopsora meibomiae*.

3. The method of claim 1, wherein the BI1 protein comprises at least one sequence which has at least 98% sequence homology with at least one BI1 consensus motif selected from the group consisting of a) H(L/I)KXVY, (SEQ ID NO: 49)

b) AXGA(Y/F)XH, (SEQ ID NO: 50)

c) NIGG, (SEQ ID NO: 51)

d) P(V/P)(Y/F)E(E/Q)(R/Q)KR, (SEQ ID NO: 52)

e) (E/Q)G(A/S)S(V/I)GPL, (SEQ ID NO: 53)

f) DP(S/G)(L/I)(I/L), (SEQ ID NO: 54)

g) V(G/A)T(A/S)(L/I)AF(A/G)CF(S/T), (SEQ ID NO: 55)

-continued h) YL(Y/F)LGG, (SEQ ID NO: 56)

i) L(L/V)SS(G/W)L(S/T)(I/M)L(L/M)W, (SEQ ID NO: 58)
and j) DTGX(I/V)(I/V)E. (SEQ ID NO: 59)

4. The method of claim 1, wherein expression of the BI1 protein is increased at least in epidermis, essentially tissue-specifically in epidermis, and/or essentially not increased in mesophyll.

5. The method of claim 1, wherein the plant additionally has:
  a) an mlo-resistant phenotype,
  b) inhibited or reduced expression or function of MLO, RacB and/or NaOx at least in epidermis in comparison with a control plant, and/or
  c) increased expression or function of PEN2, SNAP34 and/or PEN1 at least in epidermis in comparison with a control plant.

6. A recombinant expression cassette comprising a nucleic acid sequence encoding a BI1 protein operably linked to a heterologous epidermis-specific promoter, wherein the BI1 protein comprises an amino acid sequence having at least 90% sequence identity with the amino acid sequence of SEQ ID NO: 6.

7. A recombinant vector comprising the expression cassette of claim 6.

8. A recombinant soybean plant comprising at least one expression cassette of claim 6 or at least one vector comprising said expression cassette.

9. The recombinant soybean plant of claim 8, wherein the soybean plant has an mlo-resistant phenotype.

10. The method of claim 1, wherein the tissue-specific promoter is an epidermis-specific promoter.

11. The method of claim 1, wherein the BI1 protein comprises an amino acid sequence having at least 98% sequence identity with the amino acid sequence of SEQ ID NO: 6.

12. The method of claim 1, wherein the BI1 protein comprises an amino acid sequence having at least 95% sequence identity with the amino acid sequence of SEQ ID NO: 6.

13. The method of claim 1, wherein the BI1 protein comprises the amino acid sequence of SEQ ID NO: 6 or is encoded by the polynucleotide sequence of SEQ ID NO: 5.

14. The recombinant expression cassette of claim 6, wherein the BI1 protein comprises an amino acid sequence having at least 98% sequence identity with the amino acid sequence of SEQ ID NO: 6.

15. The recombinant expression cassette of claim 6, wherein the BI1 protein comprises an amino acid sequence having at least 95% sequence identity with the amino acid sequence of SEQ ID NO: 6.

16. The recombinant expression cassette of claim 6, wherein the BI1 protein comprises the amino acid sequence of SEQ ID NO: 6 or is encoded by the polynucleotide sequence of SEQ ID NO: 5.

* * * * *